(12) United States Patent
D. Reed

(10) Patent No.: US 8,993,263 B2
(45) Date of Patent: Mar. 31, 2015

(54) PKA LIGANDS AND POLYNUCLEOTIDES ENCODING PKA LIGANDS

(75) Inventor: Thomas D. Reed, Blacksburg, VA (US)

(73) Assignee: Intrexon Corporation, Blacksburg, VA (US)

( * ) Notice: Subject to any disclaimer, the term of this patent is extended or adjusted under 35 U.S.C. 154(b) by 0 days.

(21) Appl. No.: 11/834,897

(22) Filed: Aug. 7, 2007

(65) Prior Publication Data

US 2008/0032947 A1    Feb. 7, 2008

Related U.S. Application Data

(60) Provisional application No. 60/821,682, filed on Aug. 7, 2006.

(51) Int. Cl.
  C12P 21/06    (2006.01)
  C12N 15/00   (2006.01)
  C12N 1/20    (2006.01)
  C12N 9/12    (2006.01)

(52) U.S. Cl.
  CPC ........................................ *C12N 9/12* (2013.01)
  USPC ................... 435/69.1; 435/320.1; 435/252.3; 435/70.1

(58) Field of Classification Search
  CPC ....... C12N 1/00; C12N 15/00; C12N 2330/50
  USPC ........................... 435/69.1, 320.1, 252.3, 70.1
  See application file for complete search history.

(56) References Cited

U.S. PATENT DOCUMENTS

| | | |
|---|---|---|
| 6,011,013 A | 1/2000 | Carr et al. |
| 6,451,528 B1 | 9/2002 | Carr et al. |
| 7,071,295 B2 | 7/2006 | Reed |
| 2004/0185556 A1 | 9/2004 | Reed |
| 2008/0050808 A1 | 2/2008 | Reed et al. |
| 2008/0051360 A1 | 2/2008 | Reed et al. |
| 2008/0213834 A1 | 9/2008 | Reed et al. |
| 2008/0220475 A1 | 9/2008 | Reed et al. |
| 2009/0186379 A1 | 7/2009 | Reed |
| 2009/0215173 A1 | 8/2009 | Reed |
| 2009/0215866 A1 | 8/2009 | Reed |

FOREIGN PATENT DOCUMENTS

| | | |
|---|---|---|
| WO | WO 2005/040336 A2 | 5/2005 |
| WO | WO 2005/116231 A1 | 12/2005 |
| WO | WO 2007/048103 A2 | 4/2007 |
| WO | WO 2007/076166 A2 | 7/2007 |
| WO | WO 2008/119058 A2 | 10/2008 |

OTHER PUBLICATIONS

Portela et al., Characterization of yeast pyruvate kinase 1 as a protein kinase A substrate, and specificity of the phosphorylation site sequence in the whole protein. Biochem J. May 15, 2006; 396(Pt 1): 117-126.*
Voet et al., Biochemistry John Wiley and Sons, 1990, p. 126-128.*
Kimchi-Sarfaty C et al., A "silent" polymorphism in the MDR1 gene changes substrate specificity.Science. Jan. 26, 2007;315(5811):525-8.*
Ngo, in The Protein Folding Problem and Tertiary Structure Prediction, Merz et al. (eds.), Birkhauser Boston: Boston, MA, pp. 433 and 492-495, 1994.*
Pasquale et al Adeno-Associated Virus Rep78 Protein Interacts with Protein Kinase A and Its Homolog PRKX and Inhibits CREB-Dependent Transcriptional Activation J Virol. Oct. 1998;72(10):7916-25.*
Banke TG et al., Control of GluR1 AMPA receptor function by cAMP-dependent protein kinase, J Neurosci, (2000), 20:89-102.
Bhave G et al., cAMP-dependent protein kinase regulates desensitization of the capsaicin receptor (VR1) by direct phosphorylation, Neuron, (2002), 35:721-31.
Blumenthal DK et al., Dephosphorylation of cAMP-dependent protein kinase regulatory subunit (type II) by calmodulin-dependent protein phosphatase. Determinants of substrate specificity, J Biol Chem, (1986), 261:8140-5.
Boo YC, Shear stress stimulates phosphorylation of protein kinase A substrate proteins including endothelial nitric oxide synthase in endothelial cells, Exp Mol Med, (2006), 38:63-71.
Bunemann M et al., Functional regulation of L-type calcium channels via protein kinase A-mediated phosphorylation of the beta(2) subunit, J Biol Chem, (1999), 274:33851-4.
Butt E et al., cAMP- and cGMP-dependent protein kinase phosphorylation sites of the focal adhesion vasodilator-stimulated phosphoprotein (VASP) in vitro and in intact human platelets, J Biol Chem, (1994), 269:14509-17.
Chang XB et al., Protein kinase A (PKA) still activates CFTR chloride channel after mutagenesis of all 10 PKA consensus phosphorylation sites, J Biol Chem, (1993), 268:11304-11.
Chen L et al., Phosphorylation of the A-kinase-anchoring protein Yotiao contributes to protein kinase A regulation of a heart potassium channel, J Biol Chem, (2005), 280:31347-52.
Cheng HC et al., A potent synthetic peptide inhibitor of the cAMP-dependent protein kinase, J Biol Chem, (1986), 261:989-92.
Chheda MG et al., Phosphorylation of Snapin by PKA modulates its interaction with the SNARE complex, Nat Cell Biol, (2001), 3:331-8.
Collins SP et al., LKB1, a novel serine/threonine protein kinase and potential tumour suppressor, is phosphorylated by cAMP-dependent protein kinase (PKA) and prenylated in vivo, Biochem J, (2000), 345 Pt 3:673-80.
D'Souza T et al., Phosphorylation of claudin-3 at threonine 192 by cAMP-dependent protein kinase regulates tight junction barrier function in ovarian cancer cells, J Biol Chem, (2005), 280:26233-40.

(Continued)

Primary Examiner — Maria Leavitt
(74) Attorney, Agent, or Firm — Sterne, Kessler, Goldstein & Fox P.L.L.C.

(57) ABSTRACT

The invention relates to kinase ligands and polyligands. In particular, the invention relates to ligands, homopolyligands, and heteropolyligands that modulate PKA activity. The ligands and polyligands are utilized as research tools or as therapeutics. The invention includes linkage of the ligands, homopolyligands, and heteropolyligands to a cellular localization signal, epitope tag and/or a reporter. The invention also includes polynucleotides encoding the ligands and polyligands.

14 Claims, 14 Drawing Sheets

(56) References Cited

OTHER PUBLICATIONS

Day RN et al., A protein kinase inhibitor gene reduces both basal and multihormone-stimulated prolactin gene transcription, J Biol Chem, (1989), 264:431-6.
Feramisco Jr et al., Inhibition of cyclic AMP-dependent protein kinase by analogues of a synthetic peptide substrate, J Biol Chem, (1978), 253:8968-71.
Ferris CD et al., Inositol trisphosphate receptor: phosphorylation by protein kinase C and calcium calmodulin-dependent protein kinases in reconstituted lipid vesicles, Proc Natl Acad Sci U S A, (1991), 88:2232-5.
Giordano G et al., Activation of NMDA receptors induces protein kinase A-mediated phosphorylation and degradation of matrin 3. Blocking these effects prevents NMDA-induced neuronal death, J Neurochem, (2005), 94:808-18.
Glass DB et al., Primary structural determinants essential for potent inhibition of cAMP-dependent protein kinase by inhibitory peptides corresponding to the active portion of the heat-stable inhibitor protein, J Biol Chem, (1989), 264:8802-10.
Hall DD et al., Binding of protein phosphatase 2A to the L-type calcium channel Cav1.2 next to Ser1928, its main PKA site, is critical for Ser1928 dephosphorylation, Biochemistry, (2006), 45:3448-59.
Harada H et al., Phosphorylation and inactivation of BAD by mitochondria-anchored protein kinase A, Mol Cell, (1999), 3:413-22.
Horner TJ et al., Phosphorylation of GRK1 and GRK7 by cAMP-dependent protein kinase attenuates their enzymatic activities, J Biol Chem, (2005), 280:28241-50.
Hsieh-Wilson LC et al., Phosphorylation of spinophilin modulates its interaction with actin filaments, J Biol Chem, (2003), 278:1186-94.
Jarvik JW et al., Epitope tagging, Annu Rev Genet, (1998), 32:601-18.
Jay D et al., In situ determination of a PKA phosphorylation site in the C-terminal region of filamin, Mol Cell Biochem, (2004), 260:49-53.
Ji Y et al., Targeted inhibition of Ca2+/calmodulin-dependent protein kinase II in cardiac longitudinal sarcoplasmic reticulum results in decreased phospholamban phosphorylation at threonine 17, J Biol Chem, (2003), 278:25063-71.
Kameyama K et al., Involvement of a postsynaptic protein kinase A substrate in the expression of homosynaptic long-term depression, Neuron, (1998), 21:1163-75.
Kemp BE et al., Adrenergic control of the cyclic AMP-dependent protein kinase and pyruvate kinase in isolated hepatocytes. Application of a synthetic peptide substrate for measuring protein kinase activity, J Biol Chem, (1978), 253:5147-54.
Kemp BE et al., Role of multiple basic residues in determining the substrate specificity of cyclic AMP-dependent protein kinase, J Biol Chem, (1977), 252:4888-94.
Lambrechts A et al., cAMP-dependent protein kinase phosphorylation of EVL, a Mena/VASP relative, regulates its interaction with actin and SH3 domains, J Biol Chem, (2000), 275:36143-51.
Liu SJ et al., Tau becomes a more favorable substrate for GSK-3 when it is prephosphorylated by PKA in rat brain, J Biol Chem, (2004), 279:50078-88.
Lu W et al., Phosphorylation of hepatitis C virus core protein by protein kinase A and protein kinase C, Virology, (2002), 300:20-30.
Maller JL et al., In vivo phosphorylation of a synthetic peptide substrate of cyclic AMP-dependent protein kinase, Proc Natl Acad Sci U S A, (1978), 75:248-51.
Meetei AR et al., Involvement of protein kinase A in the phosphorylation of spermatidal protein TP2 and its effect on DNA condensation, Biochemistry, (2002), 41:185-95.
Pi Y et al., Phosphorylation of troponin I controls cardiac twitch dynamics: evidence from phosphorylation site mutants expressed on a troponin I-null background in mice, Circ Res, (2002), 90:649-56.
Quilliam LA et al., Rap1A is a substrate for cyclic AMP-dependent protein kinase in human neutrophils, J Immunol, (1991), 147:1628-35.
Sakthivel S et al., In vivo and in vitro analysis of cardiac troponin I phosphorylation, J Biol Chem, (2005), 280:703-14.
Schmidt M et al., Adeno-associated virus type 2 Rep78 inhibition of PKA and PRKX: fine mapping and analysis of mechanism, J Virol, (2002), 76:1033-42.
Scott JD et al., Identification of an inhibitory region of the heat-stable protein inhibitor of the cAMP-dependent protein kinase, Proc Natl Acad Sci U S A, (1985), 82:4379-83.
Scott JD et al., Primary-structure requirements for inhibition by the heat-stable inhibitor of the cAMP-dependent protein kinase, Proc Natl Acad Sci U S A, (1986), 83:1613-6.
Sette C et al., Phosphorylation and activation of a cAMP-specific phosphodiesterase by the cAMP-dependent protein kinase. Involvement of serine 54 in the enzyme activation, J Biol Chem, (1996), 271:16526-34.
Snyder PM et al., cAMP and serum and glucocorticoid-inducible kinase (SGK) regulate the epithelial Na(+) channel through convergent phosphorylation of Nedd4-2, J Biol Chem, (2004), 279:45753-8.
Taylor SS, The in vitro phosphorylation of chromatin by the catalytic subunit of cAMP-dependent protein kinase, J Biol Chem, (1982), 257:6056-63.
Walsh DA et al., Multiple pathway signal transduction by the cAMP-dependent protein kinase, Faseb J, (1994), 8:1227-36.
Wecker L et al., Phosphorylation sites within alpha4 subunits of alpha4beta2 neuronal nicotinic receptors: a comparison of substrate specificities for cAMP-dependent protein kinase (PKA) and protein kinase C (PKC), Neurochem Res, (2003), 28:431-6.
Wright De et al., Fluorometric assay for adenosine 3',5'-cyclic monophosphate-dependent protein kinase and phosphoprotein phosphatase activities, Proc Natl Acad Sci U S A, (1981), 78:6048-50.
Wullrich A et al., The multiphosphorylation domain of the phosphorylase kinase alpha M and alpha L subunits is a hotspot of differential mRNA processing and of molecular evolution, J Biol Chem, (1993), 268:23208-14.
Xu ZC et al., Phosphorylation of the ATP-sensitive, inwardly rectifying K+ channel, ROMK, by cyclic AMP-dependent protein kinase, J Biol Chem, (1996), 271:9313-9.
Yamamoto S et al., Agents that elevate cyclic AMP induce receptor phosphorylation primarily at serine 331 in HEK 293 cells overexpressing human thromboxane receptor alpha, Biochem Pharmacol, (2002), 64:375-83.
Zhou R et al., Characterization of protein kinase A-mediated phosphorylation of ezrin in gastric parietal cell activation, J Biol Chem, (2003), 278:35651-9.
U.S. Appl. No. 12/090,462, inventor Reed, Thomas D., filed Oct. 18, 2006.
U.S. Appl. No. 11/983,235, inventor Reed, Thomas D., filed Nov. 8, 2007.
Ji, Y., et al., "Targeted Inhibition of $Ca^{2+}$/Calmodulin-dependant Protein Kinase II in Cardiac Longitudinal Sarcoplasmic Reticulum Results in Decreased Phospholamban Phosphorylation at Threonine 17," J. Biol. Chem. 278:25063-25071, The American Society for Biochemistry and Molecular Biology, Inc. (2003).
U.S. Appl. No. 12/532,912, inventors Bachinsky et al.

* cited by examiner

| LIGAND X | LIGAND X |

FIGURE 1A

| LIGAND X | LIGAND X | LIGAND X |

FIGURE 1B

| LIGAND X | LIGAND X | LIGAND X | LIGAND X | LIGAND X |

FIGURE 1C

| LIGAND X | SPACER | LIGAND X |

FIGURE 2A

| LIGAND X | SPACER | LIGAND X | SPACER | LIGAND X |

FIGURE 2B

| LIGAND X | LIGAND X | SPACER | LIGAND X | SPACER | LIGAND X |

FIGURE 2C

| LIGAND X | LIGAND Y |

FIGURE 3A

| LIGAND X | LIGAND Y | LIGAND Z |

FIGURE 3B

| LIGAND X | LIGAND Y | LIGAND X | LIGAND Z | LIGAND A |

FIGURE 3C

| LIGAND A | LIGAND B | LIGAND C | LIGAND D |

FIGURE 3D

| LIGAND A | LIGAND A | LIGAND B | LIGAND C |

FIGURE 3E

| LIGAND B | SPACER | LIGAND A |

FIGURE 4A

| LIGAND X | SPACER | LIGAND Y | SPACER | LIGAND Z |

FIGURE 4B

| LIGAND X | LIGAND Y | SPACER | LIGAND Y | LIGAND X |

FIGURE 4C

| LIGAND A | SPACER | LIGAND B | SPACER | LIGAND C | SPACER | LIGAND D |

FIGURE 4D

| LIGAND A | LIGAND A | SPACER | LIGAND B | LIGAND C |

FIGURE 4E

| LIGAND X | LIGAND X | EPITOPE |

FIGURE 5A

| EPITOPE | LIGAND X | LIGAND Y |

FIGURE 5B

| LIGAND X | SPACER | LIGAND X | EPITOPE |

FIGURE 5C

| EPITOPE | LIGAND X | SPACER | LIGAND Y |

FIGURE 5D

| LIGAND X | SPACER | LIGAND Y | SPACER | LIGAND A | LIGAND B | EPITOPE |

FIGURE 5E

| EPITOPE | LIGAND X | SPACER | LIGAND Y | LIGAND A | LIGAND B |

FIGURE 5F

| LIGAND X | EPITOPE |

FIGURE 5G

| LIGAND X | LIGAND X | LOCALIZATION SIGNAL |

FIGURE 7A

| LOCALIZATION SIGNAL | LIGAND X | LIGAND Y |

FIGURE 7B

| LIGAND X | SPACER | LIGAND X | LOCALIZATION SIGNAL |

FIGURE 7C

| LOCALIZATION SIGNAL | LIGAND X | SPACER | LIGAND Y |

FIGURE 7D

| LIGAND X | SPACER | LIGAND Y | LIGAND B | LOCALIZATION SIGNAL |

FIGURE 7E

| LOCALIZATION SIGNAL | LIGAND A | LIGAND B | LIGAND C | LIGAND D |

FIGURE 7F

| LOCALIZATION SIGNAL | LIGAND Y |

FIGURE 7G

| LIGAND A | LIGAND B | LIGAND C | LIGAND D | EPITOPE | LOCALIZATION SIGNAL |

FIGURE 8A

| LOCALIZATION SIGNAL | LIGAND X | LIGAND Y | EPITOPE |

FIGURE 8B

| EPITOPE | LIGAND X | SPACER | LIGAND X | LOCALIZATION SIGNAL |

FIGURE 8C

| LOCALIZATION SIGNAL | LIGAND X | SPACER | LIGAND Y | EPITOPE |

FIGURE 8D

| EPITOPE | LIGAND X | LIGAND Y | LIGAND B | LOCALIZATION SIGNAL |

FIGURE 8E

| LOCALIZATION SIGNAL | LIGAND Z | SPACER | LIGAND Y | LIGAND B | EPITOPE |

**FIGURE

| PROMOTER | LIGAND or POLYLIGAND | EPITOPE | LOCALIZATION SIGNAL | STOP | POLY-A |
|---|---|---|---|---|---|

FIGURE 9A

| PROMOTER | OPTIONAL REPORTER | OPTIONAL EPITOPE | LIGAND or POLYLIGAND | OPTIONAL LOCALIZATION SIGNAL | STOP | POLY-A |
|---|---|---|---|---|---|---|

FIGURE 9B

| PROMOTER | LIGAND or POLYLIGAND | REPORTER | LOCALIZATION SIGNAL | STOP | POLY-A |
|---|---|---|---|---|---|

FIGURE 9C

| PROMOTER | LIGAND or POLYLIGAND | OPTIONAL EPITOPE | OPTIONAL REPORTER | OPTIONAL LOCALIZATION SIGNAL | STOP | POLY-A |
|---|---|---|---|---|---|---|

FIGURE 9D

| PROMOTER | LIGAND or POLYLIGAND | LOCALIZATION SIGNAL | STOP | POLY-A |
|---|---|---|---|---|

FIGURE 9E

| PROMOTER | LOCALIZATION SIGNAL | LIGAND or POLYLIGAND | STOP | POLY-A |
|---|---|---|---|---|

FIGURE 9F

| PROMOTER | LIGAND or POLYLIGAND | STOP | POLY-A |
|---|---|---|---|

FIGURE 9G

PKA LIGANDS AND POLYNUCLEOTIDES ENCODING PKA LIGANDS

CROSS-REFERENCE TO RELATED APPLICATION

This application claims priority to U.S. Ser. No. 60/821,682, filed 7 Aug. 2006, which is incorporated by reference.

BACKGROUND OF THE INVENTION

1. Field of the Invention

The invention relates to mammalian kinase ligands, substrates and modulators. In particular, the invention relates to polypeptides, polypeptide compositions and polynucleotides that encode polypeptides that are ligands, substrates, and/or modulators of PKA. The invention also relates to polyligands that are homopolyligands or heteropolyligands that modulate PKA activity. The invention also relates to ligands and polyligands tethered to a subcellular location.

2. Background of the Invention

Kinases are enzymes that catalyze the addition of phosphate to a molecule. The addition of phosphate by a kinase is called phosphorylation. When the kinase substrate is a protein molecule, the amino acids commonly phosphorylated are serine, threonine and tyrosine. Phosphatases are enzymes that remove phosphate from a molecule. The removal of phosphate is called dephosphorylation. Kinases and phosphatases often represent competing forces within a cell to transmit, attenuate, or otherwise modulate cellular signals and cellular control mechanisms. Kinases and phosphatases have both overlapping and unique natural substrates. Cellular signals and control mechanisms, as regulated by kinases, phosphatases, and their natural substrates are a target of research tool design and drug design.

Mammalian cyclic AMP-dependent protein kinase is also known as Protein Kinase A or PKA. PKA can phosphorylate serine and threonine residues. The enzymatic activity, activation and regulation of PKA have been studied. Many cellular and peptide substrates of PKA have been identified (See for example, Banke et al. 2000 J Neurosci 20:89-102; Bhave et al. 2002 Neuron 35:721-731; Blumenthol et al. 1986 J Biol Chem 261:8140-45; Boo 2006 Exper. Molec. Medicine 38:63-71; Bunemann et al. 1999 J Biol Chem 274:33851-54; Butt et al. 1994 J Biol Chem 269:14509-17; Chang et al. 1993 J Biol Chem 268:11304-11; Chen et al. 2005 J Biol Chem 280:31347-52; Cheng et al. 1986 J Biol Chem 261:989-992; Chheda et al. 2001 Nature Cell Biol 3:331-338; Collins et al. 2000 Biochem J 345:673-680; Day et al. 1989 J Biol Chem 264:431-436; D'Sousa et al. 2005 J Biol Chem 280:26233-40; Feramisco et al. 1978 J Biol Chem 253:8968-71; Ferris et al. 1991 Proc Natl Acad Sci USA 88:2232-35; Giordano et al. 2005 J Neurochem 94:808-818; Glass et al. 1989 J Biol Chem 264:8802-8810; Hall et al. 2006 Biochemistry 45:3448-3459; Harada et al. 1999 Molecular Cell 3:413-422; Homer et al. 2005 J Biol Chem 280:28241-50; Hsieh-Wilson et al. 2003 J Biol Chem 278-1186-94; Jay et al. 2004 Mol Cell Biochem 260:49-53; Ji et al. 2003 J Biol Chem 278:25063-71; Kameyama et al. 1998 Neuron 21:1163-75; Kemp et al. 1977 J Biol Chem 252:4888-4894; Kemp et al. 1978 J Biol Chem 253:5147-54; Lambrechts et al. 2000 J Biol Chem 275:36143-36151; Liu et al. 2004 J Biol Chem 279:50078-88; Lu et al. 2002 Virology 300:20-30; Maller et al. 1978 Proc Natl Acad Sci USA 75:248-251; Meetei et al. 2002 Biochemistry 41:185-195; Pi et al. 2002 Circ Res 90:649-656; Quilliam et al. 1991 J Immunol 147:1628-1635; Sakthivel et al. 2005 J Biol Chem 280:703-714; Schmidt et al. 2002 J Virol 76:1033-42; Scott et al. 1985 Proc Natl Acad Sci USA 82:4397-83; Scott et al. 1986 proc Natl Acad Sci USA 83:1613-16; Sette et al. 1996 J Biol Chem 271:16526-34; Snyder et al. 2004 J Biol Chem 279:45753-58; Taylor 1982 J Biol Chem 257:6056-6063; Walsh et al. 1994 FASEB J 8:1227-1236; Wecker et al. 2003 Neurochem Res 28:431-436; Wright et al. 1981 Proc Natl Acad Sci USA 78:6048-6050; Wullrich et al. 1993 J Biol Chem 268:23208-14; Xu et al. 1996 J Biol Chem 271:9313-19; Yamamoto et al. 2002 Biochem Pharmacol 64:375-383; Zhou et al. 2003 J Biol Chem 278:35651-59). Natural and synthetic polypeptides have been studied to examine PKA substrate specificity. While polypeptides and variants thereof have been studied as individual PKA substrates or ligands, mixed ligands linked together as polyligands that modulate PKA activity have not been demonstrated before this invention. An aspect of the invention is to provide novel, modular, inhibitors of PKA activity by modifying one or more natural substrates either by truncation or by amino acid substitution. A further aspect of the invention is the subcellular localization of a PKA inhibitor, ligand, or polyligand by linking to a subcellular localization signal.

Disruption of PKA binding protein interactions in sperm has been disclosed. See, for example, U.S. Pat. Nos. 6,011,013 and 6,451,528.

Further, there are several small molecule agents known in the art and used experimentally, such as H-89, HA-1004, H-7, H-8, HA-100 and staurosporine, that inhibit PKA activity.

Design and synthesis of polypeptide ligands that modulate calcium/calmodulin-dependent protein kinase and that localize to the cardiac sarco(endo)plasmic reticulum was performed by Ji et al. (J Biol Chem (2003) 278:25063-71). Ji et al. accomplished this by generating expression constructs that localized calcium/calmodulin-dependent protein kinase inhibitory polypeptide ligands to the sarcoplasmic reticulum by fusing a sarcoplasmic reticulum localization signal derived from phospholamban to a polypeptide ligand. See also U.S. Pat. No. 7,071,295.

SUMMARY OF THE INVENTION

The invention relates to polypeptide ligands and polyligands for PKA. Various embodiments of the PKA ligands and polyligands are represented in SEQ ID NOS:1-216. More specifically, the invention relates to ligands, homopolyligands, and heteropolyligands that comprise any one or more of SEQ ID NOS:55-216. Additionally, the invention relates to ligands and polyligands comprising one or more subsequences of SEQ ID NOS:12-54 or any portion thereof. Furthermore, the invention relates to polyligands with at least about 80%, 85%, 90%, 95%, 96%, 97%, 98% and 99% sequence identity to a polyligand comprising one or more of SEQ ID NOS:55-216 or any portion thereof. Furthermore, the invention relates to polyligands with at least about 80%, 85%, 90%, 95%, 96%, 97%, 98% and 99% sequence identity to a polyligand comprising one or more subsequences of SEQ ID NOS:12-54.

Polyligands, which can be homopolyligands or heteropolyligands, are chimeric ligands composed of two or more monomeric polypeptide ligands. An example of a monomeric ligand is the polypeptide represented by SEQ ID NO:55, wherein Xaa is any amino acid. SEQ ID NO:55 is a selected subsequence of wildtype full length SEQ ID NO:12, wherein the amino acid corresponding to Xaa in the wildtype sequence is a serine or threonine phosphorylatable by PKA. An example of a homopolyligand is a polypeptide comprising a dimer or multimer of SEQ ID NO:55, wherein Xaa is any amino acid. An example of a heteropolyligand is a polypeptide comprising SEQ ID NO:55 and one or more of SEQ ID NOS:56-216, wherein Xaa is any amino acid. There are numerous ways to combine SEQ ID NOS:55-216 into homopolymeric or heteropolymeric ligands. Furthermore, there are numerous ways to combine additional subsequences of SEQ ID NOS:12-54 with each other and with SEQ ID NOS:55-216 to make polymeric ligands.

The polyligands of the invention optionally comprise spacer amino acids between monomers. SEQ ID NO:1 is an embodiment of a polyligand of the structure A-S1-B-S2-C-S3-D, wherein A is SEQ ID NO:142, B is SEQ ID NO:143, C is SEQ ID NO:144, and D is SEQ ID NO:145, and wherein S1, S2, and S3 are amino acid spacers. This invention intends to capture all combinations of homopolyligands and heteropolyligands without limitation to the examples given above or below. In this description, use of the term "ligand(s)" encompasses monomeric ligands, polymeric ligands, homopolymeric ligands and/or heteropolymeric ligands.

A monomeric ligand is a polypeptide where at least a portion of the polypeptide is capable of being recognized by a PKA. The portion of the polypeptide capable of recognition is termed the recognition motif. In the present invention, recognition motifs can be natural or synthetic. Examples of recognition motifs are well known in the art and include, but are not limited to, naturally occurring PKA substrates and pseudosubstrate motifs.

A polymeric ligand comprises two or more monomeric ligands.

A homopolymeric ligand is a polymeric ligand where each of the monomeric ligands is identical in amino acid sequence, except that a phosphorylatable residue may be substituted or modified in one or more of the monomeric ligands.

A heteropolymeric ligand is a polymeric ligand where each of the monomeric ligands does not have an identical amino acid sequence.

The ligands of the invention are optionally linked to additional molecules or amino acids that provide an epitope tag, a reporter, and/or a cellular localization signal. The cellular localization signal targets the ligands to a region of a cell. The epitope tag and/or reporter and/or localization signal may be the same molecule. The epitope tag and/or reporter and/or localization signal may also be different molecules.

The invention also encompasses polynucleotides comprising a nucleotide sequence encoding ligands, homopolyligands, and heteropolyligands. The nucleic acids of the invention are optionally linked to additional nucleotide sequences encoding polypeptides with additional features, such as an epitope tag, a reporter, and/or a cellular localization signal. The polynucleotides are optionally flanked by nucleotide sequences comprising restriction endonuclease sites and other nucleotides needed for restriction endonuclease activity. The flanking sequences optionally provide unique cloning sites within a vector and optionally provide directionality of subsequence cloning. Further, the nucleic acids of the invention are optionally incorporated into vector polynucleotides. The ligands, polyligands, and polynucleotides of this invention have utility as research tools and/or therapeutics.

BRIEF DESCRIPTION OF THE DRAWINGS

FIGS. 1A-1C show examples of homopolymeric ligands without spacers.
FIGS. 2A-2C show examples of homopolymeric ligands with spacers.
FIGS. 3A-3E show examples of heteropolymeric ligands without spacers.

FIGS. 4A-4E show examples of heteropolymeric ligands with spacers.
FIGS. 5A-5G show examples of ligands and polymeric ligands linked to an optional epitope tag.
FIGS. 7A-7G show examples of ligands and polymeric ligands linked to an optional localization signal.
FIGS. 8A-8G show examples of ligands and polymeric ligands linked to an optional localization signal and an optional epitope tag.
FIGS. 9A-9G show examples of gene constructs where ligands and polyligands are linked to an optional localization signal, an optional epitope tag, and an optional reporter.

DETAILED DESCRIPTION OF THE INVENTION

Figure 6A:
FIGS. 6A-6G show examples of ligands and polymeric ligands linked to an optional reporter.
Figure 6B:
Figure 6C:
Figure 6D:
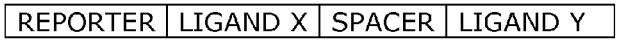
Figure 6E:
Figure 6F:
Figure 6G:

This application has subject matter related to application Ser. No. 10/724,532 (now U.S. Pat. No. 7,071,295), Ser. No. 10/682,764 (US2004/0185556, PCT/US2004/013517, WO2005/040336), Ser. No. 11/233,246, and US20040572011P (WO2005116231). Each of these patents and applications is hereby incorporated by reference.

The present invention relates to ligands and polyligands that are PKA modulators. Various embodiments of ligands and polyligands are represented in SEQ ID NOS:1-216. Polyligands are chimeric ligands comprising two or more monomeric polypeptide ligands. An example of a monomeric ligand is the polypeptide represented by SEQ ID NO:55, wherein Xaa is any amino acid. SEQ ID NO:55 is a selected subsequence of wildtype full length SEQ ID NO:12, wherein the amino acid corresponding to Xaa in the wildtype sequence is a serine or threonine phosphorylatable by PKA. Another example of a monomeric ligand is the polypeptide represented by SEQ ID NO:155. Each of SEQ ID NOS:55-216 represents an individual polypeptide ligand in monomeric form, wherein Xaa is any amino acid. SEQ ID NOS:55-132 are selected examples of subsequences of SEQ ID NOS:12-54, however, other subsequences of SEQ ID NOS:12-54 may also be utilized as monomeric ligands. Monomeric ligand subsequences of SEQ ID NOS:12-54 may be wildtype subsequences. Additionally, monomeric ligand subsequences of SEQ ID NOS:12-54 may have the PKA phosphorylatable amino acids replaced by other amino acids. Furthermore, monomeric ligands and polyligands may have at least about 80%, 85%, 90%, 95%, 96%, 97%, 98% or 99% sequence identity to a ligand comprising an amino acid sequence in one or more of SEQ ID NOS:55-216. Furthermore, monomeric ligands and polyligands may have at least about 80%, 85%, 90%, 95%, 96%, 97%, 98% and 99% sequence identity to a subsequence of SEQ ID NOS:12-54.

An example of a homopolyligand is a polypeptide comprising a dimer or multimer of SEQ ID NO:55, wherein Xaa is any amino acid. An example of a heteropolyligand is a polypeptide comprising SEQ ID NO:55 and one or more of SEQ ID NOS:56-216, wherein Xaa is any amino acid. There are numerous ways to combine SEQ ID NOS:55-216 into homopolymeric or heteropolymeric ligands. Furthermore, there are numerous ways to combine additional subsequences of SEQ ID NOS:12-54 with each other and with SEQ ID NOS:55-216 to make polymeric ligands.

Polyligands may comprise any two or more of SEQ ID NOS:55-216, wherein Xaa is any amino acid. A dimer or multimer of SEQ ID NO:91 is an example of a homopolyligand. An example of a heteropolyligand is a polypeptide comprising SEQ ID NO:216 and one or more of SEQ ID NOS:55-215. There are numerous ways to combine SEQ ID NOS:55-216 into homopolymeric or heteropolymeric ligands. SEQ ID NOS:55-132 are selected examples of subsequences of SEQ ID NOS:12-54, however, additional subsequences, wildtype or mutated, may be utilized to form polyligands. The instant invention is directed to all possible combinations of homopolyligands and heteropolyligands without limitation.

SEQ ID NOS:12-54 show proteins that contain at least one serine or threonine residue phosphorylatable by PKA, the positions of which are represented by Xaa. SEQ ID NOS:55-132 are subsequences of SEQ ID NOS:12-54 where, again, the locations of the PKA phosphorylatable residues are represented by Xaa. In nature, Xaa is, generally speaking, serine or threonine. In one embodiment of the instant invention, Xaa can be any amino acid. Ligands where Xaa is serine or threonine can be used as part of a polyligand, however in one embodiment, the phosphorylatable serine or threonine is replaced with another amino acid, such as one of the naturally occurring amino acids including, alanine, aspartate, asparagine, cysteine, glutamate, glutamine, phenylalanine, glycine, histidine, isoleucine, leucine, lysine, methionine, proline, arginine, valine, tryptophan, or tyrosine. The Xaa may also be a non-naturally occurring amino acid. In another embodiment, the PKA phosphorylatable serine(s) or threonine(s) are replaced by alanine. The ligands and polyligands of the invention are designed to modulate the endogenous effects of PKA.

In general, ligand monomers based on natural PKA substrates are built by isolating a putative PKA phosphorylation recognition motif in a PKA substrate. Sometimes it is desirable to modify the phosphorylatable residue to an amino acid other than serine or threonine. Additional monomers include the PKA recognition motif as well as amino acids adjacent and contiguous on either side of the PKA recognition motif. Monomers may therefore be any length provided the monomer includes the PKA recognition motif. For example, the monomer may comprise an PKA recognition motif and at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30-100 or more amino acids adjacent to the recognition motif.

For example, in one embodiment, the invention comprises an inhibitor of PKA comprising at least one copy of a peptide selected from the group consisting of: a) a peptide at least 80%, 85%, 90%, 95%, 96%, 97%, 98% or 99% identical to a peptide comprising amino acid residues corresponding to amino acid residues 356-362 of SEQ ID NO:12, wherein the amino acid residue corresponding to amino acid residue 362 of SEQ ID NO:12 is an amino acid residue other than serine or threonine; b) a peptide at least 80%, 85%, 90%, 95%, 96%, 97%, 98% or 99% identical to a peptide comprising amino acid residues corresponding to amino acid residues 351-367 of SEQ ID NO:12, wherein the amino acid residue corresponding to amino acid residue 362 of SEQ ID NO:12 is an amino acid residue other than serine or threonine; c) a peptide at least 80%, 85%, 90%, 95%, 96%, 97%, 98% or 99% identical to a peptide comprising amino acid residues corresponding to amino acid residues 346-372 of SEQ ID NO:12, wherein the amino acid residue corresponding to amino acid residue 362 of SEQ ID NO:12 is an amino acid residue other than serine or threonine; and d) a peptide at least 80%, 85%, 90%, 95%, 96%, 97%, 98% or 99% identical to a peptide comprising amino acid residues corresponding to amino acid residues 336-382 of SEQ ID NO:12, wherein the amino acid residue corresponding to amino acid residue 362 of SEQ ID NO:12 is an amino acid residue other than serine or threonine.

As used herein, the terms "correspond(s) to" and "corresponding to," as they relate to sequence alignment, are intended to mean enumerated positions within a reference protein, e.g., nicotininc receptor alpha (SEQ ID NO:12), and those positions that align with the positions on the reference protein. Thus, when the amino acid sequence of a subject peptide is aligned with the amino acid sequence of a reference peptide, e.g., SEQ ID NO:12, the amino acids in the subject peptide sequence that "correspond to" certain enumerated positions of the reference peptide sequence are those that align with these positions of the reference peptide sequence, but are not necessarily in these exact numerical positions of the reference sequence. Methods for aligning sequences for determining corresponding amino acids between sequences are described below.

Additional embodiments of the invention include monomers (as described above) based on any putative or real substrate for PKA, such as substrates identified by SEQ ID NOS: 12-150. Furthermore, if the substrate has more than one recognition motif, then more than one monomer may be identified therein.

Further embodiments of the invention include monomers based on PKA inhibitors and regulators, such as those identified by SEQ ID NOS:150-216 and subsequences thereof.

Another embodiment of the invention is a nucleic acid molecule comprising a polynucleotide sequence encoding at least one copy of a ligand peptide.

Another embodiment of the invention is a nucleic acid molecule wherein the polynucleotide sequence encodes one or more copies of one or more peptide ligands.

Another embodiment of the invention is a nucleic acid molecule wherein the polynucleotide sequence encodes at least a number of copies of the peptide selected from the group consisting of 2, 3, 4, 5, 6, 7, 8, 9 or 10.

Another embodiment of the invention is a vector comprising a nucleic acid molecule encoding at least one copy of a ligand or polyligand.

Another embodiment of the invention is a recombinant host cell comprising a vector comprising a nucleic acid molecule encoding at least one copy of a ligand or polyligand.

Another embodiment of the invention is a method of inhibiting PKA in a cell comprising transfecting a vector comprising a nucleic acid molecule encoding at least one copy of a ligand or polyligand into a host cell and culturing the transfected host cell under conditions suitable to produce at least one copy of the ligand or polyligand.

The invention also relates to modified inhibitors that are at least about 80%, 85%, 90% 95%, 96%, 97%, 98% or 99% identical to a reference inhibitor. A "modified inhibitor" is used to mean a peptide that can be created by addition, deletion or substitution of one or more amino acids in the primary structure (amino acid sequence) of a inhibitor protein or polypeptide. A "modified recognition motif" is a naturally occurring PKA recognition motif that has been modified by addition, deletion, or substitution of one or more amino acids in the primary structure (amino acid sequence) of the motif. For example, a modified PKA recognition motif may be a motif where the phosphorylatable amino acid has been modified to a non-phosphorylatable amino acid. The terms "protein" and "polypeptide" are used interchangeably herein. The reference inhibitor is not necessarily a wild-type protein or a portion thereof. Thus, the reference inhibitor may be a protein or peptide whose sequence was previously modified over a wild-type protein. The reference inhibitor may or may not be the wild-type protein from a particular organism.

A polypeptide having an amino acid sequence at least, for example, about 95% "identical" to a reference an amino acid sequence is understood to mean that the amino acid sequence of the polypeptide is identical to the reference sequence except that the amino acid sequence may include up to about five modifications per each 100 amino acids of the reference amino acid sequence encoding the reference peptide. In other words, to obtain a peptide having an amino acid sequence at least about 95% identical to a reference amino acid sequence, up to about 5% of the amino acid residues of the reference sequence may be deleted or substituted with another amino acid or a number of amino acids up to about 5% of the total amino acids in the reference sequence may be inserted into the reference sequence. These modifications of the reference sequence may occur at the N-terminus or C-terminus positions of the reference amino acid sequence or anywhere between those terminal positions, interspersed either individually among amino acids in the reference sequence or in one or more contiguous groups within the reference sequence.

As used herein, "identity" is a measure of the identity of nucleotide sequences or amino acid sequences compared to a reference nucleotide or amino acid sequence. In general, the sequences are aligned so that the highest order match is obtained. "Identity" per se has an art-recognized meaning and can be calculated using published techniques. (See, e.g., Computational Molecular Biology, Lesk, A. M., ed., Oxford University Press, New York (1988); Biocomputing: Informatics And Genome Projects, Smith, D. W., ed., Academic Press, New York (1993); Computer Analysis of Sequence Data, Part I, Griffin, A. M., and Griffin, H. G., eds., Humana Press, New Jersey (1994); von Heinje, G., Sequence Analysis In Molecular Biology, Academic Press (1987); and Sequence Analysis Primer, Gribskov, M. and Devereux, J., eds., M Stockton Press, New York (1991)). While there exist several methods to measure identity between two polynucleotide or polypeptide sequences, the term "identity" is well known to skilled artisans (Carillo, H. & Lipton, D., Siam J Applied Math 48:1073 (1988)). Methods commonly employed to determine identity or similarity between two sequences include, but are not limited to, those disclosed in Guide to Huge Computers, Martin J. Bishop, ed., Academic Press, San Diego (1994) and Carillo, H. & Lipton, D., Siam J Applied Math 48:1073 (1988). Computer programs may also contain methods and algorithms that calculate identity and similarity. Examples of computer program methods to determine identity and similarity between two sequences include, but are not limited to, GCG program package (Devereux, J., et al., Nucleic Acids Research 12(i):387 (1984)), BLASTP, ExPASy, BLASTN, FASTA (Atschul, S. F., et al., J Molec Biol 215:403 (1990)) and FASTDB. Examples of methods to determine identity and similarity are discussed in Michaels, G. and Garian, R., Current Protocols in Protein Science, Vol 1, John Wiley & Sons, Inc. (2000), which is incorporated by reference. In one embodiment of the present invention, the algorithm used to determine identity between two or more polypeptides is BLASTP.

In another embodiment of the present invention, the algorithm used to determine identity between two or more polypeptides is FASTDB, which is based upon the algorithm of Brutlag et al. (Comp. App. Biosci. 6:237-245 (1990), incorporated by reference). In a FASTDB sequence alignment, the query and subject sequences are amino sequences. The result of sequence alignment is in percent identity. Parameters that may be used in a FASTDB alignment of amino acid sequences to calculate percent identity include, but are not limited to: Matrix=PAM, k-tuple=2, Mismatch Penalty=1, Joining Penalty=20, Randomization Group Length=0, Cutoff Score=1, Gap Penalty=5, Gap Size Penalty 0.05, Window Size=500 or the length of the subject amino sequence, whichever is shorter.

If the subject sequence is shorter or longer than the query sequence because of N-terminus or C-terminus additions or deletions, not because of internal additions or deletions, a manual correction can be made, because the FASTDB program does not account for N-terminus and C-terminus truncations or additions of the subject sequence when calculating percent identity. For subject sequences truncated at both ends, relative to the query sequence, the percent identity is corrected by calculating the number of bases of the query sequence that are N- and C-terminus to the reference sequence that are not matched/aligned, as a percent of the total bases of the query sequence. The results of the FASTDB sequence alignment determine matching/alignment. The alignment percentage is then subtracted from the percent identity, calculated by the above FASTDB program using the specified parameters, to arrive at a final percent identity score. This corrected score can be used for the purposes of determining how alignments "correspond" to each other, as well as percentage identity. Residues of the query (subject) sequences or the reference sequence that extend past the N- or C-termini of the reference or subject sequence, respectively, may be considered for the purposes of manually adjusting the percent identity score. That is, residues that are not matched/aligned with the N- or C-termini of the comparison sequence may be counted when manually adjusting the percent identity score or alignment numbering.

For example, a 90 amino acid residue subject sequence is aligned with a 100 residue reference sequence to determine percent identity. The deletion occurs at the N-terminus of the subject sequence and therefore, the FASTDB alignment does not show a match/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 reference sequence. This time the deletions are internal deletions so there are no residues at the N- or C-termini of the subject sequence which are not matched/aligned with the query. In this case the percent identity calculated by FASTDB is not manually corrected.

The polyligands of the invention optionally comprise spacer amino acids between monomers. The length and composition of the spacer may vary. An example of a spacer is glycine, alanine, polyglycine, or polyalanine. Specific examples of spacers used between monomers in SEQ ID NO:1 are the five amino acids PGAGA, the four amino acids GGGG, and the six amino acids AAGGAA. In the instance of SEQ ID NO:1, the proline-containing spacer is intended to break an alpha helical secondary structure. Spacer amino acids may be any amino acid and are not limited to alanine, glycine and proline. SEQ ID NO:1, depicted generically in FIG. 4D, represents a specific example of a polyligand of the structure A-S1-B-S2-C-S3-D, wherein A is SEQ ID NO:142, B is SEQ ID NO:143, C is SEQ ID NO:144, and D is SEQ ID NO:145, wherein Xaa is Alanine, and wherein S1, S2 and S3 are spacers. The instant invention is directed to all combinations of homopolyligands and heteropolyligands, with or without spacers, and without limitation to the examples given above or below.

The ligands and polyligands of the invention are optionally linked to additional molecules or amino acids that provide an epitope tag, a reporter, and/or localize the ligand to a region of a cell (See FIGS. 5A-5G, FIGS. 6A-6G, FIGS. 7A-7G, and FIGS. 8A-8G). Non-limiting examples of epitope tags are FLAG™ (Kodak; Rochester, N.Y.), HA (hemaglutinin), c-Myc and His6. Additional examples of epitope tags are given in Jarvik & Telmer 1998 Annual Review of Genetics 32:601-18. Non-limiting examples of reporters are alkaline phosphatase, galactosidase, peroxidase, luciferase and green fluorescent protein (GFP). Non-limiting examples of cellular localizations are sarcoplasmic reticulum, endoplasmic reticulum, mitochondria, golgi apparatus, nucleus, plasma membrane, apical membrane, and basolateral membrane. The epitopes, reporters and localization signals are given by way of example and without limitation. The epitope tag, reporter and/or localization signal may be the same molecule. The epitope tag, reporter and/or localization signal may also be different molecules.

Ligands and polyligands and optional amino acids linked thereto can be synthesized chemically or recombinantly using techniques known in the art. Chemical synthesis techniques include but are not limited to peptide synthesis which is often performed using an automated peptide synthesizer. Peptides can also be synthesized utilizing non-automated peptide synthesis methods known in the art. Recombinant techniques include insertion of ligand-encoding nucleic acids into expression vectors, wherein nucleic acid expression products are synthesized using cellular factors and processes.

Linkage of a cellular localization signal, epitope tag, or reporter to a ligand or polyligand can include covalent or enzymatic linkage to the ligand. When the localization signal comprises material other than a polypeptide, such as a lipid or carbohydrate, a chemical reaction to link molecules may be utilized. Additionally, non-standard amino acids and amino acids modified with lipids, carbohydrates, phosphate or other molecules may be used as precursors to peptide synthesis. The ligands of the invention have therapeutic utility with or without localization signals. For example, the ligands generically depicted in FIGS. 1A-1C, FIGS. 2A-2C, FIGS. 3A-3C, and FIGS. 4A-4C represent embodiments of conventional polypeptide therapeutics. However, ligands linked to localization signals have utility as subcellular tools or therapeutics. For example, ligands depicted generically in FIGS. 7A-7G represent ligands with utility as subcellular tools or therapeutics. PKA ligand-containing gene constructs are also delivered via gene therapy. FIGS. 10B and 10C depict embodiments of gene therapy vectors for delivering and controlling polypeptide expression in vivo. Polynucleotide sequences linked to the gene construct in FIGS. 10B and 10C include genome integration domains to facilitate integration of the transgene into a viral genome and/or host genome.

Figure 10A:
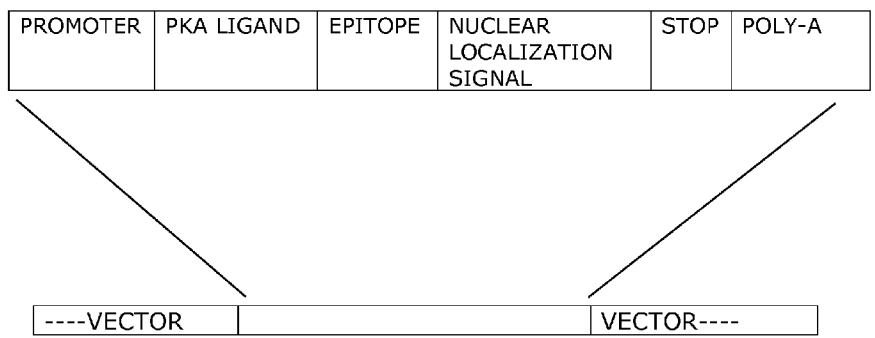
FIGS. 10A-10D show examples of vectors containing ligand gene constructs.
Figure 10B:
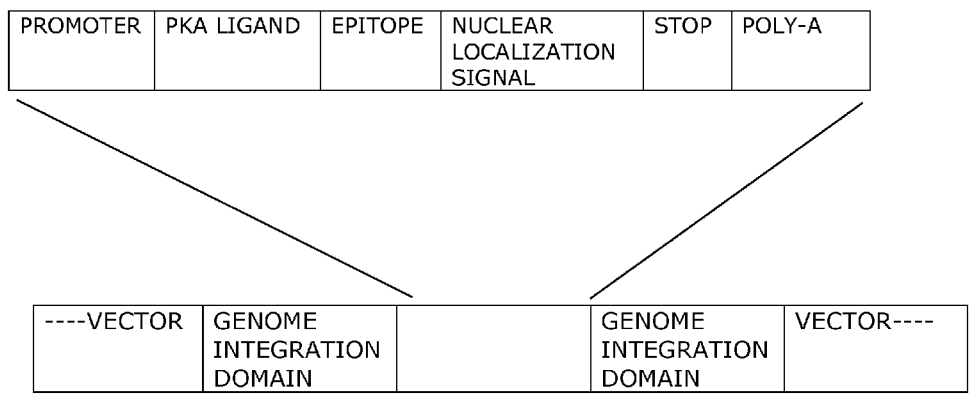
Figure 10C:
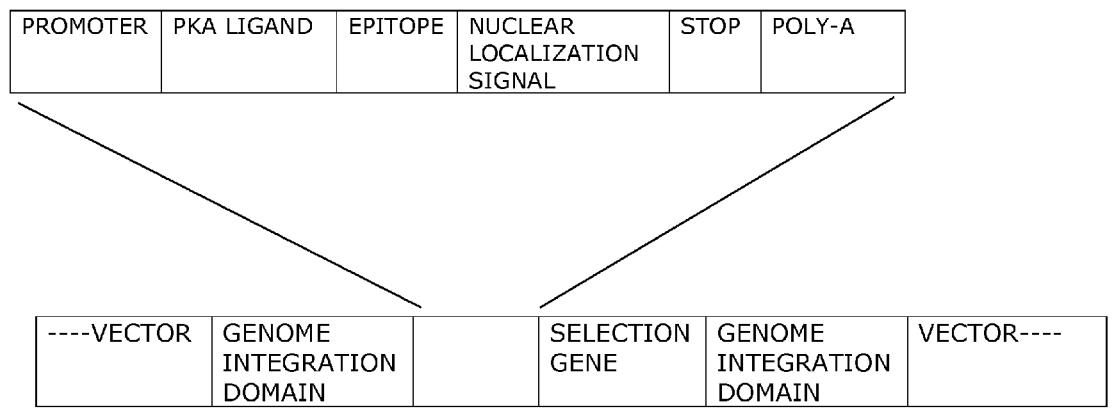

FIG. 10A shows a vector containing an PKA ligand gene construct, wherein the ligand gene construct is releasable from the vector as a unit useful for generating transgenic animals. For example, the ligand gene construct, or transgene, is released from the vector backbone by restriction endonuclease digestion. The released transgene is then injected into pronuclei of fertilized mouse eggs; or the transgene is used to transform embryonic stem cells. The vector containing a ligand gene construct of FIG. 10A is also useful for transient transfection of the transgene, wherein the promoter and codons of the transgene are optimized for the host organism. The vector containing a ligand gene construct of FIG. 10A is also useful for recombinant expression of polypeptides in fermentable organisms adaptable for small or large scale production, wherein the promoter and codons of the transgene are optimized for the fermentation host organism.

Figure 10D:
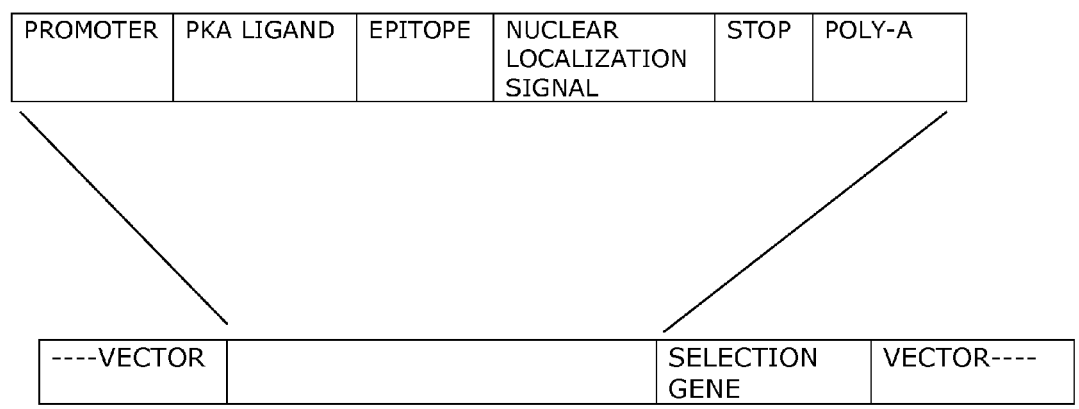

FIG. 10D shows a vector containing an PKA ligand gene construct useful for generating stable cell lines.

The invention also encompasses polynucleotides comprising nucleotide sequences encoding ligands, homopolyligands, and heteropolyligands. The polynucleotides of the invention are optionally linked to additional nucleotide sequences encoding epitopes, reporters and/or localization signals. Further, the nucleic acids of the invention are optionally incorporated into vector polynucleotides. The polynucleotides are optionally flanked by nucleotide sequences comprising restriction endonuclease sites and other nucleotides needed for restriction endonuclease activity. The flanking sequences optionally provide cloning sites within a vector. The restriction sites can include, but are not limited to, any of the commonly used sites in most commercially available cloning vectors. Examples of such sites are those recognized by BamHI, ClaI, EcoRI, EcoRV, SpeI, AflII, NdeI, NheI, XbaI, XhoI, SphI, NaeI, SexAI, HindIII, HpaI, and PstI restriction endonucleases. Sites for cleavage by other restriction enzymes, including homing endonucleases, are also used for this purpose. The polynucleotide flanking sequences also optionally provide directionality of subsequence cloning. It is preferred that 5' and 3' restriction endonuclease sites differ from each other so that double-stranded DNA can be directionally cloned into corresponding complementary sites of a cloning vector.

Ligands and polyligands with or without localization signals, epitopes or reporters are alternatively synthesized by recombinant techniques. Polynucleotide expression constructs are made containing desired components and inserted into an expression vector. The expression vector is then transfected into cells and the polypeptide products are expressed and isolated. Ligands made according to recombinant DNA techniques have utility as research tools and/or therapeutics.

The following is an example of how polynucleotides encoding ligands and polyligands are produced. Complimentary oligonucleotides encoding the ligands and flanking sequences are synthesized and annealed. The resulting double-stranded DNA molecule is inserted into a cloning vector using techniques known in the art. When the ligands and polyligands are placed in-frame adjacent to sequences within a transgenic gene construct that is translated into a protein product, they form part of a fusion protein when expressed in cells or transgenic animals.

Another embodiment of the invention relates to selective control of transgene expression in a desired cell or organism. The promotor portion of the recombinant gene can be a constitutive promoter, a non-constitutive promoter, a tissue-specific promoter (constitutive or non-constitutive) or a selectively controlled promoter. Different selectively controlled promoters are controlled by different mechanisms. For example, a tetracycline-inducible promotor is activated to express a downstream coding sequence when the cell containing the promotor and other necessary cellular factors is treated with tetracycline. When tetracycline is removed, gene expression is subsequently reduced. Other inducible promotors are activated by other drugs or factors. RheoSwitchR is an inducible promoter system available from RheoGene. Temperature sensitive promoters can also be used to increase or decrease gene expression. An embodiment of the invention comprises a ligand or polyligand gene construct whose expression is controlled by an inducible promotor. In one embodiment, the inducible promotor is tetracycline inducible.

Figure 11:
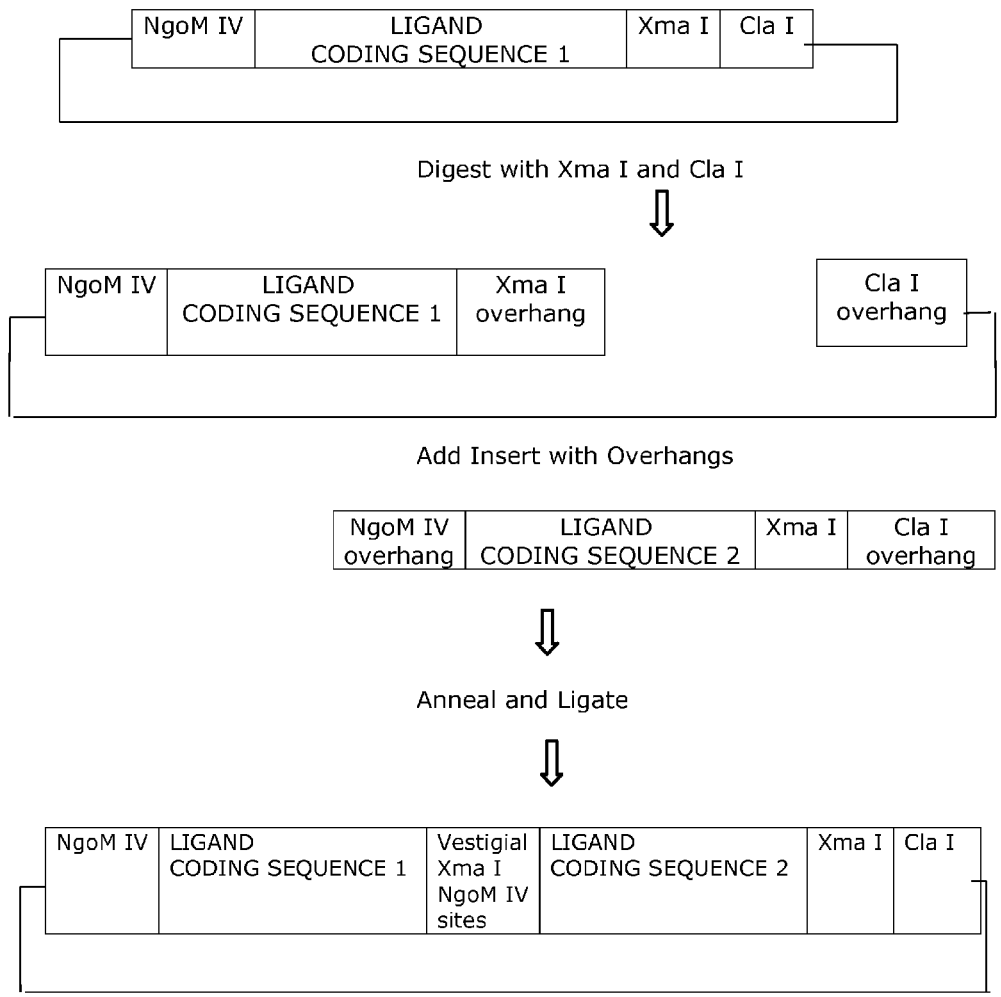
FIG. 11 shows an example of a sequential cloning process useful for combinatorial synthesis of polyligands.

Polyligands are modular in nature. An aspect of the instant invention is the combinatorial modularity of the disclosed polyligands. Another aspect of the invention are methods of making these modular polyligands easily and conveniently. In this regard, an embodiment of the invention comprises methods of modular subsequence cloning of genetic expression components. When the ligands, homopolyligands, heteropolyligands and optional amino acid expression components are synthesized recombinantly, one can consider each clonable element as a module. For speed and convenience of cloning, it is desirable to make modular elements that are compatible at cohesive ends and are easy to insert and clone sequentially. This is accomplished by exploiting the natural properties of restriction endonuclease site recognition and cleavage. One aspect of the invention encompasses module flanking sequences that, at one end of the module, are utilized for restriction enzyme digestion once, and at the other end, utilized for restriction enzyme digestion as many times as desired. In other words, a restriction site at one end of the module is utilized and destroyed in order to effect sequential cloning of modular elements. An example of restriction sites flanking a coding region module are sequences recognized by the restriction enzymes NgoM IV and Cla I; or Xma I and Cla I. Cutting a first circular DNA with NgoM IV and Cla I to yield linear DNA with a 5' NgoM IV overhang and a 3' Cla I overhang; and cutting a second circular DNA with Xma I and Cla I to yield linear DNA with a 5' Cla I overhang and a 3' Xma I overhang generates first and second DNA fragments with compatible cohesive ends. When these first and second DNA fragments are mixed together, annealed, and ligated to form a third circular DNA fragment, the NgoM IV site that was in the first DNA and the Xma I site that was in the second DNA are destroyed in the third circular DNA. Now this vestigial region of DNA is protected from further Xma I or NgoM IV digestion, but flanking sequences remaining in the third circular DNA still contain intact 5' NgoM IV and 3' Cla I sites. This process can be repeated numerous times to achieve directional, sequential, modular cloning events. Restriction sites recognized by NgoM IV, Xma I, and Cla I endonucleases represent a group of sites that permit sequential cloning when used as flanking sequences. This process is depicted in FIG. 11.

Another way to assemble coding region modules directionally and sequentially employs linear DNA in addition to circular DNA. For example, like the sequential cloning process described above, restriction sites flanking a coding region module are sequences recognized by the restriction enzymes NgoM IV and Cla I; or Xma I and Cla I. A first circular DNA is cut with NgoM IV and Cla I to yield linear DNA with a 5' NgoM IV overhang and a 3' Cla I overhang. A second linear double-stranded DNA is generated by PCR amplification or by synthesizing and annealing complimentary oligonucleotides. The second linear DNA has 5' Cla I overhang and a 3' Xma I overhang, which are compatible cohesive ends with the first DNA linearized. When these first and second DNA fragments are mixed together, annealed, and ligated to form a third circular DNA fragment, the NgoM IV site that was in the first DNA and the Xma I site that was in the second DNA are destroyed in the third circular DNA. Flanking sequences remaining in the third circular DNA still contain intact 5' NgoM IV and 3' Cla I sites. This process can be repeated numerous times to achieve directional, sequential, modular cloning events. Restriction sites recognized by NgoM IV, Xma I, and Cla I endonucleases represent a group of sites that permit sequential cloning when used as flanking sequences.

One of ordinary skill in the art recognizes that other restriction site groups can accomplish sequential, directional cloning as described herein. Preferred criteria for restriction endonuclease selection are selecting a pair of endonucleases that generate compatible cohesive ends but whose sites are destroyed upon ligation with each other. Another criteria is to select a third endonuclease site that does not generate sticky ends compatible with either of the first two. When such criteria are utilized as a system for sequential, directional cloning, ligands, polyligands and other coding regions or expression components can be combinatorially assembled as desired. The same sequential process can be utilized for epitope, reporter, and/or localization signals.

Polyligands and methods of making polyligands that modulate PKA activity are disclosed. Therapeutics include delivery of purified ligand or polyligand with or without a localization signal to a cell. Alternatively, ligands and polyligands with or without a localization signals are delivered via adenovirus, lentivirus, adeno-associated virus, or other viral constructs that express protein product in a cell.

Assays. Ligands of the invention are assayed for kinase modulating activity using one or more of the following methods.

Method 1. A biochemical assay is performed employing commercially-obtained kinase, commercially-obtained substrate, commercially-obtained kinase inhibitor (control), and semi-purified inhibitor ligand of the invention (decoy ligand). Decoy ligands are linked to an epitope tag at one end of the polypeptide for purification and/or immobilization, for example, on a microtiter plate. The tagged decoy ligand is made using an in vitro transcription/translation system such as a reticulocyte lysate system well known in the art. A vector polynucleotide comprising a promotor, such as T7 and/or T3 and/or SP6 promotor, a decoy ligand coding sequence, and an epitope tag coding sequence is employed to synthesize the tagged decoy ligand in an in vitro transcription/translation system. In vitro transcription/translation protocols are disclosed in reference manuals such as: Current Protocols in Molecular Biology (eds. Ausubel et al., Wiley, 2004 edition.) and Molecular Cloning: A Laboratory Manual (Sambrook and Russell (Cold Spring Harbor Laboratory Press, 2001, third edition). Immunoreagent-containing methods such as western blots, elisas, and immunoprecipitations are performed as described in: Using Antibodies: A Laboratory Manual (Harlow and Lane Cold Spring Harbor Laboratory Press, 1999).

Specifically, tagged decoy ligand synthesized using an in vitro transcription/translation system is semi-purified and added to a microtiter plate containing kinase enzyme and substrate immobilized by an anti-substrate specific antibody. Microtiter plates are rinsed to substantially remove non-immobilized components. Kinase activity is a direct measure of the phosphorylation of substrate by kinase employing a phospho-substrate specific secondary antibody conjugated to horseradish peroxidase (HRP) followed by the addition of 3,3',5,5'-tetramethylbenzidine (TMB) substrate solution. The catalysis of TMB by HRP results in a blue color that changes to yellow upon addition of phosphoric or sulfuric acid with a maximum absorbance at 450 nm. The Control experiments include absence of kinase enzyme, and/or absence of decoy ligand, and/or presence/absence of known kinase inhibitors. A known kinase inhibitor useful in the assay is staurosporine.

Method 2. A similar assay is performed employing the same reagents as above but the substrate is biotinylated and immobilized by binding to a streptavidin-coated plate.

Method 3. A biochemical assay is performed employing commercially-obtained kinase, commercially-obtained substrate, commercially-obtained kinase inhibitor (control), and semi-purified inhibitor ligand of the invention (decoy ligand) in a microtiter plate. A luminescent-based detection system, such as Promega's Kinase-Glo, is then added to inversely measure kinase activity.

Specifically, tagged decoy ligand synthesized using an in vitro transcription/translation system is semi-purified and added to a microtiter plate containing kinase enzyme and substrate. After the kinase assay is performed, luciferase and luciferin are added to the reaction. Luciferase utilizes any remaining ATP not used by the kinase to catalyze luciferin. The luciferase reaction results in the production of light which is inversely related to kinase activity. Control experiments include absence of kinase enzyme, and/or absence of decoy ligand, and/or presence/absence of known kinase inhibitors. A known kinase inhibitor useful in the assay is staurosporine.

Method 4. A similar cell-based assay is performed employing same reagents as above, but synthesizing the decoy ligand in a mammalian cell system instead of an in vitro transcription/translation system. Decoy ligands are linked to an epitope tag at one end of the polypeptide for immobilization and/or for purification and/or for identification in a western blot. Optionally, tagged decoy ligands are also linked to a cellular localization signal for phenotypic comparison of pancellular and localized kinase modulation. A vector polynucleotide comprising a constitutive promotor, such as the CMV promotor, a decoy ligand coding sequence, an epitope tag coding sequence, and optionally a localization signal coding sequence is employed to express the decoy ligand in cells. Transfection and expression protocols are disclosed in reference manuals such as: Current Protocols in Molecular Biology (eds. Ausubel et al., Wiley, 2004 edition) and Molecular Cloning: A Laboratory Manual (Sambrook and Russell (Cold Spring Harbor Laboratory Press, 2001, third edition). Western Blots and immunoreagent-containing methods are performed as described in: Using Antibodies: A Laboratory Manual (Harlow and Lane Cold Spring Harbor Laboratory Press, 1999).

EXAMPLE 1

A polypeptide comprising a heteropolyligand, an endoplasmic reticulum cellular localization signal, and a His6 epitope is synthesized. The structure of such a polypeptide is generically represented by FIG. 8E. The polypeptide is synthesized on an automated peptide synthesizer or is recombinantly expressed and purified. Purified polypeptide is solubilized in media and added to cells. The polypeptide is endocytosed by the cells, and transported to the endoplasmic reticulum. Verification is performed by immunohistochemical staining using an anti-His6 antibody.

EXAMPLE 2

A transgene is constructed using a human cytomegalovirus (CMV) promoter to direct expression of a fusion protein comprising SEQ ID NO:92, SEQ ID NO:146, SEQ ID NO:169 (POLYLIGAND), green fluorescent protein (REPORTER), and a plasma membrane localization signal (LOCALIZATION SIGNAL). Such a transgene is generically represented by FIG. 9C. The transgene is transfected into cells for transient expression. Verification of expression and location is performed by visualization of green fluorescent protein (GFP) by confocal microscopy.

EXAMPLE 3

A transgene construct is built to produce a protein product with expression driven by a tissue-specific promoter. The transgene comprises a synthetic gene expression unit engineered to encode three domains. Each of these three domains is synthesized as a pair of complimentary polynucleotides that are annealed in solution, ligated and inserted into a vector. Starting at the amino-terminus, the three domains in the expression unit are nucleotide sequences that encode a PKA ligand, a FLAG™ epitope, and a nuclear localization signal. The PKA ligand is a monomeric ligand, homopolymeric ligand or heteropolymeric ligand as described herein. Nucleotide sequences encoding a FLAG™ epitope are placed downstream of nucleotide sequences encoding the PKA ligand. Finally, nucleotide sequences encoding the localization signal are placed downstream of those encoding the FLAG™ epitope. The assembled gene expression unit is subsequently subcloned into an expression vector, such as that shown in FIG. 10A, and used to transiently transfect cells. Verification is performed by immunohistochemical staining using an anti-FLAG™ antibody.

EXAMPLE 4

Modulation of PKA cellular function by subcellularly localized PKA polyligand is illustrated. A transgene construct containing nucleic acids that encode a polyligand fusion protein, epitope, and nuclear localization signal is made. The expression unit contains nucleotides that encode SEQ ID NO:1 (POLYLIGAND), a c-Myc epitope (EPITOPE), and a nuclear localization signal (LOCALIZATION SIGNAL). This expression unit is subsequently subcloned into a vector between a CMV promoter and an SV40 polyadenylation signal (Generically depicted in FIG. 10A and FIG. 12). The completed transgene-containing expression vector is then used to transfect cells. Inhibition of PKA activity is demonstrated by measuring phosphorylation of endogenous substrates against controls.

EXAMPLE 5

Ligand function and localization is demonstrated in vivo by making a transgene construct used to generate mice expressing a ligand fusion protein targeted to the endoplasmic reticulum. The transgene construct is shown generically in FIG. 10B. The expression unit contains nucleotides that encode a tetramer of SEQ ID NO:202, a hemaglutinin epitope, and a mitochondrial localization signal. This expression unit is subsequently subcloned into a vector between nucleotide sequences including an inducible promoter and an SV40 polyadenylation signal. The completed transgene is then injected into pronuclei of fertilized mouse oocytes. The resultant pups are screened for the presence of the transgene by PCR. Transgenic founder mice are bred with wild-type mice. Heterozygous transgenic animals from at least the third generation are used for the following tests, with their non-transgenic littermates serving as controls.

Test 1: Southern blotting analysis is performed to determine the copy number. Southern blots are hybridized with a radio-labeled probe generated from a fragment of the transgene. The probe detects bands containing DNA from transgenic mice, but does not detect bands containing DNA from non-transgenic mice. Intensities of the transgenic mice bands are measured and compared with the transgene plasmid control bands to estimate copy number. This demonstrates that mice in Example 4 harbor the transgene in their genomes.

Test 2: Tissue homogenates are prepared for Western blot analysis. This experiment demonstrates the transgene is expressed in tissues of transgenic mice because hemaglutinin epitope is detected in transgenic homogenates but not in non-transgenic homogenates.

Test 3: Function is assessed by phenotypic observation or analysis against controls.

These examples demonstrate delivery of ligands to a localized region of a cell for therapeutic or experimental purposes. The purified polypeptide ligands can be formulated for oral or parenteral administration, topical administration, or in tablet, capsule, or liquid form, intranasal or inhaled aerosol, subcutaneous, intramuscular, intraperitoneal, or other injection; intravenous instillation; or any other routes of administration. Furthermore, the nucleotide sequences encoding the ligands permit incorporation into a vector designed to deliver and express a gene product in a cell. Such vectors include plasmids, cosmids, artificial chromosomes, and modified viruses. Delivery to eukaryotic cells can be accomplished in vivo or ex vivo. Ex vivo delivery methods include isolation of the intended recipient's cells or donor cells and delivery of the vector to those cells, followed by treatment of the recipient with the cells.

Disclosed are ligands and polyligands that modulate PKA activity and methods of making and using these ligands. The ligands and polyligands are synthesized chemically or recombinantly and are utilized as research tools or as therapeutics. The invention includes linking the ligands and polyligands to cellular localization signals for subcellular therapeutics.

SEQ ID NOS:1-11 are example polyligands and polynucleotides encoding them.

Figure 12:
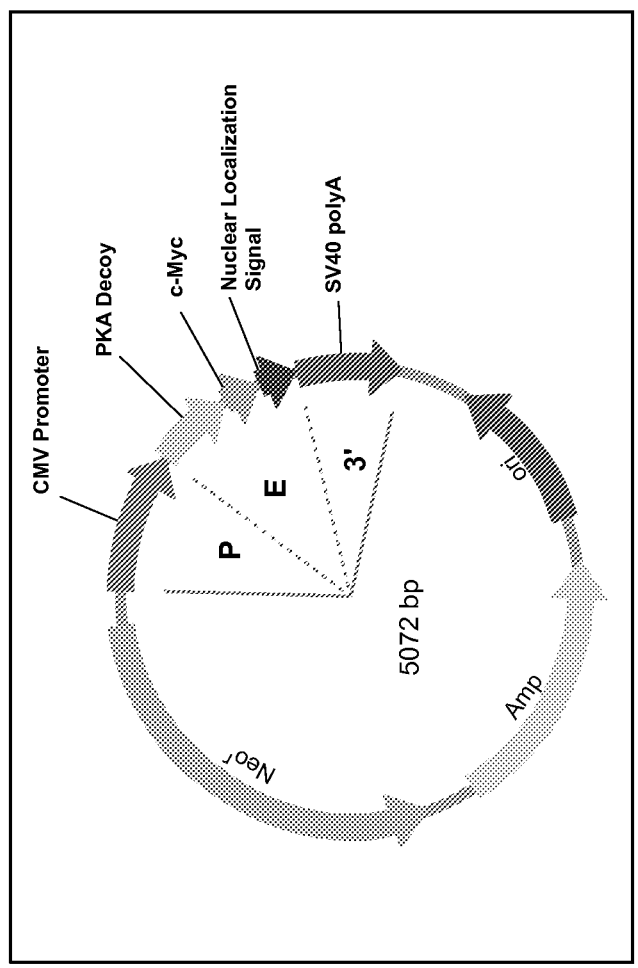
FIG. 12 shows a diagram of a vector for cell transformation.

Specifically, the PKA polyligand of SEQ ID NO:1 is encoded by SEQ ID NO:2, SEQ ID NO:3 and by SEQ ID NO:4, wherein the codons of SEQ ID NO:3 and SEQ ID NO:4 have been optimized for vector insertion. SEQ ID NO:4 includes flanking restriction sites. A vector map of a vector containing SEQ ID NO:3 is shown in FIG. 12 (labeled PKA decoy). SEQ ID NO:1 is an embodiment of a polyligand of the structure A-S1-B-S2-C-S3-D, wherein A is SEQ ID NO:142, B is SEQ ID NO:143, C is SEQ ID NO:144, and D is SEQ ID NO:145, and wherein S1 is a spacer of the amino acid sequence PGAGA, S2 is a spacer of amino acid sequence GGGG, and S3 is a spacer of amino acid sequence AAGGAA. A polyligand of structure A-S1-B-S2-C-S3-D is also called herein a heteropolyligand.

SEQ ID NO:5 is an embodiment of a polyligand of the structure X-S4-Y-S5-Z, wherein X is SEQ ID NO:153, Y is SEQ ID NO:154, and Z is SEQ ID NO:155, and wherein S4 is a spacer of amino acid sequence GAGA, and S5 is a spacer of amino acid sequence AGAG. The PKA polyligand of SEQ ID NO:5 is encoded by SEQ ID NO:6 and by SEQ ID NO:7, wherein the codons of SEQ ID NOS:6 and 7 have been optimized for vector insertion. SEQ ID NO:7 includes flanking restriction sites. A polyligand of structure X-S4-Y-S5-Z is also called herein a heteropolyligand.

SEQ ID NO:8 is an embodiment of a polyligand of the structure X-S6-Y-S7-Z-S8-A-S9-B, wherein X is SEQ ID NO:146, Y is SEQ ID NO:147, Z is SEQ ID NO:148, A is SEQ ID NO:149, and B is SEQ ID NO:150, and wherein S6 is a four amino acid spacer with the sequence PGAG, S7 is an eight amino acid spacer with the sequence PAAAGGGP, S8 is a seven amino acid spacer with sequence PAGAGAG, and S9 is a five amino acid spacer with the sequence AAAAP. The PKA polyligand of SEQ ID NO:8 is encoded by SEQ ID NO:9, SEQ ID NO:10, and by SEQ ID NO:11, wherein the codons of SEQ ID NOS:10 and 11 have been optimized for vector insertion. SEQ ID NO:11 includes flanking restriction sites. A polyligand of structure X-S6-Y-S7-Z-S8-A-S9-B is also called herein a heteropolyligand.

SEQ ID NOS:12-54 are full length PKA protein substrates. These sequences have the following public database accession numbers: NP_000735, CAA41491, CAG46757, NP_000015, AAB81869, CAA62301, NP_000483, NP_001297, AAQ24858, NP_000594, AAH23997, NP_003370, AAA92644, NP_002920, NP_631948, AAX11911, CAA40408, CAB02546, AAI06721, Q14643, NP_000209, P15381, NP_000715, AAC15742, NP_954659, AAR04685, AAP75706, BAA07606, AAA60104, CAA00804, AAB02693, P35560, P48048, NP_722451, AAD11417, AAB72005, NP_005901, NP_963998, NP_036872, P50552, AAA61273, NP_542436, NP_671714. Each of the sequences represented by these accession numbers is incorporated by reference herein. In SEQ ID NOS:12-54, the positions of the amino acid(s) phosphorylatable by PKA are represented by Xaa. In wild type proteins, Xaa is serine or threonine. In the ligands of the invention, Xaa is any amino acid.

SEQ ID NOS:55-132 are subsequences of SEQ ID NOS:12-54, which represent examples of peptide ligand sequences where the location of the PKA phosphorylatable serine or threonine in the natural polypeptide is designated as Xaa.

SEQ ID NOS:133-149 are non-endogenous, artificial peptide substrates, wherein the position of the amino acid phosphorylatable by PKA is represented by Xaa. In the ligands of the invention, Xaa is any amino acid.

SEQ ID NO:151 is human PKI with public database accession number AAB21141.

SEQ ID NO:152 is mouse PKI with public database accession number AAA39940.

SEQ ID NOS:151-214 are inhibitors of PKA, wherein SEQ ID NOS:153-214 are non-endogenous, artificial peptides.

SEQ ID NO:215 is AAV rep78 with public database accession number AAK63810.

SEQ ID NO:216 is a subsequence of AAV rep78.

SEQ ID NO:150 is a non-endogenous, artificial, hybrid inhibitor based on PKI and rep78.

SEQ ID NOS:55-216 represent examples of monomeric peptide ligand sequences.

Amino acid sequences containing Xaa encompass polypeptides where Xaa is any amino acid.

What is claimed is:

1. An isolated polynucleotide comprising a nucleotide sequence encoding a polypeptide polyligand comprising monomeric ligands, said polypeptide polyligand having at least 95% sequence identity to the polypeptide of SEQ ID NO: 1, wherein said polypeptide polyligand inhibits protein kinase A activity.

2. A vector comprising the isolated polynucleotide of claim 1.

3. The isolated polynucleotide of claim 1, wherein the polynucleotide is flanked at one terminus by a sequence cleavable by a first restriction endonuclease, and wherein the polynucleotide is flanked at the other terminus by a sequence cleavable by a second restriction endonuclease, and wherein the first and second restriction endonucleases generate non-compatible cohesive ends.

4. The isolated polynucleotide of claim 3, wherein the first restriction endonuclease and the second endonuclease are selected from the group consisting of NgoM IV, Xma I and Cla I.

5. A host cell comprising the vector of claim 2.

6. A method for inhibiting PKA in a cell comprising introducing the vector of claim 2 into a host cell and maintaining the host cell under conditions suitable to produce at least one copy of the polypeptide.

7. The method of claim 6, wherein said method is performed in vitro.

8. The isolated polynucleotide of claim 1, wherein said polypeptide is at least 96% identical to the polypeptide of SEQ ID NO: 1.

9. The isolated polynucleotide of claim 1, wherein said polypeptide is at least 97% identical to the polypeptide of SEQ ID NO: 1.

10. The isolated polynucleotide of claim 1, wherein said polypeptide is at least 98% identical to the polypeptide of SEQ ID NO: 1.

11. The isolated polynucleotide of claim 1, wherein said polypeptide is at least 99% identical to the polypeptide of SEQ ID NO: 1.

12. The isolated polynucleotide of claim 1, wherein said polynucleotide comprises SEQ ID NO: 2.

13. The isolated polynucleotide of claim 1, wherein said polynucleotide comprises SEQ ID NO: 3.

14. The isolated polynucleotide of claim 1, wherein said polynucleotide comprises SEQ ID NO: 4.

* * * * *

SEQUENCE LISTING

```
<160> NUMBER OF SEQ ID NOS: 216

<210> SEQ ID NO 1
<211> LENGTH: 113
<212> TYPE: PRT
<213> ORGANISM: artificial sequence
<220> FEATURE:
<223> OTHER INFORMATION: Synthetic

<400> SEQUENCE: 1
```

Leu Asp Ile Val Pro Arg Leu Leu Met Lys Arg Pro Ala Val Val
1               5                   10                  15

Lys Asp Asn Cys Arg Arg Leu Ile Glu Pro Gly Ala Gly Ala Pro Val
                20                  25                  30

Ser Trp Thr Glu Thr Lys Lys Gln Ala Phe Lys Gln Thr Gly Glu Phe
            35                  40                  45

Gly Glu Lys Arg Lys Asn Ala Ile Leu Asn Pro Ile Asn Gly Gly
        50                  55                  60

Gly Pro Thr Trp Leu Lys Leu Asp Lys Lys Val Ala Ala Gln Glu Val
65              70                  75                  80

Arg Lys Glu Asn Pro Ala Ala Gly Gly Ala Ala Arg Gln Arg Ala Arg
                85                  90                  95

Leu Val Ala Lys Glu Gly Arg Cys Asn Ile Glu Phe Gly Asn Val Asp
            100                 105                 110

Ala

<210> SEQ ID NO 2
<211> LENGTH: 339
<212> TYPE: DNA
<213> ORGANISM: artificial sequence
<220> FEATURE:
<223> OTHER INFORMATION: Synthetic

<400> SEQUENCE: 2
ctggacatcg tgcccaggct gctcctgatg aagaggcccg ccgtggtgaa ggacaactgc      60
aggagactga tcgagcccgg cgccggagct cccgtgagct ggaccgagac caagaagcag     120
gccttcaagc agaccggcga gttcggcgag aagaggaaga acgccatcct gaaccccatc     180
aacggcggag gcggacccac ctggctgaag ctggacaaga aggtggccgc ccaggaggtg     240
aggaaggaga accccgccgc tggcggcgct gccaggcaga gggccaggct ggtggccaag     300
gagggcaggt gcaacatcga gttcggcaac gtggacgcc                            339

<210> SEQ ID NO 3
<211> LENGTH: 339
<212> TYPE: DNA
<213> ORGANISM: artificial sequence
<220> FEATURE:
<223> OTHER INFORMATION: Synthetic

<400> SEQUENCE: 3
ctggacatcg tgcccaggct gctcctgatg aagaggcccg ccgtggtgaa ggacaactgt      60
aggagactga tcgagcccgg agccggagca cccgtgagct ggaccgagac caagaagcag     120
gctttcaagc agaccggcga gttcggcgag aagaggaaga acgccatcct gaaccccatc     180
aacggcggag gcggacccac ctggctgaag ctggacaaga aggtggccgc ccaggaggtg     240
aggaaggaga accccgccgc tggcggcgct gccaggcaga gggctaggct ggtggccaag     300
gagggcaggt gcaacatcga gttcggcaac gtggacgcc                            339

<210> SEQ ID NO 4
<211> LENGTH: 366
<212> TYPE: DNA
<213> ORGANISM: artificial sequence
<220> FEATURE:
<223> OTHER INFORMATION: Synthetic

<400> SEQUENCE: 4
gccggcctgg acatcgtgcc caggctgctc ctgatgaaga ggcccgccgt ggtgaaggac      60

```
aactgtagga gactgatcga gcccggagcc ggagcacccg tgagctggac cgagaccaag    120
aagcaggctt tcaagcagac cggcgagttc ggcgagaaga ggaagaacgc catcctgaac    180
cccatcaacg gcggaggcgg acccacctgg ctgaagctgg acaagaaggt ggccgcccag    240
gaggtgagga aggagaaccc cgccgctggc ggcgctgcca ggcagagggc taggctggtg    300
gccaaggagg gcaggtgcaa catcgagttc ggcaacgtgg acgcccccgg gggaggcgga    360
atcgat                                                               366

<210> SEQ ID NO 5
<211> LENGTH: 44
<212> TYPE: PRT
<213> ORGANISM: artificial sequence
<220> FEATURE:
<223> OTHER INFORMATION: Synthetic

<400> SEQUENCE: 5

Leu Arg Arg Ala Ala Val Ala Gly Ala Gly Ala Gly Arg Thr Gly Arg
1               5                   10                  15

Arg Asn Ala Ile Ala Gly Ala Gly Thr Thr Tyr Ala Asp Phe Ile Ala
            20                  25                  30

Ser Gly Arg Thr Gly Arg Arg Asn Ala Ile His Asp
        35                  40

<210> SEQ ID NO 6
<211> LENGTH: 132
<212> TYPE: DNA
<213> ORGANISM: artificial sequence
<220> FEATURE:
<223> OTHER INFORMATION: Synthetic

<400> SEQUENCE: 6
ctgaggagag ccgccgtggc tggcgctggc gctggcagga ccggcaggag gaacgccatc    60
gctggcgctg caccaccta cgccgacttc atcgccagcg caggaccgg caggaggaac    120 gccatccacg ac                                                       132

<210> SEQ ID NO 7
<211> LENGTH: 159
<212> TYPE: DNA
<213> ORGANISM: artificial sequence
<220> FEATURE:
<223> OTHER INFORMATION: Synthetic

<400> SEQUENCE: 7
gccggcctga ggagagccgc cgtggctggc gctggcgctg caggaccgg caggaggaac    60 gccatcgctg gcgctggcac cacctacgcc gacttcatcg ccagcggcag gaccggcagg    120
aggaacgcca tccacgaccc cgggggaggc ggaatcgat                           159

<210> SEQ ID NO 8
<211> LENGTH: 114
<212> TYPE: PRT
<213> ORGANISM: artificial sequence
<220> FEATURE:
<223> OTHER INFORMATION: Synthetic

<400> SEQUENCE: 8

Trp Ala Ala Gln Arg Tyr Gly Arg Glu Leu Arg Arg Met Ala Asp Glu
1               5                   10                  15

Phe Val Asp Ser Phe Lys Lys Gly Pro Gly Ala Gly Pro Arg Glu Lys
            20                  25                  30
```

Lys Tyr Ala Ala Thr Lys Val Val Tyr Pro Ala Ala Gly Gly Gly
          35                  40                  45

Pro Trp Gly Pro Thr Asp Pro Arg Arg Arg Ala Arg Asn Leu Gly Lys
 50                  55                  60

Val Ile Asp Thr Leu Pro Ala Gly Ala Gly Ala Gly Leu Arg Arg Trp
 65                  70                  75                  80

Ala Leu Gly Ala Ala Ala Pro Thr Thr Tyr Ala Asp Phe Ile Ala
              85                  90                  95

Ser Gly Arg Thr Gly Arg Arg Asn Ala Ile His Asp Met Leu Phe Pro
              100                 105                 110

Cys Arg

<210> SEQ ID NO 9
<211> LENGTH: 342
<212> TYPE: DNA
<213> ORGANISM: artificial sequence
<220> FEATURE:
<223> OTHER INFORMATION: Synthetic

<400> SEQUENCE: 9
tgggccgctc agaggtacgg cagggagctg agaaggatgg ccgacgagtt cgtggacagc      60
ttcaagaagg gccctggcgc tggacccagg gagaagaagt acgctgccac caaggtggtg     120
taccctgccg ctgccggcgg aggccctgg ggccccaccg accccaggag aagggccagg      180
aacctgggca aggtgatcga caccctgcct gccggcgctg cgccggact gaggaggtgg      240 gccctgggcg ctgccgctgc cctaccaca tacgccgact tcatcgccag cggcaggacc      300
ggcaggagga acgccatcca cgacatgctg ttccctgca gg                         342

<210> SEQ ID NO 10
<211> LENGTH: 342
<212> TYPE: DNA
<213> ORGANISM: artificial sequence
<220> FEATURE:
<223> OTHER INFORMATION: Synthetic

<400> SEQUENCE: 10
tgggccgctc agaggtacgg cagggagctg agaaggatgg ccgacgagtt cgtggacagc      60
ttcaagaaag gacccggcgc tggacccagg gagaagaagt acgctgctac caaggtggtg     120
taccctgccg ctgctggcgg aggaccctgg ggacccaccg accccaggag aagggctagg     180
aacctgggca aggtgatcga caccctgcct gctggcgctg gagccggact gaggaggtgg     240
gctctgggcg ctgccgctgc cctaccaca tacgccgact tcatcgccag cggcaggacc      300
ggcaggagga acgccatcca cgacatgctg ttccttgta gg                         342

<210> SEQ ID NO 11
<211> LENGTH: 369
<212> TYPE: DNA
<213> ORGANISM: artificial sequence
<220> FEATURE:
<223> OTHER INFORMATION: Synthetic

<400> SEQUENCE: 11
gccggctggg ccgctcagag gtacggcagg gagctgagaa ggatggccga cgagttcgtg      60
gacagcttca gaaaggacc cggcgctgga cccagggaga agaagtacgc tgctaccaag     120
gtggtgtacc ctgccgctgc tggcggagga ccctggggac ccaccgaccc caggagaagg     180
gctaggaacc tgggcaaggt gatcgacacc ctgcctgctg cgctggagc cggactgagg      240

```
aggtgggctc tgggcgctgc cgctgcccct accacatacg ccgacttcat cgccagcggc    300
aggaccggca ggaggaacgc catccacgac atgctgttcc cttgtaggcc cgggggaggc    360
ggaatcgat                                                              369
```

```
<210> SEQ ID NO 12
<211> LENGTH: 627
<212> TYPE: PRT
<213> ORGANISM: human
<220> FEATURE:
<221> NAME/KEY: misc_feature
<222> LOCATION: (362)..(362)
<223> OTHER INFORMATION: Xaa can be any naturally occurring amino acid
<220> FEATURE:
<221> NAME/KEY: misc_feature
<222> LOCATION: (486)..(486)
<223> OTHER INFORMATION: Xaa can be any naturally occurring amino acid

<400> SEQUENCE: 12

Met Glu Leu Gly Gly Pro Gly Ala Pro Arg Leu Leu Pro Pro Leu Leu
1               5                   10                  15

Leu Leu Leu Gly Thr Gly Leu Leu Arg Ala Ser Ser His Val Glu Thr
            20                  25                  30

Arg Ala His Ala Glu Glu Arg Leu Leu Lys Leu Phe Ser Gly Tyr
        35                  40                  45

Asn Lys Trp Ser Arg Pro Val Ala Asn Ile Ser Asp Val Val Leu Val
    50                  55                  60

Arg Phe Gly Leu Ser Ile Ala Gln Leu Ile Asp Val Asp Glu Lys Asn
65                  70                  75                  80

Gln Met Met Thr Thr Asn Val Trp Val Lys Gln Glu Trp His Asp Tyr
                85                  90                  95

Lys Leu Arg Trp Asp Pro Ala Asp Tyr Glu Asn Val Thr Ser Ile Arg
            100                 105                 110

Ile Pro Ser Glu Leu Ile Trp Arg Pro Asp Ile Val Leu Tyr Asn Asn
        115                 120                 125

Ala Asp Gly Asp Phe Ala Val Thr His Leu Thr Lys Ala His Leu Phe
    130                 135                 140

His Asp Gly Arg Val Gln Trp Thr Pro Pro Ala Ile Tyr Lys Ser Ser
145                 150                 155                 160

Cys Ser Ile Asp Val Thr Phe Phe Pro Phe Asp Gln Gln Asn Cys Thr
                165                 170                 175

Met Lys Phe Gly Ser Trp Thr Tyr Asp Lys Ala Lys Ile Asp Leu Val
            180                 185                 190

Asn Met His Ser Arg Val Asp Gln Leu Asp Phe Trp Glu Ser Gly Glu
        195                 200                 205

Trp Val Ile Val Asp Ala Val Gly Thr Tyr Asn Thr Arg Lys Tyr Glu
    210                 215                 220

Cys Cys Ala Glu Ile Tyr Pro Asp Ile Thr Tyr Ala Phe Val Ile Arg
225                 230                 235                 240

Arg Leu Pro Leu Phe Tyr Thr Ile Asn Leu Ile Ile Pro Cys Leu Leu
                245                 250                 255

Ile Ser Cys Leu Thr Val Leu Val Phe Tyr Leu Pro Ser Glu Cys Gly
            260                 265                 270

Glu Lys Ile Thr Leu Cys Ile Ser Val Leu Leu Ser Leu Thr Val Phe
        275                 280                 285

Leu Leu Leu Ile Thr Glu Ile Ile Pro Ser Thr Ser Leu Val Ile Pro
    290                 295                 300
```

```
Leu Ile Gly Glu Tyr Leu Leu Phe Thr Met Ile Phe Val Thr Leu Ser
305                 310                 315                 320

Ile Val Ile Thr Val Phe Val Leu Asn Val His His Arg Ser Pro Arg
                325                 330                 335

Thr His Thr Met Pro Thr Trp Val Arg Arg Val Phe Leu Asp Ile Val
                340                 345                 350

Pro Arg Leu Leu Leu Met Lys Arg Pro Xaa Val Val Lys Asp Asn Cys
                355                 360                 365

Arg Arg Leu Ile Glu Ser Met His Lys Met Ala Ser Ala Pro Arg Phe
        370                 375                 380

Trp Pro Glu Pro Glu Gly Glu Pro Pro Ala Thr Ser Gly Thr Gln Ser
385                 390                 395                 400

Leu His Pro Pro Ser Pro Ser Phe Cys Val Pro Leu Asp Val Pro Ala
                405                 410                 415

Glu Pro Gly Pro Ser Cys Lys Ser Pro Ser Asp Gln Leu Pro Pro Gln
                420                 425                 430

Gln Pro Leu Glu Ala Glu Lys Ala Ser Pro His Pro Ser Pro Gly Pro
        435                 440                 445

Cys Arg Pro Pro His Gly Thr Gln Ala Pro Gly Leu Ala Lys Ala Arg
450                 455                 460

Ser Leu Ser Val Gln His Met Ser Ser Pro Gly Glu Ala Val Glu Gly
465                 470                 475                 480

Gly Val Arg Cys Arg Xaa Arg Ser Ile Gln Tyr Cys Val Pro Arg Asp
                485                 490                 495

Asp Ala Ala Pro Glu Ala Asp Gly Gln Ala Ala Gly Ala Leu Ala Ser
                500                 505                 510

Arg Asn Thr His Ser Ala Glu Leu Pro Pro Asp Gln Pro Ser Pro
        515                 520                 525

Cys Lys Cys Thr Cys Lys Lys Glu Pro Ser Ser Val Ser Pro Ser Ala
530                 535                 540

Thr Val Lys Thr Arg Ser Thr Lys Ala Pro Pro Pro His Leu Pro Leu
545                 550                 555                 560

Ser Pro Ala Leu Thr Arg Ala Val Glu Gly Val Gln Tyr Ile Ala Asp
                565                 570                 575

His Leu Lys Ala Glu Asp Thr Asp Phe Ser Val Lys Glu Asp Trp Lys
                580                 585                 590

Tyr Val Ala Met Val Ile Asp Arg Ile Phe Leu Trp Met Phe Ile Ile
                595                 600                 605

Val Cys Leu Leu Gly Thr Val Gly Leu Phe Leu Pro Pro Trp Leu Ala
610                 615                 620

Gly Met Ile
625

<210> SEQ ID NO 13
<211> LENGTH: 906
<212> TYPE: PRT
<213> ORGANISM: human
<220> FEATURE:
<221> NAME/KEY: misc_feature
<222> LOCATION: (863)..(863)
<223> OTHER INFORMATION: Xaa can be any naturally occurring amino acid

<400> SEQUENCE: 13

Met Gln His Ile Phe Ala Phe Phe Cys Thr Gly Phe Leu Gly Ala Val
1               5                   10                  15
```

```
Val Gly Ala Asn Phe Pro Asn Asn Ile Gln Ile Gly Gly Leu Phe Pro
             20                  25                  30

Asn Gln Gln Ser Gln Glu His Ala Ala Phe Arg Phe Ala Leu Ser Gln
                 35                  40                  45

Leu Thr Glu Pro Pro Lys Leu Leu Pro Gln Ile Asp Ile Val Asn Ile
 50                  55                  60

Ser Asp Ser Phe Glu Met Thr Tyr Arg Phe Cys Ser Gln Phe Ser Lys
 65                  70                  75                  80

Gly Val Tyr Ala Ile Phe Gly Phe Tyr Glu Arg Arg Thr Val Asn Met
                 85                  90                  95

Leu Thr Ser Phe Cys Gly Ala Leu His Val Cys Phe Ile Thr Pro Ser
                100                 105                 110

Phe Pro Val Asp Thr Ser Asn Gln Phe Val Leu Gln Leu Arg Pro Glu
            115                 120                 125

Leu Gln Asp Ala Leu Ile Ser Ile Asp His Tyr Lys Trp Gln Lys
130                 135                 140

Phe Val Tyr Ile Tyr Asp Ala Asp Arg Gly Leu Ser Val Leu Gln Lys
145                 150                 155                 160

Val Leu Asp Thr Ala Ala Glu Lys Asn Trp Gln Val Thr Ala Val Asn
                165                 170                 175

Ile Leu Thr Thr Thr Glu Glu Gly Tyr Arg Met Leu Phe Gln Asp Leu
                180                 185                 190

Glu Lys Lys Lys Glu Arg Leu Val Val Asp Cys Glu Ser Glu Arg
            195                 200                 205

Leu Asn Ala Ile Leu Gly Gln Ile Ile Lys Leu Glu Lys Asn Gly Ile
210                 215                 220

Gly Tyr His Tyr Ile Leu Ala Asn Leu Gly Phe Met Asp Ile Asp Leu
225                 230                 235                 240

Asn Lys Phe Lys Glu Ser Gly Ala Asn Val Thr Gly Phe Gln Leu Val
                245                 250                 255

Asn Tyr Thr Asp Thr Ile Pro Ala Lys Ile Met Gln Gln Trp Lys Asn
            260                 265                 270

Ser Asp Ala Arg Asp His Thr Arg Val Asp Trp Lys Arg Pro Lys Tyr
            275                 280                 285

Thr Ser Ala Leu Thr Tyr Asp Gly Val Lys Val Met Ala Glu Ala Phe
290                 295                 300

Gln Ser Leu Arg Arg Gln Arg Ile Asp Ile Ser Arg Arg Gly Asn Ala
305                 310                 315                 320

Gly Asp Cys Leu Ala Asn Pro Ala Val Pro Trp Gly Gln Gly Ile Asp
            325                 330                 335

Ile Gln Arg Ala Leu Gln Gln Val Ala Phe Glu Gly Leu Thr Gly Asn
            340                 345                 350

Val Gln Phe Asn Glu Lys Gly Arg Arg Thr Asn Tyr Thr Leu His Val
            355                 360                 365

Ile Glu Met Lys His Asp Gly Ile Arg Lys Ile Gly Tyr Trp Asn Glu
            370                 375                 380

Asp Asp Lys Phe Val Pro Ala Ala Thr Asp Ala Gln Ala Gly Gly Asp
385                 390                 395                 400

Asn Ser Ser Val Gln Asn Arg Thr Tyr Ile Val Thr Thr Ile Leu Glu
                405                 410                 415

Asp Pro Tyr Val Met Leu Lys Lys Asn Ala Asn Gln Phe Glu Gly Asn
            420                 425                 430

Asp Arg Tyr Glu Gly Tyr Cys Val Glu Leu Ala Ala Glu Ile Ala Lys
```

```
            435                 440                 445
His Val Gly Tyr Ser Tyr Arg Leu Glu Ile Val Ser Asp Gly Lys Tyr
450                 455                 460

Gly Ala Arg Asp Pro Asp Thr Lys Ala Trp Asn Gly Met Val Gly Glu
465                 470                 475                 480

Leu Val Tyr Gly Arg Ala Asp Val Ala Val Ala Pro Leu Thr Ile Thr
                485                 490                 495

Leu Val Arg Glu Glu Val Ile Asp Phe Ser Lys Pro Phe Met Ser Leu
            500                 505                 510

Gly Ile Ser Ile Met Ile Lys Lys Pro Gln Lys Ser Lys Pro Gly Val
        515                 520                 525

Phe Ser Phe Leu Asp Pro Leu Ala Tyr Glu Ile Trp Met Cys Ile Val
    530                 535                 540

Phe Ala Tyr Ile Gly Val Ser Val Val Leu Phe Leu Val Ser Arg Phe
545                 550                 555                 560

Ser Pro Tyr Glu Trp His Ser Glu Glu Phe Glu Glu Gly Arg Asp Gln
                565                 570                 575

Thr Thr Ser Asp Gln Ser Asn Glu Phe Gly Ile Phe Asn Ser Leu Trp
            580                 585                 590

Phe Ser Leu Gly Ala Phe Met Gln Gln Gly Cys Asp Ile Ser Pro Arg
        595                 600                 605

Ser Leu Ser Gly Arg Ile Val Gly Gly Val Trp Trp Phe Phe Thr Leu
    610                 615                 620

Ile Ile Ile Ser Ser Tyr Thr Ala Asn Leu Ala Ala Phe Leu Thr Val
625                 630                 635                 640

Glu Arg Met Val Ser Pro Ile Glu Ser Ala Glu Asp Leu Ala Lys Gln
                645                 650                 655

Thr Glu Ile Ala Tyr Gly Thr Leu Glu Ala Gly Ser Thr Lys Glu Phe
            660                 665                 670

Phe Arg Arg Ser Lys Ile Ala Val Phe Glu Lys Met Trp Thr Tyr Met
        675                 680                 685

Lys Ser Ala Glu Pro Ser Val Phe Val Arg Thr Thr Glu Glu Gly Met
    690                 695                 700

Ile Arg Val Arg Lys Ser Lys Gly Lys Tyr Ala Tyr Leu Leu Glu Ser
705                 710                 715                 720

Thr Met Asn Glu Tyr Ile Glu Gln Arg Lys Pro Cys Asp Thr Met Lys
                725                 730                 735

Val Gly Gly Asn Leu Asp Ser Lys Gly Tyr Gly Ile Ala Thr Pro Lys
            740                 745                 750

Gly Ser Ala Leu Arg Asn Pro Val Asn Leu Ala Val Leu Lys Leu Asn
        755                 760                 765

Glu Gln Gly Leu Leu Asp Lys Leu Lys Asn Lys Trp Trp Tyr Asp Lys
    770                 775                 780

Gly Glu Cys Gly Ser Gly Gly Gly Asp Ser Lys Asp Lys Thr Ser Ala
785                 790                 795                 800

Leu Ser Leu Ser Asn Val Ala Gly Val Phe Tyr Ile Leu Ile Gly Gly
                805                 810                 815

Leu Gly Leu Ala Met Leu Val Ala Leu Ile Glu Phe Cys Tyr Lys Ser
            820                 825                 830

Arg Ser Glu Ser Lys Arg Met Lys Gly Phe Cys Leu Ile Pro Gln Gln
        835                 840                 845

Ser Ile Asn Glu Ala Ile Arg Thr Ser Thr Leu Pro Arg Asn Xaa Gly
    850                 855                 860
```

```
Ala Gly Ala Ser Ser Gly Gly Ser Gly Glu Asn Gly Arg Val Val Ser
865                 870                 875                 880

His Asp Phe Pro Lys Ser Met Gln Ser Ile Pro Cys Met Ser His Ser
                885                 890                 895

Ser Gly Met Pro Leu Gly Ala Thr Gly Leu
        900                 905
```

<210> SEQ ID NO 14
<211> LENGTH: 168
<212> TYPE: PRT
<213> ORGANISM: human
<220> FEATURE:
<221> NAME/KEY: misc_feature
<222> LOCATION: (118)..(118)
<223> OTHER INFORMATION: Xaa can be any naturally occurring amino acid

<400> SEQUENCE: 14

```
Met Phe Gln Ile Pro Glu Phe Glu Pro Ser Glu Gln Glu Asp Ser Ser
1               5                   10                  15

Ser Ala Glu Arg Gly Leu Gly Pro Ser Pro Ala Gly Asp Gly Pro Ser
                20                  25                  30

Gly Ser Gly Lys His His Arg Gln Ala Pro Gly Leu Leu Trp Asp Ala
            35                  40                  45

Ser His Gln Gln Glu Gln Pro Thr Ser Ser His His Gly Gly Ala
50                  55                  60

Gly Ala Val Glu Ile Arg Ser Arg His Ser Ser Tyr Pro Ala Gly Thr
65                  70                  75                  80

Glu Asp Asp Glu Gly Met Gly Glu Pro Ser Pro Phe Arg Gly Arg
                85                  90                  95

Ser Arg Ser Ala Pro Pro Asn Leu Trp Ala Ala Gln Arg Tyr Gly Arg
            100                 105                 110

Glu Leu Arg Arg Met Xaa Asp Glu Phe Val Asp Ser Phe Lys Lys Gly
        115                 120                 125

Leu Pro Arg Pro Lys Ser Ala Gly Thr Ala Thr Gln Met Arg Gln Ser
    130                 135                 140

Ser Ser Trp Thr Arg Val Phe Gln Ser Trp Trp Asp Arg Asn Leu Gly
145                 150                 155                 160

Arg Gly Ser Ser Ala Pro Ser Gln
                165
```

<210> SEQ ID NO 15
<211> LENGTH: 413
<212> TYPE: PRT
<213> ORGANISM: human
<220> FEATURE:
<221> NAME/KEY: misc_feature
<222> LOCATION: (345)..(346)
<223> OTHER INFORMATION: Xaa can be any naturally occurring amino acid

<400> SEQUENCE: 15

```
Met Gly Gln Pro Gly Asn Gly Ser Ala Phe Leu Leu Ala Pro Asn Arg
1               5                   10                  15

Ser His Ala Pro Asp His Asp Val Thr Gln Gln Arg Asp Glu Val Trp
                20                  25                  30

Val Val Gly Met Gly Ile Val Met Ser Leu Ile Val Leu Ala Ile Val
            35                  40                  45

Phe Gly Asn Val Leu Val Ile Thr Ala Ile Ala Lys Phe Glu Arg Leu
50                  55                  60
```

```
Gln Thr Val Thr Asn Tyr Phe Ile Thr Ser Leu Ala Cys Ala Asp Leu
 65                  70                  75                  80

Val Met Gly Leu Ala Val Val Pro Phe Gly Ala His Ile Leu Met
             85                  90                  95

Lys Met Trp Thr Phe Gly Asn Phe Trp Cys Glu Phe Trp Thr Ser Ile
                100                 105                 110

Asp Val Leu Cys Val Thr Ala Ser Ile Glu Thr Leu Cys Val Ile Ala
            115                 120                 125

Val Asp Arg Tyr Phe Ala Ile Thr Ser Pro Phe Lys Tyr Gln Ser Leu
        130                 135                 140

Leu Thr Lys Asn Lys Ala Arg Val Ile Ile Leu Met Val Trp Ile Val
145                 150                 155                 160

Ser Gly Leu Thr Ser Phe Leu Pro Ile Gln Met His Trp Tyr Arg Ala
                165                 170                 175

Thr His Gln Glu Ala Ile Asn Cys Tyr Ala Asn Glu Thr Cys Cys Asp
            180                 185                 190

Phe Phe Thr Asn Gln Ala Tyr Ala Ile Ala Ser Ser Ile Val Ser Phe
        195                 200                 205

Tyr Val Pro Leu Val Ile Met Val Phe Val Tyr Ser Arg Val Phe Gln
    210                 215                 220

Glu Ala Lys Arg Gln Leu Gln Lys Ile Asp Lys Ser Glu Gly Arg Phe
225                 230                 235                 240

His Val Gln Asn Leu Ser Gln Val Glu Gln Asp Gly Arg Thr Gly His
                245                 250                 255

Gly Leu Arg Arg Ser Ser Lys Phe Cys Leu Lys Glu His Lys Ala Leu
            260                 265                 270

Lys Thr Leu Gly Ile Ile Met Gly Thr Phe Thr Leu Cys Trp Leu Pro
        275                 280                 285

Phe Phe Ile Val Asn Ile Val His Val Ile Gln Asp Asn Leu Ile Arg
        290                 295                 300

Lys Glu Val Tyr Ile Leu Leu Asn Trp Ile Gly Tyr Val Asn Ser Gly
305                 310                 315                 320

Phe Asn Pro Leu Ile Tyr Cys Arg Ser Pro Asp Phe Arg Ile Ala Phe
                325                 330                 335

Gln Glu Leu Leu Cys Leu Arg Arg Xaa Xaa Leu Lys Ala Tyr Gly Asn
            340                 345                 350

Gly Tyr Ser Ser Asn Gly Asn Thr Gly Glu Gln Ser Gly Tyr His Val
        355                 360                 365

Glu Gln Glu Lys Glu Asn Lys Leu Leu Cys Glu Asp Leu Pro Gly Thr
    370                 375                 380

Glu Asp Phe Val Gly His Gln Gly Thr Val Pro Ser Asp Asn Ile Asp
385                 390                 395                 400

Ser Gln Gly Arg Asn Cys Ser Thr Asn Asp Ser Leu Leu
                405                 410

<210> SEQ ID NO 16
<211> LENGTH: 672
<212> TYPE: PRT
<213> ORGANISM: rat
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (54)..(54)
<223> OTHER INFORMATION: Xaa can be any naturally occurring amino acid
```

<220> FEATURE:
<221> NAME/KEY: misc_feature
<222> LOCATION: (74)..(74)
<223> OTHER INFORMATION: Xaa can be any naturally occurring amino acid
<220> FEATURE:
<221> NAME/KEY: misc_feature
<222> LOCATION: (119)..(119)
<223> OTHER INFORMATION: Xaa can be any naturally occurring amino acid

<400> SEQUENCE: 16

Met Met His Val Asn Thr Phe Pro Phe Arg Arg His Xaa Trp Ile Cys
1               5                   10                  15

Phe Asp Val Asp Asn Gly Thr Ser Ala Gly Arg Ser Pro Leu Asp Pro
            20                  25                  30

Met Thr Ser Pro Gly Ser Gly Leu Ile Leu Gln Ala Asn Phe Val His
        35                  40                  45

Ser Gln Arg Arg Glu Xaa Phe Leu Tyr Arg Ser Asp Ser Asp Tyr Asp
    50                  55                  60

Leu Ser Pro Lys Ser Met Ser Arg Asn Xaa Ser Ile Ala Ser Asp Ile
65                  70                  75                  80

His Gly Asp Asp Leu Ile Val Thr Pro Phe Ala Gln Val Leu Ala Ser
                85                  90                  95

Leu Arg Thr Val Arg Asn Asn Phe Ala Ala Leu Thr Asn Leu Gln Asp
            100                 105                 110

Arg Ala Pro Ser Lys Arg Xaa Pro Met Cys Asn Gln Pro Ser Ile Asn
        115                 120                 125

Lys Ala Thr Ile Thr Glu Glu Ala Tyr Gln Lys Leu Ala Ser Glu Thr
    130                 135                 140

Leu Glu Glu Leu Asp Trp Cys Leu Asp Gln Leu Glu Thr Leu Gln Thr
145                 150                 155                 160

Arg His Ser Val Ser Glu Met Ala Ser Asn Lys Phe Lys Arg Met Leu
                165                 170                 175

Asn Arg Glu Leu Thr His Leu Ser Glu Met Ser Arg Ser Gly Asn Gln
            180                 185                 190

Val Ser Glu Tyr Ile Ser Asn Thr Phe Leu Asp Lys Gln His Glu Val
        195                 200                 205

Glu Ile Pro Ser Pro Thr Gln Lys Glu Lys Glu Lys Lys Lys Arg Pro
    210                 215                 220

Met Ser Gln Ile Ser Gly Val Lys Lys Leu Met His Ser Ser Ser Leu
225                 230                 235                 240

Thr Asn Ser Cys Ile Pro Arg Phe Gly Val Lys Thr Glu Gln Glu Asp
                245                 250                 255

Val Leu Ala Lys Glu Leu Glu Asp Val Asn Lys Trp Gly Leu His Val
            260                 265                 270

Phe Arg Ile Ala Glu Leu Ser Gly Asn Arg Pro Leu Thr Val Ile Met
        275                 280                 285

His Thr Ile Phe Gln Glu Arg Asp Leu Leu Lys Thr Phe Lys Ile Pro
    290                 295                 300

Val Asp Thr Leu Ile Thr Tyr Leu Met Thr Leu Glu Asp His Tyr His
305                 310                 315                 320

Ala Asp Val Ala Tyr His Asn Asn Ile His Ala Ala Asp Val Val Gln
                325                 330                 335

Ser Thr His Val Leu Leu Ser Thr Pro Ala Leu Glu Ala Val Phe Thr
            340                 345                 350

Asp Leu Glu Ile Leu Ala Ala Ile Phe Ala Ser Ala Ile His Asp Val
        355                 360                 365

-continued

```
Asp His Pro Gly Val Ser Asn Gln Phe Leu Ile Asn Thr Asn Ser Glu
        370                 375                 380

Leu Ala Leu Met Tyr Asn Asp Ser Ser Val Leu Glu Asn His His Leu
385                 390                 395                 400

Ala Val Gly Phe Lys Leu Leu Gln Glu Glu Asn Cys Asp Ile Phe Gln
                405                 410                 415

Asn Leu Thr Lys Lys Gln Arg Gln Ser Leu Arg Lys Met Ala Ile Asp
            420                 425                 430

Ile Val Leu Ala Thr Asp Met Ser Lys His Met Asn Leu Leu Ala Asp
        435                 440                 445

Leu Lys Thr Met Val Glu Thr Lys Lys Val Thr Ser Ser Gly Val Leu
450                 455                 460

Leu Leu Asp Asn Tyr Ser Asp Arg Ile Gln Val Leu Gln Asn Met Val
465                 470                 475                 480

His Cys Ala Asp Leu Ser Asn Pro Thr Lys Pro Leu Gln Leu Tyr Arg
                485                 490                 495

Gln Trp Thr Asp Arg Ile Met Glu Glu Phe Phe Arg Gln Gly Asp Arg
            500                 505                 510

Glu Arg Glu Arg Gly Met Glu Ile Ser Pro Met Cys Asp Lys His Asn
        515                 520                 525

Ala Ser Val Glu Lys Ser Gln Val Gly Phe Ile Asp Tyr Ile Val His
530                 535                 540

Pro Leu Trp Glu Thr Trp Ala Asp Leu Val His Pro Asp Ala Gln Asp
545                 550                 555                 560

Ile Leu Asp Thr Leu Glu Asp Asn Arg Glu Trp Tyr Gln Ser Thr Ile
                565                 570                 575

Pro Gln Ser Pro Ser Pro Ala Pro Asp Asp Gln Glu Asp Gly Arg Gln
            580                 585                 590

Gly Gln Thr Glu Lys Phe Gln Phe Glu Leu Thr Leu Glu Glu Asp Gly
        595                 600                 605

Glu Ser Asp Thr Glu Lys Asp Ser Gly Ser Gln Val Glu Glu Asp Thr
610                 615                 620

Ser Cys Ser Asp Ser Lys Thr Leu Cys Thr Gln Asp Ser Glu Ser Thr
625                 630                 635                 640

Glu Ile Pro Leu Asp Glu Gln Val Glu Glu Ala Val Ala Glu Glu
                645                 650                 655

Glu Ser Gln Pro Gln Thr Gly Val Ala Asp Asp Cys Cys Pro Asp Thr
            660                 665                 670
```

<210> SEQ ID NO 17
<211> LENGTH: 210
<212> TYPE: PRT
<213> ORGANISM: human
<220> FEATURE:
<221> NAME/KEY: misc_feature
<222> LOCATION: (23)..(24)
<223> OTHER INFORMATION: Xaa can be any naturally occurring amino acid

<400> SEQUENCE: 17

```
Met Ala Asp Gly Ser Ser Asp Ala Ala Arg Glu Pro Arg Pro Ala
1               5                   10                  15

Ala Pro Ile Arg Arg Arg Xaa Xaa Asn Tyr Arg Ala Tyr Ala Thr Glu
                20                  25                  30

Pro His Ala Lys Lys Lys Ser Lys Ile Ser Ala Ser Arg Lys Leu Gln
            35                  40                  45
```

```
Leu Lys Thr Leu Leu Leu Gln Ile Ala Lys Gln Glu Leu Glu Arg Glu
 50                  55                  60

Ala Glu Glu Arg Arg Gly Glu Lys Gly Arg Ala Leu Ser Thr Arg Cys
 65                  70                  75                  80

Gln Pro Leu Glu Leu Ala Gly Leu Gly Phe Ala Glu Leu Gln Asp Leu
                 85                  90                  95

Cys Arg Gln Leu His Ala Arg Val Asp Lys Val Asp Glu Glu Arg Tyr
                100                 105                 110

Asp Ile Glu Ala Lys Val Thr Lys Asn Ile Thr Glu Ile Ala Asp Leu
            115                 120                 125

Thr Gln Lys Ile Phe Asp Leu Arg Gly Lys Phe Lys Arg Pro Thr Leu
130                 135                 140

Arg Arg Val Arg Ile Ser Ala Asp Ala Met Met Gln Ala Leu Leu Gly
145                 150                 155                 160

Ala Arg Ala Lys Glu Ser Leu Asp Leu Arg Ala His Leu Lys Gln Val
                165                 170                 175

Lys Lys Glu Asp Thr Glu Lys Glu Asn Arg Glu Val Gly Asp Trp Arg
                180                 185                 190

Lys Asn Ile Asp Ala Leu Ser Gly Met Glu Gly Arg Lys Lys Lys Phe
            195                 200                 205

Glu Ser
    210

<210> SEQ ID NO 18
<211> LENGTH: 1480
<212> TYPE: PRT
<213> ORGANISM: human
<220> FEATURE:
<221> NAME/KEY: misc_feature
<222> LOCATION: (422)..(422)
<223> OTHER INFORMATION: Xaa can be any naturally occurring amino acid
<220> FEATURE:
<221> NAME/KEY: misc_feature
<222> LOCATION: (660)..(660)
<223> OTHER INFORMATION: Xaa can be any naturally occurring amino acid
<220> FEATURE:
<221> NAME/KEY: misc_feature
<222> LOCATION: (686)..(686)
<223> OTHER INFORMATION: Xaa can be any naturally occurring amino acid
<220> FEATURE:
<221> NAME/KEY: misc_feature
<222> LOCATION: (700)..(700)
<223> OTHER INFORMATION: Xaa can be any naturally occurring amino acid
<220> FEATURE:
<221> NAME/KEY: misc_feature
<222> LOCATION: (712)..(712)
<223> OTHER INFORMATION: Xaa can be any naturally occurring amino acid
<220> FEATURE:
<221> NAME/KEY: misc_feature
<222> LOCATION: (737)..(737)
<223> OTHER INFORMATION: Xaa can be any naturally occurring amino acid
<220> FEATURE:
<221> NAME/KEY: misc_feature
<222> LOCATION: (768)..(768)
<223> OTHER INFORMATION: Xaa can be any naturally occurring amino acid
<220> FEATURE:
<221> NAME/KEY: misc_feature
<222> LOCATION: (788)..(788)
<223> OTHER INFORMATION: Xaa can be any naturally occurring amino acid
<220> FEATURE:
<221> NAME/KEY: misc_feature
<222> LOCATION: (795)..(795)
<223> OTHER INFORMATION: Xaa can be any naturally occurring amino acid
<220> FEATURE:
<221> NAME/KEY: misc_feature
<222> LOCATION: (813)..(813)
<223> OTHER INFORMATION: Xaa can be any naturally occurring amino acid
```

<400> SEQUENCE: 18

```
Met Gln Arg Ser Pro Leu Glu Lys Ala Ser Val Ser Lys Leu Phe
1               5                   10                  15

Phe Ser Trp Thr Arg Pro Ile Leu Arg Lys Gly Tyr Arg Gln Arg Leu
                20                  25                  30

Glu Leu Ser Asp Ile Tyr Gln Ile Pro Ser Val Asp Ser Ala Asp Asn
            35                  40                  45

Leu Ser Glu Lys Leu Glu Arg Glu Trp Asp Arg Glu Leu Ala Ser Lys
    50                  55                  60

Lys Asn Pro Lys Leu Ile Asn Ala Leu Arg Arg Cys Phe Phe Trp Arg
65                  70                  75                  80

Phe Met Phe Tyr Gly Ile Phe Leu Tyr Leu Gly Glu Val Thr Lys Ala
                85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
        115                 120                 125

Leu Leu Phe Ile Val Arg Thr Leu Leu Leu His Pro Ala Ile Phe Gly
    130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
        195                 200                 205

Ala Leu Leu Met Gly Leu Ile Trp Glu Leu Leu Gln Ala Ser Ala Phe
    210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
            260                 265                 270

Lys Ala Tyr Cys Trp Glu Glu Ala Met Glu Lys Met Ile Glu Asn Leu
        275                 280                 285

Arg Gln Thr Glu Leu Lys Leu Thr Arg Lys Ala Ala Tyr Val Arg Tyr
    290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
            340                 345                 350

Gln Phe Pro Trp Ala Val Gln Thr Trp Tyr Asp Ser Leu Gly Ala Ile
        355                 360                 365

Asn Lys Ile Gln Asp Phe Leu Gln Lys Gln Glu Tyr Lys Thr Leu Glu
    370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415
```

-continued

```
Asn Asn Arg Lys Thr Xaa Asn Gly Asp Asp Ser Leu Phe Phe Ser Asn
            420                 425                 430

Phe Ser Leu Leu Gly Thr Pro Val Leu Lys Asp Ile Asn Phe Lys Ile
        435                 440                 445

Glu Arg Gly Gln Leu Leu Ala Val Ala Gly Ser Thr Gly Ala Gly Lys
    450                 455                 460

Thr Ser Leu Leu Met Val Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Phe Gly Val Ser Tyr
            500                 505                 510

Asp Glu Tyr Arg Tyr Arg Ser Val Ile Lys Ala Cys Gln Leu Glu Glu
        515                 520                 525

Asp Ile Ser Lys Phe Ala Glu Lys Asp Asn Ile Val Leu Gly Glu Gly
    530                 535                 540

Gly Ile Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
                565                 570                 575

Tyr Leu Asp Val Leu Thr Glu Lys Glu Ile Phe Glu Ser Cys Val Cys
            580                 585                 590

Lys Leu Met Ala Asn Lys Thr Arg Ile Leu Val Thr Ser Lys Met Glu
        595                 600                 605

His Leu Lys Lys Ala Asp Lys Ile Leu Ile Leu His Glu Gly Ser Ser
    610                 615                 620

Tyr Phe Tyr Gly Thr Phe Ser Glu Leu Gln Asn Leu Gln Pro Asp Phe
625                 630                 635                 640

Ser Ser Lys Leu Met Gly Cys Asp Ser Phe Asp Gln Phe Ser Ala Glu
                645                 650                 655

Arg Arg Asn Xaa Ile Leu Thr Glu Thr Leu His Arg Phe Ser Leu Glu
            660                 665                 670

Gly Asp Ala Pro Val Ser Trp Thr Glu Thr Lys Lys Gln Xaa Phe Lys
        675                 680                 685

Gln Thr Gly Glu Phe Gly Glu Lys Arg Lys Asn Xaa Ile Leu Asn Pro
    690                 695                 700

Ile Asn Ser Ile Arg Lys Phe Xaa Ile Val Gln Lys Thr Pro Leu Gln
705                 710                 715                 720

Met Asn Gly Ile Glu Glu Asp Ser Asp Glu Pro Leu Glu Arg Arg Leu
                725                 730                 735

Xaa Leu Val Pro Asp Ser Glu Gln Gly Glu Ala Ile Leu Pro Arg Ile
            740                 745                 750

Ser Val Ile Ser Thr Gly Pro Thr Leu Gln Ala Arg Arg Arg Gln Xaa
        755                 760                 765

Val Leu Asn Leu Met Thr His Ser Val Asn Gln Gly Gln Asn Ile His
    770                 775                 780

Arg Lys Thr Xaa Ala Ser Thr Arg Lys Val Xaa Leu Ala Pro Gln Ala
785                 790                 795                 800

Asn Leu Thr Glu Leu Asp Ile Tyr Ser Arg Arg Leu Xaa Gln Glu Thr
                805                 810                 815

Gly Leu Glu Ile Ser Glu Glu Ile Asn Glu Glu Asp Leu Lys Glu Cys
            820                 825                 830
```

```
Phe Phe Asp Asp Met Glu Ser Ile Pro Ala Val Thr Trp Asn Thr
            835                 840                 845

Tyr Leu Arg Tyr Ile Thr Val His Lys Ser Leu Ile Phe Val Leu Ile
    850                 855                 860

Trp Cys Leu Val Ile Phe Leu Ala Glu Val Ala Ala Ser Leu Val Val
865                 870                 875                 880

Leu Trp Leu Leu Gly Asn Thr Pro Leu Gln Asp Lys Gly Asn Ser Thr
                885                 890                 895

His Ser Arg Asn Asn Ser Tyr Ala Val Ile Ile Thr Ser Thr Ser Ser
            900                 905                 910

Tyr Tyr Val Phe Tyr Ile Tyr Val Gly Val Ala Asp Thr Leu Leu Ala
        915                 920                 925

Met Gly Phe Phe Arg Gly Leu Pro Leu Val His Thr Leu Ile Thr Val
    930                 935                 940

Ser Lys Ile Leu His His Lys Met Leu His Ser Val Leu Gln Ala Pro
945                 950                 955                 960

Met Ser Thr Leu Asn Thr Leu Lys Ala Gly Gly Ile Leu Asn Arg Phe
                965                 970                 975

Ser Lys Asp Ile Ala Ile Leu Asp Asp Leu Leu Pro Leu Thr Ile Phe
            980                 985                 990

Asp Phe Ile Gln Leu Leu Leu Ile Val Ile Gly Ala Ile Ala Val Val
        995                 1000                1005

Ala Val Leu Gln Pro Tyr Ile Phe Val Ala Thr Val Pro Val Ile
    1010                1015                1020

Val Ala Phe Ile Met Leu Arg Ala Tyr Phe Leu Gln Thr Ser Gln
    1025                1030                1035

Gln Leu Lys Gln Leu Glu Ser Glu Gly Arg Ser Pro Ile Phe Thr
    1040                1045                1050

His Leu Val Thr Ser Leu Lys Gly Leu Trp Thr Leu Arg Ala Phe
    1055                1060                1065

Gly Arg Gln Pro Tyr Phe Glu Thr Leu Phe His Lys Ala Leu Asn
    1070                1075                1080

Leu His Thr Ala Asn Trp Phe Leu Tyr Leu Ser Thr Leu Arg Trp
    1085                1090                1095

Phe Gln Met Arg Ile Glu Met Ile Phe Val Ile Phe Phe Ile Ala
    1100                1105                1110

Val Thr Phe Ile Ser Ile Leu Thr Thr Gly Glu Gly Glu Gly Arg
    1115                1120                1125

Val Gly Ile Ile Leu Thr Leu Ala Met Asn Ile Met Ser Thr Leu
    1130                1135                1140

Gln Trp Ala Val Asn Ser Ser Ile Asp Val Asp Ser Leu Met Arg
    1145                1150                1155

Ser Val Ser Arg Val Phe Lys Phe Ile Asp Met Pro Thr Glu Gly
    1160                1165                1170

Lys Pro Thr Lys Ser Thr Lys Pro Tyr Lys Asn Gly Gln Leu Ser
    1175                1180                1185

Lys Val Met Ile Ile Glu Asn Ser His Val Lys Lys Asp Asp Ile
    1190                1195                1200

Trp Pro Ser Gly Gly Gln Met Thr Val Lys Asp Leu Thr Ala Lys
    1205                1210                1215

Tyr Thr Glu Gly Gly Asn Ala Ile Leu Glu Asn Ile Ser Phe Ser
    1220                1225                1230

Ile Ser Pro Gly Gln Arg Val Gly Leu Leu Gly Arg Thr Gly Ser
```

-continued

```
            1235                1240                1245

Gly Lys Ser Thr Leu Leu Ser Ala Phe Leu Arg Leu Leu Asn Thr
        1250                1255                1260

Glu Gly Glu Ile Gln Ile Asp Gly Val Ser Trp Asp Ser Ile Thr
    1265                1270                1275

Leu Gln Gln Trp Arg Lys Ala Phe Gly Val Ile Pro Gln Lys Val
1280                1285                1290

Phe Ile Phe Ser Gly Thr Phe Arg Lys Asn Leu Asp Pro Tyr Glu
    1295                1300                1305

Gln Trp Ser Asp Gln Glu Ile Trp Lys Val Ala Asp Glu Val Gly
    1310                1315                1320

Leu Arg Ser Val Ile Glu Gln Phe Pro Gly Lys Leu Asp Phe Val
    1325                1330                1335

Leu Val Asp Gly Gly Cys Val Leu Ser His Gly His Lys Gln Leu
    1340                1345                1350

Met Cys Leu Ala Arg Ser Val Leu Ser Lys Ala Lys Ile Leu Leu
    1355                1360                1365

Leu Asp Glu Pro Ser Ala His Leu Asp Pro Val Thr Tyr Gln Ile
    1370                1375                1380

Ile Arg Arg Thr Leu Lys Gln Ala Phe Ala Asp Cys Thr Val Ile
    1385                1390                1395

Leu Cys Glu His Arg Ile Glu Ala Met Leu Glu Cys Gln Gln Phe
    1400                1405                1410

Leu Val Ile Glu Glu Asn Lys Val Arg Gln Tyr Asp Ser Ile Gln
    1415                1420                1425

Lys Leu Leu Asn Glu Arg Ser Leu Phe Arg Gln Ala Ile Ser Pro
    1430                1435                1440

Ser Asp Arg Val Lys Leu Phe Pro His Arg Asn Ser Ser Lys Cys
    1445                1450                1455

Lys Ser Lys Pro Gln Ile Ala Ala Leu Lys Glu Glu Thr Glu Glu
    1460                1465                1470

Glu Val Gln Asp Thr Arg Leu
    1475                1480

<210> SEQ ID NO 19
<211> LENGTH: 220
<212> TYPE: PRT
<213> ORGANISM: human
<220> FEATURE:
<221> NAME/KEY: misc_feature
<222> LOCATION: (192)..(192)
<223> OTHER INFORMATION: Xaa can be any naturally occurring amino acid

<400> SEQUENCE: 19

Met Ser Met Gly Leu Glu Ile Thr Gly Thr Ala Leu Ala Val Leu Gly
1               5                   10                  15

Trp Leu Gly Thr Ile Val Cys Cys Ala Leu Pro Met Trp Arg Val Ser
                20                  25                  30

Ala Phe Ile Gly Ser Asn Ile Ile Thr Ser Gln Asn Ile Trp Glu Gly
            35                  40                  45

Leu Trp Met Asn Cys Val Val Gln Ser Thr Gly Gln Met Gln Cys Lys
        50                  55                  60

Val Tyr Asp Ser Leu Leu Ala Leu Pro Gln Asp Leu Gln Ala Ala Arg
65                  70                  75                  80

Ala Leu Ile Val Val Ala Ile Leu Leu Ala Ala Phe Gly Leu Leu Val
                85                  90                  95
```

```
Ala Leu Val Gly Ala Gln Cys Thr Asn Cys Val Gln Asp Asp Thr Ala
            100                 105                 110

Lys Ala Lys Ile Thr Ile Val Ala Gly Val Leu Phe Leu Leu Ala Ala
            115                 120                 125

Leu Leu Thr Leu Val Pro Val Ser Trp Ser Ala Asn Thr Ile Ile Arg
130                 135                 140

Asp Phe Tyr Asn Pro Val Val Pro Glu Ala Gln Lys Arg Glu Met Gly
145                 150                 155                 160

Ala Gly Leu Tyr Val Gly Trp Ala Ala Ala Leu Gln Leu Leu Gly
            165                 170                 175

Gly Ala Leu Leu Cys Cys Ser Cys Pro Pro Arg Glu Lys Lys Tyr Xaa
            180                 185                 190

Ala Thr Lys Val Val Tyr Ser Ala Pro Arg Ser Thr Gly Pro Gly Ala
            195                 200                 205

Ser Leu Gly Thr Gly Tyr Asp Arg Lys Asp Tyr Val
            210                 215                 220

<210> SEQ ID NO 20
<211> LENGTH: 230
<212> TYPE: PRT
<213> ORGANISM: human
<220> FEATURE:
<221> NAME/KEY: misc_feature
<222> LOCATION: (133)..(133)
<223> OTHER INFORMATION: Xaa can be any naturally occurring amino acid

<400> SEQUENCE: 20

Met Thr Met Glu Ser Gly Ala Glu Asn Gln Gln Ser Gly Asp Ala Ala
1               5                   10                  15

Val Thr Glu Ala Glu Asn Gln Gln Met Thr Val Gln Ala Gln Pro Gln
            20                  25                  30

Ile Ala Thr Leu Ala Gln Val Ser Met Pro Ala Ala His Ala Thr Ser
            35                  40                  45

Ser Ala Pro Thr Val Thr Leu Val Gln Leu Pro Asn Gly Gln Thr Val
        50                  55                  60

Gln Val His Gly Val Ile Gln Ala Ala Gln Pro Ser Val Ile Gln Ser
65                  70                  75                  80

Pro Gln Val Gln Thr Val Gln Ser Ser Cys Lys Asp Leu Lys Arg Leu
                85                  90                  95

Phe Ser Gly Thr Gln Ile Ser Thr Ile Ala Glu Ser Glu Asp Ser Gln
            100                 105                 110

Glu Ser Val Asp Ser Val Thr Asp Ser Gln Lys Arg Arg Glu Ile Leu
            115                 120                 125

Ser Arg Arg Pro Xaa Tyr Arg Lys Ile Leu Asn Asp Leu Ser Ser Asp
130                 135                 140

Ala Pro Gly Val Pro Arg Ile Glu Glu Glu Lys Ser Glu Glu Glu Thr
145                 150                 155                 160

Ser Ala Leu Pro Thr Gln Pro Ala Glu Ala Ala Arg Lys Arg Glu
            165                 170                 175

Val Arg Leu Met Glu Asn Arg Glu Ala Ala Arg Glu Cys Arg Arg Lys
            180                 185                 190

Lys Lys Glu Tyr Val Lys Cys Leu Glu Asn Arg Val Ala Val Leu Glu
            195                 200                 205

Asn Gln Asn Lys Thr Leu Ile Glu Glu Leu Lys Ala Leu Lys Asp Leu
            210                 215                 220
```

-continued

```
Tyr Cys His Lys Ser Asp
225                 230

<210> SEQ ID NO 21
<211> LENGTH: 1203
<212> TYPE: PRT
<213> ORGANISM: human
<220> FEATURE:
<221> NAME/KEY: misc_feature
<222> LOCATION: (633)..(634)
<223> OTHER INFORMATION: Xaa can be any naturally occurring amino acid
<220> FEATURE:
<221> NAME/KEY: misc_feature
<222> LOCATION: (1177)..(1177)
<223> OTHER INFORMATION: Xaa can be any naturally occurring amino acid
<220> FEATURE:
<221> NAME/KEY: misc_feature
<222> LOCATION: (1179)..(1179)
<223> OTHER INFORMATION: Xaa can be any naturally occurring amino acid

<400> SEQUENCE: 21

Met Gly Asn Leu Lys Ser Val Ala Gln Glu Pro Gly Pro Pro Cys Gly
1               5                   10                  15

Leu Gly Leu Gly Leu Gly Leu Cys Gly Lys Gln Gly Pro Ala
            20                  25                  30

Thr Pro Ala Pro Glu Pro Ser Arg Ala Pro Ala Ser Leu Leu Pro Pro
            35                  40                  45

Ala Pro Glu His Ser Pro Ser Ser Pro Leu Thr Gln Pro Pro Glu
 50                 55                  60

Gly Pro Lys Phe Pro Arg Val Lys Asn Trp Glu Val Gly Ser Ile Thr
65                  70                  75                  80

Tyr Asp Thr Leu Ser Ala Gln Ala Gln Asp Gly Pro Cys Thr Pro
                85                  90                  95

Arg Arg Cys Leu Gly Ser Leu Val Phe Pro Arg Lys Leu Gln Gly Arg
                100                 105                 110

Pro Ser Pro Gly Pro Pro Ala Pro Glu Gln Leu Leu Ser Gln Ala Arg
            115                 120                 125

Asp Phe Ile Asn Gln Tyr Tyr Ser Ser Ile Lys Arg Ser Gly Ser Gln
130                 135                 140

Ala His Glu Gln Arg Leu Gln Glu Val Glu Ala Glu Val Ala Ala Thr
145                 150                 155                 160

Gly Thr Tyr Gln Leu Arg Glu Ser Glu Leu Val Phe Gly Ala Lys Gln
                165                 170                 175

Ala Trp Arg Asn Ala Pro Arg Cys Val Gly Arg Ile Gln Trp Gly Lys
            180                 185                 190

Leu Gln Val Phe Asp Ala Arg Asp Cys Arg Ser Ala Gln Glu Met Phe
        195                 200                 205

Thr Tyr Ile Cys Asn His Ile Lys Tyr Ala Thr Asn Arg Gly Asn Leu
210                 215                 220

Arg Ser Ala Ile Thr Val Phe Pro Gln Arg Cys Pro Gly Arg Gly Asp
225                 230                 235                 240

Phe Arg Ile Trp Asn Ser Gln Leu Val Arg Tyr Ala Gly Tyr Arg Gln
                245                 250                 255

Gln Asp Gly Ser Val Arg Gly Asp Pro Ala Asn Val Glu Ile Thr Glu
            260                 265                 270

Leu Cys Ile Gln His Gly Trp Thr Pro Gly Asn Gly Arg Phe Asp Val
        275                 280                 285

Leu Pro Leu Leu Leu Gln Ala Pro Asp Asp Pro Pro Glu Leu Phe Leu
290                 295                 300
```

-continued

```
Leu Pro Pro Glu Leu Val Leu Glu Val Pro Leu His Pro Thr Leu
305                 310                 315                 320

Glu Trp Phe Ala Ala Leu Gly Leu Arg Trp Tyr Ala Leu Pro Ala Val
                325                 330                 335

Ser Asn Met Leu Leu Glu Ile Gly Gly Leu Glu Phe Pro Ala Ala Pro
            340                 345                 350

Phe Ser Gly Trp Tyr Met Ser Thr Glu Ile Gly Thr Arg Asn Leu Cys
        355                 360                 365

Asp Pro His Arg Tyr Asn Ile Leu Glu Asp Val Ala Val Cys Met Asp
    370                 375                 380

Leu Asp Thr Arg Thr Thr Ser Ser Leu Trp Lys Asp Lys Ala Ala Val
385                 390                 395                 400

Glu Ile Asn Val Ala Val Leu His Ser Tyr Gln Leu Ala Lys Val Thr
                405                 410                 415

Ile Val Asp His His Ala Ala Thr Ala Ser Phe Met Lys His Leu Glu
            420                 425                 430

Asn Glu Gln Lys Ala Arg Gly Gly Cys Pro Ala Asp Trp Ala Trp Ile
        435                 440                 445

Val Pro Pro Ile Ser Gly Ser Leu Thr Pro Val Phe His Gln Glu Met
    450                 455                 460

Val Asn Tyr Phe Leu Ser Pro Ala Phe Arg Tyr Gln Pro Asp Pro Trp
465                 470                 475                 480

Lys Gly Ser Ala Ala Lys Gly Thr Gly Ile Thr Arg Lys Lys Thr Phe
                485                 490                 495

Lys Glu Val Ala Asn Ala Val Lys Ile Ser Ala Ser Leu Met Gly Thr
            500                 505                 510

Val Met Ala Lys Arg Val Lys Ala Thr Ile Leu Tyr Gly Ser Glu Thr
        515                 520                 525

Gly Arg Ala Gln Ser Tyr Ala Gln Gln Leu Gly Arg Leu Phe Arg Lys
    530                 535                 540

Ala Phe Asp Pro Arg Val Leu Cys Met Asp Glu Tyr Asp Val Val Ser
545                 550                 555                 560

Leu Glu His Glu Thr Leu Val Leu Val Val Thr Ser Thr Phe Gly Asn
                565                 570                 575

Gly Asp Pro Pro Glu Asn Gly Glu Ser Phe Ala Ala Ala Leu Met Glu
            580                 585                 590

Met Ser Gly Pro Tyr Asn Ser Ser Pro Arg Pro Glu Gln His Lys Ser
        595                 600                 605

Tyr Lys Ile Arg Phe Asn Ser Ile Ser Cys Ser Asp Pro Leu Val Ser
    610                 615                 620

Ser Trp Arg Arg Lys Arg Lys Glu Xaa Xaa Asn Thr Asp Ser Ala Gly
625                 630                 635                 640

Ala Leu Gly Thr Leu Arg Phe Cys Val Phe Gly Leu Gly Ser Arg Ala
                645                 650                 655

Tyr Pro His Phe Cys Ala Phe Ala Arg Ala Val Asp Thr Arg Leu Glu
            660                 665                 670

Glu Leu Gly Gly Glu Arg Leu Leu Gln Leu Gly Gln Gly Asp Glu Leu
        675                 680                 685

Cys Gly Gln Glu Glu Ala Phe Arg Gly Trp Ala Gln Ala Ala Phe Gln
    690                 695                 700

Ala Ala Cys Glu Thr Phe Cys Val Gly Glu Asp Ala Lys Ala Ala Ala
705                 710                 715                 720
```

```
Arg Asp Ile Phe Ser Pro Lys Arg Ser Trp Lys Arg Gln Arg Tyr Arg
            725                 730                 735

Leu Ser Ala Gln Ala Glu Gly Leu Gln Leu Leu Pro Gly Leu Ile His
        740                 745                 750

Val His Arg Arg Lys Met Phe Gln Ala Thr Ile Arg Ser Val Glu Asn
            755                 760                 765

Leu Gln Ser Ser Lys Ser Thr Arg Ala Thr Ile Leu Val Arg Leu Asp
        770                 775                 780

Thr Gly Gly Gln Glu Gly Leu Gln Tyr Gln Pro Gly Asp His Ile Gly
785                 790                 795                 800

Val Cys Pro Pro Asn Arg Pro Gly Leu Val Glu Ala Leu Leu Ser Arg
                805                 810                 815

Val Glu Asp Pro Pro Ala Pro Thr Glu Pro Val Ala Val Glu Gln Leu
                820                 825                 830

Glu Lys Gly Ser Pro Gly Gly Pro Pro Gly Trp Val Arg Asp Pro
            835                 840                 845

Arg Leu Pro Pro Cys Thr Leu Arg Gln Ala Leu Thr Phe Phe Leu Asp
        850                 855                 860

Ile Thr Ser Pro Pro Ser Pro Gln Leu Leu Arg Leu Leu Ser Thr Leu
865                 870                 875                 880

Ala Glu Glu Pro Arg Glu Gln Gln Gly Leu Glu Ala Leu Ser Gln Asp
                885                 890                 895

Pro Arg Arg Tyr Glu Glu Trp Lys Trp Phe Arg Cys Pro Thr Leu Leu
            900                 905                 910

Glu Val Leu Glu Gln Phe Pro Ser Val Ala Leu Pro Ala Pro Leu Leu
            915                 920                 925

Leu Thr Gln Leu Pro Leu Leu Gln Pro Arg Tyr Tyr Ser Val Ser Ser
        930                 935                 940

Ala Pro Ser Thr His Pro Gly Glu Ile His Leu Thr Val Ala Val Leu
945                 950                 955                 960

Ala Tyr Arg Thr Gln Asp Gly Leu Gly Pro Leu His Tyr Gly Val Cys
                965                 970                 975

Ser Thr Trp Leu Ser Gln Leu Lys Pro Gly Asp Pro Val Pro Cys Phe
            980                 985                 990

Ile Arg Gly Ala Pro Ser Phe Arg Leu Pro Pro Asp Pro Ser Leu Pro
            995                1000                1005

Cys Ile Leu Val Gly Pro Gly Thr Gly Ile Ala Pro Phe Arg Gly
        1010                1015                1020

Phe Trp Gln Glu Arg Leu His Asp Ile Glu Ser Lys Gly Leu Gln
        1025                1030                1035

Pro Thr Pro Met Thr Leu Val Phe Gly Cys Arg Cys Ser Gln Leu
        1040                1045                1050

Asp His Leu Tyr Arg Asp Glu Val Gln Asn Ala Gln Gln Arg Gly
        1055                1060                1065

Val Phe Gly Arg Val Leu Thr Ala Phe Ser Arg Glu Pro Asp Asn
        1070                1075                1080

Pro Lys Thr Tyr Val Gln Asp Ile Leu Arg Thr Glu Leu Ala Ala
        1085                1090                1095

Glu Val His Arg Val Leu Cys Leu Glu Arg Gly His Met Phe Val
        1100                1105                1110

Cys Gly Asp Val Thr Met Ala Thr Asn Val Leu Gln Thr Val Gln
        1115                1120                1125

Arg Ile Leu Ala Thr Glu Gly Asp Met Glu Leu Asp Glu Ala Gly
```

```
                    1130                1135                1140

Asp Val Ile Gly Val Leu Arg Asp Gln Gln Arg Tyr His Glu Asp
        1145                1150                1155

Ile Phe Gly Leu Thr Leu Arg Thr Gln Glu Val Thr Ser Arg Ile
    1160                1165                1170

Arg Thr Gln Xaa Phe Xaa Leu Gln Glu Arg Gln Leu Arg Gly Ala
1175                1180                1185

Val Pro Trp Ala Phe Asp Pro Pro Gly Ser Asp Thr Asn Ser Pro
    1190                1195                1200

<210> SEQ ID NO 22
<211> LENGTH: 416
<212> TYPE: PRT
<213> ORGANISM: human
<220> FEATURE:
<221> NAME/KEY: misc_feature
<222> LOCATION: (158)..(158)
<223> OTHER INFORMATION: Xaa can be any naturally occurring amino acid

<400> SEQUENCE: 22

Met Ser Glu Gln Ser Ile Cys Gln Ala Arg Ala Ser Val Met Val Tyr
1               5                   10                  15

Asp Asp Thr Ser Lys Lys Trp Val Pro Ile Lys Pro Gly Gln Gln Gly
            20                  25                  30

Phe Ser Arg Ile Asn Ile Tyr His Asn Thr Ala Ser Asn Thr Phe Arg
        35                  40                  45

Val Val Gly Val Lys Leu Gln Asp Gln Gln Val Val Ile Asn Tyr Ser
    50                  55                  60

Ile Val Lys Gly Leu Lys Tyr Asn Gln Ala Thr Pro Thr Phe His Gln
65                  70                  75                  80

Trp Arg Asp Ala Arg Gln Val Tyr Gly Leu Asn Phe Ala Ser Lys Glu
                85                  90                  95

Glu Ala Thr Thr Phe Ser Asn Ala Met Leu Phe Ala Leu Asn Ile Met
            100                 105                 110

Asn Ser Gln Glu Gly Gly Pro Ser Ser Gln Arg Gln Val Gln Asn Gly
        115                 120                 125

Pro Ser Pro Asp Glu Met Asp Ile Gln Arg Arg Gln Val Met Glu Gln
    130                 135                 140

His Gln Gln Gln Arg Gln Glu Ser Leu Glu Arg Arg Thr Xaa Ala Thr
145                 150                 155                 160

Gly Pro Ile Leu Pro Pro Gly His Pro Ser Ser Ala Ala Ser Ala Pro
                165                 170                 175

Val Ser Cys Ser Gly Pro Pro Pro Pro Pro Pro Pro Val Pro Pro
            180                 185                 190

Pro Pro Thr Gly Ala Thr Pro Pro Pro Pro Pro Leu Pro Ala Gly
        195                 200                 205

Gly Ala Gln Gly Ser Ser His Asp Glu Ser Ser Met Ser Gly Leu Ala
    210                 215                 220

Ala Ala Ile Ala Gly Ala Lys Leu Arg Arg Val Gln Arg Pro Glu Asp
225                 230                 235                 240

Ala Ser Gly Gly Ser Ser Pro Ser Gly Thr Ser Lys Ser Asp Ala Asn
                245                 250                 255

Arg Ala Ser Ser Gly Gly Gly Gly Gly Leu Met Glu Glu Met Asn
            260                 265                 270

Lys Leu Leu Ala Lys Arg Arg Lys Ala Ala Ser Gln Ser Asp Lys Pro
        275                 280                 285
```

```
Ala Glu Lys Lys Glu Asp Glu Ser Gln Met Glu Asp Pro Ser Thr Ser
    290                 295                 300
Pro Ser Pro Gly Thr Arg Ala Ala Ser Gln Pro Asn Ser Ser Glu
305                 310                 315                 320
Ala Gly Arg Lys Pro Trp Glu Arg Ser Asn Ser Val Glu Lys Pro Val
                325                 330                 335
Ser Ser Ile Leu Ser Arg Thr Pro Ser Val Ala Lys Ser Pro Glu Ala
                340                 345                 350
Lys Ser Pro Leu Gln Ser Gln Pro His Ser Arg Met Lys Pro Ala Gly
            355                 360                 365
Ser Val Asn Asp Met Ala Leu Asp Ala Phe Asp Leu Asp Arg Met Lys
    370                 375                 380
Gln Glu Ile Leu Glu Glu Val Val Arg Glu Leu His Lys Val Lys Glu
385                 390                 395                 400
Glu Ile Ile Asp Ala Ile Arg Gln Glu Leu Ser Gly Ile Ser Thr Thr
                405                 410                 415
```

<210> SEQ ID NO 23
<211> LENGTH: 586
<212> TYPE: PRT
<213> ORGANISM: human
<220> FEATURE:
<221> NAME/KEY: misc_feature
<222> LOCATION: (66)..(66)
<223> OTHER INFORMATION: Xaa can be any naturally occurring amino acid

<400> SEQUENCE: 23

```
Met Pro Lys Pro Ile Asn Val Arg Val Thr Thr Met Asp Ala Glu Leu
1               5                   10                  15
Glu Phe Ala Ile Gln Pro Asn Thr Thr Gly Lys Gln Leu Phe Asp Gln
                20                  25                  30
Val Val Lys Thr Ile Gly Leu Arg Glu Val Trp Tyr Phe Gly Leu His
            35                  40                  45
Tyr Val Asp Asn Lys Gly Phe Pro Thr Trp Leu Lys Leu Asp Lys Lys
    50                  55                  60
Val Xaa Ala Gln Glu Val Arg Lys Glu Asn Pro Leu Gln Phe Lys Phe
65                  70                  75                  80
Arg Ala Lys Phe Tyr Pro Glu Asp Val Ala Glu Glu Leu Ile Gln Asp
                85                  90                  95
Ile Thr Gln Lys Leu Phe Phe Leu Gln Val Lys Glu Gly Ile Leu Ser
                100                 105                 110
Asp Glu Ile Tyr Cys Pro Pro Glu Thr Ala Val Leu Leu Gly Ser Tyr
            115                 120                 125
Ala Val Gln Ala Lys Phe Gly Asp Tyr Asn Lys Glu Val His Lys Ser
    130                 135                 140
Gly Tyr Leu Ser Ser Glu Arg Leu Ile Pro Gln Arg Val Met Asp Gln
145                 150                 155                 160
His Lys Leu Thr Arg Asp Gln Trp Glu Asp Arg Ile Gln Val Trp His
                165                 170                 175
Ala Glu His Arg Gly Met Leu Lys Asp Asn Ala Met Leu Glu Tyr Leu
                180                 185                 190
Lys Ile Ala Gln Asp Leu Glu Met Tyr Gly Ile Asn Tyr Phe Glu Ile
            195                 200                 205
Lys Asn Lys Lys Gly Thr Asp Leu Trp Leu Gly Val Asp Ala Leu Gly
    210                 215                 220
```

```
Leu Asn Ile Tyr Glu Lys Asp Asp Lys Leu Thr Pro Lys Ile Gly Phe
225                 230                 235                 240

Pro Trp Ser Glu Ile Arg Asn Ile Ser Phe Asn Asp Lys Lys Phe Val
            245                 250                 255

Ile Lys Pro Ile Asp Lys Lys Ala Pro Asp Phe Val Phe Tyr Ala Pro
        260                 265                 270

Arg Leu Arg Ile Asn Lys Arg Ile Leu Gln Leu Cys Met Gly Asn His
    275                 280                 285

Glu Leu Tyr Met Arg Arg Lys Pro Asp Thr Ile Glu Val Gln Gln
290                 295                 300

Met Lys Ala Gln Ala Arg Glu Glu Lys His Gln Lys Gln Leu Glu Arg
305                 310                 315                 320

Gln Gln Leu Glu Thr Glu Lys Lys Arg Glu Thr Val Glu Arg Glu
                325                 330                 335

Lys Glu Gln Met Met Arg Glu Lys Glu Glu Leu Met Leu Arg Leu Gln
                340                 345                 350

Asp Tyr Glu Glu Lys Thr Lys Lys Ala Glu Arg Glu Leu Ser Glu Gln
                355                 360                 365

Ile Gln Arg Ala Leu Gln Leu Glu Glu Glu Arg Lys Arg Ala Gln Glu
370                 375                 380

Glu Ala Glu Arg Leu Glu Ala Asp Arg Met Ala Ala Leu Arg Ala Lys
385                 390                 395                 400

Glu Glu Leu Glu Arg Gln Ala Val Asp Gln Ile Lys Ser Gln Glu Gln
                405                 410                 415

Leu Ala Ala Glu Leu Ala Glu Tyr Thr Ala Lys Ile Ala Leu Leu Glu
            420                 425                 430

Glu Ala Arg Arg Arg Lys Glu Asp Glu Val Glu Glu Trp Gln His Arg
        435                 440                 445

Ala Lys Glu Ala Gln Asp Asp Leu Val Lys Thr Lys Glu Glu Leu His
    450                 455                 460

Leu Val Met Thr Ala Pro Pro Pro Pro Pro Val Tyr Glu Pro
465                 470                 475                 480

Val Ser Tyr His Val Gln Glu Ser Leu Gln Asp Glu Gly Ala Glu Pro
                485                 490                 495

Thr Gly Tyr Ser Ala Glu Leu Ser Ser Glu Gly Ile Arg Asp Asp Arg
            500                 505                 510

Asn Glu Glu Lys Arg Ile Thr Glu Ala Glu Lys Asn Glu Arg Val Gln
        515                 520                 525

Arg Gln Leu Leu Thr Leu Ser Ser Glu Leu Ser Gln Ala Arg Asp Glu
    530                 535                 540

Asn Lys Arg Thr His Asn Asp Ile Ile His Asn Glu Asn Met Arg Gln
545                 550                 555                 560

Gly Arg Asp Lys Tyr Lys Thr Leu Arg Gln Ile Arg Gln Gly Asn Thr
                565                 570                 575

Lys Gln Arg Ile Asp Glu Phe Glu Ala Leu
            580                 585

<210> SEQ ID NO 24
<211> LENGTH: 2647
<212> TYPE: PRT
<213> ORGANISM: human
<220> FEATURE:
<221> NAME/KEY: misc_feature
<222> LOCATION: (2152)..(2152)
<223> OTHER INFORMATION: Xaa can be any naturally occurring amino acid
<220> FEATURE:
```

-continued

```
<221> NAME/KEY: misc_feature
<222> LOCATION: (2336)..(2336)
<223> OTHER INFORMATION: Xaa can be any naturally occurring amino acid

<400> SEQUENCE: 24

Met Ser Ser Ser His Ser Arg Ala Gly Gln Ser Ala Ala Gly Ala Ala
1               5                   10                  15

Pro Gly Gly Gly Val Asp Thr Arg Asp Ala Glu Met Pro Ala Thr Glu
            20                  25                  30

Lys Asp Leu Ala Glu Asp Ala Pro Trp Lys Lys Ile Gln Gln Asn Thr
        35                  40                  45

Phe Thr Arg Trp Cys Asn Glu His Leu Lys Cys Val Ser Lys Arg Ile
    50                  55                  60

Ala Asn Leu Gln Thr Asp Leu Ser Asp Gly Leu Arg Leu Ile Ala Leu
65                  70                  75                  80

Leu Glu Val Leu Ser Gln Lys Lys Met His Arg Lys His Asn Gln Arg
                85                  90                  95

Pro Thr Phe Arg Gln Met Gln Leu Glu Asn Val Ser Val Ala Leu Glu
            100                 105                 110

Phe Leu Asp Arg Glu Ser Ile Lys Leu Val Ser Ile Asp Ser Lys Ala
        115                 120                 125

Ile Val Asp Gly Asn Leu Lys Leu Ile Leu Gly Leu Ile Trp Thr Leu
    130                 135                 140

Ile Leu His Tyr Ser Ile Ser Met Pro Met Trp Asp Glu Glu Glu Asp
145                 150                 155                 160

Glu Glu Ala Lys Lys Gln Thr Pro Lys Gln Arg Leu Leu Gly Trp Ile
                165                 170                 175

Gln Asn Lys Leu Pro Gln Leu Pro Ile Thr Asn Phe Ser Arg Asp Trp
            180                 185                 190

Gln Ser Gly Arg Ala Leu Gly Ala Leu Val Asp Ser Cys Ala Pro Gly
        195                 200                 205

Leu Cys Pro Asp Trp Asp Ser Trp Asp Ala Ser Lys Pro Val Thr Asn
    210                 215                 220

Ala Arg Glu Ala Met Gln Gln Ala Asp Asp Trp Leu Gly Ile Pro Gln
225                 230                 235                 240

Val Ile Thr Pro Glu Glu Ile Val Asp Pro Asn Val Asp Glu His Ser
                245                 250                 255

Val Met Thr Tyr Leu Ser Gln Phe Pro Lys Ala Lys Leu Lys Pro Gly
            260                 265                 270

Ala Pro Leu Arg Pro Lys Leu Asn Pro Lys Lys Ala Arg Ala Tyr Gly
        275                 280                 285

Pro Gly Ile Glu Pro Thr Gly Asn Met Val Lys Lys Arg Ala Glu Phe
    290                 295                 300

Thr Val Glu Thr Arg Ser Ala Gly Gln Gly Glu Val Leu Val Tyr Val
305                 310                 315                 320

Glu Asp Pro Ala Gly His Gln Glu Glu Ala Lys Val Thr Ala Asn Asn
                325                 330                 335

Asp Lys Asn Arg Thr Phe Ser Val Trp Tyr Val Pro Glu Val Thr Gly
            340                 345                 350

Thr His Lys Val Thr Val Leu Phe Ala Gly Gln His Ile Ala Lys Ser
        355                 360                 365

Pro Phe Glu Val Tyr Val Asp Lys Ser Gln Gly Asp Ala Ser Lys Val
    370                 375                 380

Thr Ala Gln Gly Pro Gly Leu Glu Pro Ser Gly Asn Ile Ala Asn Lys
```

```
            385                 390                 395                 400
        Thr Thr Tyr Phe Glu Ile Phe Thr Ala Gly Ala Gly Thr Gly Glu Val
                        405                 410                 415

Glu Val Val Ile Gln Asp Pro Met Gly Gln Lys Gly Thr Val Glu Pro
                        420                 425                 430

Gln Leu Glu Ala Arg Gly Asp Ser Thr Tyr Arg Cys Ser Tyr Gln Pro
                    435                 440                 445

Thr Met Glu Gly Val His Thr Val His Val Thr Phe Ala Gly Val Pro
                    450                 455                 460

Ile Pro Arg Ser Pro Tyr Thr Val Thr Val Gly Gln Ala Cys Asn Pro
        465                 470                 475                 480

Ser Ala Cys Arg Ala Val Gly Arg Gly Leu Gln Pro Lys Gly Val Arg
                            485                 490                 495

Val Lys Glu Thr Ala Asp Phe Lys Val Tyr Thr Lys Gly Ala Gly Ser
                        500                 505                 510

Gly Glu Leu Lys Val Thr Val Lys Gly Pro Lys Gly Glu Glu Arg Val
                    515                 520                 525

Lys Gln Lys Asp Leu Gly Asp Gly Val Tyr Gly Phe Glu Tyr Tyr Pro
                    530                 535                 540

Met Val Pro Gly Thr Tyr Ile Val Thr Ile Thr Trp Gly Gly Gln Asn
        545                 550                 555                 560

Ile Gly Arg Ser Pro Phe Glu Val Lys Val Gly Thr Glu Cys Gly Asn
                            565                 570                 575

Gln Lys Val Arg Ala Trp Gly Pro Gly Leu Glu Gly Gly Val Val Gly
                        580                 585                 590

Lys Ser Ala Asp Phe Val Val Glu Ala Ile Gly Asp Asp Val Gly Thr
                    595                 600                 605

Leu Gly Phe Ser Val Glu Gly Pro Ser Gln Ala Lys Ile Glu Cys Asp
                    610                 615                 620

Asp Lys Gly Asp Gly Ser Cys Asp Val Arg Tyr Trp Pro Gln Glu Ala
        625                 630                 635                 640

Gly Glu Tyr Ala Val His Val Leu Cys Asn Ser Glu Asp Ile Arg Leu
                            645                 650                 655

Ser Pro Phe Met Ala Asp Ile Arg Asp Ala Pro Gln Asp Phe His Pro
                        660                 665                 670

Asp Arg Val Lys Ala Arg Gly Pro Gly Leu Glu Lys Thr Gly Val Ala
                    675                 680                 685

Val Asn Lys Pro Ala Glu Phe Thr Val Asp Ala Lys His Gly Gly Lys
                    690                 695                 700

Ala Pro Leu Arg Val Gln Val Gln Asp Asn Glu Gly Cys Pro Val Glu
        705                 710                 715                 720

Ala Leu Val Lys Asp Asn Gly Asn Gly Thr Tyr Ser Cys Ser Tyr Val
                            725                 730                 735

Pro Arg Lys Pro Val Lys His Thr Ala Met Val Ser Trp Gly Gly Val
                        740                 745                 750

Ser Ile Pro Asn Ser Pro Phe Arg Val Asn Val Gly Ala Gly Ser His
                    755                 760                 765

Pro Asn Lys Val Lys Val Tyr Gly Pro Gly Val Ala Lys Thr Gly Leu
                    770                 775                 780

Lys Ala His Glu Pro Thr Tyr Phe Thr Val Asp Cys Ala Glu Ala Gly
        785                 790                 795                 800

Gln Gly Asp Val Ser Ile Gly Ile Lys Cys Ala Pro Gly Val Val Gly
                            805                 810                 815
```

-continued

Pro Ala Glu Ala Asp Ile Asp Phe Asp Ile Ile Arg Asn Asp Asn Asp
            820                 825                 830

Thr Phe Thr Val Lys Tyr Thr Pro Arg Gly Ala Gly Ser Tyr Thr Ile
        835                 840                 845

Met Val Leu Phe Ala Asp Gln Ala Thr Pro Thr Ser Pro Ile Arg Val
    850                 855                 860

Lys Val Glu Pro Ser His Asp Ala Ser Lys Val Lys Ala Glu Gly Pro
865                 870                 875                 880

Gly Leu Ser Arg Thr Gly Val Glu Leu Gly Lys Pro Thr His Phe Thr
                885                 890                 895

Val Asn Ala Lys Ala Ala Gly Lys Gly Lys Leu Asp Val Gln Phe Ser
            900                 905                 910

Gly Leu Thr Lys Gly Asp Ala Val Arg Asp Val Asp Ile Ile Asp His
        915                 920                 925

His Asp Asn Thr Tyr Thr Val Lys Tyr Thr Pro Val Gln Gln Gly Pro
    930                 935                 940

Val Gly Val Asn Val Thr Tyr Gly Gly Asp Pro Ile Pro Lys Ser Pro
945                 950                 955                 960

Phe Ser Val Ala Val Ser Pro Ser Leu Asp Leu Ser Lys Ile Lys Val
                965                 970                 975

Ser Gly Leu Gly Glu Lys Val Asp Val Gly Lys Asp Gln Glu Phe Thr
            980                 985                 990

Val Lys Ser Lys Gly Ala Gly Gly Gln Gly Lys Val Ala Ser Lys Ile
        995                 1000                1005

Val Gly Pro Ser Gly Ala Ala Val Pro Cys Lys Val Glu Pro Gly
    1010                1015                1020

Leu Gly Ala Asp Asn Ser Val Val Arg Phe Leu Pro Arg Glu Glu
    1025                1030                1035

Gly Pro Tyr Glu Val Glu Val Thr Tyr Asp Gly Val Pro Val Pro
    1040                1045                1050

Gly Ser Pro Phe Pro Leu Glu Ala Val Ala Pro Thr Lys Pro Ser
    1055                1060                1065

Lys Val Lys Ala Phe Gly Pro Gly Leu Gln Gly Gly Ser Ala Gly
    1070                1075                1080

Ser Pro Ala Arg Phe Thr Ile Asp Thr Lys Gly Ala Gly Thr Gly
    1085                1090                1095

Gly Leu Gly Leu Thr Val Glu Gly Pro Cys Glu Ala Gln Leu Glu
    1100                1105                1110

Cys Leu Asp Asn Gly Asp Gly Thr Cys Ser Val Ser Tyr Val Pro
    1115                1120                1125

Thr Glu Pro Gly Asp Tyr Asn Ile Asn Ile Leu Phe Ala Asp Thr
    1130                1135                1140

His Ile Pro Gly Ser Pro Phe Lys Ala His Val Val Pro Cys Phe
    1145                1150                1155

Asp Ala Ser Lys Val Lys Cys Ser Gly Pro Gly Leu Glu Arg Ala
    1160                1165                1170

Thr Ala Gly Glu Val Gly Gln Phe Gln Val Asp Cys Ser Ser Ala
    1175                1180                1185

Gly Ser Ala Glu Leu Thr Ile Glu Ile Cys Ser Glu Ala Gly Leu
    1190                1195                1200

Pro Ala Glu Val Tyr Ile Gln Asp His Gly Asp Gly Thr His Thr
    1205                1210                1215

```
Ile  Thr  Tyr  Ile  Pro  Leu  Cys  Pro  Gly  Ala  Tyr  Thr  Val  Thr  Ile
1220                1225                1230

Lys  Tyr  Gly  Gly  Gln  Pro  Val  Pro  Asn  Phe  Pro  Ser  Lys  Leu  Gln
1235                1240                1245

Val  Glu  Pro  Ala  Val  Asp  Thr  Ser  Gly  Val  Gln  Cys  Tyr  Gly  Pro
1250                1255                1260

Gly  Ile  Glu  Gly  Gln  Gly  Val  Phe  Arg  Glu  Ala  Thr  Thr  Glu  Phe
1265                1270                1275

Ser  Val  Asp  Ala  Arg  Ala  Leu  Thr  Gln  Thr  Gly  Gly  Pro  His  Val
1280                1285                1290

Lys  Ala  Arg  Val  Ala  Asn  Pro  Ser  Gly  Asn  Leu  Thr  Glu  Thr  Tyr
1295                1300                1305

Val  Gln  Asp  Arg  Gly  Asp  Gly  Met  Tyr  Lys  Val  Glu  Tyr  Thr  Pro
1310                1315                1320

Tyr  Glu  Glu  Gly  Leu  His  Ser  Val  Asp  Val  Thr  Tyr  Asp  Gly  Ser
1325                1330                1335

Pro  Val  Pro  Ser  Ser  Pro  Phe  Gln  Val  Pro  Val  Thr  Glu  Gly  Cys
1340                1345                1350

Asp  Pro  Ser  Arg  Val  Arg  Val  His  Gly  Pro  Gly  Ile  Gln  Ser  Gly
1355                1360                1365

Thr  Thr  Asn  Lys  Pro  Asn  Lys  Phe  Thr  Val  Glu  Thr  Arg  Gly  Ala
1370                1375                1380

Gly  Thr  Gly  Gly  Leu  Gly  Leu  Ala  Val  Glu  Gly  Pro  Ser  Glu  Ala
1385                1390                1395

Lys  Met  Ser  Cys  Met  Asp  Asn  Lys  Asp  Gly  Ser  Cys  Ser  Val  Glu
1400                1405                1410

Tyr  Ile  Pro  Tyr  Glu  Ala  Gly  Thr  Tyr  Ser  Leu  Asn  Val  Thr  Tyr
1415                1420                1425

Gly  Gly  His  Gln  Val  Pro  Gly  Ser  Pro  Phe  Lys  Val  Pro  Val  His
1430                1435                1440

Asp  Val  Thr  Asp  Ala  Ser  Lys  Val  Lys  Cys  Ser  Gly  Pro  Gly  Leu
1445                1450                1455

Ser  Pro  Gly  Met  Val  Arg  Ala  Asn  Leu  Pro  Gln  Ser  Phe  Gln  Val
1460                1465                1470

Asp  Thr  Ser  Lys  Ala  Gly  Val  Ala  Pro  Leu  Gln  Val  Lys  Val  Gln
1475                1480                1485

Gly  Pro  Lys  Gly  Leu  Val  Glu  Pro  Val  Asp  Val  Val  Asp  Asn  Ala
1490                1495                1500

Asp  Gly  Thr  Gln  Thr  Val  Asn  Tyr  Val  Pro  Ser  Arg  Glu  Gly  Pro
1505                1510                1515

Tyr  Ser  Ile  Ser  Val  Leu  Tyr  Gly  Asp  Glu  Glu  Val  Pro  Arg  Ser
1520                1525                1530

Pro  Phe  Lys  Val  Lys  Val  Leu  Pro  Thr  His  Asp  Ala  Ser  Lys  Val
1535                1540                1545

Lys  Ala  Ser  Gly  Pro  Gly  Leu  Asn  Thr  Thr  Gly  Val  Pro  Ala  Ser
1550                1555                1560

Leu  Pro  Val  Glu  Phe  Thr  Ile  Asp  Ala  Lys  Asp  Ala  Gly  Glu  Gly
1565                1570                1575

Leu  Leu  Ala  Val  Gln  Ile  Thr  Asp  Pro  Glu  Gly  Lys  Pro  Lys  Lys
1580                1585                1590

Thr  His  Ile  Gln  Asp  Asn  His  Asp  Gly  Thr  Tyr  Thr  Val  Ala  Tyr
1595                1600                1605

Val  Pro  Asp  Val  Thr  Gly  Arg  Tyr  Thr  Ile  Leu  Ile  Lys  Tyr  Gly
```

-continued

```
                1610                1615                1620
Gly Asp Glu Ile Pro Phe Ser Pro Tyr Arg Val Arg Ala Val Pro
        1625                1630                1635
Thr Gly Asp Ala Ser Lys Cys Thr Val Thr Val Ser Ile Gly Gly
        1640                1645                1650
His Gly Leu Gly Ala Gly Ile Gly Pro Thr Ile Gln Ile Gly Glu
        1655                1660                1665
Glu Thr Val Ile Thr Val Asp Thr Lys Ala Ala Gly Lys Gly Lys
        1670                1675                1680
Val Thr Cys Thr Val Cys Thr Pro Asp Gly Ser Glu Val Asp Val
        1685                1690                1695
Asp Val Val Glu Asn Glu Asp Gly Thr Phe Asp Ile Phe Tyr Thr
        1700                1705                1710
Ala Pro Gln Pro Gly Lys Tyr Val Ile Cys Val Arg Phe Gly Gly
        1715                1720                1725
Glu His Val Pro Asn Ser Pro Phe Gln Val Thr Ala Leu Ala Gly
        1730                1735                1740
Asp Gln Pro Ser Val Gln Pro Pro Leu Arg Ser Gln Gln Leu Ala
        1745                1750                1755
Pro Gln Tyr Thr Tyr Ala Gln Gly Gly Gln Gln Thr Trp Ala Pro
        1760                1765                1770
Glu Arg Pro Leu Val Gly Val Asn Gly Leu Asp Val Thr Ser Leu
        1775                1780                1785
Arg Pro Phe Asp Leu Val Ile Pro Phe Thr Ile Lys Lys Gly Glu
        1790                1795                1800
Ile Thr Gly Glu Val Arg Met Pro Ser Gly Lys Val Ala Gln Pro
        1805                1810                1815
Thr Ile Thr Asp Asn Lys Asp Gly Thr Val Thr Val Arg Tyr Ala
        1820                1825                1830
Pro Ser Glu Ala Gly Leu His Glu Met Asp Ile Arg Tyr Asp Asn
        1835                1840                1845
Met His Ile Pro Gly Ser Pro Leu Gln Phe Tyr Val Asp Tyr Val
        1850                1855                1860
Asn Cys Gly His Val Thr Ala Tyr Gly Pro Gly Leu Thr His Gly
        1865                1870                1875
Val Val Asn Lys Pro Ala Thr Phe Thr Val Asn Thr Lys Asp Ala
        1880                1885                1890
Gly Glu Gly Gly Leu Ser Leu Ala Ile Glu Gly Pro Ser Lys Ala
        1895                1900                1905
Glu Ile Ser Cys Thr Asp Asn Gln Asp Gly Thr Cys Ser Val Ser
        1910                1915                1920
Tyr Leu Pro Val Leu Pro Gly Asp Tyr Ser Ile Leu Val Lys Tyr
        1925                1930                1935
Asn Glu Gln His Val Pro Gly Ser Pro Phe Thr Ala Arg Val Thr
        1940                1945                1950
Gly Asp Asp Ser Met Arg Met Ser His Leu Lys Val Gly Ser Ala
        1955                1960                1965
Ala Asp Ile Pro Ile Asn Ile Ser Glu Thr Asp Leu Ser Leu Leu
        1970                1975                1980
Thr Ala Thr Val Val Pro Pro Ser Gly Arg Glu Glu Pro Cys Leu
        1985                1990                1995
Leu Lys Arg Leu Arg Asn Gly His Val Gly Ile Ser Phe Val Pro
        2000                2005                2010
```

-continued

Lys Glu Thr Gly Glu His Leu Val His Val Lys Lys Asn Gly Gln
2015                2020                2025

His Val Ala Ser Ser Pro Ile Pro Val Val Ile Ser Gln Ser Glu
2030                2035                2040

Ile Gly Asp Ala Ser Arg Val Arg Val Ser Gly Gln Gly Leu His
2045                2050                2055

Glu Gly His Thr Phe Glu Pro Ala Glu Phe Ile Ile Asp Thr Arg
2060                2065                2070

Asp Ala Gly Tyr Gly Gly Leu Ser Leu Ser Ile Glu Gly Pro Ser
2075                2080                2085

Lys Val Asp Ile Asn Thr Glu Asp Leu Glu Asp Gly Thr Cys Arg
2090                2095                2100

Val Thr Tyr Cys Pro Thr Glu Pro Gly Asn Tyr Ile Ile Asn Ile
2105                2110                2115

Lys Phe Ala Asp Gln His Val Pro Gly Ser Pro Phe Ser Val Lys
2120                2125                2130

Val Thr Gly Glu Gly Arg Val Lys Glu Ser Ile Thr Arg Arg Arg
2135                2140                2145

Arg Ala Pro Xaa Val Ala Asn Val Gly Ser His Cys Asp Leu Ser
2150                2155                2160

Leu Lys Ile Pro Glu Ile Ser Ile Gln Asp Met Thr Ala Gln Val
2165                2170                2175

Thr Ser Pro Ser Gly Lys Thr His Glu Ala Glu Ile Val Glu Gly
2180                2185                2190

Glu Asn His Thr Tyr Cys Ile Arg Phe Val Pro Ala Glu Met Gly
2195                2200                2205

Thr His Thr Val Ser Val Lys Tyr Lys Gly Gln His Val Pro Gly
2210                2215                2220

Ser Pro Phe Gln Phe Thr Val Gly Pro Leu Gly Glu Gly Gly Ala
2225                2230                2235

His Lys Val Arg Ala Gly Gly Pro Gly Leu Glu Arg Ala Glu Ala
2240                2245                2250

Gly Val Pro Ala Glu Phe Ser Ile Trp Thr Arg Glu Ala Gly Ala
2255                2260                2265

Gly Gly Leu Ala Ile Ala Val Glu Gly Pro Ser Lys Ala Glu Ile
2270                2275                2280

Ser Phe Glu Asp Arg Lys Asp Gly Ser Cys Gly Val Ala Tyr Val
2285                2290                2295

Val Gln Glu Pro Gly Asp Tyr Glu Val Ser Val Lys Phe Asn Glu
2300                2305                2310

Glu His Ile Pro Asp Ser Pro Phe Val Val Pro Val Ala Ser Pro
2315                2320                2325

Ser Gly Asp Ala Arg Arg Leu Xaa Val Ser Ser Leu Gln Glu Ser
2330                2335                2340

Gly Leu Lys Val Asn Gln Pro Ala Ser Phe Ala Val Ser Leu Asn
2345                2350                2355

Gly Ala Lys Gly Ala Ile Asp Ala Lys Val His Ser Pro Ser Gly
2360                2365                2370

Ala Leu Glu Glu Cys Tyr Val Thr Glu Ile Asp Gln Asp Lys Tyr
2375                2380                2385

Ala Val Arg Phe Ile Pro Arg Glu Asn Gly Val Tyr Leu Ile Asp
2390                2395                2400

-continued

```
Val Lys Phe Asn Gly Thr His Ile Pro Gly Ser Pro Phe Lys Ile
    2405                2410                2415

Arg Val Gly Glu Pro Gly His Gly Gly Asp Pro Gly Leu Val Ser
    2420                2425                2430

Ala Tyr Gly Ala Gly Leu Glu Gly Gly Val Thr Gly Asn Pro Ala
    2435                2440                2445

Glu Phe Val Val Asn Thr Ser Asn Ala Gly Ala Gly Ala Leu Ser
    2450                2455                2460

Val Thr Ile Asp Gly Pro Ser Lys Val Lys Met Asp Cys Gln Glu
    2465                2470                2475

Cys Pro Glu Gly Tyr Arg Val Thr Tyr Thr Pro Met Ala Pro Gly
    2480                2485                2490

Ser Tyr Leu Ile Ser Ile Lys Tyr Gly Gly Pro Tyr His Ile Gly
    2495                2500                2505

Gly Ser Pro Phe Lys Ala Lys Val Thr Gly Pro Arg Leu Val Ser
    2510                2515                2520

Asn His Ser Leu His Glu Thr Ser Ser Val Phe Val Asp Ser Leu
    2525                2530                2535

Thr Lys Ala Thr Cys Ala Pro Gln His Gly Ala Pro Gly Pro Gly
    2540                2545                2550

Pro Ala Asp Ala Ser Lys Val Val Ala Lys Gly Leu Gly Leu Ser
    2555                2560                2565

Lys Ala Tyr Val Gly Gln Lys Ser Ser Phe Thr Val Asp Cys Ser
    2570                2575                2580

Lys Ala Gly Asn Asn Met Leu Leu Val Gly Val His Gly Pro Arg
    2585                2590                2595

Thr Pro Cys Glu Glu Ile Leu Val Lys His Val Gly Ser Arg Leu
    2600                2605                2610

Tyr Ser Val Ser Tyr Leu Leu Lys Asp Lys Gly Glu Tyr Thr Leu
    2615                2620                2625

Val Val Lys Trp Gly Asp Glu His Ile Pro Gly Ser Pro Tyr Arg
    2630                2635                2640

Val Val Val Pro
    2645

<210> SEQ ID NO 25
<211> LENGTH: 563
<212> TYPE: PRT
<213> ORGANISM: human
<220> FEATURE:
<221> NAME/KEY: misc_feature
<222> LOCATION: (21)..(21)
<223> OTHER INFORMATION: Xaa can be any naturally occurring amino acid

<400> SEQUENCE: 25

Met Asp Phe Gly Ser Leu Glu Thr Val Val Ala Asn Ser Ala Phe Ile
1               5                   10                  15

Ala Ala Arg Gly Xaa Phe Asp Gly Ser Ser Ser Gln Pro Ser Arg Asp
            20                  25                  30

Lys Lys Tyr Leu Ala Lys Leu Lys Leu Pro Pro Leu Ser Lys Cys Glu
        35                  40                  45

Ser Leu Arg Asp Ser Leu Ser Leu Glu Phe Glu Ser Val Cys Leu Glu
    50                  55                  60

Gln Pro Ile Gly Lys Lys Leu Phe Gln Gln Phe Leu Gln Ser Ala Glu
65                  70                  75                  80

Lys His Leu Pro Ala Leu Glu Leu Trp Lys Asp Ile Glu Asp Tyr Asp
```

```
                    85                  90                  95
Thr Ala Asp Asn Asp Leu Gln Pro Gln Lys Ala Gln Thr Ile Leu Ala
            100                 105                 110
Gln Tyr Leu Asp Pro Gln Ala Lys Leu Phe Cys Ser Phe Leu Asp Glu
            115                 120                 125
Gly Ile Val Ala Lys Phe Lys Glu Gly Pro Val Glu Ile Gln Asp Gly
        130                 135                 140
Leu Phe Gln Pro Leu Leu Gln Ala Thr Leu Ala His Leu Gly Gln Ala
145                 150                 155                 160
Pro Phe Gln Glu Tyr Leu Gly Ser Leu Tyr Phe Leu Arg Phe Leu Gln
                165                 170                 175
Trp Lys Trp Leu Glu Ala Gln Pro Met Gly Glu Asp Trp Phe Leu Asp
            180                 185                 190
Phe Arg Val Leu Gly Lys Gly Phe Gly Glu Val Ser Ala Cys Gln
            195                 200                 205
Met Lys Ala Thr Gly Lys Leu Tyr Ala Cys Lys Lys Leu Asn Lys Lys
        210                 215                 220
Arg Leu Lys Lys Arg Lys Gly Tyr Gln Gly Ala Met Val Glu Lys Lys
225                 230                 235                 240
Ile Leu Met Lys Val His Ser Arg Phe Ile Val Ser Leu Ala Tyr Ala
                245                 250                 255
Phe Glu Thr Lys Ala Asp Leu Cys Leu Val Met Thr Ile Met Asn Gly
            260                 265                 270
Gly Asp Ile Arg Tyr His Ile Tyr Asn Val Asn Glu Glu Asn Pro Gly
            275                 280                 285
Phe Pro Glu Pro Arg Ala Leu Phe Tyr Thr Ala Gln Ile Ile Cys Gly
290                 295                 300
Leu Glu His Leu His Gln Arg Arg Ile Val Tyr Arg Asp Leu Lys Pro
305                 310                 315                 320
Glu Asn Val Leu Leu Asp Asn Asp Gly Asn Val Arg Ile Ser Asp Leu
                325                 330                 335
Gly Leu Ala Val Glu Leu Leu Asp Gly Gln Ser Lys Thr Lys Gly Tyr
            340                 345                 350
Ala Gly Thr Pro Gly Phe Met Ala Pro Glu Leu Leu Gln Gly Glu Glu
            355                 360                 365
Tyr Asp Phe Ser Val Asp Tyr Phe Ala Leu Gly Val Thr Leu Tyr Glu
            370                 375                 380
Met Ile Ala Ala Arg Gly Pro Phe Arg Ala Arg Gly Glu Lys Val Glu
385                 390                 395                 400
Asn Lys Glu Leu Lys His Arg Ile Ile Ser Glu Pro Val Lys Tyr Pro
                405                 410                 415
Asp Lys Phe Ser Gln Ala Ser Lys Asp Phe Cys Glu Ala Leu Leu Glu
            420                 425                 430
Lys Asp Pro Glu Lys Arg Leu Gly Phe Arg Asp Glu Thr Cys Asp Lys
            435                 440                 445
Leu Arg Ala His Pro Leu Phe Lys Asp Leu Asn Trp Arg Gln Leu Glu
        450                 455                 460
Ala Gly Met Leu Met Pro Pro Phe Ile Pro Asp Ser Lys Thr Val Tyr
465                 470                 475                 480
Ala Lys Asp Ile Gln Asp Val Gly Ala Phe Ser Thr Val Lys Gly Val
                485                 490                 495
Ala Phe Asp Lys Thr Asp Thr Glu Phe Phe Gln Glu Phe Ala Thr Gly
            500                 505                 510
```

```
Asn Cys Pro Ile Pro Trp Gln Glu Glu Met Ile Glu Thr Gly Ile Phe
            515                 520                 525

Gly Glu Leu Asn Val Trp Arg Ser Asp Gly Gln Met Pro Asp Asp Met
        530                 535                 540

Lys Gly Ile Ser Gly Ser Ser Ser Ser Lys Ser Gly Met Cys
545                 550                 555                 560

Leu Val Ser

<210> SEQ ID NO 26
<211> LENGTH: 553
<212> TYPE: PRT
<213> ORGANISM: human
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid

<400> SEQUENCE: 26

Met Val Asp Met Gly Ala Leu Asp Asn Leu Ile Ala Asn Thr Ala Tyr
1               5                   10                  15

Leu Gln Ala Arg Lys Pro Xaa Asp Cys Asp Ser Lys Glu Leu Gln Arg
            20                  25                  30

Arg Arg Arg Xaa Leu Ala Leu Pro Gly Leu Gln Gly Cys Ala Glu Leu
        35                  40                  45

Arg Gln Lys Leu Ser Leu Asn Phe His Ser Leu Cys Glu Gln Gln Pro
50                  55                  60

Ile Gly Arg Arg Leu Phe Arg Asp Phe Leu Ala Thr Val Pro Thr Phe
65                  70                  75                  80

Arg Lys Ala Ala Thr Phe Leu Glu Asp Val Gln Asn Trp Glu Leu Ala
                85                  90                  95

Glu Glu Gly Pro Thr Lys Asp Ser Ala Leu Gln Gly Leu Val Ala Thr
            100                 105                 110

Cys Ala Ser Ala Pro Ala Pro Gly Asn Pro Gln Pro Phe Leu Ser Gln
        115                 120                 125

Ala Val Ala Thr Lys Cys Gln Ala Ala Thr Glu Glu Glu Arg Val
130                 135                 140

Ala Ala Val Thr Leu Ala Lys Ala Glu Ala Met Ala Phe Leu Gln Glu
145                 150                 155                 160

Gln Pro Phe Lys Asp Phe Val Thr Ser Ala Phe Tyr Asp Lys Phe Leu
                165                 170                 175

Gln Trp Lys Leu Phe Glu Met Gln Pro Val Ser Asp Lys Tyr Phe Thr
            180                 185                 190

Glu Phe Arg Val Leu Gly Lys Gly Gly Phe Gly Glu Val Cys Ala Val
        195                 200                 205

Gln Val Lys Asn Thr Gly Lys Met Tyr Ala Cys Lys Lys Leu Asp Lys
    210                 215                 220

Lys Arg Leu Lys Lys Lys Gly Gly Glu Lys Met Ala Leu Leu Glu Lys
225                 230                 235                 240

Glu Ile Leu Glu Lys Val Ser Ser Pro Phe Ile Val Ser Leu Ala Tyr
                245                 250                 255

Ala Phe Glu Ser Lys Thr His Leu Cys Leu Val Met Ser Leu Met Asn
            260                 265                 270
```

```
Gly Gly Asp Leu Lys Phe His Ile Tyr Asn Val Gly Thr Arg Gly Leu
            275                 280                 285

Asp Met Ser Arg Val Ile Phe Tyr Ser Ala Gln Ile Ala Cys Gly Met
        290                 295                 300

Leu His Leu His Glu Leu Gly Ile Val Tyr Arg Asp Met Lys Pro Glu
305                 310                 315                 320

Asn Val Leu Leu Asp Asp Leu Gly Asn Cys Arg Leu Ser Asp Leu Gly
                325                 330                 335

Leu Ala Val Glu Met Lys Gly Gly Lys Pro Ile Thr Gln Arg Ala Gly
            340                 345                 350

Thr Asn Gly Tyr Met Ala Pro Glu Ile Leu Met Glu Lys Val Ser Tyr
        355                 360                 365

Ser Tyr Pro Val Asp Trp Phe Ala Met Gly Cys Ser Ile Tyr Glu Met
370                 375                 380

Val Ala Gly Arg Thr Pro Phe Lys Asp Tyr Lys Glu Lys Val Ser Lys
385                 390                 395                 400

Glu Asp Leu Lys Gln Arg Thr Leu Gln Asp Glu Val Lys Phe Gln His
                405                 410                 415

Asp Asn Phe Thr Glu Glu Ala Lys Asp Ile Cys Arg Leu Phe Leu Ala
            420                 425                 430

Lys Lys Pro Glu Gln Arg Leu Gly Ser Arg Glu Lys Ser Asp Asp Pro
        435                 440                 445

Arg Lys His His Phe Phe Lys Thr Ile Asn Phe Pro Arg Leu Glu Ala
450                 455                 460

Gly Leu Ile Glu Pro Pro Phe Val Pro Asp Pro Ser Val Val Tyr Ala
465                 470                 475                 480

Lys Asp Ile Ala Glu Ile Asp Asp Phe Ser Glu Val Arg Gly Val Glu
                485                 490                 495

Phe Asp Asp Lys Asp Lys Gln Phe Phe Lys Asn Phe Ala Thr Gly Ala
            500                 505                 510

Val Pro Ile Ala Trp Gln Glu Ile Ile Glu Thr Gly Leu Phe Glu
        515                 520                 525

Glu Leu Asn Asp Pro Asn Arg Pro Thr Gly Cys Glu Glu Gly Asn Ser
530                 535                 540

Ser Lys Ser Gly Val Cys Leu Leu Leu
545                 550

<210> SEQ ID NO 27
<211> LENGTH: 191
<212> TYPE: PRT
<213> ORGANISM: viral
<220> FEATURE:
<221> NAME/KEY: misc_feature
<222> LOCATION: (116)..(116)
<223> OTHER INFORMATION: Xaa can be any naturally occurring amino acid

<400> SEQUENCE: 27

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Gln Pro Glu Gly Arg Ala Trp Ala Gln Pro Gly
```

```
                65                  70                  75                  80
Tyr Pro Trp Pro Leu Tyr Gly Asn Glu Gly Met Gly Trp Ala Gly Trp
                    85                  90                  95

Leu Leu Ser Pro Arg Gly Ser Arg Pro Ser Trp Gly Pro Thr Asp Pro
                100                 105                 110

Arg Arg Arg Xaa Arg Asn Leu Gly Lys Val Ile Asp Thr Leu Thr Cys
                115                 120                 125

Gly Phe Ala Asp Leu Met Gly Tyr Ile Pro Leu Val Gly Ala Pro Leu
130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Ile Pro Ala Ser Ala
                180                 185                 190

<210> SEQ ID NO 28
<211> LENGTH: 213
<212> TYPE: PRT
<213> ORGANISM: human
<220> FEATURE:
<221> NAME/KEY: misc_feature
<222> LOCATION: (36)..(36)
<223> OTHER INFORMATION: Xaa can be any naturally occurring amino acid

<400> SEQUENCE: 28

Met Ser Glu Thr Ala Pro Ala Ala Pro Ala Ala Ala Pro Pro Ala Glu
1               5                   10                  15

Lys Ala Pro Val Lys Lys Lys Ala Ala Lys Ala Gly Gly Thr Pro
            20                  25                  30

Arg Lys Ala Xaa Gly Pro Pro Val Ser Glu Leu Ile Thr Lys Ala Val
                35                  40                  45

Ala Ala Ser Lys Glu Arg Ser Gly Val Ser Leu Ala Ala Leu Lys Lys
        50                  55                  60

Ala Leu Ala Ala Ala Gly Tyr Asp Val Glu Lys Asn Asn Ser Arg Ile
65                  70                  75                  80

Lys Leu Gly Leu Lys Ser Leu Val Ser Lys Gly Thr Leu Val Gln Thr
                85                  90                  95

Lys Gly Thr Gly Ala Ser Gly Ser Phe Lys Leu Asn Lys Lys Ala Ala
                100                 105                 110

Ser Gly Glu Ala Lys Pro Lys Val Lys Lys Ala Gly Gly Thr Lys Pro
            115                 120                 125

Lys Lys Pro Val Gly Ala Ala Lys Lys Pro Lys Lys Ala Ala Gly Gly
130                 135                 140

Ala Thr Pro Lys Lys Ser Ala Lys Lys Thr Pro Lys Lys Ala Lys Lys
145                 150                 155                 160

Pro Ala Ala Ala Thr Val Thr Lys Lys Val Ala Lys Ser Pro Lys Lys
                165                 170                 175

Ala Lys Val Ala Lys Pro Lys Lys Ala Ala Lys Ser Ala Ala Lys Ala
                180                 185                 190

Val Lys Pro Lys Ala Ala Lys Pro Lys Val Val Lys Pro Lys Lys Ala
                195                 200                 205

Ala Pro Lys Lys Lys
            210

<210> SEQ ID NO 29
```

```
<211> LENGTH: 136
<212> TYPE: PRT
<213> ORGANISM: human
<220> FEATURE:
<221> NAME/KEY: misc_feature
<222> LOCATION: (11)..(11)
<223> OTHER INFORMATION: Xaa can be any naturally occurring amino acid

<400> SEQUENCE: 29
```

Met Ala Arg Thr Lys Gln Thr Ala Arg Lys Xaa Thr Gly Gly Lys Ala
1               5                   10                  15

Pro Arg Lys Gln Leu Ala Thr Lys Ala Ala Arg Lys Ser Ala Pro Ala
                20                  25                  30

Thr Gly Gly Val Lys Lys Pro His Arg Tyr Arg Pro Gly Thr Val Ala
            35                  40                  45

Leu Arg Glu Ile Arg Arg Tyr Gln Lys Ser Thr Glu Leu Leu Ile Arg
        50                  55                  60

Lys Leu Pro Phe Gln Arg Leu Val Arg Glu Ile Ala Gln Asp Phe Lys
65                  70                  75                  80

Thr Asp Leu Arg Phe Gln Ser Ser Ala Val Met Ala Leu Gln Glu Ala
                85                  90                  95

Cys Glu Ala Thr Leu Val Gly Leu Phe Glu Asp Thr Asn Leu Cys Ala
            100                 105                 110

Ile His Ala Lys Arg Val Thr Ile Met Pro Lys Asp Ile Gln Leu Ala
        115                 120                 125

Arg Arg Ile Arg Gly Glu Arg Ala
        130                 135

```
<210> SEQ ID NO 30
<211> LENGTH: 126
<212> TYPE: PRT
<213> ORGANISM: human
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid

<400> SEQUENCE: 30
```

Met Pro Asp Pro Ala Lys Ser Ala Pro Ala Pro Lys Lys Gly Ser Lys
1               5                   10                  15

Lys Ala Val Thr Lys Ala Gln Lys Lys Asp Gly Lys Lys Arg Lys Arg
                20                  25                  30

Xaa Arg Lys Glu Xaa Tyr Ser Ile Tyr Val Tyr Lys Val Leu Lys Gln
        35                  40                  45

Val His Pro Asp Thr Gly Ile Ser Ser Lys Ala Met Gly Ile Met Asn
        50                  55                  60

Ser Phe Val Asn Asp Ile Phe Glu Arg Ile Ala Gly Glu Ala Ser Arg
65                  70                  75                  80

Leu Ala His Tyr Asn Lys Arg Ser Thr Ile Thr Ser Arg Glu Ile Gln
                85                  90                  95

Thr Ala Val Arg Leu Leu Leu Pro Gly Glu Leu Ala Lys His Ala Val
            100                 105                 110

Ser Glu Gly Thr Lys Ala Val Thr Lys Tyr Thr Ser Ser Lys
        115                 120                 125

```
<210> SEQ ID NO 31
```

```
<211> LENGTH: 2758
<212> TYPE: PRT
<213> ORGANISM: human
<220> FEATURE:
<221> NAME/KEY: misc_feature
<222> LOCATION: (1598)..(1598)
<223> OTHER INFORMATION: Xaa can be any naturally occurring amino acid
<220> FEATURE:
<221> NAME/KEY: misc_feature
<222> LOCATION: (1764)..(1764)
<223> OTHER INFORMATION: Xaa can be any naturally occurring amino acid

<400> SEQUENCE: 31

Met Ser Asp Lys Met Ser Ser Phe Leu His Ile Gly Asp Ile Cys Ser
1               5                   10                  15

Leu Tyr Ala Glu Gly Ser Thr Asn Gly Phe Ile Ser Thr Leu Gly Leu
            20                  25                  30

Val Asp Asp Arg Cys Val Val Gln Pro Glu Thr Gly Asp Leu Asn Asn
        35                  40                  45

Pro Pro Lys Lys Phe Arg Asp Cys Leu Phe Lys Leu Cys Pro Met Asn
    50                  55                  60

Arg Tyr Ser Ala Gln Lys Gln Phe Trp Lys Ala Ala Lys Pro Gly Ala
65                  70                  75                  80

Asn Ser Thr Thr Asp Ala Val Leu Leu Asn Lys Leu His His Ala Ala
                85                  90                  95

Asp Leu Glu Lys Lys Gln Asn Glu Thr Glu Asn Arg Lys Leu Leu Gly
            100                 105                 110

Thr Val Ile Gln Tyr Gly Asn Val Ile Gln Leu Leu His Leu Lys Ser
        115                 120                 125

Asn Lys Tyr Leu Thr Val Asn Lys Arg Leu Pro Ala Leu Leu Glu Lys
130                 135                 140

Asn Ala Met Arg Val Thr Leu Asp Glu Ala Gly Asn Glu Gly Ser Trp
145                 150                 155                 160

Phe Tyr Ile Gln Pro Phe Tyr Lys Leu Arg Ser Ile Gly Asp Ser Val
                165                 170                 175

Val Ile Gly Asp Lys Val Val Leu Asn Pro Val Asn Ala Gly Gln Pro
            180                 185                 190

Leu His Ala Ser Ser His Gln Leu Val Asp Asn Pro Gly Cys Asn Glu
        195                 200                 205

Val Asn Ser Val Asn Cys Asn Thr Ser Trp Lys Ile Val Leu Phe Met
    210                 215                 220

Lys Trp Ser Asp Asn Lys Asp Asp Ile Leu Lys Gly Gly Asp Val Val
225                 230                 235                 240

Arg Leu Phe His Ala Glu Gln Glu Lys Phe Leu Thr Cys Asp Glu His
                245                 250                 255

Arg Lys Lys Gln His Val Phe Leu Arg Thr Thr Gly Arg Gln Ser Ala
            260                 265                 270

Thr Ser Ala Thr Ser Ser Lys Ala Leu Trp Glu Val Glu Val Val Gln
        275                 280                 285

His Asp Pro Cys Arg Gly Gly Ala Gly Tyr Trp Asn Ser Leu Phe Arg
    290                 295                 300

Phe Lys His Leu Ala Thr Gly His Tyr Leu Ala Ala Glu Val Asp Pro
305                 310                 315                 320

Asp Phe Glu Glu Glu Cys Leu Glu Phe Gln Pro Ser Val Asp Pro Asp
                325                 330                 335

Gln Asp Ala Ser Arg Ser Arg Leu Arg Asn Ala Gln Glu Lys Met Val
            340                 345                 350
```

```
Tyr Ser Leu Val Ser Val Pro Glu Gly Asn Asp Ile Ser Ser Ile Phe
        355                 360                 365

Glu Leu Asp Pro Thr Thr Leu Arg Gly Gly Asp Ser Leu Val Pro Arg
    370                 375                 380

Asn Ser Tyr Val Arg Leu Arg His Leu Cys Thr Asn Thr Trp Val His
385                 390                 395                 400

Ser Thr Asn Ile Pro Ile Asp Lys Glu Glu Lys Pro Val Met Leu
                405                 410                 415

Lys Ile Gly Thr Ser Pro Val Lys Glu Asp Lys Glu Ala Phe Ala Ile
            420                 425                 430

Val Pro Val Ser Pro Ala Glu Val Arg Asp Leu Asp Phe Ala Asn Asp
            435                 440                 445

Ala Ser Lys Val Leu Gly Ser Ile Ala Gly Lys Leu Glu Lys Gly Thr
        450                 455                 460

Ile Thr Gln Asn Glu Arg Arg Ser Val Thr Lys Leu Leu Glu Asp Leu
465                 470                 475                 480

Val Tyr Phe Val Thr Gly Gly Thr Asn Ser Gly Gln Asp Val Leu Glu
                485                 490                 495

Val Val Phe Ser Lys Pro Asn Arg Glu Arg Gln Lys Leu Met Arg Glu
            500                 505                 510

Gln Asn Ile Leu Lys Gln Ile Phe Lys Leu Leu Gln Ala Pro Phe Thr
        515                 520                 525

Asp Cys Gly Asp Gly Pro Met Leu Arg Leu Glu Glu Leu Gly Asp Gln
    530                 535                 540

Arg His Ala Pro Phe Arg His Ile Cys Arg Leu Cys Tyr Arg Val Leu
545                 550                 555                 560

Arg His Ser Gln Gln Asp Tyr Arg Lys Asn Gln Glu Tyr Ile Ala Lys
                565                 570                 575

Gln Phe Gly Phe Met Gln Lys Gln Ile Gly Tyr Asp Val Leu Ala Glu
            580                 585                 590

Asp Thr Ile Thr Ala Leu Leu His Asn Asn Arg Lys Leu Leu Glu Lys
        595                 600                 605

His Ile Thr Ala Ala Glu Ile Asp Thr Phe Val Ser Leu Val Arg Lys
    610                 615                 620

Asn Arg Glu Pro Arg Phe Leu Asp Tyr Leu Ser Asp Leu Cys Val Ser
625                 630                 635                 640

Met Asn Lys Ser Ile Pro Val Thr Gln Glu Leu Ile Cys Lys Ala Val
                645                 650                 655

Leu Asn Pro Thr Asn Ala Asp Ile Leu Ile Glu Thr Lys Leu Val Leu
            660                 665                 670

Ser Arg Phe Glu Phe Glu Gly Val Ser Ser Thr Gly Glu Asn Ala Leu
        675                 680                 685

Glu Ala Gly Glu Asp Glu Glu Val Trp Leu Phe Trp Arg Asp Ser
    690                 695                 700

Asn Lys Glu Ile Arg Ser Lys Ser Val Arg Glu Leu Ala Gln Asp Ala
705                 710                 715                 720

Lys Glu Gly Gln Lys Glu Asp Arg Asp Val Leu Ser Tyr Tyr Arg Tyr
                725                 730                 735

Gln Leu Asn Leu Phe Ala Arg Met Cys Leu Asp Arg Gln Tyr Leu Ala
            740                 745                 750

Ile Asn Glu Ile Ser Gly Gln Leu Asp Val Asp Leu Ile Leu Arg Cys
        755                 760                 765
```

Met Ser Asp Glu Asn Leu Pro Tyr Asp Leu Arg Ala Ser Phe Cys Arg
770                 775                 780

Leu Met Leu His Met His Val Asp Arg Asp Pro Gln Glu Gln Val Thr
785                 790                 795                 800

Pro Val Lys Tyr Ala Arg Leu Trp Ser Glu Ile Pro Ser Glu Ile Ala
            805                 810                 815

Ile Asp Asp Tyr Asp Ser Ser Gly Ala Ser Lys Asp Glu Ile Lys Glu
            820                 825                 830

Arg Phe Ala Gln Thr Met Glu Phe Val Glu Glu Tyr Leu Arg Asp Val
            835                 840                 845

Val Cys Gln Arg Phe Pro Phe Ser Asp Lys Lys Asn Lys Leu Thr
850                 855                 860

Phe Glu Val Val Asn Leu Ala Arg Asn Leu Ile Tyr Phe Gly Phe Tyr
865                 870                 875                 880

Asn Phe Ser Asp Leu Leu Arg Leu Thr Lys Ile Leu Leu Ala Ile Leu
                885                 890                 895

Asp Cys Val His Val Thr Thr Ile Phe Pro Ile Ser Lys Met Ala Lys
            900                 905                 910

Gly Glu Glu Asn Lys Gly Asn Asn Asp Val Glu Lys Leu Lys Ser Ser
            915                 920                 925

Asn Val Met Arg Ser Ile His Gly Val Gly Glu Leu Met Thr Gln Val
930                 935                 940

Val Leu Arg Gly Gly Gly Phe Leu Pro Met Thr Pro Met Ala Ala Ala
945                 950                 955                 960

Pro Glu Gly Asn Val Lys Gln Ala Glu Pro Gly Lys Glu Asp Ile Met
            965                 970                 975

Val Met Asp Thr Lys Leu Lys Ile Ile Glu Ile Leu Gln Phe Ile Leu
            980                 985                 990

Asn Val Arg Leu Asp Tyr Arg Ile Ser Cys Leu Leu Cys Ile Phe Lys
            995                 1000                1005

Arg Glu Phe Asp Glu Ser Asn Ser Gln Thr Ser Glu Thr Ser Ser
    1010                1015                1020

Gly Asn Ser Ser Gln Glu Gly Pro Ser Asn Val Pro Gly Ala Leu
    1025                1030                1035

Asp Phe Glu His Ile Glu Glu Gln Ala Glu Gly Ile Phe Gly Gly
    1040                1045                1050

Ser Glu Glu Asn Thr Pro Leu Asp Leu Asp Asp His Gly Gly Arg
    1055                1060                1065

Thr Phe Leu Arg Val Leu Leu His Leu Thr Met His Asp Tyr Pro
    1070                1075                1080

Pro Leu Val Ser Gly Ala Leu Gln Leu Leu Phe Arg His Phe Ser
    1085                1090                1095

Gln Arg Gln Glu Val Leu Gln Ala Phe Lys Gln Val Gln Leu Leu
    1100                1105                1110

Val Thr Ser Gln Asp Val Asp Asn Tyr Lys Gln Ile Lys Gln Asp
    1115                1120                1125

Leu Asp Gln Leu Arg Ser Ile Val Glu Lys Ser Glu Leu Trp Val
    1130                1135                1140

Tyr Lys Gly Gln Gly Pro Asp Glu Thr Met Asp Gly Ala Ser Gly
    1145                1150                1155

Glu Asn Glu His Lys Lys Thr Glu Glu Gly Asn Asn Lys Pro Gln
    1160                1165                1170

Lys His Glu Ser Thr Ser Ser Tyr Asn Tyr Arg Val Val Lys Glu

-continued

|      | 1175 |      |      |      | 1180 |      |      |      | 1185 |      |      |
| Ile  | Leu  | Ile  | Arg  | Leu  | Ser  | Lys  | Leu  | Cys  | Val  | Gln  | Glu  | Ser  | Ala  | Ser  |
|      | 1190 |      |      |      | 1195 |      |      |      | 1200 |      |      |

Val Arg Lys Ser Arg Lys Gln Gln Gln Arg Leu Leu Arg Asn Met
        1205            1210            1215

Gly Ala His Ala Val Val Leu Glu Leu Leu Gln Ile Pro Tyr Glu
        1220            1225            1230

Lys Ala Glu Asp Thr Lys Met Gln Glu Ile Met Arg Leu Ala His
        1235            1240            1245

Glu Phe Leu Gln Asn Phe Cys Ala Gly Asn Gln Gln Asn Gln Ala
        1250            1255            1260

Leu Leu His Lys His Ile Asn Leu Phe Leu Asn Pro Gly Ile Leu
        1265            1270            1275

Glu Ala Val Thr Met Gln His Ile Phe Met Asn Asn Phe Gln Leu
        1280            1285            1290

Cys Ser Glu Ile Asn Glu Arg Val Val Gln His Phe Val His Cys
        1295            1300            1305

Ile Glu Thr His Gly Arg Asn Val Gln Tyr Ile Lys Phe Leu Gln
        1310            1315            1320

Thr Ile Val Lys Ala Glu Gly Lys Phe Ile Lys Lys Cys Gln Asp
        1325            1330            1335

Met Val Met Ala Glu Leu Val Asn Ser Gly Glu Asp Val Leu Val
        1340            1345            1350

Phe Tyr Asn Asp Arg Ala Ser Phe Gln Thr Leu Ile Gln Met Met
        1355            1360            1365

Arg Ser Glu Arg Asp Arg Met Asp Glu Asn Ser Pro Leu Met Tyr
        1370            1375            1380

His Ile His Leu Val Glu Leu Leu Ala Val Cys Thr Glu Gly Lys
        1385            1390            1395

Asn Val Tyr Thr Glu Ile Lys Cys Asn Ser Leu Leu Pro Leu Asp
        1400            1405            1410

Asp Ile Val Arg Val Val Thr His Glu Asp Cys Ile Pro Glu Val
        1415            1420            1425

Lys Ile Ala Tyr Ile Asn Phe Leu Asn His Cys Tyr Val Asp Thr
        1430            1435            1440

Glu Val Glu Met Lys Glu Ile Tyr Thr Ser Asn His Met Trp Lys
        1445            1450            1455

Leu Phe Glu Asn Phe Leu Val Asp Ile Cys Arg Ala Cys Asn Asn
        1460            1465            1470

Thr Ser Asp Arg Lys His Ala Asp Ser Ile Leu Glu Lys Tyr Val
        1475            1480            1485

Thr Glu Ile Val Met Ser Ile Val Thr Thr Phe Phe Ser Ser Pro
        1490            1495            1500

Phe Ser Asp Gln Ser Thr Thr Leu Gln Thr Arg Gln Pro Val Phe
        1505            1510            1515

Val Gln Leu Leu Gln Gly Val Phe Arg Val Tyr His Cys Asn Trp
        1520            1525            1530

Leu Met Pro Ser Gln Lys Ala Ser Val Glu Ser Cys Ile Arg Val
        1535            1540            1545

Leu Ser Asp Val Ala Lys Ser Arg Ala Ile Ala Ile Pro Val Asp
        1550            1555            1560

Leu Asp Ser Gln Val Asn Asn Leu Phe Leu Lys Ser His Ser Ile
        1565            1570            1575

```
Val Gln Lys Thr Ala Met Asn Trp Arg Leu Ser Ala Arg Asn Ala
1580            1585                1590

Ala Arg Arg Asp Xaa Val Leu Ala Ala Ser Arg Asp Tyr Arg Asn
1595            1600                1605

Ile Ile Glu Arg Leu Gln Asp Ile Val Ser Ala Leu Glu Asp Arg
1610            1615                1620

Leu Arg Pro Leu Val Gln Ala Glu Leu Ser Val Leu Val Asp Val
1625            1630                1635

Leu His Arg Pro Glu Leu Leu Phe Pro Glu Asn Thr Asp Ala Arg
1640            1645                1650

Arg Lys Cys Glu Ser Gly Gly Phe Ile Cys Lys Leu Ile Lys His
1655            1660                1665

Thr Lys Gln Leu Leu Glu Glu Asn Glu Glu Lys Leu Cys Ile Lys
1670            1675                1680

Val Leu Gln Thr Leu Arg Glu Met Met Thr Lys Asp Arg Gly Tyr
1685            1690                1695

Gly Glu Lys Leu Ile Ser Ile Asp Glu Leu Asp Asn Ala Glu Leu
1700            1705                1710

Pro Pro Ala Pro Asp Ser Glu Asn Ser Thr Glu Glu Leu Glu Pro
1715            1720                1725

Ser Pro Pro Leu Arg Gln Leu Glu Asp His Lys Arg Gly Glu Ala
1730            1735                1740

Leu Arg Gln Val Leu Val Asn Arg Tyr Tyr Gly Asn Val Arg Pro
1745            1750                1755

Ser Gly Arg Arg Glu Xaa Leu Thr Ser Phe Gly Asn Gly Pro Leu
1760            1765                1770

Ser Ala Gly Gly Pro Gly Lys Pro Gly Gly Gly Gly Gly Gly Ser
1775            1780                1785

Gly Ser Ser Ser Met Ser Arg Gly Glu Met Ser Leu Ala Glu Val
1790            1795                1800

Gln Cys His Leu Asp Lys Glu Gly Ala Ser Asn Leu Val Ile Asp
1805            1810                1815

Leu Ile Met Asn Ala Ser Ser Asp Arg Val Phe His Glu Ser Ile
1820            1825                1830

Leu Leu Ala Ile Ala Leu Leu Glu Gly Gly Asn Thr Thr Ile Gln
1835            1840                1845

His Ser Phe Phe Cys Arg Leu Thr Glu Asp Lys Lys Ser Glu Lys
1850            1855                1860

Phe Phe Lys Val Phe Tyr Asp Arg Met Lys Val Ala Gln Gln Glu
1865            1870                1875

Ile Lys Ala Thr Val Thr Val Asn Thr Ser Asp Leu Gly Asn Lys
1880            1885                1890

Lys Lys Asp Asp Glu Val Asp Arg Asp Ala Pro Ser Arg Lys Lys
1895            1900                1905

Ala Lys Glu Pro Thr Thr Gln Ile Thr Glu Glu Val Arg Asp Gln
1910            1915                1920

Leu Leu Glu Ala Ser Ala Ala Thr Arg Lys Ala Phe Thr Thr Phe
1925            1930                1935

Arg Arg Glu Ala Asp Pro Asp Asp His Tyr Gln Pro Gly Glu Gly
1940            1945                1950

Thr Gln Ala Thr Ala Asp Lys Ala Lys Asp Asp Leu Glu Met Ser
1955            1960                1965
```

Ala Val Ile Thr Ile Met Gln Pro Ile Leu Arg Phe Leu Gln Leu
1970                1975                1980

Leu Cys Glu Asn His Asn Arg Asp Leu Gln Asn Phe Leu Arg Cys
1985                1990                1995

Gln Asn Asn Lys Thr Asn Tyr Asn Leu Val Cys Glu Thr Leu Gln
2000                2005                2010

Phe Leu Asp Cys Ile Cys Gly Ser Thr Gly Gly Leu Gly Leu
2015                2020                2025

Leu Gly Leu Tyr Ile Asn Glu Lys Asn Val Ala Leu Ile Asn Gln
2030                2035                2040

Thr Leu Glu Ser Leu Thr Glu Tyr Cys Gln Gly Pro Cys His Glu
2045                2050                2055

Asn Gln Asn Cys Ile Ala Thr His Glu Ser Asn Gly Ile Asp Ile
2060                2065                2070

Ile Thr Ala Leu Ile Leu Asn Asp Ile Asn Pro Leu Gly Lys Lys
2075                2080                2085

Arg Met Asp Leu Val Leu Glu Leu Lys Asn Asn Ala Ser Lys Leu
2090                2095                2100

Leu Leu Ala Ile Met Glu Ser Arg His Asp Ser Glu Asn Ala Glu
2105                2110                2115

Arg Ile Leu Tyr Asn Met Arg Pro Lys Glu Leu Val Glu Val Ile
2120                2125                2130

Lys Lys Ala Tyr Met Gln Gly Glu Val Glu Phe Glu Asp Gly Glu
2135                2140                2145

Asn Gly Glu Asp Gly Ala Ala Ser Pro Arg Asn Val Gly His Asn
2150                2155                2160

Ile Tyr Ile Leu Ala His Gln Leu Ala Arg His Asn Lys Glu Leu
2165                2170                2175

Gln Ser Met Leu Lys Pro Gly Gly Gln Val Asp Gly Asp Glu Ala
2180                2185                2190

Leu Glu Phe Tyr Ala Lys His Thr Ala Gln Ile Glu Ile Val Arg
2195                2200                2205

Leu Asp Arg Thr Met Glu Gln Ile Val Phe Pro Val Pro Ser Ile
2210                2215                2220

Cys Glu Phe Leu Thr Lys Glu Ser Lys Leu Arg Ile Tyr Tyr Thr
2225                2230                2235

Thr Glu Arg Asp Glu Gln Gly Ser Lys Ile Asn Asp Phe Phe Leu
2240                2245                2250

Arg Ser Glu Asp Leu Phe Asn Glu Met Asn Trp Gln Lys Lys Leu
2255                2260                2265

Arg Ala Gln Pro Val Leu Tyr Trp Cys Ala Arg Asn Met Ser Phe
2270                2275                2280

Trp Ser Ser Ile Ser Phe Asn Leu Ala Val Leu Met Asn Leu Leu
2285                2290                2295

Val Ala Phe Phe Tyr Pro Phe Lys Gly Val Arg Gly Gly Thr Leu
2300                2305                2310

Glu Pro His Trp Ser Gly Leu Leu Trp Thr Ala Met Leu Ile Ser
2315                2320                2325

Leu Ala Ile Val Ile Ala Leu Pro Lys Pro His Gly Ile Arg Ala
2330                2335                2340

Leu Ile Ala Ser Thr Ile Leu Arg Leu Ile Phe Ser Val Gly Leu
2345                2350                2355

Gln Pro Thr Leu Phe Leu Leu Gly Ala Phe Asn Val Cys Asn Lys

```
            2360                2365                2370
Ile Ile Phe Leu Met Ser Phe Val Gly Asn Cys Gly Thr Phe Thr
    2375                2380                2385
Arg Gly Tyr Arg Ala Met Val Leu Asp Val Glu Phe Leu Tyr His
    2390                2395                2400
Leu Leu Tyr Leu Val Ile Cys Ala Met Gly Leu Phe Val His Glu
    2405                2410                2415
Phe Phe Tyr Ser Leu Leu Phe Asp Leu Val Tyr Arg Glu Glu
    2420                2425                2430
Thr Leu Leu Asn Val Ile Lys Ser Val Thr Arg Asn Gly Arg Ser
    2435                2440                2445
Ile Ile Leu Thr Ala Val Leu Ala Leu Ile Leu Val Tyr Leu Phe
    2450                2455                2460
Ser Ile Val Gly Tyr Leu Phe Phe Lys Asp Asp Phe Ile Leu Glu
    2465                2470                2475
Val Asp Arg Leu Pro Asn Glu Thr Ala Val Pro Glu Thr Gly Glu
    2480                2485                2490
Ser Leu Ala Ser Glu Phe Leu Phe Ser Asp Val Cys Arg Val Glu
    2495                2500                2505
Ser Gly Glu Asn Cys Ser Ser Pro Ala Pro Arg Glu Glu Leu Val
    2510                2515                2520
Pro Ala Glu Glu Thr Glu Gln Asp Lys Glu His Thr Cys Glu Thr
    2525                2530                2535
Leu Leu Met Cys Ile Val Thr Val Leu Ser His Gly Leu Arg Ser
    2540                2545                2550
Gly Gly Gly Val Gly Asp Val Leu Arg Lys Pro Ser Lys Glu Glu
    2555                2560                2565
Pro Leu Phe Ala Ala Arg Val Ile Tyr Asp Leu Leu Phe Phe Phe
    2570                2575                2580
Met Val Ile Ile Ile Val Leu Asn Leu Ile Phe Gly Val Ile Ile
    2585                2590                2595
Asp Thr Phe Ala Asp Leu Arg Ser Glu Lys Gln Lys Lys Glu Glu
    2600                2605                2610
Ile Leu Lys Thr Thr Cys Phe Ile Cys Gly Leu Glu Arg Asp Lys
    2615                2620                2625
Phe Asp Asn Lys Thr Val Thr Phe Glu Glu His Ile Lys Glu Glu
    2630                2635                2640
His Asn Met Trp His Tyr Leu Cys Phe Ile Val Leu Val Lys Val
    2645                2650                2655
Lys Asp Ser Thr Glu Tyr Thr Gly Pro Glu Ser Tyr Val Ala Glu
    2660                2665                2670
Met Ile Lys Glu Arg Asn Leu Asp Trp Phe Pro Arg Met Arg Ala
    2675                2680                2685
Met Ser Leu Val Ser Ser Asp Ser Glu Gly Glu Gln Asn Glu Leu
    2690                2695                2700
Arg Asn Leu Gln Glu Lys Leu Glu Ser Thr Met Lys Leu Val Thr
    2705                2710                2715
Asn Leu Ser Gly Gln Leu Ser Glu Leu Lys Asp Gln Met Thr Glu
    2720                2725                2730
Gln Arg Lys Gln Lys Gln Arg Ile Gly Leu Leu Gly His Pro Pro
    2735                2740                2745
His Met Asn Val Asn Pro Gln Gln Pro Ala
    2750                2755
```

```
<210> SEQ ID NO 32
<211> LENGTH: 676
<212> TYPE: PRT
<213> ORGANISM: human
<220> FEATURE:
<221> NAME/KEY: misc_feature
<222> LOCATION: (27)..(27)
<223> OTHER INFORMATION: Xaa can be any naturally occurring amino acid

<400> SEQUENCE: 32

Met Ala Ala Ser Ser Pro Pro Arg Ala Glu Arg Lys Arg Trp Gly
1               5                  10                  15

Trp Gly Arg Leu Pro Gly Ala Arg Arg Gly Xaa Ala Gly Leu Ala Lys
            20                  25                  30

Lys Cys Pro Phe Ser Leu Glu Leu Ala Glu Gly Gly Pro Ala Gly Gly
            35                  40                  45

Ala Leu Tyr Ala Pro Ile Ala Pro Gly Ala Pro Gly Pro Ala Pro Pro
        50                  55                  60

Ala Ser Pro Ala Ala Pro Ala Ala Pro Pro Val Ala Ser Asp Leu Gly
65                  70                  75                  80

Pro Arg Pro Pro Val Ser Leu Asp Pro Arg Val Ser Ile Tyr Ser Thr
                85                  90                  95

Arg Arg Pro Val Leu Ala Arg Thr His Val Gln Gly Arg Val Tyr Asn
            100                 105                 110

Phe Leu Glu Arg Pro Thr Gly Trp Lys Cys Phe Val Tyr His Phe Ala
        115                 120                 125

Val Phe Leu Ile Val Leu Val Cys Leu Ile Phe Ser Val Leu Ser Thr
130                 135                 140

Ile Glu Gln Tyr Ala Ala Leu Ala Thr Gly Thr Leu Phe Trp Met Glu
145                 150                 155                 160

Ile Val Leu Val Val Phe Phe Gly Thr Glu Tyr Val Val Arg Leu Trp
                165                 170                 175

Ser Ala Gly Cys Arg Ser Lys Tyr Val Gly Leu Trp Gly Arg Leu Arg
            180                 185                 190

Phe Ala Arg Lys Pro Ile Ser Ile Ile Asp Leu Ile Val Val Val Ala
        195                 200                 205

Ser Met Val Val Leu Cys Val Gly Ser Lys Gly Gln Val Phe Ala Thr
210                 215                 220

Ser Ala Ile Arg Gly Ile Arg Phe Leu Gln Ile Leu Arg Met Leu His
225                 230                 235                 240

Val Asp Arg Gln Gly Gly Thr Trp Arg Leu Leu Gly Ser Val Val Phe
                245                 250                 255

Ile His Arg Gln Glu Leu Ile Thr Thr Leu Tyr Ile Gly Phe Leu Gly
            260                 265                 270

Leu Ile Phe Ser Ser Tyr Phe Val Tyr Leu Ala Glu Lys Asp Ala Val
        275                 280                 285

Asn Glu Ser Gly Arg Val Glu Phe Gly Ser Tyr Ala Asp Ala Leu Trp
290                 295                 300

Trp Gly Val Val Thr Val Thr Thr Ile Gly Tyr Gly Asp Lys Val Pro
305                 310                 315                 320

Gln Thr Trp Val Gly Lys Thr Ile Ala Ser Cys Phe Ser Val Phe Ala
                325                 330                 335

Ile Ser Phe Phe Ala Leu Pro Ala Gly Ile Leu Gly Ser Gly Phe Ala
            340                 345                 350
```

```
Leu Lys Val Gln Gln Lys Gln Arg Gln Lys His Phe Asn Arg Gln Ile
            355                 360                 365

Pro Ala Ala Ser Leu Ile Gln Thr Ala Trp Arg Cys Tyr Ala Ala
370                 375                 380

Glu Asn Pro Asp Ser Ser Thr Trp Lys Ile Tyr Ile Arg Lys Ala Pro
385                 390                 395                 400

Arg Ser His Thr Leu Leu Ser Pro Ser Pro Lys Pro Lys Lys Ser Val
                405                 410                 415

Val Val Lys Lys Lys Phe Lys Leu Asp Lys Asp Asn Gly Val Thr
            420                 425                 430

Pro Gly Glu Lys Met Leu Thr Val Pro His Ile Thr Cys Asp Pro Pro
            435                 440                 445

Glu Glu Arg Arg Leu Asp His Phe Ser Val Asp Gly Tyr Asp Ser Ser
450                 455                 460

Val Arg Lys Ser Pro Thr Leu Leu Glu Val Ser Met Pro His Phe Met
465                 470                 475                 480

Arg Thr Asn Ser Phe Ala Glu Asp Leu Asp Leu Glu Gly Glu Thr Leu
                485                 490                 495

Leu Thr Pro Ile Thr His Ile Ser Gln Leu Arg Glu His His Arg Ala
            500                 505                 510

Thr Ile Lys Val Ile Arg Arg Met Gln Tyr Phe Val Ala Lys Lys Lys
            515                 520                 525

Phe Gln Gln Ala Arg Lys Pro Tyr Asp Val Arg Asp Val Ile Glu Gln
            530                 535                 540

Tyr Ser Gln Gly His Leu Asn Leu Met Val Arg Ile Lys Glu Leu Gln
545                 550                 555                 560

Arg Arg Leu Asp Gln Ser Ile Gly Lys Pro Ser Leu Phe Ile Ser Val
                565                 570                 575

Ser Glu Lys Ser Lys Asp Arg Gly Ser Asn Thr Ile Gly Ala Arg Leu
                580                 585                 590

Asn Arg Val Glu Asp Lys Val Thr Gln Leu Asp Gln Arg Leu Ala Leu
            595                 600                 605

Ile Thr Asp Met Leu His Gln Leu Leu Ser Leu His Gly Gly Ser Thr
610                 615                 620

Pro Gly Ser Gly Gly Pro Arg Glu Gly Gly Ala His Ile Thr Gln
625                 630                 635                 640

Pro Cys Gly Ser Gly Ser Val Asp Pro Glu Leu Phe Leu Pro Ser
                645                 650                 655

Asn Thr Leu Pro Thr Tyr Glu Gln Leu Thr Val Pro Arg Arg Gly Pro
                660                 665                 670

Asp Glu Gly Ser
            675

<210> SEQ ID NO 33
<211> LENGTH: 2171
<212> TYPE: PRT
<213> ORGANISM: human
<220> FEATURE:
<221> NAME/KEY: misc_feature
<222> LOCATION: (1928)..(1928)
<223> OTHER INFORMATION: Xaa can be any naturally occurring amino acid

<400> SEQUENCE: 33

Met Leu Arg Ala Leu Val Gln Pro Ala Thr Pro Ala Tyr Gln Pro Leu
1               5                   10                  15

Pro Ser His Leu Ser Ala Glu Thr Glu Ser Thr Cys Lys Gly Thr Val
```

```
                 20                  25                  30
Val His Glu Ala Gln Leu Asn His Phe Tyr Ile Ser Pro Gly Gly Ser
             35                  40                  45

Asn Tyr Gly Ser Pro Arg Pro Ala His Ala Asn Met Asn Ala Asn Ala
 50                  55                  60

Ala Ala Gly Leu Ala Pro Glu His Ile Pro Thr Pro Gly Ala Ala Leu
 65                  70                  75                  80

Ser Trp Gln Ala Ala Ile Asp Ala Ala Arg Gln Ala Lys Leu Met Gly
                 85                  90                  95

Ser Ala Gly Asn Ala Thr Ile Ser Thr Val Ser Ser Thr Gln Arg Lys
            100                 105                 110

Arg Gln Gln Tyr Gly Lys Pro Lys Lys Gln Gly Ser Thr Thr Ala Thr
            115                 120                 125

Arg Pro Pro Arg Ala Leu Leu Cys Leu Thr Leu Lys Asn Pro Ile Arg
            130                 135                 140

Arg Ala Cys Ile Ser Ile Val Glu Trp Lys Pro Phe Glu Ile Ile Ile
145                 150                 155                 160

Leu Leu Thr Ile Phe Ala Asn Cys Val Ala Leu Ala Ile Tyr Ile Pro
                165                 170                 175

Phe Pro Glu Asp Asp Ser Asn Ala Thr Asn Ser Asn Leu Glu Arg Val
            180                 185                 190

Glu Tyr Leu Phe Leu Ile Ile Phe Thr Val Glu Ala Phe Leu Lys Val
            195                 200                 205

Ile Ala Tyr Gly Leu Leu Phe His Pro Asn Ala Tyr Leu Arg Asn Gly
            210                 215                 220

Trp Asn Leu Leu Asp Phe Ile Ile Val Val Gly Leu Phe Ser Ala
225                 230                 235                 240

Ile Leu Glu Gln Ala Thr Lys Ala Asp Gly Ala Asn Ala Leu Gly Gly
                245                 250                 255

Lys Gly Ala Gly Phe Asp Val Lys Ala Leu Arg Ala Phe Arg Val Leu
            260                 265                 270

Arg Pro Leu Arg Leu Val Ser Gly Val Pro Ser Leu Gln Val Val Leu
            275                 280                 285

Asn Ser Ile Ile Lys Ala Met Val Pro Leu Leu His Ile Ala Leu Leu
            290                 295                 300

Val Leu Phe Val Ile Ile Tyr Ala Ile Ile Gly Leu Glu Leu Phe
305                 310                 315                 320

Met Gly Lys Met His Lys Thr Cys Tyr Asn Gln Glu Gly Val Ala Asp
                325                 330                 335

Val Pro Ala Glu Asp Asp Pro Ser Pro Cys Ala Leu Glu Thr Gly His
            340                 345                 350

Gly Arg Gln Cys Gln Asn Gly Thr Val Cys Lys Pro Gly Trp Asp Gly
            355                 360                 365

Pro Lys His Gly Ile Thr Asn Phe Asp Asn Phe Ala Phe Ala Met Leu
            370                 375                 380

Thr Val Phe Gln Cys Ile Thr Met Glu Gly Trp Thr Asp Val Leu Tyr
385                 390                 395                 400

Trp Met Gln Asp Ala Met Gly Tyr Glu Leu Pro Trp Val Tyr Phe Val
                405                 410                 415

Ser Leu Val Ile Phe Gly Ser Phe Phe Val Leu Asn Leu Val Leu Gly
            420                 425                 430

Val Leu Ser Gly Glu Phe Ser Lys Glu Arg Glu Lys Ala Lys Ala Arg
            435                 440                 445
```

```
Gly Asp Phe Gln Lys Leu Arg Glu Lys Gln Leu Glu Glu Asp Leu
    450                 455                 460

Lys Gly Tyr Leu Asp Trp Ile Thr Gln Ala Glu Asp Ile Asp Pro Glu
465                 470                 475                 480

Asn Glu Asp Glu Gly Met Asp Glu Glu Lys Pro Arg Asn Met Ser Met
                485                 490                 495

Pro Thr Ser Glu Thr Glu Ser Val Asn Thr Glu Asn Val Ala Gly Gly
            500                 505                 510

Asp Ile Glu Gly Glu Asn Cys Gly Ala Arg Leu Ala His Arg Ile Ser
        515                 520                 525

Lys Ser Lys Phe Ser Arg Tyr Trp Arg Arg Trp Asn Arg Phe Cys Arg
530                 535                 540

Arg Lys Cys Arg Ala Ala Val Lys Ser Asn Val Phe Tyr Trp Leu Val
545                 550                 555                 560

Ile Phe Leu Val Phe Leu Asn Thr Leu Thr Ile Ala Ser Glu His Tyr
                565                 570                 575

Asn Gln Pro His Trp Leu Thr Glu Val Gln Asp Thr Ala Asn Lys Ala
            580                 585                 590

Leu Leu Ala Leu Phe Thr Ala Glu Met Leu Leu Lys Met Tyr Ser Leu
        595                 600                 605

Gly Leu Gln Ala Tyr Phe Val Ser Leu Phe Asn Arg Phe Asp Cys Phe
    610                 615                 620

Ile Val Cys Gly Gly Ile Leu Glu Thr Ile Leu Val Glu Thr Lys Val
625                 630                 635                 640

Met Ser Pro Leu Gly Ile Ser Val Leu Arg Cys Val Arg Leu Leu Arg
                645                 650                 655

Ile Phe Lys Ile Thr Arg Tyr Trp Asn Ser Leu Ser Asn Leu Val Ala
            660                 665                 670

Ser Leu Leu Asn Ser Val Arg Ser Ile Ala Ser Leu Leu Leu Leu Leu
        675                 680                 685

Phe Leu Phe Ile Ile Ile Phe Ser Leu Leu Gly Met Gln Leu Phe Gly
    690                 695                 700

Gly Lys Phe Asn Phe Asp Glu Met Gln Thr Arg Arg Ser Thr Phe Asp
705                 710                 715                 720

Asn Phe Pro Gln Ser Leu Leu Thr Val Phe Gln Ile Leu Thr Gly Glu
                725                 730                 735

Asp Trp Asn Ser Val Met Tyr Asp Gly Ile Met Ala Tyr Gly Gly Pro
            740                 745                 750

Ser Phe Pro Gly Met Leu Val Cys Ile Tyr Phe Ile Ile Leu Phe Ile
        755                 760                 765

Cys Gly Asn Tyr Ile Leu Leu Asn Val Phe Leu Ala Ile Ala Val Asp
    770                 775                 780

Asn Leu Ala Asp Ala Glu Ser Leu Thr Ser Ala Gln Lys Glu Glu Glu
785                 790                 795                 800

Glu Glu Lys Glu Arg Lys Lys Leu Ala Arg Thr Ala Ser Pro Glu Lys
                805                 810                 815

Lys Gln Glu Val Val Gly Lys Pro Ala Leu Glu Glu Ala Lys Glu Glu
            820                 825                 830

Lys Ile Glu Leu Lys Ser Ile Thr Ala Asp Gly Glu Ser Pro Pro Thr
        835                 840                 845

Thr Lys Ile Asn Met Asp Asp Leu Gln Pro Asn Glu Ser Glu Asp Lys
    850                 855                 860
```

-continued

Ser Pro Tyr Pro Asn Pro Glu Thr Gly Glu Glu Asp Glu Glu Glu
865                 870                 875                 880

Pro Glu Met Pro Val Gly Pro Arg Pro Arg Pro Leu Ser Glu Leu His
            885                 890                 895

Leu Lys Glu Lys Ala Val Pro Met Pro Glu Ala Ser Ala Phe Phe Ile
            900                 905                 910

Phe Ser Pro Asn Asn Arg Phe Arg Leu Gln Cys His Arg Ile Val Asn
            915                 920                 925

Asp Thr Ile Phe Thr Asn Leu Ile Leu Phe Phe Ile Leu Leu Ser Ser
    930                 935                 940

Ile Ser Leu Ala Ala Glu Asp Pro Val Gln His Thr Ser Phe Arg Asn
945                 950                 955                 960

His Ile Leu Phe Tyr Phe Asp Ile Val Phe Thr Thr Ile Phe Thr Ile
            965                 970                 975

Glu Ile Ala Leu Lys Met Thr Ala Tyr Gly Ala Phe Leu His Lys Gly
            980                 985                 990

Ser Phe Cys Arg Asn Tyr Phe Asn Ile Leu Asp Leu Leu Val Val Ser
            995                 1000                1005

Val Ser Leu Ile Ser Phe Gly Ile Gln Ser Ser Ala Ile Asn Val
    1010            1015                1020

Val Lys Ile Leu Arg Val Leu Arg Val Leu Arg Pro Leu Arg Ala
    1025            1030                1035

Ile Asn Arg Ala Lys Gly Leu Lys His Val Val Gln Cys Val Phe
    1040            1045                1050

Val Ala Ile Arg Thr Ile Gly Asn Ile Val Ile Val Thr Thr Leu
    1055            1060                1065

Leu Gln Phe Met Phe Ala Cys Ile Gly Val Gln Leu Phe Lys Gly
    1070            1075                1080

Lys Leu Tyr Thr Cys Ser Asp Ser Ser Lys Gln Thr Glu Ala Glu
    1085            1090                1095

Cys Lys Gly Asn Tyr Ile Thr Tyr Lys Asp Gly Glu Val Asp His
    1100            1105                1110

Pro Ile Ile Gln Pro Arg Ser Trp Glu Asn Ser Lys Phe Asp Phe
    1115            1120                1125

Asp Asn Val Leu Ala Ala Met Met Ala Leu Phe Thr Val Ser Thr
    1130            1135                1140

Phe Glu Gly Trp Pro Glu Leu Leu Tyr Arg Ser Ile Asp Ser His
    1145            1150                1155

Thr Glu Asp Lys Gly Pro Ile Tyr Asn Tyr Arg Val Glu Ile Ser
    1160            1165                1170

Ile Phe Phe Ile Ile Tyr Ile Ile Ile Ala Phe Phe Met Met
    1175            1180                1185

Asn Ile Phe Val Gly Phe Val Ile Val Thr Phe Gln Glu Gln Gly
    1190            1195                1200

Glu Gln Glu Tyr Lys Asn Cys Glu Leu Asp Lys Asn Gln Arg Gln
    1205            1210                1215

Cys Val Glu Tyr Ala Leu Lys Ala Arg Pro Leu Arg Arg Tyr Ile
    1220            1225                1230

Pro Lys Asn Gln His Gln Tyr Lys Val Trp Tyr Val Val Asn Ser
    1235            1240                1245

Thr Tyr Phe Glu Tyr Leu Met Phe Val Leu Ile Leu Leu Asn Thr
    1250            1255                1260

Ile Cys Leu Ala Met Gln His Tyr Gly Gln Ser Cys Leu Phe Lys

-continued

```
            1265                1270                1275

Ile Ala Met Asn Ile Leu Asn Met Leu Phe Thr Gly Leu Phe Thr
            1280                1285                1290

Val Glu Met Ile Leu Lys Leu Ile Ala Phe Lys Pro Lys Gly Tyr
            1295                1300                1305

Phe Ser Asp Pro Trp Asn Val Phe Asp Phe Leu Ile Val Ile Gly
            1310                1315                1320

Ser Ile Ile Asp Val Ile Leu Ser Glu Thr Asn Pro Ala Glu His
            1325                1330                1335

Thr Gln Cys Ser Pro Ser Met Asn Ala Glu Glu Asn Ser Arg Ile
            1340                1345                1350

Ser Ile Thr Phe Phe Arg Leu Phe Arg Val Met Arg Leu Val Lys
            1355                1360                1365

Leu Leu Ser Arg Gly Glu Gly Ile Arg Thr Leu Leu Trp Thr Phe
            1370                1375                1380

Ile Lys Ser Phe Gln Ala Leu Pro Tyr Val Ala Leu Leu Ile Val
            1385                1390                1395

Met Leu Phe Phe Ile Tyr Ala Val Ile Gly Met Gln Val Phe Gly
            1400                1405                1410

Lys Ile Ala Leu Asn Asp Thr Thr Glu Ile Asn Arg Asn Asn Asn
            1415                1420                1425

Phe Gln Thr Phe Pro Gln Ala Val Leu Leu Leu Phe Arg Cys Ala
            1430                1435                1440

Thr Gly Glu Ala Trp Gln Asp Ile Met Leu Ala Cys Met Pro Gly
            1445                1450                1455

Lys Lys Cys Ala Pro Glu Ser Glu Pro His Asn Ser Thr Glu Gly
            1460                1465                1470

Glu Thr Pro Cys Gly Ser Ser Phe Ala Val Phe Tyr Phe Ile Ser
            1475                1480                1485

Phe Tyr Met Leu Cys Ala Phe Leu Ile Ile Asn Leu Phe Val Ala
            1490                1495                1500

Val Ile Met Asp Asn Phe Asp Tyr Leu Thr Arg Asp Trp Ser Ile
            1505                1510                1515

Leu Gly Pro His His Leu Asp Glu Phe Lys Arg Ile Trp Ala Glu
            1520                1525                1530

Tyr Asp Pro Glu Ala Lys Gly Arg Ile Lys His Leu Asp Val Val
            1535                1540                1545

Thr Leu Leu Arg Arg Ile Gln Pro Pro Leu Gly Phe Gly Lys Leu
            1550                1555                1560

Cys Pro His Arg Val Ala Cys Lys Arg Leu Val Ser Met Asn Met
            1565                1570                1575

Pro Leu Asn Ser Asp Gly Thr Val Met Phe Asn Ala Thr Leu Phe
            1580                1585                1590

Ala Leu Val Arg Thr Ala Leu Arg Ile Lys Thr Glu Gly Asn Leu
            1595                1600                1605

Glu Gln Ala Asn Glu Glu Leu Arg Ala Ile Ile Lys Lys Ile Trp
            1610                1615                1620

Lys Arg Thr Ser Met Lys Leu Leu Asp Gln Val Val Pro Pro Ala
            1625                1630                1635

Gly Asp Asp Glu Val Thr Val Gly Lys Phe Tyr Ala Thr Phe Leu
            1640                1645                1650

Ile Gln Glu Tyr Phe Arg Lys Phe Lys Lys Arg Lys Glu Gln Gly
            1655                1660                1665
```

```
Leu Val Gly Lys Pro Ser Gln Arg Asn Ala Leu Ser Leu Gln Ala
    1670                1675                1680

Gly Leu Arg Thr Leu His Asp Ile Gly Pro Glu Ile Arg Arg Ala
    1685                1690                1695

Ile Ser Gly Asp Leu Thr Ala Glu Glu Leu Asp Lys Ala Met
    1700                1705                1710

Lys Glu Ala Val Ser Ala Ala Ser Glu Asp Asp Ile Phe Arg Arg
    1715                1720                1725

Ala Gly Gly Leu Phe Gly Asn His Val Ser Tyr Tyr Gln Ser Asp
    1730                1735                1740

Ser Arg Ser Ala Phe Pro Gln Thr Phe Thr Thr Gln Arg Pro Leu
    1745                1750                1755

His Ile Ser Lys Ala Gly Asn Asn Gln Gly Asp Thr Glu Ser Pro
    1760                1765                1770

Ser His Glu Lys Leu Val Asp Ser Thr Phe Thr Pro Ser Ser Tyr
    1775                1780                1785

Ser Ser Thr Gly Ser Asn Ala Asn Ile Asn Asn Ala Asn Asn Thr
    1790                1795                1800

Ala Leu Gly Arg Leu Pro Arg Pro Ala Gly Tyr Pro Ser Thr Val
    1805                1810                1815

Ser Thr Val Glu Gly His Gly Ser Pro Leu Ser Pro Ala Val Arg
    1820                1825                1830

Ala Gln Glu Ala Ala Trp Lys Leu Ser Ser Lys Arg Cys His Ser
    1835                1840                1845

Gln Glu Ser Gln Ile Ala Met Ala Cys Gln Glu Gly Ala Ser Gln
    1850                1855                1860

Asp Asp Asn Tyr Asp Val Arg Ile Gly Glu Asp Ala Glu Cys Cys
    1865                1870                1875

Ser Glu Pro Ser Leu Leu Ser Thr Glu Met Leu Ser Tyr Gln Asp
    1880                1885                1890

Asp Glu Asn Arg Gln Leu Ala Pro Pro Glu Glu Glu Lys Arg Asp
    1895                1900                1905

Ile Arg Leu Ser Pro Lys Lys Gly Phe Leu Arg Ser Ala Ser Leu
    1910                1915                1920

Gly Arg Arg Ala Xaa Phe His Leu Glu Cys Leu Lys Arg Gln Lys
    1925                1930                1935

Asn Gln Gly Gly Asp Ile Ser Gln Lys Thr Val Leu Pro Leu His
    1940                1945                1950

Leu Val His His Gln Ala Leu Ala Val Ala Gly Leu Ser Pro Leu
    1955                1960                1965

Leu Gln Arg Ser His Ser Pro Thr Ser Leu Pro Arg Pro Cys Ala
    1970                1975                1980

Thr Pro Pro Ala Thr Pro Gly Ser Arg Gly Trp Pro Pro Gln Pro
    1985                1990                1995

Ile Pro Thr Leu Arg Leu Glu Gly Ala Asp Ser Ser Glu Lys Leu
    2000                2005                2010

Asn Ser Ser Phe Pro Ser Ile His Cys Gly Ser Trp Ser Gly Glu
    2015                2020                2025

Asn Ser Pro Cys Arg Gly Asp Ser Ser Ala Ala Arg Arg Ala Arg
    2030                2035                2040

Pro Val Ser Leu Thr Val Pro Ser Gln Ala Gly Ala Gln Gly Arg
    2045                2050                2055
```

```
Gln Phe His Gly Ser Ala Ser Ser Leu Val Glu Ala Val Leu Ile
    2060                2065                2070

Ser Glu Gly Leu Gly Gln Phe Ala Gln Asp Pro Lys Phe Ile Glu
    2075                2080                2085

Val Thr Thr Gln Glu Leu Ala Asp Ala Cys Asp Leu Thr Ile Glu
    2090                2095                2100

Glu Met Glu Asn Ala Ala Asp Asp Ile Leu Ser Gly Gly Ala Arg
    2105                2110                2115

Gln Ser Pro Asn Gly Thr Leu Leu Pro Phe Val Asn Arg Arg Asp
    2120                2125                2130

Pro Gly Arg Asp Arg Ala Gly Gln Asn Glu Gln Asp Ala Ser Gly
    2135                2140                2145

Ala Cys Ala Pro Gly Cys Gly Gln Ser Glu Glu Ala Leu Ala Asp
    2150                2155                2160

Arg Arg Ala Gly Val Ser Ser Leu
    2165                2170

<210> SEQ ID NO 34
<211> LENGTH: 605
<212> TYPE: PRT
<213> ORGANISM: human
<220> FEATURE:
<221> NAME/KEY: misc_feature
<222> LOCATION: (459)..(459)
<223> OTHER INFORMATION: Xaa can be any naturally occurring amino acid
<220> FEATURE:
<221> NAME/KEY: misc_feature
<222> LOCATION: (478)..(479)
<223> OTHER INFORMATION: Xaa can be any naturally occurring amino acid

<400> SEQUENCE: 34

Met Gln Cys Cys Gly Leu Val His Arg Arg Val Arg Val Ser Tyr
1               5                   10                  15

Gly Ser Ala Asp Ser Tyr Thr Ser Arg Pro Ser Asp Ser Asp Val Ser
            20                  25                  30

Leu Glu Glu Asp Arg Glu Ala Val Arg Arg Glu Ala Glu Arg Gln Ala
        35                  40                  45

Gln Ala Gln Leu Glu Lys Ala Lys Thr Lys Pro Val Ala Phe Ala Val
    50                  55                  60

Arg Thr Asn Val Ser Tyr Ser Ala Ala His Glu Asp Asp Val Pro Val
65                  70                  75                  80

Pro Gly Met Ala Ile Ser Phe Glu Ala Lys Asp Phe Leu His Val Lys
                85                  90                  95

Glu Lys Phe Asn Asn Asp Trp Trp Ile Gly Arg Leu Val Lys Glu Gly
            100                 105                 110

Cys Glu Ile Gly Phe Ile Pro Ser Pro Val Lys Leu Glu Asn Met Arg
        115                 120                 125

Leu Gln His Glu Gln Arg Ala Lys Gln Gly Lys Phe Tyr Ser Ser Lys
    130                 135                 140

Ser Gly Gly Asn Ser Ser Ser Ser Leu Gly Asp Ile Val Pro Ser Ser
145                 150                 155                 160

Arg Lys Ser Thr Pro Pro Ser Ser Ala Ile Asp Ile Asp Ala Thr Gly
                165                 170                 175

Leu Asp Ala Glu Glu Asn Asp Ile Pro Ala Asn His Arg Ser Pro Lys
            180                 185                 190

Pro Ser Ala Asn Ser Val Thr Ser Pro His Ser Lys Glu Lys Arg Met
        195                 200                 205
```

```
Pro Phe Phe Lys Lys Thr Glu His Thr Pro Pro Tyr Asp Val Val Pro
210                 215                 220

Ser Met Arg Pro Val Val Leu Val Gly Pro Ser Leu Lys Gly Tyr Glu
225                 230                 235                 240

Val Thr Asp Met Met Gln Lys Ala Leu Phe Asp Phe Leu Lys His Arg
            245                 250                 255

Phe Glu Gly Arg Ile Ser Ile Thr Arg Val Thr Ala Asp Ile Ser Leu
                260                 265                 270

Ala Lys Arg Ser Val Leu Asn Asn Pro Ser Lys His Ala Ile Ile Glu
            275                 280                 285

Arg Ser Asn Thr Arg Ser Ser Leu Ala Glu Val Gln Ser Glu Ile Glu
290                 295                 300

Arg Ile Phe Glu Leu Ala Arg Thr Leu Gln Leu Val Val Leu Asp Ala
305                 310                 315                 320

Asp Thr Ile Asn His Pro Ala Gln Leu Ser Lys Thr Ser Leu Ala Pro
                325                 330                 335

Ile Ile Val Tyr Val Lys Ile Ser Ser Pro Lys Val Leu Gln Arg Leu
                340                 345                 350

Ile Lys Ser Arg Gly Lys Ser Gln Ala Lys His Leu Asn Val Gln Met
            355                 360                 365

Val Ala Ala Asp Lys Leu Ala Gln Cys Pro Pro Glu Leu Phe Asp Val
370                 375                 380

Ile Leu Asp Glu Asn Gln Leu Glu Asp Ala Cys Glu His Leu Ala Asp
385                 390                 395                 400

Tyr Leu Glu Ala Tyr Trp Lys Ala Thr His Pro Pro Ser Ser Ser Leu
                405                 410                 415

Pro Asn Pro Leu Leu Ser Arg Thr Leu Ala Thr Ser Ser Leu Pro Leu
                420                 425                 430

Ser Pro Thr Leu Ala Ser Asn Ser Gln Gly Ser Gln Gly Asp Gln Arg
            435                 440                 445

Thr Asp Arg Ser Ala Pro Ile Arg Ser Ala Xaa Gln Ala Glu Glu Glu
450                 455                 460

Pro Ser Val Glu Pro Val Lys Lys Ser Gln His Arg Ser Xaa Xaa Ser
465                 470                 475                 480

Ala Pro His His Asn His Arg Ser Gly Thr Ser Arg Gly Leu Ser Arg
                485                 490                 495

Gln Glu Thr Phe Asp Ser Glu Thr Gln Glu Ser Arg Asp Ser Ala Tyr
                500                 505                 510

Val Glu Pro Lys Glu Asp Tyr Ser His Asp His Val Asp His Tyr Ala
            515                 520                 525

Ser His Arg Asp His Asn His Arg Asp Glu Thr His Gly Ser Ser Asp
530                 535                 540

His Arg His Arg Glu Ser Arg His Arg Ser Arg Asp Val Asp Arg Glu
545                 550                 555                 560

Gln Asp His Asn Glu Cys Asn Lys Gln Arg Ser Arg His Lys Ser Lys
                565                 570                 575

Asp Arg Tyr Cys Glu Lys Asp Gly Glu Val Ile Ser Lys Lys Arg Asn
                580                 585                 590

Glu Ala Gly Glu Trp Asn Arg Asp Val Tyr Ile Pro Gln
            595                 600                 605

<210> SEQ ID NO 35
<211> LENGTH: 433
<212> TYPE: PRT
```

<213> ORGANISM: human
<220> FEATURE:
<221> NAME/KEY: misc_feature
<222> LOCATION: (428)..(428)
<223> OTHER INFORMATION: Xaa can be any naturally occurring amino acid

<400> SEQUENCE: 35

```
Met Glu Val Val Asp Pro Gln Gln Leu Gly Met Phe Thr Glu Gly Glu
1               5                   10                  15

Leu Met Ser Val Gly Met Asp Thr Phe Ile His Arg Ile Asp Ser Thr
            20                  25                  30

Glu Val Ile Tyr Gln Pro Arg Arg Lys Arg Ala Lys Leu Ile Gly Lys
        35                  40                  45

Tyr Leu Met Gly Asp Leu Leu Gly Glu Gly Ser Tyr Gly Lys Val Lys
50                  55                  60

Glu Val Leu Asp Ser Glu Thr Leu Cys Arg Arg Ala Val Lys Ile Leu
65                  70                  75                  80

Lys Lys Lys Lys Leu Arg Arg Ile Pro Asn Gly Glu Ala Asn Val Lys
                85                  90                  95

Lys Glu Ile Gln Leu Leu Arg Arg Leu Arg His Lys Asn Val Ile Gln
            100                 105                 110

Leu Val Asp Val Leu Tyr Asn Glu Glu Lys Gln Lys Met Tyr Met Val
        115                 120                 125

Met Glu Tyr Cys Val Cys Gly Met Gln Glu Met Leu Asp Ser Val Pro
130                 135                 140

Glu Lys Arg Phe Pro Val Cys Gln Ala His Gly Tyr Phe Cys Gln Leu
145                 150                 155                 160

Ile Asp Gly Leu Glu Tyr Leu His Ser Gln Gly Ile Val His Lys Asp
                165                 170                 175

Ile Lys Pro Gly Asn Leu Leu Leu Thr Thr Gly Gly Thr Leu Lys Ile
            180                 185                 190

Ser Asp Leu Gly Val Ala Glu Ala Leu His Pro Phe Ala Ala Asp Asp
        195                 200                 205

Thr Cys Arg Thr Ser Gln Gly Ser Pro Ala Phe Gln Pro Pro Glu Ile
210                 215                 220

Ala Asn Gly Leu Asp Thr Phe Ser Gly Phe Lys Val Asp Ile Trp Ser
225                 230                 235                 240

Ala Gly Val Thr Leu Tyr Asn Ile Thr Thr Gly Leu Tyr Pro Phe Glu
                245                 250                 255

Gly Asp Asn Ile Tyr Lys Leu Phe Glu Asn Ile Gly Lys Gly Ser Tyr
            260                 265                 270

Ala Ile Pro Gly Asp Cys Gly Pro Pro Leu Ser Asp Leu Leu Lys Gly
        275                 280                 285

Met Leu Glu Tyr Glu Pro Ala Lys Arg Phe Ser Ile Arg Gln Ile Arg
290                 295                 300

Gln His Ser Trp Phe Arg Lys Lys His Pro Pro Ala Glu Ala Pro Val
305                 310                 315                 320

Pro Ile Pro Pro Ser Pro Asp Thr Lys Asp Arg Trp Arg Ser Met Thr
                325                 330                 335

Val Val Pro Tyr Leu Glu Asp Leu His Gly Ala Asp Glu Asp Glu Asp
            340                 345                 350

Leu Phe Asp Ile Glu Asp Asp Ile Ile Tyr Thr Gln Asp Phe Thr Val
        355                 360                 365

Pro Gly Gln Val Pro Glu Glu Glu Ala Ser His Asn Gly Gln Arg Arg
370                 375                 380
```

```
Gly Leu Pro Lys Ala Val Cys Met Asn Gly Thr Glu Ala Ala Gln Leu
385                 390                 395                 400

Ser Thr Lys Ser Arg Ala Glu Gly Arg Ala Pro Asn Pro Ala Arg Lys
            405                 410                 415

Ala Cys Ser Ala Ser Ser Lys Ile Arg Arg Leu Xaa Ala Cys Lys Gln
            420                 425                 430

Gln

<210> SEQ ID NO 36
<211> LENGTH: 847
<212> TYPE: PRT
<213> ORGANISM: human
<220> FEATURE:
<221> NAME/KEY: misc_feature
<222> LOCATION: (188)..(188)
<223> OTHER INFORMATION: Xaa can be any naturally occurring amino acid

<400> SEQUENCE: 36

Met Ser Lys Ser Phe Gln Gln Ser Ser Leu Ser Arg Asp Ser Gln Gly
1               5                   10                  15

His Gly Arg Asp Leu Ser Ala Ala Gly Ile Gly Leu Leu Ala Ala Ala
            20                  25                  30

Thr Gln Ser Leu Ser Met Pro Ala Ser Leu Gly Arg Met Asn Gln Gly
        35                  40                  45

Thr Ala Arg Leu Ala Ser Leu Met Asn Leu Gly Met Ser Ser Ser Leu
    50                  55                  60

Asn Gln Gln Gly Ala His Ser Ala Leu Ser Ser Ala Ser Thr Ser Ser
65                  70                  75                  80

His Asn Leu Gln Ser Ile Phe Asn Ile Gly Ser Arg Gly Pro Leu Pro
                85                  90                  95

Leu Ser Ser Gln His Arg Gly Asp Ala Asp Gln Ala Ser Asn Ile Leu
            100                 105                 110

Ala Ser Phe Gly Leu Ser Ala Arg Asp Leu Asp Glu Leu Ser Arg Tyr
        115                 120                 125

Pro Glu Asp Lys Ile Thr Pro Glu Asn Leu Pro Gln Ile Leu Leu Gln
130                 135                 140

Leu Lys Arg Arg Arg Thr Glu Glu Gly Pro Thr Leu Ser Tyr Gly Arg
145                 150                 155                 160

Asp Gly Arg Ser Ala Thr Arg Glu Pro Pro Tyr Arg Val Pro Arg Asp
                165                 170                 175

Asp Trp Glu Glu Lys Arg His Phe Arg Arg Asp Xaa Phe Asp Asp Arg
            180                 185                 190

Gly Pro Ser Leu Asn Pro Val Leu Asp Tyr Asp His Gly Ser Arg Ser
        195                 200                 205

Gln Glu Ser Gly Tyr Tyr Asp Arg Met Asp Tyr Glu Asp Asp Arg Leu
    210                 215                 220

Arg Asp Gly Glu Arg Cys Arg Asp Asp Ser Phe Phe Gly Glu Thr Ser
225                 230                 235                 240

His Asn Tyr His Lys Phe Asp Ser Glu Tyr Glu Arg Met Gly Arg Gly
                245                 250                 255

Pro Gly Pro Leu Gln Glu Arg Ser Leu Phe Glu Lys Lys Arg Gly Ala
            260                 265                 270

Pro Pro Ser Ser Asn Ile Glu Asp Phe His Gly Leu Leu Pro Lys Gly
        275                 280                 285

Tyr Pro His Leu Cys Ser Ile Cys Asp Leu Pro Val His Ser Asn Lys
```

```
            290                 295                 300
Glu Trp Ser Gln His Ile Asn Gly Ala Ser His Ser Arg Arg Cys Gln
305                 310                 315                 320

Leu Leu Leu Glu Ile Tyr Pro Glu Trp Asn Pro Asp Asn Asp Thr Gly
                325                 330                 335

His Thr Met Gly Asp Pro Phe Met Leu Gln Gln Ser Thr Asn Pro Ala
                340                 345                 350

Pro Gly Ile Leu Gly Pro Pro Pro Ser Phe His Leu Gly Gly Pro
        355                 360                 365

Ala Val Gly Pro Arg Gly Asn Leu Gly Ala Gly Asn Gly Asn Leu Gln
        370                 375                 380

Gly Pro Arg His Met Gln Lys Gly Arg Val Glu Thr Ser Arg Val Val
385                 390                 395                 400

His Ile Met Asp Phe Gln Arg Gly Lys Asn Leu Arg Tyr Gln Leu Leu
                405                 410                 415

Gln Leu Val Glu Pro Phe Gly Val Ile Ser Asn His Leu Ile Leu Asn
                420                 425                 430

Lys Ile Asn Glu Ala Phe Ile Glu Met Ala Thr Thr Glu Asp Ala Gln
            435                 440                 445

Ala Ala Val Asp Tyr Tyr Thr Thr Pro Ala Leu Val Phe Gly Lys
        450                 455                 460

Pro Val Arg Val His Leu Ser Gln Lys Tyr Lys Arg Ile Lys Lys Pro
465                 470                 475                 480

Glu Gly Lys Pro Asp Gln Lys Phe Asp Gln Lys Gln Glu Leu Gly Arg
                485                 490                 495

Val Ile His Leu Ser Asn Leu Pro His Ser Gly Tyr Ser Asp Ser Ala
                500                 505                 510

Val Leu Lys Leu Ala Glu Pro Tyr Gly Lys Ile Lys Asn Tyr Ile Leu
            515                 520                 525

Met Arg Met Lys Ser Gln Ala Phe Ile Glu Met Glu Thr Arg Glu Asp
        530                 535                 540

Ala Met Ala Met Val Asp His Cys Leu Lys Lys Ala Leu Trp Phe Gln
545                 550                 555                 560

Gly Arg Cys Val Lys Val Asp Leu Ser Glu Lys Tyr Lys Lys Leu Val
                565                 570                 575

Leu Arg Ile Pro Asn Arg Gly Ile Asp Leu Leu Lys Lys Asp Lys Ser
            580                 585                 590

Arg Lys Arg Ser Tyr Ser Pro Asp Gly Lys Glu Ser Pro Ser Asp Lys
        595                 600                 605

Lys Ser Lys Thr Asp Gly Ser Gln Lys Thr Glu Ser Thr Glu Gly
        610                 615                 620

Lys Glu Gln Glu Glu Lys Ser Gly Glu Asp Gly Glu Lys Asp Thr Lys
625                 630                 635                 640

Asp Asp Gln Thr Glu Gln Glu Pro Asn Met Leu Leu Glu Ser Glu Asp
                645                 650                 655

Glu Leu Leu Val Asp Glu Glu Ala Ala Leu Leu Glu Ser Gly
                660                 665                 670

Ser Ser Val Gly Asp Glu Thr Asp Leu Ala Asn Leu Gly Asp Val Ala
        675                 680                 685

Ser Asp Gly Lys Lys Glu Pro Ser Asp Lys Ala Val Lys Lys Asp Gly
        690                 695                 700

Ser Ala Ser Ala Ala Ala Lys Lys Lys Leu Lys Lys Val Asp Lys Ile
705                 710                 715                 720
```

```
Glu Glu Leu Asp Gln Glu Asn Glu Ala Ala Leu Glu Asn Gly Ile Lys
                725                 730                 735

Asn Glu Glu Asn Thr Glu Pro Gly Ala Glu Ser Ser Glu Asn Ala Asp
            740                 745                 750

Asp Pro Asn Lys Asp Thr Ser Glu Asn Ala Asp Gly Gln Ser Asp Glu
            755                 760                 765

Asn Lys Asp Asp Tyr Thr Ile Pro Asp Glu Tyr Arg Ile Gly Pro Tyr
    770                 775                 780

Gln Pro Asn Val Pro Val Gly Ile Asp Tyr Val Ile Pro Lys Thr Gly
785                 790                 795                 800

Phe Tyr Cys Lys Leu Cys Ser Leu Phe Tyr Thr Asn Glu Glu Val Ala
                805                 810                 815

Lys Asn Thr His Cys Ser Ser Leu Pro His Tyr Gln Lys Leu Lys Lys
            820                 825                 830

Phe Leu Asn Lys Leu Ala Glu Glu Arg Arg Gln Lys Lys Glu Thr
            835                 840                 845

<210> SEQ ID NO 37
<211> LENGTH: 570
<212> TYPE: PRT
<213> ORGANISM: human
<220> FEATURE:
<221> NAME/KEY: misc_feature
<222> LOCATION: (265)..(266)
<223> OTHER INFORMATION: Xaa can be any naturally occurring amino acid
<220> FEATURE:
<221> NAME/KEY: misc_feature
<222> LOCATION: (405)..(405)
<223> OTHER INFORMATION: Xaa can be any naturally occurring amino acid

<400> SEQUENCE: 37

Met Ser Glu Gln Ser Ile Cys Gln Ala Arg Ala Ala Val Met Val Tyr
1               5                   10                  15

Asp Asp Ala Asn Lys Lys Trp Val Pro Ala Gly Gly Ser Thr Gly Phe
            20                  25                  30

Ser Arg Val His Ile Tyr His His Thr Gly Asn Asn Thr Phe Arg Val
        35                  40                  45

Val Gly Arg Lys Ile Gln Asp His Gln Val Val Ile Asn Cys Ala Ile
    50                  55                  60

Pro Lys Gly Leu Lys Tyr Asn Gln Ala Thr Gln Thr Phe His Gln Trp
65                  70                  75                  80

Arg Asp Ala Arg Gln Val Tyr Gly Leu Asn Phe Gly Ser Lys Glu Asp
                85                  90                  95

Ala Asn Val Phe Ala Ser Ala Met Met His Ala Leu Glu Val Leu Asn
            100                 105                 110

Ser Gln Glu Thr Gly Pro Thr Leu Pro Arg Gln Asn Ser Gln Leu Pro
        115                 120                 125

Ala Gln Val Gln Asn Gly Pro Ser Gln Glu Glu Leu Glu Ile Gln Arg
    130                 135                 140

Arg Gln Leu Gln Glu Gln Arg Gln Lys Glu Leu Glu Arg Glu Arg
145                 150                 155                 160

Leu Glu Arg Glu Arg Met Glu Arg Glu Arg Leu Glu Arg Glu Arg Leu
                165                 170                 175

Glu Arg Glu Arg Leu Glu Arg Glu Arg Leu Glu Gln Glu Gln Leu Glu
            180                 185                 190

Arg Glu Arg Gln Glu Arg Glu Arg Gln Glu Arg Leu Glu Arg Gln Glu
        195                 200                 205
```

```
Arg Leu Glu Arg Gln Glu Arg Leu Glu Arg Gln Glu Arg Leu Asp Arg
    210                 215                 220

Glu Arg Gln Glu Arg Gln Arg Glu Arg Leu Glu Arg Leu Glu Arg
225                 230                 235                 240

Glu Arg Gln Glu Arg Glu Arg Gln Glu Gln Leu Glu Arg Glu Gln Leu
                245                 250                 255

Glu Trp Glu Arg Glu Arg Arg Ile Xaa Xaa Ala Ala Ala Pro Ala Ser
                260                 265                 270

Val Glu Thr Pro Leu Asn Ser Val Leu Gly Asp Ser Ala Ser Glu
            275                 280                 285

Pro Gly Leu Gln Ala Ala Ser Gln Pro Ala Glu Thr Pro Ser Gln Gln
    290                 295                 300

Gly Ile Val Leu Gly Pro Leu Ala Pro Pro Pro Pro Pro Leu Pro
305                 310                 315                 320

Pro Gly Pro Ala Gln Ala Ser Val Ala Leu Pro Pro Pro Gly Pro
                325                 330                 335

Pro Pro Pro Pro Pro Leu Pro Ser Thr Gly Pro Pro Pro Pro Pro
                340                 345                 350

Pro Pro Pro Leu Pro Asn Gln Val Pro Pro Pro Pro Pro Pro Pro
            355                 360                 365

Ala Pro Pro Leu Pro Ala Ser Gly Phe Phe Leu Ala Ser Met Ser Glu
    370                 375                 380

Asp Asn Arg Pro Leu Thr Gly Leu Ala Ala Ile Ala Gly Ala Lys
385                 390                 395                 400

Leu Arg Lys Val Xaa Arg Met Glu Asp Thr Ser Phe Pro Ser Gly Gly
                405                 410                 415

Asn Ala Ile Gly Val Asn Ser Ala Ser Ser Lys Thr Asp Thr Gly Arg
            420                 425                 430

Gly Asn Gly Pro Leu Pro Leu Gly Gly Ser Gly Leu Met Glu Glu Met
                435                 440                 445

Ser Ala Leu Leu Ala Arg Arg Arg Ile Ala Glu Lys Gly Ser Thr
    450                 455                 460

Ile Glu Thr Glu Gln Lys Glu Asp Lys Gly Glu Asp Ser Glu Pro Val
465                 470                 475                 480

Thr Ser Lys Ala Ser Ser Thr Ser Thr Pro Glu Pro Thr Arg Lys Pro
                485                 490                 495

Trp Glu Arg Thr Asn Thr Met Asn Gly Ser Lys Ser Pro Val Ile Ser
                500                 505                 510

Arg Pro Lys Ser Thr Pro Leu Ser Gln Pro Ser Ala Asn Gly Val Gln
            515                 520                 525

Thr Glu Gly Leu Asp Tyr Asp Arg Leu Lys Gln Asp Ile Leu Asp Glu
    530                 535                 540

Met Arg Lys Glu Leu Thr Lys Leu Lys Glu Glu Leu Ile Asp Ala Ile
545                 550                 555                 560

Arg Gln Glu Leu Ser Lys Ser Asn Thr Ala
                565                 570

<210> SEQ ID NO 38
<211> LENGTH: 975
<212> TYPE: PRT
<213> ORGANISM: human
<220> FEATURE:
<221> NAME/KEY: misc_feature
<222> LOCATION: (342)..(342)
<223> OTHER INFORMATION: Xaa can be any naturally occurring amino acid
```

```
<220> FEATURE:
<221> NAME/KEY: misc_feature
<222> LOCATION: (367)..(367)
<223> OTHER INFORMATION: Xaa can be any naturally occurring amino acid
<220> FEATURE:
<221> NAME/KEY: misc_feature
<222> LOCATION: (448)..(448)
<223> OTHER INFORMATION: Xaa can be any naturally occurring amino acid

<400> SEQUENCE: 38
```

| | | | | | | | | | | | | | | |
|---|---|---|---|---|---|---|---|---|---|---|---|---|---|---|
| Met | Ala | Thr | Gly | Leu | Gly | Glu | Pro | Val | Tyr | Gly | Leu | Ser | Asp | Glu |
| 1 | | | | 5 | | | | | 10 | | | | | 15 |
| Gly | Glu | Ser | Arg | Ile | Leu | Arg | Val | Lys | Val | Ser | Gly | Ile | Asp | Leu |
| | | | 20 | | | | | 25 | | | | | 30 | |
| Ala | Lys | Lys | Asp | Ile | Phe | Gly | Ala | Ser | Asp | Pro | Tyr | Val | Lys | Leu | Ser |
| | | 35 | | | | | 40 | | | | | 45 | | |
| Leu | Tyr | Val | Ala | Asp | Glu | Asn | Arg | Glu | Leu | Ala | Leu | Val | Gln | Thr | Lys |
| | 50 | | | | | 55 | | | | | 60 | | | | |
| Thr | Ile | Lys | Lys | Thr | Leu | Asn | Pro | Lys | Trp | Asn | Glu | Glu | Phe | Tyr | Phe |
| 65 | | | | | 70 | | | | | 75 | | | | | 80 |
| Arg | Val | Asn | Pro | Ser | Asn | His | Arg | Leu | Leu | Phe | Glu | Val | Phe | Asp | Glu |
| | | | | 85 | | | | | 90 | | | | | 95 | |
| Asn | Arg | Leu | Thr | Arg | Asp | Asp | Phe | Leu | Gly | Gln | Val | Asp | Val | Pro | Leu |
| | | | 100 | | | | | 105 | | | | | 110 | | |
| Ser | His | Leu | Pro | Thr | Glu | Asp | Pro | Thr | Met | Glu | Arg | Pro | Tyr | Thr | Phe |
| | | 115 | | | | | 120 | | | | | 125 | | | |
| Lys | Asp | Phe | Leu | Leu | Arg | Pro | Arg | Ser | His | Lys | Ser | Arg | Val | Lys | Gly |
| | 130 | | | | | 135 | | | | | 140 | | | | |
| Phe | Leu | Arg | Leu | Lys | Met | Ala | Tyr | Met | Pro | Lys | Asn | Gly | Gly | Gln | Asp |
| 145 | | | | | 150 | | | | | 155 | | | | | 160 |
| Glu | Glu | Asn | Ser | Asp | Gln | Arg | Asp | Asp | Met | Glu | His | Gly | Trp | Glu | Val |
| | | | | 165 | | | | | 170 | | | | | 175 | |
| Val | Asp | Ser | Asn | Asp | Ser | Ala | Ser | Gln | His | Gln | Lys | Glu | Leu | Pro | Pro |
| | | | 180 | | | | | 185 | | | | | 190 | | |
| Pro | Pro | Leu | Pro | Pro | Gly | Trp | Glu | Glu | Lys | Val | Asp | Asn | Leu | Gly | Arg |
| | | 195 | | | | | 200 | | | | | 205 | | | |
| Thr | Tyr | Tyr | Val | Asn | His | Asn | Asn | Arg | Thr | Thr | Gln | Trp | His | Arg | Pro |
| | 210 | | | | | 215 | | | | | 220 | | | | |
| Ser | Leu | Met | Asp | Val | Ser | Ser | Glu | Ser | Asp | Asn | Asn | Ile | Arg | Gln | Ile |
| 225 | | | | | 230 | | | | | 235 | | | | | 240 |
| Asn | Gln | Glu | Ala | Ala | His | Arg | Arg | Phe | Arg | Ser | Arg | Arg | His | Ile | Ser |
| | | | | 245 | | | | | 250 | | | | | 255 | |
| Glu | Asp | Leu | Glu | Pro | Glu | Pro | Ser | Glu | Gly | Gly | Asp | Val | Pro | Glu | Pro |
| | | | 260 | | | | | 265 | | | | | 270 | | |
| Trp | Glu | Thr | Ile | Ser | Glu | Glu | Val | Asn | Ile | Ala | Gly | Asp | Ser | Leu | Gly |
| | | 275 | | | | | 280 | | | | | 285 | | | |
| Leu | Ala | Leu | Pro | Pro | Pro | Pro | Ala | Ser | Pro | Gly | Ser | Arg | Thr | Ser | Pro |
| | 290 | | | | | 295 | | | | | 300 | | | | |
| Gln | Glu | Leu | Ser | Glu | Glu | Leu | Ser | Arg | Arg | Leu | Gln | Ile | Thr | Pro | Asp |
| 305 | | | | | 310 | | | | | 315 | | | | | 320 |
| Ser | Asn | Gly | Glu | Gln | Phe | Ser | Ser | Leu | Ile | Gln | Arg | Glu | Pro | Ser | Ser |
| | | | | 325 | | | | | 330 | | | | | 335 | |
| Arg | Leu | Arg | Ser | Cys | Xaa | Val | Thr | Asp | Ala | Val | Ala | Glu | Gln | Gly | His |
| | | | 340 | | | | | 345 | | | | | 350 | | |
| Leu | Pro | Pro | Pro | Ser | Ala | Pro | Ala | Gly | Arg | Ala | Arg | Ser | Ser | Xaa | Val |
| | | 355 | | | | | 360 | | | | | 365 | | | |

```
Thr Gly Gly Glu Glu Pro Thr Pro Ser Val Ala Tyr Val His Thr Thr
        370                 375                 380

Pro Gly Leu Pro Ser Gly Trp Glu Glu Arg Lys Asp Ala Lys Gly Arg
385                 390                 395                 400

Thr Tyr Tyr Val Asn His Asn Asn Arg Thr Thr Thr Trp Thr Arg Pro
                405                 410                 415

Ile Met Gln Leu Ala Glu Asp Gly Ala Ser Gly Ser Ala Thr Asn Ser
                420                 425                 430

Asn Asn His Leu Ile Glu Pro Gln Ile Arg Arg Pro Arg Ser Leu Xaa
            435                 440                 445

Ser Pro Thr Val Thr Leu Ser Ala Pro Leu Gly Ala Lys Asp Ser
450                 455                 460

Pro Val Arg Arg Ala Val Lys Asp Thr Leu Ser Asn Pro Gln Ser Pro
465                 470                 475                 480

Gln Pro Ser Pro Tyr Asn Ser Pro Lys Pro Gln His Lys Val Thr Gln
                485                 490                 495

Ser Phe Leu Pro Pro Gly Trp Glu Met Arg Ile Ala Pro Asn Gly Arg
                500                 505                 510

Pro Phe Phe Ile Asp His Asn Thr Lys Thr Thr Thr Trp Glu Asp Pro
            515                 520                 525

Arg Leu Lys Phe Pro Val His Met Arg Ser Lys Thr Ser Leu Asn Pro
530                 535                 540

Asn Asp Leu Gly Pro Leu Pro Pro Gly Trp Glu Glu Arg Ile His Leu
545                 550                 555                 560

Asp Gly Arg Thr Phe Tyr Ile Asp His Asn Ser Lys Ile Thr Gln Trp
                565                 570                 575

Glu Asp Pro Arg Leu Gln Asn Pro Ala Ile Thr Gly Pro Ala Val Pro
            580                 585                 590

Tyr Ser Arg Glu Phe Lys Gln Lys Tyr Asp Tyr Phe Arg Lys Lys Leu
            595                 600                 605

Lys Lys Pro Ala Asp Ile Pro Asn Arg Phe Glu Met Lys Leu His Arg
610                 615                 620

Asn Asn Ile Phe Glu Glu Ser Tyr Arg Arg Ile Met Ser Val Lys Arg
625                 630                 635                 640

Pro Asp Val Leu Lys Ala Arg Leu Trp Ile Glu Phe Glu Ser Glu Lys
                645                 650                 655

Gly Leu Asp Tyr Gly Gly Val Ala Arg Glu Trp Phe Leu Leu Ser
                660                 665                 670

Lys Glu Met Phe Asn Pro Tyr Tyr Gly Leu Phe Glu Tyr Ser Ala Thr
            675                 680                 685

Asp Asn Tyr Thr Leu Gln Ile Asn Pro Asn Ser Gly Leu Cys Asn Glu
690                 695                 700

Asp His Leu Ser Tyr Phe Thr Phe Ile Gly Arg Val Ala Gly Leu Ala
705                 710                 715                 720

Val Phe His Gly Lys Leu Leu Asp Gly Phe Phe Ile Arg Pro Phe Tyr
                725                 730                 735

Lys Met Met Leu Gly Lys Gln Ile Thr Leu Asn Asp Met Glu Ser Val
                740                 745                 750

Asp Ser Glu Tyr Tyr Asn Ser Leu Lys Trp Ile Leu Glu Asn Asp Pro
            755                 760                 765

Thr Glu Leu Asp Leu Met Phe Cys Ile Asp Glu Glu Asn Phe Gly Gln
        770                 775                 780
```

```
Thr Tyr Gln Val Asp Leu Lys Pro Asn Gly Ser Glu Ile Met Val Thr
785                 790                 795                 800

Asn Glu Asn Lys Arg Glu Tyr Ile Asp Leu Val Ile Gln Trp Arg Phe
            805                 810                 815

Val Asn Arg Val Gln Lys Gln Met Asn Ala Phe Leu Glu Gly Phe Thr
        820                 825                 830

Glu Leu Leu Pro Ile Asp Leu Ile Lys Ile Phe Asp Glu Asn Glu Leu
    835                 840                 845

Glu Leu Leu Met Cys Gly Leu Gly Asp Val Asp Val Asn Asp Trp Arg
    850                 855                 860

Gln His Ser Ile Tyr Lys Asn Gly Tyr Cys Pro Asn His Pro Val Ile
865                 870                 875                 880

Gln Trp Phe Trp Lys Ala Val Leu Leu Met Asp Ala Glu Lys Arg Ile
            885                 890                 895

Arg Leu Leu Gln Phe Val Thr Gly Thr Ser Arg Val Pro Met Asn Gly
        900                 905                 910

Phe Ala Glu Leu Tyr Gly Ser Asn Gly Pro Gln Leu Phe Thr Ile Glu
    915                 920                 925

Gln Trp Gly Ser Pro Glu Lys Leu Pro Arg Ala His Thr Cys Phe Asn
    930                 935                 940

Arg Leu Asp Leu Pro Pro Tyr Glu Thr Phe Glu Asp Leu Arg Glu Lys
945                 950                 955                 960

Leu Leu Met Ala Val Glu Asn Ala Gln Gly Phe Glu Gly Val Asp
                965                 970                 975

<210> SEQ ID NO 39
<211> LENGTH: 1235
<212> TYPE: PRT
<213> ORGANISM: human
<220> FEATURE:
<221> NAME/KEY: misc_feature
<222> LOCATION: (1015)..(1015)
<223> OTHER INFORMATION: Xaa can be any naturally occurring amino acid

<400> SEQUENCE: 39

Met Arg Ser Arg Ser Asn Ser Gly Val Arg Leu Asp Gly Tyr Ala Arg
1               5                   10                  15

Leu Val Gln Gln Thr Ile Leu Cys Tyr Gln Asn Pro Val Thr Gly Leu
                20                  25                  30

Leu Ser Ala Ser His Glu Gln Lys Asp Ala Trp Val Arg Asp Asn Ile
            35                  40                  45

Tyr Ser Ile Leu Ala Val Trp Gly Leu Gly Met Ala Tyr Arg Lys Asn
    50                  55                  60

Ala Asp Arg Asp Glu Asp Lys Ala Lys Ala Tyr Glu Leu Glu Gln Asn
65                  70                  75                  80

Val Val Lys Leu Met Arg Gly Leu Leu Gln Cys Met Met Arg Gln Val
                85                  90                  95

Ala Lys Val Glu Lys Phe Lys His Thr Gln Ser Thr Lys Asp Ser Leu
                100                 105                 110

His Ala Lys Tyr Asn Thr Ala Thr Cys Gly Thr Val Val Gly Asp Asp
            115                 120                 125

Gln Trp Gly His Leu Gln Val Asp Ala Thr Ser Leu Phe Leu Leu Phe
    130                 135                 140

Leu Ala Gln Met Thr Ala Ser Gly Leu Arg Ile Ile Phe Thr Leu Asp
145                 150                 155                 160

Glu Val Ala Phe Ile Gln Asn Leu Val Phe Tyr Ile Glu Ala Ala Tyr
```

```
                165                 170                 175
Lys Val Ala Asp Tyr Gly Met Trp Glu Arg Gly Asp Lys Thr Asn Gln
                180                 185                 190

Gly Ile Pro Glu Leu Asn Ala Ser Ser Val Gly Met Ala Lys Ala Ala
                195                 200                 205

Leu Glu Ala Ile Asp Glu Leu Asp Leu Phe Gly Ala His Gly Gly Arg
                210                 215                 220

Lys Ser Val Ile His Val Leu Pro Asp Glu Val Glu His Cys Gln Ser
225                 230                 235                 240

Ile Leu Phe Ser Met Leu Pro Arg Ala Ser Thr Ser Lys Glu Ile Asp
                245                 250                 255

Ala Gly Leu Leu Ser Ile Ile Ser Phe Pro Ala Phe Ala Val Glu Asp
                260                 265                 270

Val Asn Leu Val Asn Val Thr Lys Asn Glu Ile Ile Ser Lys Leu Gln
                275                 280                 285

Gly Arg Tyr Gly Cys Cys Arg Phe Leu Arg Asp Gly Tyr Lys Thr Pro
                290                 295                 300

Arg Glu Asp Pro Asn Arg Leu His Tyr Asp Pro Ala Glu Leu Lys Leu
305                 310                 315                 320

Phe Glu Asn Ile Glu Cys Glu Trp Pro Val Phe Trp Thr Tyr Phe Ile
                325                 330                 335

Ile Asp Gly Val Phe Ser Gly Asp Ala Val Gln Val Gln Glu Tyr Arg
                340                 345                 350

Glu Ala Leu Glu Gly Ile Leu Ile Arg Gly Lys Asn Gly Ile Arg Leu
                355                 360                 365

Val Pro Glu Leu Tyr Ala Val Pro Pro Asn Lys Val Asp Glu Glu Tyr
                370                 375                 380

Lys Asn Pro His Thr Val Asp Arg Val Pro Met Gly Lys Val Pro His
385                 390                 395                 400

Leu Trp Gly Gln Ser Leu Tyr Ile Leu Ser Ser Leu Leu Ala Glu Gly
                405                 410                 415

Phe Leu Ala Ala Gly Glu Ile Asp Pro Leu Asn Arg Arg Phe Ser Thr
                420                 425                 430

Ser Val Lys Pro Asp Val Val Gln Val Thr Val Leu Ala Glu Asn
                435                 440                 445

Asn His Ile Lys Asp Leu Leu Arg Lys His Gly Val Asn Val Gln Ser
                450                 455                 460

Ile Ala Asp Ile His Pro Ile Gln Val Gln Pro Gly Arg Ile Leu Ser
465                 470                 475                 480

His Ile Tyr Ala Lys Leu Gly Arg Asn Lys Asn Met Asn Leu Ser Gly
                485                 490                 495

Arg Pro Tyr Arg His Ile Gly Val Leu Gly Thr Ser Lys Leu Tyr Val
                500                 505                 510

Ile Arg Asn Gln Ile Phe Thr Phe Thr Pro Gln Phe Thr Asp Gln His
                515                 520                 525

His Phe Tyr Leu Ala Leu Asp Asn Glu Met Ile Val Glu Met Leu Arg
                530                 535                 540

Ile Glu Leu Ala Tyr Leu Cys Thr Cys Trp Arg Met Thr Gly Arg Pro
545                 550                 555                 560

Thr Leu Thr Phe Pro Ile Ser Arg Thr Met Leu Thr Asn Asp Gly Ser
                565                 570                 575

Asp Ile His Ser Ala Val Leu Ser Thr Ile Arg Lys Leu Glu Asp Gly
                580                 585                 590
```

```
Tyr Phe Gly Gly Ala Arg Val Lys Leu Gly Asn Leu Ser Glu Phe Leu
        595                 600                 605

Thr Thr Ser Phe Tyr Thr Tyr Leu Thr Phe Leu Asp Pro Asp Cys Asp
    610                 615                 620

Glu Lys Leu Phe Asp Asn Ala Ser Glu Gly Thr Phe Ser Pro Asp Ser
625                 630                 635                 640

Asp Ser Asp Leu Val Gly Tyr Leu Glu Asp Thr Cys Asn Gln Glu Ser
            645                 650                 655

Gln Asp Glu Leu Asp His Tyr Ile Asn His Leu Leu Gln Ser Thr Ser
                660                 665                 670

Leu Arg Ser Tyr Leu Pro Pro Leu Cys Lys Asn Thr Glu Asp Arg His
        675                 680                 685

Val Phe Ser Ala Ile His Ser Thr Arg Asp Ile Leu Ser Val Met Ala
    690                 695                 700

Lys Ala Lys Gly Leu Glu Val Pro Phe Val Pro Met Thr Leu Pro Thr
705                 710                 715                 720

Lys Val Leu Ser Ala His Arg Lys Ser Leu Asn Leu Val Asp Ser Pro
            725                 730                 735

Gln Pro Leu Leu Glu Lys Val Pro Glu Ser Asp Phe Gln Trp Pro Arg
                740                 745                 750

Asp Asp His Gly Asp Val Asp Cys Glu Lys Leu Val Glu Gln Leu Lys
        755                 760                 765

Asp Cys Ser Asn Leu Gln Asp Gln Ala Asp Ile Leu Tyr Ile Leu Tyr
    770                 775                 780

Val Ile Lys Gly Pro Ser Trp Asp Thr Asn Leu Ser Gly Gln His Gly
785                 790                 795                 800

Val Thr Val Gln Asn Leu Leu Gly Glu Leu Tyr Gly Lys Ala Gly Leu
            805                 810                 815

Asn Gln Glu Trp Gly Leu Ile Arg Tyr Ile Ser Gly Leu Leu Arg Lys
                820                 825                 830

Lys Val Glu Val Leu Ala Glu Ala Cys Thr Asp Leu Leu Ser His Gln
        835                 840                 845

Lys Gln Leu Thr Val Gly Leu Pro Pro Glu Pro Arg Glu Lys Ile Ile
    850                 855                 860

Ser Ala Pro Leu Pro Pro Glu Leu Thr Lys Leu Ile Tyr Glu Ala
865                 870                 875                 880

Ser Gly Gln Asp Ile Ser Ile Ala Val Leu Thr Gln Glu Ile Val Val
            885                 890                 895

Tyr Leu Ala Met Tyr Val Arg Ala Gln Pro Ser Leu Phe Val Glu Met
                900                 905                 910

Leu Arg Leu Arg Ile Gly Leu Ile Ile Gln Val Met Ala Thr Glu Leu
        915                 920                 925

Ala Arg Ser Leu Asn Cys Ser Gly Glu Glu Ala Ser Glu Ser Leu Met
    930                 935                 940

Asn Leu Ser Pro Phe Asp Met Lys Asn Leu Leu His Ile Leu Ser
945                 950                 955                 960

Gly Lys Glu Phe Gly Val Glu Arg Ser Val Arg Pro Ile His Ser Ser
            965                 970                 975

Thr Ser Ser Pro Thr Ile Ser Ile His Glu Val Gly His Thr Gly Val
                980                 985                 990

Thr Lys Thr Glu Arg Ser Gly Ile  Asn Arg Leu Arg Ser  Glu Met Lys
        995                 1000                 1005
```

```
Gln Met Thr Arg Arg Phe Xaa Ala Asp Glu Gln Phe Phe Ser Val
    1010                1015                1020

Gly Gln Ala Ala Ser Ser Ser Ala His Ser Ser Lys Ser Ala Arg
    1025                1030                1035

Ser Ser Thr Pro Ser Ser Pro Thr Gly Thr Ser Ser Ser Asp Ser
    1040                1045                1050

Gly Gly His His Ile Gly Trp Gly Glu Arg Gln Gly Gln Trp Leu
    1055                1060                1065

Arg Arg Arg Arg Leu Asp Gly Ala Ile Asn Arg Val Pro Val Gly
    1070                1075                1080

Phe Tyr Gln Arg Val Trp Lys Ile Leu Gln Lys Cys His Gly Leu
    1085                1090                1095

Ser Ile Asp Gly Tyr Val Leu Pro Ser Ser Thr Thr Arg Glu Met
    1100                1105                1110

Thr Pro His Glu Ile Lys Phe Ala Val His Val Glu Ser Val Leu
    1115                1120                1125

Asn Arg Val Pro Gln Pro Glu Tyr Arg Gln Leu Leu Val Glu Ala
    1130                1135                1140

Ile Met Val Leu Thr Leu Leu Ser Asp Thr Glu Met Thr Ser Ile
    1145                1150                1155

Gly Gly Ile Ile His Val Asp Gln Ile Val Gln Met Ala Ser Gln
    1160                1165                1170

Leu Phe Leu Gln Asp Gln Val Ser Ile Gly Ala Met Asp Thr Leu
    1175                1180                1185

Glu Lys Asp Gln Ala Thr Gly Ile Cys His Phe Phe Tyr Asp Ser
    1190                1195                1200

Ala Pro Ser Gly Ala Tyr Gly Thr Met Thr Tyr Leu Thr Arg Ala
    1205                1210                1215

Val Ala Ser Tyr Leu Gln Glu Leu Leu Pro Asn Ser Gly Cys Gln
    1220                1225                1230

Met Gln
    1235

<210> SEQ ID NO 40
<211> LENGTH: 543
<212> TYPE: PRT
<213> ORGANISM: human
<220> FEATURE:
<221> NAME/KEY: misc_feature
<222> LOCATION: (12)..(12)
<223> OTHER INFORMATION: Xaa can be any naturally occurring amino acid

<400> SEQUENCE: 40

Met Glu Gly Pro Ala Gly Tyr Leu Arg Arg Ala Xaa Val Ala Gln Leu
1               5                   10                  15

Thr Gln Glu Leu Gly Thr Ala Phe Phe Gln Gln Gln Leu Pro Ala
            20                  25                  30

Ala Met Ala Asp Thr Phe Leu Glu His Leu Cys Leu Leu Asp Ile Asp
            35                  40                  45

Ser Glu Pro Val Ala Ala Arg Ser Thr Ser Ile Ile Ala Thr Ile Gly
    50                  55                  60

Pro Ala Ser Arg Ser Val Glu Arg Leu Lys Glu Met Ile Lys Ala Gly
65                  70                  75                  80

Met Asn Ile Ala Arg Leu Asn Phe Ser His Gly Ser His Glu Tyr His
                85                  90                  95

Ala Glu Thr Ile Ala Asn Val Arg Glu Ala Val Glu Ser Phe Ala Gly
```

```
            100                 105                 110
Ser Pro Leu Ser Tyr Arg Pro Val Ala Ile Ala Leu Asp Thr Lys Gly
            115                 120                 125

Pro Glu Ile Arg Thr Gly Ile Leu Gln Gly Gly Pro Glu Ser Glu Val
            130                 135                 140

Glu Leu Val Lys Gly Ser Gln Val Leu Val Thr Val Asp Pro Ala Phe
145                 150                 155                 160

Arg Thr Arg Gly Asn Ala Asn Thr Val Trp Val Asp Tyr Pro Asn Ile
                165                 170                 175

Val Arg Val Val Pro Val Gly Gly Arg Ile Tyr Ile Asp Asp Gly Leu
            180                 185                 190

Ile Ser Leu Val Val Gln Lys Ile Ser Pro Glu Gly Leu Val Thr Gln
            195                 200                 205

Val Glu Asn Gly Gly Val Leu Gly Ser Arg Lys Gly Val Asn Leu Pro
            210                 215                 220

Gly Ala Gln Val Asp Leu Pro Gly Leu Ser Glu Gln Asp Val Arg Asp
225                 230                 235                 240

Leu Arg Phe Gly Val Glu His Gly Val Asp Ile Val Phe Ala Ser Phe
                245                 250                 255

Val Arg Lys Ala Ser Asp Val Ala Ala Val Arg Ala Ala Leu Gly Pro
            260                 265                 270

Glu Gly His Gly Ile Lys Ile Ile Ser Lys Ile Glu Asn His Glu Gly
            275                 280                 285

Val Lys Arg Phe Asp Glu Ile Leu Glu Val Ser Asp Gly Ile Met Val
            290                 295                 300

Ala Arg Gly Asp Leu Gly Ile Glu Ile Pro Ala Glu Lys Val Phe Leu
305                 310                 315                 320

Ala Gln Lys Met Met Ile Gly Arg Cys Asn Leu Ala Gly Lys Pro Val
                325                 330                 335

Val Cys Ala Thr Gln Met Leu Glu Ser Met Ile Thr Lys Pro Arg Pro
            340                 345                 350

Thr Arg Ala Glu Thr Ser Asp Val Ala Asn Ala Val Leu Asp Gly Ala
            355                 360                 365

Asp Cys Ile Met Leu Ser Gly Glu Thr Ala Lys Gly Asn Phe Pro Val
            370                 375                 380

Glu Ala Val Lys Met Gln His Arg Ile Ala Arg Glu Ala Glu Ala Ala
385                 390                 395                 400

Val Tyr His Arg Gln Leu Phe Glu Glu Leu Arg Arg Ala Ala Pro Leu
                405                 410                 415

Ser Arg Asp Pro Thr Glu Val Thr Ala Ile Gly Ala Val Glu Ala Ala
            420                 425                 430

Phe Lys Cys Cys Ala Ala Ala Ile Val Leu Thr Thr Thr Gly Arg
            435                 440                 445

Ser Ala Gln Leu Leu Ser Arg Tyr Arg Pro Arg Ala Ala Val Ile Ala
            450                 455                 460

Val Thr Arg Ser Ala Gln Ala Ala Arg Gln Val His Leu Cys Arg Gly
465                 470                 475                 480

Val Phe Pro Leu Leu Tyr Arg Glu Pro Pro Glu Ala Ile Trp Ala Asp
                485                 490                 495

Asp Val Asp Arg Arg Val Gln Phe Gly Ile Glu Ser Gly Lys Leu Arg
            500                 505                 510

Gly Phe Leu Arg Val Gly Asp Leu Val Ile Val Val Thr Gly Trp Arg
            515                 520                 525
```

-continued

Pro Gly Ser Gly Tyr Thr Asn Ile Met Arg Val Leu Ser Ile Ser
    530                 535                 540

<210> SEQ ID NO 41
<211> LENGTH: 184
<212> TYPE: PRT
<213> ORGANISM: human
<220> FEATURE:
<221> NAME/KEY: misc_feature
<222> LOCATION: (180)..(180)
<223> OTHER INFORMATION: Xaa can be any naturally occurring amino acid

<400> SEQUENCE: 41

Met Arg Glu Tyr Lys Leu Val Val Leu Gly Ser Gly Gly Val Gly Lys
1               5                   10                  15

Ser Ala Leu Thr Val Gln Phe Val Gln Gly Ile Phe Val Glu Lys Tyr
            20                  25                  30

Asp Pro Thr Ile Glu Asp Ser Tyr Arg Lys Gln Val Glu Val Asp Cys
        35                  40                  45

Gln Gln Cys Met Leu Glu Ile Leu Asp Thr Ala Gly Thr Glu Gln Phe
    50                  55                  60

Thr Ala Met Arg Asp Leu Tyr Met Lys Asn Gly Gln Gly Phe Ala Leu
65                  70                  75                  80

Val Tyr Ser Ile Thr Ala Gln Ser Thr Phe Asn Asp Leu Gln Asp Leu
                85                  90                  95

Arg Glu Gln Ile Leu Arg Val Lys Asp Thr Glu Asp Val Pro Met Ile
            100                 105                 110

Leu Val Gly Asn Lys Cys Asp Leu Glu Asp Glu Arg Val Val Gly Lys
        115                 120                 125

Glu Gln Gly Gln Asn Leu Ala Arg Gln Trp Cys Asn Cys Ala Phe Leu
    130                 135                 140

Glu Ser Ser Ala Lys Ser Lys Ile Asn Val Asn Glu Ile Phe Tyr Asp
145                 150                 155                 160

Leu Val Arg Gln Ile Asn Arg Lys Thr Pro Val Glu Lys Lys Lys Pro
                165                 170                 175

Lys Lys Lys Xaa Cys Leu Leu Leu
            180

<210> SEQ ID NO 42
<211> LENGTH: 114
<212> TYPE: PRT
<213> ORGANISM: rat
<220> FEATURE:
<221> NAME/KEY: misc_feature
<222> LOCATION: (101)..(101)
<223> OTHER INFORMATION: Xaa can be any naturally occurring amino acid
<220> FEATURE:
<221> NAME/KEY: misc_feature
<222> LOCATION: (109)..(109)
<223> OTHER INFORMATION: Xaa can be any naturally occurring amino acid

<400> SEQUENCE: 42

Met Asp Thr Lys Met Gln Ser Leu Pro Thr Thr His Pro His Pro His
1               5                   10                  15

Ser Ser Ser Arg Pro Gln Ser His Thr Asn Asn Gln Cys Ala Cys Ser
            20                  25                  30

His His Cys Arg Ser Cys Ser Gln Ala Gly His Pro Ser Ser Ser Ser
        35                  40                  45

Ser Pro Ser Pro Gly Pro Pro Thr Lys His Pro Lys Thr Pro Met His
    50                  55                  60

```
Ser Arg Tyr Ser Pro Ser Arg Pro Ser His Arg Gly Ser Cys Pro Lys
 65                  70                  75                  80

Asn Arg Lys Thr Leu Glu Gly Lys Val Ser Arg Lys Ala Val Arg
                 85                  90                  95

Arg Arg Lys Arg Xaa His Arg Ala Lys Arg Arg Ser Xaa Gly Arg Arg
            100                 105                 110

Tyr Lys
```

<210> SEQ ID NO 43
<211> LENGTH: 391
<212> TYPE: PRT
<213> ORGANISM: rat
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (219)..(219)
<223> OTHER INFORMATION: Xaa can be any naturally occurring amino acid
<220> FEATURE:
<221> NAME/KEY: misc_feature
<222> LOCATION: (313)..(313)
<223> OTHER INFORMATION: Xaa can be any naturally occurring amino acid

<400> SEQUENCE: 43

```
Met Gly Ala Ser Glu Arg Ser Val Phe Arg Val Leu Ile Arg Ala Leu
  1               5                  10                  15

Thr Glu Arg Met Phe Lys His Leu Arg Arg Trp Phe Ile Thr His Ile
                 20                  25                  30

Phe Gly Arg Ser Arg Gln Arg Ala Arg Leu Val Xaa Lys Glu Gly Arg
             35                  40                  45

Cys Asn Ile Glu Phe Gly Asn Val Asp Ala Gln Ser Arg Phe Ile Phe
 50                  55                  60

Phe Val Asp Ile Trp Thr Thr Val Leu Asp Leu Lys Trp Arg Tyr Lys
 65                  70                  75                  80

Met Thr Val Phe Ile Thr Ala Phe Leu Gly Ser Trp Phe Leu Phe Gly
                 85                  90                  95

Leu Leu Trp Tyr Val Val Ala Tyr Val His Lys Asp Leu Pro Glu Phe
            100                 105                 110

Tyr Pro Pro Asp Asn Arg Thr Pro Cys Val Glu Asn Ile Asn Gly Met
            115                 120                 125

Thr Ser Ala Phe Leu Phe Ser Leu Glu Thr Gln Val Thr Ile Gly Tyr
130                 135                 140

Gly Phe Arg Phe Val Thr Glu Gln Cys Ala Thr Ala Ile Phe Leu Leu
145                 150                 155                 160

Ile Phe Gln Ser Ile Leu Gly Val Ile Ile Asn Ser Phe Met Cys Gly
                165                 170                 175

Ala Ile Leu Ala Lys Ile Ser Arg Pro Lys Lys Arg Ala Lys Thr Ile
            180                 185                 190

Thr Phe Ser Lys Asn Ala Val Ile Ser Lys Arg Gly Gly Lys Leu Cys
            195                 200                 205

Leu Leu Ile Arg Val Ala Asn Leu Arg Lys Xaa Leu Leu Ile Gly Ser
        210                 215                 220

His Ile Tyr Gly Lys Leu Leu Lys Thr Thr Ile Thr Pro Glu Gly Glu
225                 230                 235                 240

Thr Ile Ile Leu Asp Gln Thr Asn Ile Asn Phe Val Val Asp Ala Gly
                245                 250                 255
```

Asn Glu Asn Leu Phe Phe Ile Ser Pro Leu Thr Ile Tyr His Ile Ile
            260                 265                 270

Asp His Asn Ser Pro Phe Phe His Met Ala Ala Glu Thr Leu Ser Gln
        275                 280                 285

Gln Asp Phe Glu Leu Val Val Phe Leu Asp Gly Thr Val Glu Ser Thr
    290                 295                 300

Ser Ala Thr Cys Gln Val Arg Thr Xaa Tyr Val Pro Glu Glu Val Leu
305                 310                 315                 320

Trp Gly Tyr Arg Phe Val Pro Ile Val Ser Lys Thr Lys Glu Gly Lys
                325                 330                 335

Tyr Arg Val Asp Phe His Asn Phe Gly Lys Thr Val Glu Val Glu Thr
            340                 345                 350

Pro His Cys Ala Met Cys Leu Tyr Asn Glu Lys Asp Ala Arg Ala Arg
        355                 360                 365

Met Lys Arg Gly Tyr Asp Asn Pro Asn Phe Val Leu Ser Glu Val Asp
    370                 375                 380

Glu Thr Asp Asp Thr Gln Met
385                 390

<210> SEQ ID NO 44
<211> LENGTH: 391
<212> TYPE: PRT
<213> ORGANISM: human
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (219)..(219)
<223> OTHER INFORMATION: Xaa can be any naturally occurring amino acid
<220> FEATURE:
<221> NAME/KEY: misc_feature
<222> LOCATION: (313)..(313)
<223> OTHER INFORMATION: Xaa can be any naturally occurring amino acid

<400> SEQUENCE: 44

Met Asn Ala Ser Ser Arg Asn Val Phe Asp Thr Leu Ile Arg Val Leu
1               5                   10                  15

Thr Glu Ser Met Phe Lys His Leu Arg Lys Trp Val Val Thr Arg Phe
            20                  25                  30

Phe Gly His Ser Arg Gln Arg Ala Arg Leu Val Xaa Lys Asp Gly Arg
        35                  40                  45

Cys Asn Ile Glu Phe Gly Asn Val Glu Ala Gln Ser Arg Phe Ile Phe
    50                  55                  60

Phe Val Asp Ile Trp Thr Thr Val Leu Asp Leu Lys Trp Arg Tyr Lys
65                  70                  75                  80

Met Thr Ile Phe Ile Thr Ala Phe Leu Gly Ser Trp Phe Phe Gly
                85                  90                  95

Leu Leu Trp Tyr Ala Val Ala Tyr Ile His Lys Asp Leu Pro Glu Phe
            100                 105                 110

His Pro Ser Ala Asn His Thr Pro Cys Val Glu Asn Ile Asn Gly Leu
        115                 120                 125

Thr Ser Ala Phe Leu Phe Ser Leu Glu Thr Gln Val Thr Ile Gly Tyr
    130                 135                 140

Gly Phe Arg Cys Val Thr Glu Gln Cys Ala Thr Ala Ile Phe Leu Leu
145                 150                 155                 160

Ile Phe Gln Ser Ile Leu Gly Val Ile Ile Asn Ser Phe Met Cys Gly

```
                    165                 170                 175
Ala Ile Leu Ala Lys Ile Ser Arg Pro Lys Lys Arg Ala Lys Thr Ile
                180                 185                 190

Thr Phe Ser Lys Asn Ala Val Ile Ser Lys Arg Gly Gly Lys Leu Cys
            195                 200                 205

Leu Leu Ile Arg Val Ala Asn Leu Arg Lys Xaa Leu Leu Ile Gly Ser
        210                 215                 220

His Ile Tyr Gly Lys Leu Leu Lys Thr Thr Val Thr Pro Glu Gly Glu
225                 230                 235                 240

Thr Ile Ile Leu Asp Gln Ile Asn Ile Asn Phe Val Val Asp Ala Gly
                245                 250                 255

Asn Glu Asn Leu Phe Phe Ile Ser Pro Leu Thr Ile Tyr His Val Ile
            260                 265                 270

Asp His Asn Ser Pro Phe Phe His Met Ala Ala Glu Thr Leu Leu Gln
        275                 280                 285

Gln Asp Phe Glu Leu Val Val Phe Leu Asp Gly Thr Val Glu Ser Thr
    290                 295                 300

Ser Ala Thr Cys Gln Val Arg Thr Xaa Tyr Val Pro Glu Glu Val Leu
305                 310                 315                 320

Trp Gly Tyr Arg Phe Ala Pro Ile Val Ser Lys Thr Lys Glu Gly Lys
                325                 330                 335

Tyr Arg Val Asp Phe His Asn Phe Ser Lys Thr Val Glu Val Glu Thr
            340                 345                 350

Pro His Cys Ala Met Cys Leu Tyr Asn Glu Lys Asp Val Arg Ala Arg
        355                 360                 365

Met Lys Arg Gly Tyr Asp Asn Pro Asn Phe Ile Leu Ser Glu Val Asn
    370                 375                 380

Glu Thr Asp Asp Thr Lys Met
385                 390

<210> SEQ ID NO 45
<211> LENGTH: 372
<212> TYPE: PRT
<213> ORGANISM: human
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (200)..(200)
<223> OTHER INFORMATION: Xaa can be any naturally occurring amino acid
<220> FEATURE:
<221> NAME/KEY: misc_feature
<222> LOCATION: (294)..(294)
<223> OTHER INFORMATION: Xaa can be any naturally occurring amino acid

<400> SEQUENCE: 45

Met Phe Lys His Leu Arg Lys Trp Val Thr Arg Phe Phe Gly His
1               5                   10                  15

Ser Arg Gln Arg Ala Arg Leu Val Xaa Lys Asp Gly Arg Cys Asn Ile
                20                  25                  30

Glu Phe Gly Asn Val Glu Ala Gln Ser Arg Phe Ile Phe Phe Val Asp
            35                  40                  45

Ile Trp Thr Thr Val Leu Asp Leu Lys Trp Arg Tyr Lys Met Thr Ile
        50                  55                  60

Phe Ile Thr Ala Phe Leu Gly Ser Trp Phe Phe Gly Leu Leu Trp
65                  70                  75                  80
```

```
Tyr Ala Val Ala Tyr Ile His Lys Asp Leu Pro Glu Phe His Pro Ser
                85                  90                  95
Ala Asn His Thr Pro Cys Val Glu Asn Ile Asn Gly Leu Thr Ser Ala
           100                 105                 110
Phe Leu Phe Ser Leu Glu Thr Gln Val Thr Ile Gly Tyr Gly Phe Arg
           115                 120                 125
Cys Val Thr Glu Gln Cys Ala Thr Ala Ile Phe Leu Leu Ile Phe Gln
           130                 135                 140
Ser Ile Leu Gly Val Ile Ile Asn Ser Phe Met Cys Gly Ala Ile Leu
145                 150                 155                 160
Ala Lys Ile Ser Arg Pro Lys Lys Arg Ala Lys Thr Ile Thr Phe Ser
                165                 170                 175
Lys Asn Ala Val Ile Ser Lys Arg Gly Gly Lys Leu Cys Leu Leu Ile
           180                 185                 190
Arg Val Ala Asn Leu Arg Lys Xaa Leu Leu Ile Gly Ser His Ile Tyr
           195                 200                 205
Gly Lys Leu Leu Lys Thr Thr Val Thr Pro Glu Gly Glu Thr Ile Ile
           210                 215                 220
Leu Asp Gln Ile Asn Ile Asn Phe Val Val Asp Ala Gly Asn Glu Asn
225                 230                 235                 240
Leu Phe Phe Ile Ser Pro Leu Thr Ile Tyr His Val Ile Asp His Asn
                245                 250                 255
Ser Pro Phe Phe His Met Ala Ala Glu Thr Leu Leu Gln Gln Asp Phe
           260                 265                 270
Glu Leu Val Val Phe Leu Asp Gly Thr Val Glu Ser Thr Ser Ala Thr
           275                 280                 285
Cys Gln Val Arg Thr Xaa Tyr Val Pro Glu Glu Val Leu Trp Gly Tyr
290                 295                 300
Arg Phe Ala Pro Ile Val Ser Lys Thr Lys Glu Gly Lys Tyr Arg Val
305                 310                 315                 320
Asp Phe His Asn Phe Ser Lys Thr Val Glu Val Glu Thr Pro His Cys
                325                 330                 335
Ala Met Cys Leu Tyr Asn Glu Lys Asp Val Arg Ala Arg Met Lys Arg
           340                 345                 350
Gly Tyr Asp Asn Pro Asn Phe Ile Leu Ser Glu Val Asn Glu Thr Asp
           355                 360                 365
Asp Thr Lys Met
    370

<210> SEQ ID NO 46
<211> LENGTH: 136
<212> TYPE: PRT
<213> ORGANISM: human
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (112)..(112)
<223> OTHER INFORMATION: Xaa can be any naturally occurring amino acid
<220> FEATURE:
<221> NAME/KEY: misc_feature
<222> LOCATION: (126)..(126)
<223> OTHER INFORMATION: Xaa can be any naturally occurring amino acid

<400> SEQUENCE: 46

Met Ala Gly Ala Gly Ser Ala Ala Val Ser Gly Ala Gly Thr Pro Val
1               5                   10                  15
```

```
Ala Gly Pro Thr Gly Arg Asp Leu Phe Ala Glu Gly Leu Leu Glu Phe
            20                  25                  30

Leu Arg Pro Ala Val Gln Gln Leu Asp Ser His Val His Ala Val Arg
        35                  40                  45

Glu Xaa Gln Val Glu Leu Arg Glu Gln Ile Asp Asn Leu Ala Thr Glu
 50                  55                  60

Leu Cys Arg Ile Asn Glu Asp Gln Lys Val Ala Leu Asp Leu Asp Pro
 65                  70                  75                  80

Tyr Val Lys Lys Leu Leu Asn Ala Arg Arg Val Val Leu Val Asn
                85                  90                  95

Asn Ile Leu Gln Asn Ala Gln Glu Arg Leu Arg Arg Leu Asn His Xaa
            100                 105                 110

Val Ala Lys Glu Thr Ala Arg Arg Ala Met Leu Asp Xaa Gly Ile
        115                 120                 125

Tyr Pro Pro Gly Ser Pro Gly Lys
    130                 135
```

<210> SEQ ID NO 47
<211> LENGTH: 817
<212> TYPE: PRT
<213> ORGANISM: rat
<220> FEATURE:
<221> NAME/KEY: misc_feature
<222> LOCATION: (94)..(94)
<223> OTHER INFORMATION: Xaa can be any naturally occurring amino acid
<220> FEATURE:
<221> NAME/KEY: misc_feature
<222> LOCATION: (177)..(177)
<223> OTHER INFORMATION: Xaa can be any naturally occurring amino acid

<400> SEQUENCE: 47

```
Met Met Lys Thr Glu Pro Arg Gly Pro Gly Pro Leu Arg Ser Ala
 1               5                  10                  15

Ser Pro His Arg Ser Ala Tyr Glu Ala Gly Ile Gln Ala Leu Lys Pro
            20                  25                  30

Pro Asp Ala Pro Gly Pro Asp Glu Ala Pro Lys Ala Ala His His Lys
        35                  40                  45

Lys Tyr Gly Ser Asn Val His Arg Ile Lys Ser Met Phe Leu Gln Met
 50                  55                  60

Gly Thr Thr Thr Gly Pro Pro Gly Glu Ala Gly Gly Ala Ser Gly Met
 65                  70                  75                  80

Ala Glu Ala Pro Arg Ala Ser Asp Arg Gly Val Arg Leu Xaa Leu Pro
            85                  90                  95

Arg Ala Ser Ser Leu Asn Glu Asn Val Asp His Ser Ala Leu Leu Lys
        100                 105                 110

Leu Gly Thr Ser Val Ser Glu Arg Val Ser Arg Phe Asp Ser Lys Pro
        115                 120                 125

Ala Pro Ser Ala Gln Pro Ala Pro Pro His Pro Pro Ser Arg Leu
    130                 135                 140

Gln Glu Thr Arg Lys Leu Phe Glu Arg Ser Val Pro Ala Ala Ser Gly
145                 150                 155                 160

Gly Asp Lys Glu Ala Val Ala Arg Arg Leu Leu Arg Gln Glu Arg Ala
                165                 170                 175

Xaa Leu Gln Asp Arg Lys Leu Asp Val Val Arg Phe Asn Gly Ser
    180                 185                 190

Thr Glu Ala Leu Asp Lys Leu Asp Ala Asp Ala Val Ser Pro Thr Val
        195                 200                 205
```

```
Ser Gln Leu Ser Ala Val Phe Glu Lys Ala Asp Ser Arg Thr Gly Leu
    210                 215                 220

His Arg Ala Pro Gly Pro Arg Ala Ala Gly Ala Pro Gln Val Asn
225                 230                 235                 240

Ser Lys Leu Val Thr Lys Arg Ser Arg Val Phe Gln Pro Pro Pro
                245                 250                 255

Pro Pro Ala Pro Ser Gly Asp Ala Ala Thr Glu Lys Asp Arg Gly Pro
            260                 265                 270

Gly Gly Gln Gln Pro Pro Gln His Arg Val Ala Pro Ala Arg Pro Pro
            275                 280                 285

Pro Lys Pro Arg Glu Val Arg Lys Ile Lys Pro Val Glu Val Glu Glu
        290                 295                 300

Ser Gly Glu Ser Glu Ala Glu Ser Ala Pro Gly Glu Val Ile Gln Ala
305                 310                 315                 320

Glu Val Thr Val His Ala Ala Leu Glu Asn Gly Ser Thr Thr Ala Thr
                325                 330                 335

Thr Ala Ser Pro Ala Pro Glu Pro Lys Ala Glu Ala Val Pro Glu
                340                 345                 350

Glu Glu Ala Ser Ser Val Ala Thr Leu Glu Arg Gly Val Asp Asn
        355                 360                 365

Gly Arg Ala Pro Asp Met Ala Pro Glu Glu Val Asp Glu Ser Lys Lys
370                 375                 380

Glu Asp Phe Ser Glu Ala Asp Leu Val Asp Val Ser Ala Tyr Ser Gly
385                 390                 395                 400

Leu Gly Glu Asp Ser Gly Gly Ser Ala Leu Glu Glu Asp Asp Glu Glu
                405                 410                 415

Asp Glu Glu Asp Gly Glu Pro Pro Tyr Glu Pro Glu Ser Gly Cys Val
            420                 425                 430

Glu Ile Pro Gly Leu Ser Glu Glu Asp Pro Ala Pro Ser Arg Lys
        435                 440                 445

Ile His Phe Ser Thr Ala Pro Ile Gln Val Phe Ser Thr Tyr Ser Asn
    450                 455                 460

Glu Asp Tyr Asp Arg Arg Asn Glu Asp Val Asp Pro Met Ala Ala Ser
465                 470                 475                 480

Ala Glu Tyr Glu Leu Glu Lys Arg Val Glu Arg Leu Glu Leu Phe Pro
                485                 490                 495

Val Glu Leu Glu Lys Asp Ser Glu Gly Leu Gly Ile Ser Ile Ile Gly
            500                 505                 510

Met Gly Ala Gly Ala Asp Met Gly Leu Glu Lys Leu Gly Ile Phe Val
        515                 520                 525

Lys Thr Val Thr Glu Gly Gly Ala Ala His Arg Asp Gly Arg Ile Gln
    530                 535                 540

Val Asn Asp Leu Leu Val Glu Val Asp Gly Thr Ser Leu Val Gly Val
545                 550                 555                 560

Thr Gln Ser Phe Ala Ala Ser Val Leu Arg Asn Thr Lys Gly Arg Val
                565                 570                 575

Arg Phe Met Ile Gly Arg Glu Arg Pro Gly Glu Gln Ser Glu Val Ala
            580                 585                 590

Gln Leu Ile Gln Gln Thr Leu Glu Gln Glu Arg Trp Gln Arg Glu Met
        595                 600                 605

Met Glu Gln Arg Tyr Ala Gln Tyr Gly Glu Asp Glu Glu Thr Gly
    610                 615                 620
```

| | | | | | | | | | | | | | | | |
|---|---|---|---|---|---|---|---|---|---|---|---|---|---|---|---|
|Glu|Tyr|Ala|Thr|Asp|Glu|Asp|Glu|Leu|Ser|Pro|Thr|Phe|Pro|Gly|
|625| | | | |630| | | | |635| | | | |640|

Gly Glu Met Ala Ile Glu Val Phe Glu Leu Ala Glu Asn Glu Asp Ala
                              645                       650                           655

Leu Ser Pro Val Glu Met Glu Pro Glu Lys Leu Val His Lys Phe Lys
               660                       665                         670

Glu Leu Gln Ile Lys His Ala Val Thr Glu Ala Glu Ile Gln Gln Leu
             675                     680                       685

Lys Arg Lys Leu Gln Ser Leu Glu Gln Glu Lys Gly Arg Trp Arg Val
     690                   695                   700

Glu Lys Ala Gln Leu Glu Gln Ser Val Glu Glu Asn Lys Glu Arg Met
705                  710                   715               720

Glu Lys Leu Glu Gly Tyr Trp Gly Glu Ala Gln Ser Leu Cys Gln Ala
             725                     730                       735

Val Asp Glu His Leu Arg Glu Thr Gln Ala Gln Tyr Gln Ala Leu Glu
               740                     745                   750

Arg Lys Tyr Ser Lys Ala Lys Arg Leu Ile Lys Asp Tyr Gln Gln Lys
         755                   760                   765

Glu Ile Glu Phe Leu Lys Lys Glu Thr Ala Gln Arg Arg Val Leu Glu
     770                   775                   780

Glu Ser Glu Leu Ala Arg Lys Glu Met Asp Lys Leu Leu Asp Lys
785                  790                   795               800

Ile Ser Glu Leu Glu Gly Asn Leu Gln Thr Leu Arg Asn Ser Asn Ser
         805                   810                   815

Thr

<210> SEQ ID NO 48
<211> LENGTH: 441
<212> TYPE: PRT
<213> ORGANISM: human
<220> FEATURE:
<221> NAME/KEY: misc_feature
<222> LOCATION: (198)..(199)
<223> OTHER INFORMATION: Xaa can be any naturally occurring amino acid
<220> FEATURE:
<221> NAME/KEY: misc_feature
<222> LOCATION: (202)..(202)
<223> OTHER INFORMATION: Xaa can be any naturally occurring amino acid
<220> FEATURE:
<221> NAME/KEY: misc_feature
<222> LOCATION: (214)..(214)
<223> OTHER INFORMATION: Xaa can be any naturally occurring amino acid
<220> FEATURE:
<221> NAME/KEY: misc_feature
<222> LOCATION: (262)..(262)
<223> OTHER INFORMATION: Xaa can be any naturally occurring amino acid
<220> FEATURE:
<221> NAME/KEY: misc_feature
<222> LOCATION: (356)..(356)
<223> OTHER INFORMATION: Xaa can be any naturally occurring amino acid
<220> FEATURE:
<221> NAME/KEY: misc_feature
<222> LOCATION: (396)..(396)
<223> OTHER INFORMATION: Xaa can be any naturally occurring amino acid

<400> SEQUENCE: 48

Met Ala Glu Pro Arg Gln Glu Phe Glu Val Met Glu Asp His Ala Gly
1                  5                    10                   15

Thr Tyr Gly Leu Gly Asp Arg Lys Asp Gln Gly Gly Tyr Thr Met His
              20                   25                  30

Gln Asp Gln Glu Gly Asp Thr Asp Ala Gly Leu Lys Glu Ser Pro Leu
         35                  40                  45

```
Gln Thr Pro Thr Glu Asp Gly Ser Glu Pro Gly Ser Glu Thr Ser
     50                  55                  60

Asp Ala Lys Ser Thr Pro Thr Ala Glu Asp Val Thr Ala Pro Leu Val
 65                  70                  75                  80

Asp Glu Gly Ala Pro Gly Lys Gln Ala Ala Gln Pro His Thr Glu
                 85                  90                  95

Ile Pro Glu Gly Thr Thr Ala Glu Glu Ala Gly Ile Gly Asp Thr Pro
                100                 105                 110

Ser Leu Glu Asp Glu Ala Ala Gly His Val Thr Gln Ala Arg Met Val
            115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Ser Ser Gly Glu Pro Lys Ser Gly
            180                 185                 190                 Gly

Asp Arg Ser Gly Tyr Xaa Xaa Pro Gly Xaa Pro Gly Thr Pro Gly Ser
    195                 200                 205

Arg Ser Arg Thr Pro Xaa Leu Pro Thr Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Xaa Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Xaa Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
    370                 375                 380

Lys Thr Asp His Gly Ala Glu Ile Val Tyr Lys Xaa Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
    435                 440

<210> SEQ ID NO 49
<211> LENGTH: 369
<212> TYPE: PRT
```

```
<213> ORGANISM: human
<220> FEATURE:
<221> NAME/KEY: misc_feature
<222> LOCATION: (331)..(331)
<223> OTHER INFORMATION: Xaa can be any naturally occurring amino acid

<400> SEQUENCE: 49

Met Trp Pro Asn Gly Ser Ser Leu Gly Pro Cys Phe Arg Pro Thr Asn
1               5                   10                  15

Ile Thr Leu Glu Glu Arg Arg Leu Ile Ala Ser Pro Trp Phe Ala Ala
            20                  25                  30

Ser Phe Cys Val Val Gly Leu Ala Ser Asn Leu Leu Ala Leu Ser Val
        35                  40                  45

Leu Ala Gly Ala Arg Gln Gly Ser His Thr Arg Ser Ser Phe Leu
50                  55                  60

Thr Phe Leu Cys Gly Leu Val Leu Thr Asp Phe Leu Gly Leu Leu Val
65                  70                  75                  80

Thr Gly Thr Ile Val Ser Gln His Ala Ala Leu Phe Glu Trp His
                85                  90                  95

Ala Val Asp Pro Gly Cys Arg Leu Cys Arg Phe Met Gly Val Val Met
            100                 105                 110

Ile Phe Phe Gly Leu Ser Pro Leu Leu Leu Gly Ala Ala Met Ala Ser
            115                 120                 125

Glu Arg Tyr Leu Gly Ile Thr Arg Pro Phe Ser Arg Pro Ala Val Ala
            130                 135                 140

Ser Gln Arg Arg Ala Trp Ala Thr Val Gly Leu Val Trp Ala Ala Ala
145                 150                 155                 160

Leu Ala Leu Gly Leu Leu Pro Leu Leu Gly Val Gly Arg Tyr Thr Val
                165                 170                 175

Gln Tyr Pro Gly Ser Trp Cys Phe Leu Thr Leu Gly Ala Glu Ser Gly
            180                 185                 190

Asp Val Ala Phe Gly Leu Leu Phe Ser Met Leu Gly Gly Leu Ser Val
            195                 200                 205

Gly Leu Ser Phe Leu Leu Asn Thr Val Ser Val Ala Thr Leu Cys His
210                 215                 220

Val Tyr His Gly Gln Glu Ala Ala Gln Gln Arg Pro Arg Asp Ser Glu
225                 230                 235                 240

Val Glu Met Met Ala Gln Leu Leu Gly Ile Met Val Val Ala Ser Val
                245                 250                 255

Cys Trp Leu Pro Leu Leu Val Phe Ile Ala Gln Thr Val Leu Arg Asn
            260                 265                 270

Pro Pro Ala Met Ser Pro Ala Gly Gln Leu Ser Arg Thr Thr Glu Lys
            275                 280                 285

Glu Leu Leu Ile Tyr Leu Arg Val Ala Thr Trp Asn Gln Ile Leu Asp
            290                 295                 300

Pro Trp Val Tyr Ile Leu Phe Arg Arg Ala Val Leu Arg Arg Leu Gln
305                 310                 315                 320

Pro Arg Leu Ser Thr Arg Pro Ser Gly Val Xaa Leu Cys Gly Pro Ala
                325                 330                 335

Trp Ser Thr Val Ala Arg Ser Arg Leu Thr Ala Thr Ser Ala Ser Arg
            340                 345                 350

Val Gln Ala Ile Leu Val Pro Gln Pro Glu Gln Leu Gly Leu Gln
        355                 360                 365

Ala
```

<210> SEQ ID NO 50
<211> LENGTH: 498
<212> TYPE: PRT
<213> ORGANISM: rat
<220> FEATURE:
<221> NAME/KEY: misc_feature
<222> LOCATION: (40)..(40)
<223> OTHER INFORMATION: Xaa can be any naturally occurring amino acid

<400> SEQUENCE: 50

```
Met Pro Thr Pro Ser Ala Pro Ser Pro Gln Pro Lys Gly Phe Arg Arg
1               5                   10                  15

Ala Val Ser Glu Gln Asp Ala Lys Gln Ala Glu Ala Val Thr Ser Pro
            20                  25                  30

Arg Phe Ile Gly Arg Arg Gln Xaa Leu Ile Glu Asp Ala Arg Lys Glu
        35                  40                  45

Arg Glu Ala Ala Ala Ala Ala Ala Ala Ala Val Ala Ser Ser Glu
    50                  55                  60

Pro Gly Asn Pro Leu Glu Ala Val Val Phe Glu Arg Asp Gly Asn
65                  70                  75                  80

Ala Val Leu Asn Leu Leu Phe Ser Leu Arg Gly Thr Lys Pro Ser Ser
                85                  90                  95

Leu Ser Arg Ala Val Lys Val Phe Glu Thr Phe Glu Ala Lys Ile His
            100                 105                 110

His Leu Glu Thr Arg Pro Ala Gln Arg Pro Leu Ala Gly Ser Pro His
        115                 120                 125

Leu Glu Tyr Phe Val Arg Phe Glu Val Pro Ser Gly Asp Leu Ala Ala
    130                 135                 140

Leu Leu Ser Ser Val Arg Arg Val Ser Asp Asp Val Arg Ser Ala Arg
145                 150                 155                 160

Glu Asp Lys Val Pro Trp Phe Pro Arg Lys Val Ser Glu Leu Asp Lys
                165                 170                 175

Cys His His Leu Val Thr Lys Phe Asp Pro Asp Leu Asp Leu Asp His
            180                 185                 190

Pro Gly Phe Ser Asp Gln Val Tyr Arg Gln Arg Arg Lys Leu Ile Ala
        195                 200                 205

Glu Ile Ala Phe Gln Tyr Lys His Gly Glu Pro Ile Pro His Val Glu
    210                 215                 220

Tyr Thr Ala Glu Glu Ile Ala Thr Trp Lys Glu Val Tyr Val Thr Leu
225                 230                 235                 240

Lys Gly Leu Tyr Ala Thr His Ala Cys Arg Glu His Leu Glu Gly Phe
                245                 250                 255

Gln Leu Leu Glu Arg Tyr Cys Gly Tyr Arg Glu Asp Ser Ile Pro Gln
            260                 265                 270

Leu Glu Asp Val Ser Arg Phe Leu Lys Glu Arg Thr Gly Phe Gln Leu
        275                 280                 285

Arg Pro Val Ala Gly Leu Leu Ser Ala Arg Asp Phe Leu Ala Ser Leu
    290                 295                 300

Ala Phe Arg Val Phe Gln Cys Thr Gln Tyr Ile Arg His Ala Ser Ser
305                 310                 315                 320

Pro Met His Ser Pro Glu Pro Asp Cys Cys His Glu Leu Leu Gly His
                325                 330                 335

Val Pro Met Leu Ala Asp Arg Thr Phe Ala Gln Phe Ser Gln Asp Ile
            340                 345                 350

Gly Leu Ala Ser Leu Gly Ala Ser Asp Glu Glu Ile Glu Lys Leu Ser
```

```
                    355                 360                 365
Thr Val Tyr Trp Phe Thr Val Glu Phe Gly Leu Cys Lys Gln Asn Gly
            370                 375                 380

Glu Leu Lys Ala Tyr Gly Ala Gly Leu Leu Ser Ser Tyr Gly Glu Leu
385                 390                 395                 400

Leu His Ser Leu Ser Glu Glu Pro Glu Val Arg Ala Phe Asp Pro Asp
                405                 410                 415

Thr Ala Ala Val Gln Pro Tyr Gln Asp Gln Thr Tyr Gln Pro Val Tyr
            420                 425                 430

Phe Val Ser Glu Ser Phe Asn Asp Ala Lys Asp Lys Leu Arg Asn Tyr
            435                 440                 445

Ala Ser Arg Ile Gln Arg Pro Phe Ser Val Lys Phe Asp Pro Tyr Thr
            450                 455                 460

Leu Ala Ile Asp Val Leu Asp Ser Pro His Thr Ile Gln Arg Ser Leu
465                 470                 475                 480

Glu Gly Val Gln Asp Glu Leu His Thr Leu Ala His Ala Leu Ser Ala
                485                 490                 495

Ile Ser

<210> SEQ ID NO 51
<211> LENGTH: 380
<212> TYPE: PRT
<213> ORGANISM: human
<220> FEATURE:
<221> NAME/KEY: misc_feature
<222> LOCATION: (157)..(157)
<223> OTHER INFORMATION: Xaa can be any naturally occurring amino acid
<220> FEATURE:
<221> NAME/KEY: misc_feature
<222> LOCATION: (239)..(239)
<223> OTHER INFORMATION: Xaa can be any naturally occurring amino acid
<220> FEATURE:
<221> NAME/KEY: misc_feature
<222> LOCATION: (278)..(278)
<223> OTHER INFORMATION: Xaa can be any naturally occurring amino acid

<400> SEQUENCE: 51

Met Ser Glu Thr Val Ile Cys Ser Ser Arg Ala Thr Val Met Leu Tyr
1               5                   10                  15

Asp Asp Gly Asn Lys Arg Trp Leu Pro Ala Gly Thr Gly Pro Gln Ala
            20                  25                  30

Phe Ser Arg Val Gln Ile Tyr His Asn Pro Thr Ala Asn Ser Phe Arg
        35                  40                  45

Val Val Gly Arg Lys Met Gln Pro Asp Gln Val Val Ile Asn Cys
    50                  55                  60

Ala Ile Val Arg Gly Val Lys Tyr Asn Gln Ala Thr Pro Asn Phe His
65                  70                  75                  80

Gln Trp Arg Asp Ala Arg Gln Val Trp Gly Leu Asn Phe Gly Ser Lys
                85                  90                  95

Glu Asp Ala Ala Gln Phe Ala Ala Gly Met Ala Ser Ala Leu Glu Ala
            100                 105                 110

Leu Glu Gly Gly Gly Pro Pro Pro Pro Ala Leu Pro Thr Trp Ser
        115                 120                 125

Val Pro Asn Gly Pro Ser Pro Glu Glu Val Glu Gln Gln Lys Arg Gln
    130                 135                 140

Gln Pro Gly Pro Ser Glu His Ile Glu Arg Arg Val Xaa Asn Ala Gly
145                 150                 155                 160

Gly Pro Pro Ala Pro Pro Ala Gly Gly Pro Pro Pro Pro Pro Gly Pro
```

```
                165                 170                 175
Pro Pro Pro Pro Gly Pro Pro Pro Pro Gly Leu Pro Pro Ser Gly
            180                 185                 190

Val Pro Ala Ala His Gly Ala Gly Gly Pro Pro Pro Ala Pro
        195                 200                 205

Pro Leu Pro Ala Ala Gln Gly Pro Gly Gly Gly Ala Gly Ala Pro
    210                 215                 220

Gly Leu Ala Ala Ala Ile Ala Gly Ala Lys Leu Arg Lys Val Xaa Lys
225                 230                 235                 240

Gln Glu Glu Ala Ser Gly Gly Pro Thr Ala Pro Lys Ala Glu Ser Gly
                245                 250                 255

Arg Ser Gly Gly Gly Leu Met Glu Glu Met Asn Ala Met Leu Ala
            260                 265                 270

Arg Arg Arg Lys Ala Xaa Gln Val Gly Glu Lys Thr Pro Lys Asp Glu
            275                 280                 285

Ser Ala Asn Gln Glu Glu Pro Glu Ala Arg Val Pro Ala Gln Ser Glu
    290                 295                 300

Ser Val Arg Arg Pro Trp Glu Lys Asn Ser Thr Thr Leu Pro Arg Met
305                 310                 315                 320

Lys Ser Ser Ser Val Thr Thr Ser Glu Thr Gln Pro Cys Thr Pro
                325                 330                 335

Ser Ser Ser Asp Tyr Ser Asp Leu Gln Arg Val Lys Gln Glu Leu Leu
            340                 345                 350

Glu Glu Val Lys Lys Glu Leu Gln Lys Val Lys Glu Glu Ile Ile Glu
            355                 360                 365

Ala Phe Val Gln Glu Leu Arg Lys Arg Gly Ser Pro
            370                 375                 380

<210> SEQ ID NO 52
<211> LENGTH: 427
<212> TYPE: PRT
<213> ORGANISM: human
<220> FEATURE:
<221> NAME/KEY: misc_feature
<222> LOCATION: (182)..(182)
<223> OTHER INFORMATION: Xaa can be any naturally occurring amino acid

<400> SEQUENCE: 52

Met Glu Ala Met Ala Ala Ser Thr Ser Leu Pro Asp Pro Gly Asp Phe
1               5                   10                  15

Asp Arg Asn Val Pro Arg Ile Cys Gly Val Cys Gly Asp Arg Ala Thr
            20                  25                  30

Gly Phe His Phe Asn Ala Met Thr Cys Glu Gly Cys Lys Gly Phe Phe
        35                  40                  45

Arg Arg Ser Met Lys Arg Lys Ala Leu Phe Thr Cys Pro Phe Asn Gly
    50                  55                  60

Asp Cys Arg Ile Thr Lys Asp Asn Arg Arg His Cys Gln Ala Cys Arg
65                  70                  75                  80

Leu Lys Arg Cys Val Asp Ile Gly Met Met Lys Glu Phe Ile Leu Thr
                85                  90                  95

Asp Glu Glu Val Gln Arg Lys Arg Glu Met Ile Leu Lys Arg Lys Glu
            100                 105                 110

Glu Glu Ala Leu Lys Asp Ser Leu Arg Pro Lys Leu Ser Glu Glu Gln
        115                 120                 125

Gln Arg Ile Ile Ala Ile Leu Leu Asp Ala His His Lys Thr Tyr Asp
    130                 135                 140
```

-continued

```
Pro Thr Tyr Ser Asp Phe Cys Gln Phe Arg Pro Pro Val Arg Val Asn
145                 150                 155                 160

Asp Gly Gly Gly Ser His Pro Ser Arg Pro Asn Ser Arg His Thr Pro
                165                 170                 175

Ser Phe Ser Gly Asp Xaa Ser Ser Cys Ser Asp His Cys Ile Thr
            180                 185                 190

Ser Ser Asp Met Met Asp Ser Ser Phe Ser Asn Leu Asp Leu Ser
        195                 200                 205

Glu Glu Asp Ser Asp Asp Pro Ser Val Thr Leu Glu Leu Ser Gln Leu
210                 215                 220

Ser Met Leu Pro His Leu Ala Asp Leu Val Ser Tyr Ser Ile Gln Lys
225                 230                 235                 240

Val Ile Gly Phe Ala Lys Met Ile Pro Gly Phe Arg Asp Leu Thr Ser
                245                 250                 255

Glu Asp Gln Ile Val Leu Leu Lys Ser Ser Ala Ile Glu Val Ile Met
            260                 265                 270

Leu Arg Ser Asn Glu Ser Phe Thr Met Asp Asp Met Ser Trp Thr Cys
        275                 280                 285

Gly Asn Gln Asp Tyr Lys Tyr Arg Val Ser Asp Val Thr Lys Ala Gly
290                 295                 300

His Ser Leu Glu Leu Ile Glu Pro Leu Ile Lys Phe Gln Val Gly Leu
305                 310                 315                 320

Lys Lys Leu Asn Leu His Glu Glu His Val Leu Leu Met Ala Ile
                325                 330                 335

Cys Ile Val Ser Pro Asp Arg Pro Gly Val Gln Asp Ala Ala Leu Ile
            340                 345                 350

Glu Ala Ile Gln Asp Arg Leu Ser Asn Thr Leu Gln Thr Tyr Ile Arg
        355                 360                 365

Cys Arg His Pro Pro Pro Gly Ser His Leu Leu Tyr Ala Lys Met Ile
370                 375                 380

Gln Lys Leu Ala Asp Leu Arg Ser Leu Asn Glu Glu His Ser Lys Gln
385                 390                 395                 400

Tyr Arg Cys Leu Ser Phe Gln Pro Glu Cys Ser Met Lys Leu Thr Pro
                405                 410                 415

Leu Val Leu Glu Val Phe Gly Asn Glu Ile Ser
            420                 425

<210> SEQ ID NO 53
<211> LENGTH: 839
<212> TYPE: PRT
<213> ORGANISM: human
<220> FEATURE:
<221> NAME/KEY: misc_feature
<222> LOCATION: (117)..(117)
<223> OTHER INFORMATION: Xaa can be any naturally occurring amino acid

<400> SEQUENCE: 53

Met Lys Lys Trp Ser Ser Thr Asp Leu Gly Ala Ala Ala Asp Pro Leu
1               5                   10                  15

Gln Lys Asp Thr Cys Pro Asp Pro Leu Asp Gly Asp Pro Asn Ser Arg
                20                  25                  30

Pro Pro Pro Ala Lys Pro Gln Leu Ser Thr Ala Lys Ser Arg Thr Arg
            35                  40                  45

Leu Phe Gly Lys Gly Asp Ser Glu Glu Ala Phe Pro Val Asp Cys Pro
50                  55                  60
```

```
His Glu Glu Gly Glu Leu Asp Ser Cys Pro Thr Ile Thr Val Ser Pro
 65                  70                  75                  80

Val Ile Thr Ile Gln Arg Pro Gly Asp Pro Thr Gly Ala Arg Leu
             85                  90                  95

Leu Ser Gln Asp Ser Val Ala Ala Ser Thr Glu Lys Thr Leu Arg Leu
            100                 105                 110

Tyr Asp Arg Arg Xaa Ile Phe Glu Ala Val Ala Gln Asn Asn Cys Gln
            115                 120                 125

Asp Leu Glu Ser Leu Leu Phe Leu Gln Lys Ser Lys Lys His Leu
130                 135                 140

Thr Asp Asn Glu Phe Lys Asp Pro Glu Thr Gly Lys Thr Cys Leu Leu
145                 150                 155                 160

Lys Ala Met Leu Asn Leu His Asp Gly Gln Asn Thr Thr Ile Pro Leu
                165                 170                 175

Leu Leu Glu Ile Ala Arg Gln Thr Asp Ser Leu Lys Glu Leu Val Asn
                180                 185                 190

Ala Ser Tyr Thr Asp Ser Tyr Tyr Lys Gly Gln Thr Ala Leu His Ile
            195                 200                 205

Ala Ile Glu Arg Arg Asn Met Ala Leu Val Thr Leu Leu Val Glu Asn
210                 215                 220

Gly Ala Asp Val Gln Ala Ala His Gly Asp Phe Phe Lys Lys Thr
225                 230                 235                 240

Lys Gly Arg Pro Gly Phe Tyr Phe Gly Glu Leu Pro Leu Ser Leu Ala
                245                 250                 255

Ala Cys Thr Asn Gln Leu Gly Ile Val Lys Phe Leu Leu Gln Asn Ser
            260                 265                 270

Trp Gln Thr Ala Asp Ile Ser Ala Arg Asp Ser Val Gly Asn Thr Val
275                 280                 285

Leu His Ala Leu Val Glu Val Ala Asp Asn Thr Ala Asp Asn Thr Lys
    290                 295                 300

Phe Val Thr Ser Met Tyr Asn Glu Ile Leu Met Leu Gly Ala Lys Leu
305                 310                 315                 320

His Pro Thr Leu Lys Leu Glu Glu Leu Thr Asn Lys Lys Gly Met Thr
                325                 330                 335

Pro Leu Ala Leu Ala Ala Gly Thr Gly Lys Ile Gly Val Leu Ala Tyr
            340                 345                 350

Ile Leu Gln Arg Glu Ile Gln Glu Pro Glu Cys Arg His Leu Ser Arg
            355                 360                 365

Lys Phe Thr Glu Trp Ala Tyr Gly Pro Val His Ser Ser Leu Tyr Asp
    370                 375                 380

Leu Ser Cys Ile Asp Thr Cys Glu Lys Asn Ser Val Leu Glu Val Ile
385                 390                 395                 400

Ala Tyr Ser Ser Ser Glu Thr Pro Asn Arg His Asp Met Leu Leu Val
                405                 410                 415

Glu Pro Leu Asn Arg Leu Leu Gln Asp Lys Trp Asp Arg Phe Val Lys
            420                 425                 430

Arg Ile Phe Tyr Phe Asn Phe Leu Val Tyr Cys Leu Tyr Met Ile Ile
        435                 440                 445

Phe Thr Met Ala Ala Tyr Tyr Arg Pro Val Asp Gly Leu Pro Pro Phe
    450                 455                 460

Lys Met Glu Lys Thr Gly Asp Tyr Phe Arg Val Thr Gly Glu Ile Leu
465                 470                 475                 480

Ser Val Leu Gly Gly Val Tyr Phe Phe Phe Arg Gly Ile Gln Tyr Phe
```

485                 490                 495

Leu Gln Arg Arg Pro Ser Met Lys Thr Leu Phe Val Asp Ser Tyr Ser
            500                 505                 510

Glu Met Leu Phe Phe Leu Gln Ser Leu Phe Met Leu Ala Thr Val Val
        515                 520                 525

Leu Tyr Phe Ser His Leu Lys Glu Tyr Val Ala Ser Met Val Phe Ser
    530                 535                 540

Leu Ala Leu Gly Trp Thr Asn Met Leu Tyr Tyr Thr Arg Gly Phe Gln
545                 550                 555                 560

Gln Met Gly Ile Tyr Ala Val Met Ile Glu Lys Met Ile Leu Arg Asp
            565                 570                 575

Leu Cys Arg Phe Met Phe Val Tyr Ile Val Phe Leu Phe Gly Phe Ser
        580                 585                 590

Thr Ala Val Val Thr Leu Ile Glu Asp Gly Lys Asn Asp Ser Leu Pro
    595                 600                 605

Ser Glu Ser Thr Ser His Arg Trp Arg Gly Pro Ala Cys Arg Pro Pro
610                 615                 620

Asp Ser Ser Tyr Asn Ser Leu Tyr Ser Thr Cys Leu Glu Leu Phe Lys
625                 630                 635                 640

Phe Thr Ile Gly Met Gly Asp Leu Glu Phe Thr Glu Asn Tyr Asp Phe
            645                 650                 655

Lys Ala Val Phe Ile Ile Leu Leu Leu Ala Tyr Val Ile Leu Thr Tyr
        660                 665                 670

Ile Leu Leu Leu Asn Met Leu Ile Ala Leu Met Gly Glu Thr Val Asn
    675                 680                 685

Lys Ile Ala Gln Glu Ser Lys Asn Ile Trp Lys Leu Gln Arg Ala Ile
690                 695                 700

Thr Ile Leu Asp Thr Glu Lys Ser Phe Leu Lys Cys Met Arg Lys Ala
705                 710                 715                 720

Phe Arg Ser Gly Lys Leu Leu Gln Val Gly Tyr Thr Pro Asp Gly Lys
            725                 730                 735

Asp Asp Tyr Arg Trp Cys Phe Arg Val Asp Glu Val Asn Trp Thr Thr
        740                 745                 750

Trp Asn Thr Asn Val Gly Ile Ile Asn Glu Asp Pro Gly Asn Cys Glu
    755                 760                 765

Gly Val Lys Arg Thr Leu Ser Phe Ser Leu Arg Ser Ser Arg Val Ser
770                 775                 780

Gly Arg His Trp Lys Asn Phe Ala Leu Val Pro Leu Leu Arg Glu Ala
785                 790                 795                 800

Ser Ala Arg Asp Arg Gln Ser Ala Gln Pro Glu Glu Val Tyr Leu Arg
            805                 810                 815

Gln Phe Ser Gly Ser Leu Lys Pro Glu Asp Ala Glu Val Phe Lys Ser
        820                 825                 830

Pro Ala Ala Ser Gly Glu Lys
        835

<210> SEQ ID NO 54
<211> LENGTH: 3899
<212> TYPE: PRT
<213> ORGANISM: human
<220> FEATURE:
<221> NAME/KEY: misc_feature
<222> LOCATION: (43)..(44)
<223> OTHER INFORMATION: Xaa can be any naturally occurring amino acid

<400> SEQUENCE: 54

```
Met Glu Asp Glu Glu Arg Gln Lys Lys Leu Glu Ala Gly Lys Ala Lys
1               5                   10                  15

Leu Ala Gln Phe Arg Gln Arg Lys Ala Gln Ser Asp Gly Gln Ser Pro
            20                  25                  30

Ser Lys Lys Gln Lys Lys Arg Lys Thr Xaa Xaa Ser Lys His Asp
        35                  40                  45

Val Ser Ala His His Asp Leu Asn Ile Asp Gln Ser Gln Cys Asn Glu
    50              55                  60

Met Tyr Ile Asn Ser Ser Gln Arg Val Glu Ser Thr Val Ile Pro Glu
65              70                  75                  80

Ser Thr Ile Met Arg Thr Leu His Ser Gly Glu Ile Thr Ser His Glu
                85                  90                  95

Gln Gly Phe Ser Val Glu Leu Glu Ser Glu Ile Ser Thr Thr Ala Asp
                100                 105                 110

Asp Cys Ser Ser Glu Val Asn Gly Cys Ser Phe Val Met Arg Thr Gly
        115                 120                 125

Lys Pro Thr Asn Leu Leu Arg Glu Glu Phe Gly Val Asp Asp Ser
        130                 135                 140

Tyr Ser Glu Gln Gly Ala Gln Asp Ser Pro Thr His Leu Glu Met Met
145                 150                 155                 160

Glu Ser Glu Leu Ala Gly Lys Gln His Glu Ile Glu Glu Leu Asn Arg
                165                 170                 175

Glu Leu Glu Glu Met Arg Val Thr Tyr Gly Thr Glu Gly Leu Gln Gln
                180                 185                 190

Leu Gln Glu Phe Glu Ala Ala Ile Lys Gln Arg Asp Gly Ile Ile Thr
            195                 200                 205

Gln Leu Thr Ala Asn Leu Gln Gln Ala Arg Arg Glu Lys Asp Glu Thr
        210                 215                 220

Met Arg Glu Phe Leu Glu Leu Thr Glu Gln Ser Gln Lys Leu Gln Ile
225                 230                 235                 240

Gln Phe Gln Gln Leu Gln Ala Ser Glu Thr Leu Arg Asn Ser Thr His
            245                 250                 255

Ser Ser Thr Ala Ala Asp Leu Leu Gln Ala Lys Gln Gln Ile Leu Thr
            260                 265                 270

His Gln Gln Gln Leu Glu Glu Gln Asp His Leu Leu Glu Asp Tyr Gln
        275                 280                 285

Lys Lys Lys Glu Asp Phe Thr Met Gln Ile Ser Phe Leu Gln Glu Lys
        290                 295                 300

Ile Lys Val Tyr Glu Met Glu Gln Asp Lys Lys Val Glu Asn Ser Asn
305                 310                 315                 320

Lys Glu Glu Ile Gln Glu Lys Glu Thr Ile Ile Glu Glu Leu Asn Thr
                325                 330                 335

Lys Ile Ile Glu Glu Lys Lys Thr Leu Glu Leu Lys Asp Lys Leu
                340                 345                 350

Thr Thr Ala Asp Lys Leu Leu Gly Glu Leu Gln Glu Gln Ile Val Gln
            355                 360                 365

Lys Asn Gln Glu Ile Lys Asn Met Lys Leu Glu Leu Thr Asn Ser Lys
    370                 375                 380

Gln Lys Glu Arg Gln Ser Ser Glu Glu Ile Lys Gln Leu Met Gly Thr
385                 390                 395                 400

Val Glu Glu Leu Gln Lys Arg Asn His Lys Asp Ser Gln Phe Glu Thr
                405                 410                 415
```

```
Asp Ile Val Gln Arg Met Glu Gln Glu Thr Gln Arg Lys Leu Glu Gln
            420                 425                 430
Leu Arg Ala Glu Leu Asp Glu Met Tyr Gly Gln Gln Ile Val Gln Met
        435                 440                 445
Lys Gln Glu Leu Ile Arg Gln His Met Ala Gln Met Glu Glu Met Lys
    450                 455                 460
Thr Arg His Lys Gly Glu Met Glu Asn Ala Leu Arg Ser Tyr Ser Asn
465                 470                 475                 480
Ile Thr Val Asn Glu Asp Gln Ile Lys Leu Met Asn Val Ala Ile Asn
            485                 490                 495
Glu Leu Asn Ile Lys Leu Gln Asp Thr Asn Ser Gln Lys Glu Lys Leu
        500                 505                 510
Lys Glu Glu Leu Gly Leu Ile Leu Glu Glu Lys Cys Ala Leu Gln Arg
    515                 520                 525
Gln Leu Glu Asp Leu Val Glu Glu Leu Ser Phe Ser Arg Glu Gln Ile
    530                 535                 540
Gln Arg Ala Arg Gln Thr Ile Ala Glu Gln Glu Ser Lys Leu Asn Glu
545                 550                 555                 560
Ala His Lys Ser Leu Ser Thr Val Glu Asp Leu Lys Ala Glu Ile Val
            565                 570                 575
Ser Ala Ser Glu Ser Arg Lys Glu Leu Glu Leu Lys His Glu Ala Glu
        580                 585                 590
Val Thr Asn Tyr Lys Ile Lys Leu Glu Met Leu Glu Lys Glu Lys Asn
    595                 600                 605
Ala Val Leu Asp Arg Met Ala Glu Ser Gln Glu Ala Glu Leu Glu Arg
610                 615                 620
Leu Arg Thr Gln Leu Leu Phe Ser His Glu Glu Leu Ser Lys Leu
625                 630                 635                 640
Lys Glu Asp Leu Glu Ile Glu His Arg Ile Asn Ile Glu Lys Leu Lys
            645                 650                 655
Asp Asn Leu Gly Ile His Tyr Lys Gln Gln Ile Asp Gly Leu Gln Asn
        660                 665                 670
Glu Met Ser Gln Lys Ile Glu Thr Met Gln Phe Glu Lys Asp Asn Leu
    675                 680                 685
Ile Thr Lys Gln Asn Gln Leu Ile Leu Glu Ile Ser Lys Leu Lys Asp
    690                 695                 700
Leu Gln Gln Ser Leu Val Asn Ser Lys Ser Glu Glu Met Thr Leu Gln
705                 710                 715                 720
Ile Asn Glu Leu Gln Lys Glu Ile Glu Ile Leu Arg Gln Glu Glu Lys
            725                 730                 735
Glu Lys Gly Thr Leu Glu Gln Glu Val Gln Glu Leu Gln Leu Lys Thr
        740                 745                 750
Glu Leu Leu Glu Lys Gln Met Lys Glu Lys Glu Asn Asp Leu Gln Glu
    755                 760                 765
Lys Phe Ala Gln Leu Glu Ala Glu Asn Ser Ile Leu Lys Asp Glu Lys
    770                 775                 780
Lys Thr Leu Glu Asp Met Leu Lys Ile His Thr Pro Val Ser Gln Glu
785                 790                 795                 800
Glu Arg Leu Ile Phe Leu Asp Ser Ile Lys Ser Lys Ser Lys Asp Ser
            805                 810                 815
Val Trp Glu Lys Glu Ile Glu Ile Leu Ile Glu Glu Asn Glu Asp Leu
        820                 825                 830
Lys Gln Gln Cys Ile Gln Leu Asn Glu Glu Ile Glu Lys Gln Arg Asn
```

-continued

```
              835                 840                 845
Thr Phe Ser Phe Ala Glu Lys Asn Phe Glu Val Asn Tyr Gln Glu Leu
    850                 855                 860

Gln Glu Glu Tyr Ala Cys Leu Leu Lys Val Lys Asp Asp Leu Glu Asp
865                 870                 875                 880

Ser Lys Asn Lys Gln Glu Leu Glu Tyr Lys Ser Lys Leu Lys Ala Leu
                885                 890                 895

Asn Glu Glu Leu His Leu Gln Arg Ile Asn Pro Thr Thr Val Lys Met
            900                 905                 910

Lys Ser Ser Val Phe Asp Glu Asp Lys Thr Phe Val Ala Glu Thr Leu
                915                 920                 925

Glu Met Gly Glu Val Val Glu Lys Asp Thr Thr Glu Leu Met Glu Lys
        930                 935                 940

Leu Glu Val Thr Lys Arg Glu Lys Leu Glu Leu Ser Gln Arg Leu Ser
945                 950                 955                 960

Asp Leu Ser Glu Gln Leu Lys Gln Lys His Gly Glu Ile Ser Phe Leu
                965                 970                 975

Asn Glu Glu Val Lys Ser Leu Lys Gln Glu Lys Glu Gln Val Ser Leu
            980                 985                 990

Arg Cys Arg Glu Leu Glu Ile Ile Ile Asn His Asn Arg Ala Glu Asn
        995                 1000                1005

Val Gln Ser Cys Asp Thr Gln Val Ser Ser Leu Leu Asp Gly Val
    1010                1015                1020

Val Thr Met Thr Ser Arg Gly Ala Glu Gly Ser Val Ser Lys Val
    1025                1030                1035

Asn Lys Ser Phe Gly Glu Glu Ser Lys Ile Met Val Glu Asp Lys
    1040                1045                1050

Val Ser Phe Glu Asn Met Thr Val Gly Glu Glu Ser Lys Gln Glu
    1055                1060                1065

Gln Leu Ile Leu Asp His Leu Pro Ser Val Thr Lys Glu Ser Ser
    1070                1075                1080

Leu Arg Ala Thr Gln Pro Ser Glu Asn Asp Lys Leu Gln Lys Glu
    1085                1090                1095

Leu Asn Val Leu Lys Ser Glu Gln Asn Asp Leu Arg Leu Gln Met
    1100                1105                1110

Glu Ala Gln Arg Ile Cys Leu Ser Leu Val Tyr Ser Thr His Val
    1115                1120                1125

Asp Gln Val Arg Glu Tyr Met Glu Asn Glu Lys Asp Lys Ala Leu
    1130                1135                1140

Cys Ser Leu Lys Glu Glu Leu Ile Phe Ala Gln Glu Glu Lys Ile
    1145                1150                1155

Lys Glu Leu Gln Lys Ile His Gln Leu Glu Leu Gln Thr Met Lys
    1160                1165                1170

Thr Gln Glu Thr Gly Asp Glu Gly Lys Pro Leu His Leu Leu Ile
    1175                1180                1185

Gly Lys Leu Gln Lys Ala Val Ser Glu Glu Cys Ser Tyr Phe Leu
    1190                1195                1200

Gln Thr Leu Cys Ser Val Leu Gly Glu Tyr Tyr Thr Pro Ala Leu
    1205                1210                1215

Lys Cys Glu Val Asn Ala Glu Asp Lys Glu Asn Ser Gly Asp Tyr
    1220                1225                1230

Ile Ser Glu Asn Glu Asp Pro Glu Leu Gln Asp Tyr Arg Tyr Glu
    1235                1240                1245
```

```
Val Gln Asp Phe Gln Glu Asn Met His Thr Leu Leu Asn Lys Val
    1250                1255                1260

Thr Glu Glu Tyr Asn Lys Leu Leu Val Leu Gln Thr Arg Leu Ser
    1265                1270                1275

Lys Ile Trp Gly Gln Gln Thr Asp Gly Met Lys Leu Glu Phe Gly
    1280                1285                1290

Glu Glu Asn Leu Pro Lys Glu Glu Thr Glu Phe Leu Ser Ile His
    1295                1300                1305

Ser Gln Met Thr Asn Leu Glu Asp Ile Asp Val Asn His Lys Ser
    1310                1315                1320

Lys Leu Ser Ser Leu Gln Asp Leu Glu Lys Thr Lys Leu Glu Glu
    1325                1330                1335

Gln Val Gln Glu Leu Glu Ser Leu Ile Ser Ser Leu Gln Gln Gln
    1340                1345                1350

Leu Lys Glu Thr Glu Gln Asn Tyr Glu Ala Glu Ile His Cys Leu
    1355                1360                1365

Gln Lys Arg Leu Gln Ala Val Ser Glu Ser Thr Val Pro Pro Ser
    1370                1375                1380

Leu Pro Val Asp Ser Val Val Ile Thr Glu Ser Asp Ala Gln Arg
    1385                1390                1395

Thr Met Tyr Pro Gly Ser Cys Val Lys Lys Asn Ile Asp Gly Thr
    1400                1405                1410

Ile Glu Phe Ser Gly Glu Phe Gly Val Lys Glu Glu Thr Asn Ile
    1415                1420                1425

Val Lys Leu Leu Glu Lys Gln Tyr Gln Glu Gln Leu Glu Glu Glu
    1430                1435                1440

Val Ala Lys Val Ile Val Ser Met Ser Ile Ala Phe Ala Gln Gln
    1445                1450                1455

Thr Glu Leu Ser Arg Ile Ser Gly Gly Lys Glu Asn Thr Ala Ser
    1460                1465                1470

Ser Lys Gln Ala His Ala Val Cys Gln Gln Glu Gln His Tyr Phe
    1475                1480                1485

Asn Glu Met Lys Leu Ser Gln Asp Gln Ile Gly Phe Gln Thr Phe
    1490                1495                1500

Glu Thr Val Asp Val Lys Phe Lys Glu Glu Phe Lys Pro Leu Ser
    1505                1510                1515

Lys Glu Leu Gly Glu His Gly Lys Glu Ile Leu Leu Ser Asn Ser
    1520                1525                1530

Asp Pro His Asp Ile Pro Glu Ser Lys Asp Cys Val Leu Thr Ile
    1535                1540                1545

Ser Glu Glu Met Phe Ser Lys Asp Lys Thr Phe Ile Val Arg Gln
    1550                1555                1560

Ser Ile His Asp Glu Ile Ser Val Ser Ser Met Asp Ala Ser Arg
    1565                1570                1575

Gln Leu Met Leu Asn Glu Glu Gln Leu Glu Asp Met Arg Gln Glu
    1580                1585                1590

Leu Val Arg Gln Tyr Gln Glu His Gln Gln Ala Thr Glu Leu Leu
    1595                1600                1605

Arg Gln Ala His Met Arg Gln Met Glu Arg Gln Arg Glu Asp Gln
    1610                1615                1620

Glu Gln Leu Gln Glu Glu Ile Lys Arg Leu Asn Arg Gln Leu Ala
    1625                1630                1635
```

-continued

```
Gln Arg Ser Ser Ile Asp Asn Glu Asn Leu Val Ser Glu Arg Glu
    1640                1645                1650

Arg Val Leu Leu Glu Glu Leu Glu Ala Leu Lys Gln Leu Ser Leu
    1655                1660                1665

Ala Gly Arg Glu Lys Leu Cys Cys Glu Leu Arg Asn Ser Ser Thr
    1670                1675                1680

Gln Thr Gln Asn Gly Asn Glu Asn Gln Gly Glu Val Glu Glu Gln
    1685                1690                1695

Thr Phe Lys Glu Lys Glu Leu Asp Arg Lys Pro Glu Asp Val Pro
    1700                1705                1710

Pro Glu Ile Leu Ser Asn Glu Arg Tyr Ala Leu Gln Lys Ala Asn
    1715                1720                1725

Asn Arg Leu Leu Lys Ile Leu Leu Glu Val Val Lys Thr Thr Ala
    1730                1735                1740

Ala Val Glu Glu Thr Ile Gly Arg His Val Leu Gly Ile Leu Asp
    1745                1750                1755

Arg Ser Ser Lys Ser Gln Ser Ser Ala Ser Leu Ile Trp Arg Ser
    1760                1765                1770

Glu Ala Glu Ala Ser Val Lys Ser Cys Val His Glu Glu His Thr
    1775                1780                1785

Arg Val Thr Asp Glu Ser Ile Pro Ser Tyr Ser Gly Ser Asp Met
    1790                1795                1800

Pro Arg Asn Asp Ile Asn Met Trp Ser Lys Val Thr Glu Glu Gly
    1805                1810                1815

Thr Glu Leu Ser Gln Arg Leu Val Arg Ser Gly Phe Ala Gly Thr
    1820                1825                1830

Glu Ile Asp Pro Glu Asn Glu Glu Leu Met Leu Asn Ile Ser Ser
    1835                1840                1845

Arg Leu Gln Ala Ala Val Glu Lys Leu Leu Glu Ala Ile Ser Glu
    1850                1855                1860

Thr Ser Ser Gln Leu Glu His Ala Lys Val Thr Gln Thr Glu Leu
    1865                1870                1875

Met Arg Glu Ser Phe Arg Gln Lys Gln Glu Ala Thr Glu Ser Leu
    1880                1885                1890

Lys Cys Gln Glu Glu Leu Arg Glu Arg Leu His Glu Glu Ser Arg
    1895                1900                1905

Ala Arg Glu Gln Leu Ala Val Glu Leu Ser Lys Ala Glu Gly Val
    1910                1915                1920

Ile Asp Gly Tyr Ala Asp Glu Lys Thr Leu Phe Glu Arg Gln Ile
    1925                1930                1935

Gln Glu Lys Thr Asp Ile Ile Asp Arg Leu Glu Gln Glu Leu Leu
    1940                1945                1950

Cys Ala Ser Asn Arg Leu Gln Glu Leu Glu Ala Glu Gln Gln Gln
    1955                1960                1965

Ile Gln Glu Glu Arg Glu Leu Leu Ser Arg Gln Lys Glu Ala Met
    1970                1975                1980

Lys Ala Glu Ala Gly Pro Val Glu Gln Gln Leu Leu Gln Glu Thr
    1985                1990                1995

Glu Lys Leu Met Lys Glu Lys Leu Glu Val Gln Cys Gln Ala Glu
    2000                2005                2010

Lys Val Arg Asp Asp Leu Gln Lys Gln Val Lys Ala Leu Glu Ile
    2015                2020                2025

Asp Val Glu Glu Gln Val Ser Arg Phe Ile Glu Leu Glu Gln Glu
```

```
                    2030                2035                2040

Lys Asn Thr Glu Leu Met Asp Leu Arg Gln Gln Asn Gln Ala Leu
    2045                2050                2055

Glu Lys Gln Leu Glu Lys Met Arg Lys Phe Leu Asp Glu Gln Ala
    2060                2065                2070

Ile Asp Arg Glu His Glu Arg Asp Val Phe Gln Gln Glu Ile Gln
    2075                2080                2085

Lys Leu Glu Gln Gln Leu Lys Val Val Pro Arg Phe Gln Pro Ile
    2090                2095                2100

Ser Glu His Gln Thr Arg Glu Val Glu Gln Leu Ala Asn His Leu
    2105                2110                2115

Lys Glu Lys Thr Asp Lys Cys Ser Glu Leu Leu Leu Ser Lys Glu
    2120                2125                2130

Gln Leu Gln Arg Asp Ile Gln Glu Arg Asn Glu Glu Ile Glu Lys
    2135                2140                2145

Leu Glu Phe Arg Val Arg Glu Leu Glu Gln Ala Leu Leu Val Glu
    2150                2155                2160

Asp Arg Lys His Phe Gly Ala Val Glu Ala Lys Pro Glu Leu Ser
    2165                2170                2175

Leu Glu Val Gln Leu Gln Ala Glu Arg Asp Ala Ile Asp Arg Lys
    2180                2185                2190

Glu Lys Glu Ile Thr Asn Leu Glu Glu Gln Leu Glu Gln Phe Arg
    2195                2200                2205

Glu Glu Leu Glu Asn Lys Asn Glu Glu Val Gln Gln Leu His Met
    2210                2215                2220

Gln Leu Glu Ile Gln Lys Lys Glu Ser Thr Thr Arg Leu Gln Glu
    2225                2230                2235

Leu Glu Gln Glu Asn Lys Leu Phe Lys Asp Asp Met Glu Lys Leu
    2240                2245                2250

Gly Leu Ala Ile Lys Glu Ser Asp Ala Met Ser Thr Gln Asp Gln
    2255                2260                2265

His Val Leu Phe Gly Lys Phe Ala Gln Ile Ile Gln Glu Lys Glu
    2270                2275                2280

Val Glu Ile Asp Gln Leu Asn Glu Gln Val Thr Lys Leu Gln Gln
    2285                2290                2295

Gln Leu Lys Ile Thr Thr Asp Asn Lys Val Ile Glu Glu Lys Asn
    2300                2305                2310

Glu Leu Ile Arg Asp Leu Glu Thr Gln Ile Glu Cys Leu Met Ser
    2315                2320                2325

Asp Gln Glu Cys Val Lys Arg Asn Arg Glu Glu Ile Glu Gln
    2330                2335                2340

Leu Asn Glu Val Ile Glu Lys Leu Gln Gln Glu Leu Ala Asn Ile
    2345                2350                2355

Gly Gln Lys Thr Ser Met Asn Ala His Ser Leu Ser Glu Glu Ala
    2360                2365                2370

Asp Ser Leu Lys His Gln Leu Asp Val Val Ile Ala Glu Lys Leu
    2375                2380                2385

Ala Leu Glu Gln Gln Val Glu Thr Ala Asn Glu Glu Met Thr Phe
    2390                2395                2400

Met Lys Asn Val Leu Lys Glu Thr Asn Phe Lys Met Asn Gln Leu
    2405                2410                2415

Thr Gln Glu Leu Phe Ser Leu Lys Arg Glu Arg Glu Ser Val Glu
    2420                2425                2430
```

-continued

Lys Ile Gln Ser Ile Pro Glu Asn Ser Val Asn Val Ala Ile Asp
2435                2440                2445

His Leu Ser Lys Asp Lys Pro Glu Leu Glu Val Val Leu Thr Glu
2450                2455                2460

Asp Ala Leu Lys Ser Leu Glu Asn Gln Thr Tyr Phe Lys Ser Phe
2465                2470                2475

Glu Glu Asn Gly Lys Gly Ser Ile Ile Asn Leu Glu Thr Arg Leu
2480                2485                2490

Leu Gln Leu Glu Ser Thr Val Ser Ala Lys Asp Leu Glu Leu Thr
2495                2500                2505

Gln Cys Tyr Lys Gln Ile Lys Asp Met Gln Glu Gln Gly Gln Phe
2510                2515                2520

Glu Thr Glu Met Leu Gln Lys Lys Ile Val Asn Leu Gln Lys Ile
2525                2530                2535

Val Glu Glu Lys Val Ala Ala Leu Val Ser Gln Ile Gln Leu
2540                2545                2550

Glu Ala Val Gln Glu Tyr Ala Lys Phe Cys Gln Asp Asn Gln Thr
2555                2560                2565

Ile Ser Ser Glu Pro Glu Arg Thr Asn Ile Gln Asn Leu Asn Gln
2570                2575                2580

Leu Arg Glu Asp Glu Leu Gly Ser Asp Ile Ser Ala Leu Thr Leu
2585                2590                2595

Arg Ile Ser Glu Leu Glu Ser Gln Val Val Glu Met His Thr Ser
2600                2605                2610

Leu Ile Leu Glu Lys Glu Gln Val Glu Ile Ala Glu Lys Asn Val
2615                2620                2625

Leu Glu Lys Glu Lys Lys Leu Leu Glu Leu Gln Lys Leu Leu Glu
2630                2635                2640

Gly Asn Glu Lys Lys Gln Arg Glu Lys Glu Lys Arg Ser Pro
2645                2650                2655

Gln Asp Val Glu Val Leu Lys Thr Thr Thr Glu Leu Phe His Ser
2660                2665                2670

Asn Glu Glu Ser Gly Phe Phe Asn Glu Leu Glu Ala Leu Arg Ala
2675                2680                2685

Glu Ser Val Ala Thr Lys Ala Glu Leu Ala Ser Tyr Lys Glu Lys
2690                2695                2700

Ala Glu Lys Leu Gln Glu Glu Leu Leu Val Lys Glu Thr Asn Met
2705                2710                2715

Thr Ser Leu Gln Lys Asp Leu Ser Gln Val Arg Asp His Leu Ala
2720                2725                2730

Glu Ala Lys Glu Lys Leu Ser Ile Leu Glu Lys Glu Asp Glu Thr
2735                2740                2745

Glu Val Gln Glu Ser Lys Lys Ala Cys Met Phe Glu Pro Leu Pro
2750                2755                2760

Ile Lys Leu Ser Lys Ser Ile Ala Ser Gln Thr Asp Gly Thr Leu
2765                2770                2775

Lys Ile Ser Ser Ser Asn Gln Thr Pro Gln Ile Leu Val Lys Asn
2780                2785                2790

Ala Gly Ile Gln Ile Asn Leu Gln Ser Glu Cys Ser Ser Glu Glu
2795                2800                2805

Val Thr Glu Ile Ile Ser Gln Phe Thr Glu Lys Ile Glu Lys Met
2810                2815                2820

```
Gln Glu Leu His Ala Ala Glu Ile Leu Asp Met Glu Ser Arg His
2825                2830                2835

Ile Ser Glu Thr Glu Thr Leu Lys Arg Glu His Tyr Val Ala Val
2840                2845                2850

Gln Leu Leu Lys Glu Glu Cys Gly Thr Leu Lys Ala Val Ile Gln
2855                2860                2865

Cys Leu Arg Ser Lys Glu Gly Ser Ser Ile Pro Glu Leu Ala His
2870                2875                2880

Ser Asp Ala Tyr Gln Thr Arg Glu Ile Cys Ser Ser Asp Ser Gly
2885                2890                2895

Ser Asp Trp Gly Gln Gly Ile Tyr Leu Thr His Ser Gln Gly Phe
2900                2905                2910

Asp Ile Ala Ser Glu Gly Arg Gly Glu Glu Ser Glu Ser Ala Thr
2915                2920                2925

Asp Ser Phe Pro Lys Lys Ile Lys Gly Leu Leu Arg Ala Val His
2930                2935                2940

Asn Glu Gly Met Gln Val Leu Ser Leu Thr Glu Ser Pro Tyr Ser
2945                2950                2955

Asp Gly Glu Asp His Ser Ile Gln Gln Val Ser Glu Pro Trp Leu
2960                2965                2970

Glu Glu Arg Lys Ala Tyr Ile Asn Thr Ile Ser Ser Leu Lys Asp
2975                2980                2985

Leu Ile Thr Lys Met Gln Leu Gln Arg Glu Ala Glu Val Tyr Asp
2990                2995                3000

Ser Ser Gln Ser His Glu Ser Phe Ser Asp Trp Arg Gly Glu Leu
3005                3010                3015

Leu Leu Ala Leu Gln Gln Val Phe Leu Glu Glu Arg Ser Val Leu
3020                3025                3030

Leu Ala Ala Phe Arg Thr Glu Leu Thr Ala Leu Gly Thr Thr Asp
3035                3040                3045

Ala Val Gly Leu Leu Asn Cys Leu Glu Gln Arg Ile Gln Glu Gln
3050                3055                3060

Gly Val Glu Tyr Gln Ala Ala Met Glu Cys Leu Gln Lys Ala Asp
3065                3070                3075

Arg Arg Ser Leu Leu Ser Glu Ile Gln Ala Leu His Ala Gln Met
3080                3085                3090

Asn Gly Arg Lys Ile Thr Leu Lys Arg Glu Gln Glu Ser Glu Lys
3095                3100                3105

Pro Ser Gln Glu Leu Leu Glu Tyr Asn Ile Gln Gln Lys Gln Ser
3110                3115                3120

Gln Met Leu Glu Met Gln Val Glu Leu Ser Ser Met Lys Asp Arg
3125                3130                3135

Ala Thr Glu Leu Gln Glu Gln Leu Ser Ser Glu Lys Met Val Val
3140                3145                3150

Ala Glu Leu Lys Ser Glu Leu Ala Gln Thr Lys Leu Glu Leu Glu
3155                3160                3165

Thr Thr Leu Lys Ala Gln His Lys His Leu Lys Glu Leu Glu Ala
3170                3175                3180

Phe Arg Leu Glu Val Lys Asp Lys Thr Asp Glu Val His Leu Leu
3185                3190                3195

Asn Asp Thr Leu Ala Ser Glu Gln Lys Lys Ser Arg Glu Leu Gln
3200                3205                3210

Trp Ala Leu Glu Lys Glu Lys Ala Lys Leu Gly Arg Ser Glu Glu
```

```
            3215                3220                3225

Arg Asp Lys Glu Glu Leu Glu  Asp Leu Lys Phe Ser  Leu Glu Ser
        3230                3235                3240

Gln Lys Gln Arg Asn Leu Gln  Leu Asn Leu Leu Leu  Glu Gln Gln
        3245                3250                3255

Lys Gln Leu Leu Asn Glu Ser  Gln Gln Lys Ile Glu  Ser Gln Arg
        3260                3265                3270

Met Leu Tyr Asp Ala Gln Leu  Ser Glu Glu Gln Gly  Arg Asn Leu
        3275                3280                3285

Glu Leu Gln Val Leu Leu Glu  Ser Glu Lys Val Arg  Ile Arg Glu
        3290                3295                3300

Met Ser Ser Thr Leu Asp Arg  Glu Arg Glu Leu His  Ala Gln Leu
        3305                3310                3315

Gln Ser Ser Asp Gly Thr Gly  Gln Ser Arg Pro Pro  Leu Pro Ser
        3320                3325                3330

Glu Asp Leu Leu Lys Glu Leu  Gln Lys Gln Leu Glu  Glu Lys His
        3335                3340                3345

Ser Arg Ile Val Glu Leu Leu  Asn Glu Thr Glu Lys  Tyr Lys Leu
        3350                3355                3360

Asp Ser Leu Gln Thr Arg Gln  Gln Met Glu Lys Asp  Arg Gln Val
        3365                3370                3375

His Arg Lys Thr Leu Gln Thr  Glu Gln Glu Ala Asn  Thr Glu Gly
        3380                3385                3390

Gln Lys Lys Met His Glu Leu  Gln Ser Lys Val Glu  Asp Leu Gln
        3395                3400                3405

Arg Gln Leu Glu Glu Lys Arg  Gln Gln Val Tyr Lys  Leu Asp Leu
        3410                3415                3420

Glu Gly Gln Arg Leu Gln Gly  Ile Met Gln Glu Phe  Gln Lys Gln
        3425                3430                3435

Glu Leu Glu Arg Glu Glu Lys  Arg Glu Ser Arg Arg  Ile Leu Tyr
        3440                3445                3450

Gln Asn Leu Asn Glu Pro Thr  Thr Trp Ser Leu Thr  Ser Asp Arg
        3455                3460                3465

Thr Arg Asn Trp Val Leu Gln  Gln Lys Ile Glu Gly  Glu Thr Lys
        3470                3475                3480

Glu Ser Asn Tyr Ala Lys Leu  Ile Glu Met Asn Gly  Gly Gly Thr
        3485                3490                3495

Gly Cys Asn His Glu Leu Glu  Met Ile Arg Gln Lys  Leu Gln Cys
        3500                3505                3510

Val Ala Ser Lys Leu Gln Val  Leu Pro Gln Lys Ala  Ser Glu Arg
        3515                3520                3525

Leu Gln Phe Glu Thr Ala Asp  Asp Glu Asp Phe Ile  Trp Val Gln
        3530                3535                3540

Glu Asn Ile Asp Glu Ile Ile  Leu Gln Leu Gln Lys  Leu Thr Gly
        3545                3550                3555

Gln Gln Gly Glu Glu Pro Ser  Leu Val Ser Pro Ser  Thr Ser Cys
        3560                3565                3570

Gly Ser Leu Thr Glu Arg Leu  Leu Arg Gln Asn Ala  Glu Leu Thr
        3575                3580                3585

Gly His Ile Ser Gln Leu Thr  Glu Glu Lys Asn Asp  Leu Arg Asn
        3590                3595                3600

Met Val Met Lys Leu Glu Glu  Gln Ile Arg Trp Tyr  Arg Gln Thr
        3605                3610                3615
```

```
Gly Ala Gly Arg Asp Asn Ser  Ser Arg Phe Ser Leu  Asn Gly Gly
    3620            3625                 3630

Ala Asn Ile Glu Ala Ile Ile  Ala Ser Glu Lys Glu  Val Trp Asn
    3635            3640                 3645

Arg Glu Lys Leu Thr Leu Gln  Lys Ser Leu Lys Arg  Ala Glu Ala
    3650            3655                 3660

Glu Val Tyr Lys Leu Lys Ala  Glu Leu Arg Asn Asp  Ser Leu Leu
    3665            3670                 3675

Gln Thr Leu Ser Pro Asp Ser  Glu His Val Thr Leu  Lys Arg Ile
    3680            3685                 3690

Tyr Gly Lys Tyr Leu Arg Ala  Glu Ser Phe Arg Lys  Ala Leu Ile
    3695            3700                 3705

Tyr Gln Lys Lys Tyr Leu Leu  Leu Leu Leu Gly Gly  Phe Gln Glu
    3710            3715                 3720

Cys Glu Asp Ala Thr Leu Ala  Leu Leu Ala Arg Met  Gly Gly Gln
    3725            3730                 3735

Pro Ala Phe Thr Asp Leu Glu  Val Ile Thr Asn Arg  Pro Lys Gly
    3740            3745                 3750

Phe Thr Arg Phe Arg Ser Ala  Val Arg Val Ser Ile  Ala Ile Ser
    3755            3760                 3765

Arg Met Lys Phe Leu Val Arg  Arg Trp His Arg Val  Thr Gly Ser
    3770            3775                 3780

Val Ser Ile Asn Ile Asn Arg  Asp Gly Phe Gly Leu  Asn Gln Gly
    3785            3790                 3795

Ala Glu Lys Thr Asp Ser Phe  Tyr His Ser Ser Gly  Gly Leu Glu
    3800            3805                 3810

Leu Tyr Gly Glu Pro Arg His  Thr Thr Tyr Arg Ser  Arg Ser Asp
    3815            3820                 3825

Leu Asp Tyr Ile Arg Ser Pro  Leu Pro Phe Gln Asn  Arg Tyr Pro
    3830            3835                 3840

Gly Thr Pro Ala Asp Phe Asn  Pro Gly Ser Leu Ala  Cys Ser Gln
    3845            3850                 3855

Leu Gln Asn Tyr Asp Pro Asp  Arg Ala Leu Thr Asp  Tyr Ile Thr
    3860            3865                 3870

Arg Leu Glu Ala Leu Gln Arg  Arg Leu Gly Thr Ile  Gln Ser Gly
    3875            3880                 3885

Ser Thr Thr Gln Phe His Ala  Gly Met Arg Arg
    3890            3895

<210> SEQ ID NO 55
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 55

Leu Leu Met Lys Arg Pro Xaa Val Val Lys
1               5                   10

<210> SEQ ID NO 56
<211> LENGTH: 10
<212> TYPE: PRT
```

```
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 56

Ala Lys Ala Arg Ser Leu Xaa Val Gln His
1               5                   10

<210> SEQ ID NO 57
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 57

Gly Gly Val Arg Cys Arg Xaa Arg Ser Ile
1               5                   10

<210> SEQ ID NO 58
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 58

Thr Leu Pro Arg Asn Xaa Gly Ala Gly Ala
1               5                   10

<210> SEQ ID NO 59
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 59

Arg Glu Leu Arg Arg Met Xaa Asp Glu Phe
1               5                   10

<210> SEQ ID NO 60
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 60

Leu Cys Leu Arg Arg Xaa Ser Leu Lys Ala
```

<210> SEQ ID NO 61
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 61

Leu Cys Leu Arg Arg Ser Xaa Leu Lys Ala
1               5                   10

<210> SEQ ID NO 62
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 62

Phe Pro Phe Arg Arg His Xaa Trp Ile Cys
1               5                   10

<210> SEQ ID NO 63
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 63

His Ser Gln Arg Arg Glu Xaa Phe Leu Tyr
1               5                   10

<210> SEQ ID NO 64
<211> LENGTH: 9
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 64

Ala Pro Ser Lys Arg Xaa Pro Met Cys
1               5

<210> SEQ ID NO 65
<211> LENGTH: 11
<212> TYPE: PRT
<213> ORGANISM: artificial sequence
<220> FEATURE:
<223> OTHER INFORMATION: Synthetic
<220> FEATURE:
<221> NAME/KEY: misc_feature

```
<222> LOCATION: (8)..(8)
<223> OTHER INFORMATION: Xaa can be any naturally occurring amino acid

<400> SEQUENCE: 65

Ala Pro Ile Arg Arg Arg Ser Xaa Asn Tyr Arg
1               5                   10

<210> SEQ ID NO 66
<211> LENGTH: 11
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 66

Ala Pro Ile Arg Arg Arg Xaa Ser Asn Tyr Arg
1               5                   10

<210> SEQ ID NO 67
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 67

Asn Asn Asn Arg Lys Thr Xaa Asn Gly Asp
1               5                   10

<210> SEQ ID NO 68
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 68

Thr Glu Thr Lys Lys Gln Xaa Phe Lys Gln
1               5                   10

<210> SEQ ID NO 69
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 69

Gly Glu Lys Arg Lys Asn Xaa Ile Leu Asn
1               5                   10

<210> SEQ ID NO 70
<211> LENGTH: 10
```

```
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 70

Asn Ser Ile Arg Lys Phe Xaa Ile Val Gln
1               5                   10

<210> SEQ ID NO 71
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 71

Pro Leu Glu Arg Arg Leu Xaa Leu Val Pro
1               5                   10

<210> SEQ ID NO 72
<211> LENGTH: 11
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: Xaa can be any naturally occurring amino acid

<400> SEQUENCE: 72

Leu Gln Ala Arg Arg Arg Gln Xaa Val Leu Asn
1               5                   10

<210> SEQ ID NO 73
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 73

Asn Ile His Arg Lys Thr Xaa Ala Ser Thr
1               5                   10

<210> SEQ ID NO 74
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 74
```

```
Ala Ser Thr Arg Lys Val Xaa Leu Ala Pro
1               5                  10
```

```
<210> SEQ ID NO 75
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 75

Ile Tyr Ser Arg Arg Leu Xaa Gln Glu Thr
1               5                  10
```

```
<210> SEQ ID NO 76
<211> LENGTH: 36
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid

<400> SEQUENCE: 76

Thr Glu Thr Lys Lys Gln Xaa Phe Lys Gln Thr Gly Glu Phe Gly Glu
1               5                  10                  15

Lys Arg Lys Asn Xaa Ile Leu Asn Pro Ile Asn Ser Ile Arg Lys Phe
            20                  25                  30

Xaa Ile Val Gln
        35
```

```
<210> SEQ ID NO 77
<211> LENGTH: 17
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 77

Asn Ile His Arg Lys Thr Xaa Ala Ser Thr Arg Lys Val Xaa Leu Ala
1               5                  10                  15

Pro
```

```
<210> SEQ ID NO 78
<211> LENGTH: 10
<212> TYPE: PRT
<213> ORGANISM: artificial sequence
```

```
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 78

Pro Arg Glu Lys Lys Tyr Xaa Ala Thr Lys
1               5                   10

<210> SEQ ID NO 79
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 79

Ile Leu Ser Arg Arg Pro Xaa Tyr Arg Lys
1               5                   10

<210> SEQ ID NO 80
<211> LENGTH: 11
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 80

Arg Arg Lys Arg Lys Glu Xaa Ser Asn Thr Asp
1               5                   10

<210> SEQ ID NO 81
<211> LENGTH: 11
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: Xaa can be any naturally occurring amino acid

<400> SEQUENCE: 81

Arg Arg Lys Arg Lys Glu Ser Xaa Asn Thr Asp
1               5                   10

<210> SEQ ID NO 82
<211> LENGTH: 14
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (11)..(11)
<223> OTHER INFORMATION: Xaa can be any naturally occurring amino acid

<400> SEQUENCE: 82

Val Thr Ser Arg Ile Arg Thr Gln Ser Phe Xaa Leu Gln Glu
1               5                   10
```

```
<210> SEQ ID NO 83
<211> LENGTH: 14
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: Xaa can be any naturally occurring amino acid

<400> SEQUENCE: 83

Val Thr Ser Arg Ile Arg Thr Gln Xaa Phe Ser Leu Gln Glu
1               5                   10

<210> SEQ ID NO 84
<211> LENGTH: 14
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 84

Val Thr Ser Arg Ile Arg Xaa Gln Ser Phe Ser Leu Gln Glu
1               5                   10

<210> SEQ ID NO 85
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 85

Ser Leu Glu Arg Arg Thr Xaa Ala Thr Gly
1               5                   10

<210> SEQ ID NO 86
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 86

Lys Leu Asp Lys Lys Val Xaa Ala Gln Glu
1               5                   10

<210> SEQ ID NO 87
<211> LENGTH: 11
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (8)..(8)
```

<223> OTHER INFORMATION: Xaa can be any naturally occurring amino acid

<400> SEQUENCE: 87

Thr Arg Arg Arg Arg Ala Pro Xaa Val Ala Asn
1               5                   10

<210> SEQ ID NO 88
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 88

Gly Asp Ala Arg Arg Leu Xaa Val Ser Ser
1               5                   10

<210> SEQ ID NO 89
<211> LENGTH: 9
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 89

Ile Ala Ala Arg Gly Xaa Phe Asp Gly
1               5

<210> SEQ ID NO 90
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 90

Leu Gln Ala Arg Lys Pro Xaa Asp Cys Asp
1               5                   10

<210> SEQ ID NO 91
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 91

Leu Gln Arg Arg Arg Arg Xaa Leu Ala Leu
1               5                   10

<210> SEQ ID NO 92
<211> LENGTH: 23
<212> TYPE: PRT

```
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid

<400> SEQUENCE: 92

Leu Gln Ala Arg Lys Pro Xaa Asp Cys Asp Ser Lys Glu Leu Gln Arg
1               5                   10                  15

Arg Arg Arg Xaa Leu Ala Leu
            20

<210> SEQ ID NO 93
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 93

Thr Asp Pro Arg Arg Arg Xaa Arg Asn Leu
1               5                   10

<210> SEQ ID NO 94
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 94

Gly Thr Pro Arg Lys Ala Xaa Gly Pro Pro
1               5                   10

<210> SEQ ID NO 95
<211> LENGTH: 9
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 95

Gln Thr Ala Arg Lys Xaa Thr Gly Gly
1               5

<210> SEQ ID NO 96
<211> LENGTH: 15
<212> TYPE: PRT
<213> ORGANISM: artificial sequence
<220> FEATURE:
<223> OTHER INFORMATION: Synthetic
<220> FEATURE:
```

-continued

```
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 96

Asp Gly Lys Lys Arg Lys Arg Xaa Arg Lys Glu Xaa Tyr Ser Ile
1               5                   10                  15

<210> SEQ ID NO 97
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 97

Asn Ala Ala Arg Arg Asp Xaa Val Leu Ala
1               5                   10

<210> SEQ ID NO 98
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 98

Pro Ser Gly Arg Arg Glu Xaa Leu Thr Ser
1               5                   10

<210> SEQ ID NO 99
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 99

Pro Gly Ala Arg Arg Gly Xaa Ala Gly Leu
1               5                   10

<210> SEQ ID NO 100
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 100

Ser Leu Gly Arg Arg Ala Xaa Phe His Leu
```

<210> SEQ ID NO 101
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: Xaa can be any naturally occurring amino acid

<400> SEQUENCE: 101

```
Ser Ala Pro Ile Arg Ser Ala Xaa Gln Ala
1               5                   10
```

<210> SEQ ID NO 102
<211> LENGTH: 9
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 102

```
Gln His Arg Ser Ser Ser Xaa Ala Pro
1               5
```

<210> SEQ ID NO 103
<211> LENGTH: 11
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: Xaa can be any naturally occurring amino acid

<400> SEQUENCE: 103

```
Ser Ser Lys Ile Arg Arg Leu Xaa Ala Cys Lys
1               5                   10
```

<210> SEQ ID NO 104
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 104

```
Arg His Phe Arg Arg Asp Xaa Phe Asp Asp
1               5                   10
```

<210> SEQ ID NO 105
<211> LENGTH: 11
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: Xaa can be any naturally occurring amino acid

<400> SEQUENCE: 105

Glu Arg Glu Arg Arg Ile Ser Xaa Ala Ala Ala
1               5                   10

<210> SEQ ID NO 106
<211> LENGTH: 9
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 106

Lys Leu Arg Lys Val Xaa Arg Met Glu
1               5

<210> SEQ ID NO 107
<211> LENGTH: 132
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (129)..(129)
<223> OTHER INFORMATION: Xaa can be any naturally occurring amino acid

<400> SEQUENCE: 107

Asp Ser Asn Gly Glu Gln Phe Ser Ser Leu Ile Gln Arg Glu Pro Ser
1               5                   10                  15

Ser Arg Leu Arg Ser Cys Xaa Val Thr Asp Ala Val Ala Glu Gln Gly
            20                  25                  30

His Leu Pro Pro Pro Ser Ala Pro Ala Gly Arg Ala Arg Ser Ser Xaa
        35                  40                  45

Val Thr Gly Gly Glu Glu Pro Thr Pro Ser Val Ala Tyr Val His Thr
    50                  55                  60

Thr Pro Gly Leu Pro Ser Gly Trp Glu Glu Arg Lys Asp Ala Lys Gly
65                  70                  75                  80

Arg Thr Tyr Tyr Val Asn His Asn Asn Arg Thr Thr Thr Trp Thr Arg
                85                  90                  95

Pro Ile Met Gln Leu Ala Glu Asp Gly Ala Ser Gly Ser Ala Thr Asn
            100                 105                 110

Ser Asn Asn His Leu Ile Glu Pro Gln Ile Arg Arg Pro Arg Ser Leu
        115                 120                 125

Xaa Ser Pro Thr
    130

<210> SEQ ID NO 108
<211> LENGTH: 10
<212> TYPE: PRT
<213> ORGANISM: artificial sequence

```
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 108

Ser Arg Leu Arg Ser Cys Xaa Val Thr Asp
1               5                   10

<210> SEQ ID NO 109
<211> LENGTH: 9
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 109

Arg Ala Arg Ser Ser Xaa Val Thr Gly
1               5

<210> SEQ ID NO 110
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 110

Arg Arg Pro Arg Ser Leu Xaa Ser Pro Thr
1               5                   10

<210> SEQ ID NO 111
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 111

Gln Met Thr Arg Arg Phe Xaa Ala Asp Glu
1               5                   10

<210> SEQ ID NO 112
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 112

Gly Tyr Leu Arg Arg Ala Xaa Val Ala Gln
1               5                   10
```

<210> SEQ ID NO 113
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 113

Lys Lys Pro Lys Lys Lys Xaa Cys Leu Leu
1               5                   10

<210> SEQ ID NO 114
<211> LENGTH: 21
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid

<400> SEQUENCE: 114

Arg Lys Ala Val Arg Arg Lys Arg Xaa His Arg Ala Lys Arg Arg
1               5                   10                  15

Ser Xaa Gly Arg Arg
            20

<210> SEQ ID NO 115
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 115

Gln Arg Ala Arg Leu Val Xaa Lys Asp Gly
1               5                   10

<210> SEQ ID NO 116
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 116

Val Ala Asn Leu Arg Lys Xaa Leu Leu Ile
1               5                   10

<210> SEQ ID NO 117
<211> LENGTH: 9

```
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 117

Cys Gln Val Arg Thr Xaa Tyr Val Pro
1               5

<210> SEQ ID NO 118
<211> LENGTH: 12
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: Xaa can be any naturally occurring amino acid

<400> SEQUENCE: 118

Ser Arg Gln Arg Ala Arg Leu Val Xaa Lys Asp Gly
1               5                   10

<210> SEQ ID NO 119
<211> LENGTH: 136
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (112)..(112)
<223> OTHER INFORMATION: Xaa can be any naturally occurring amino acid
<220> FEATURE:
<221> NAME/KEY: misc_feature
<222> LOCATION: (126)..(126)
<223> OTHER INFORMATION: Xaa can be any naturally occurring amino acid

<400> SEQUENCE: 119

Met Ala Gly Ala Gly Ser Ala Ala Val Ser Gly Ala Gly Thr Pro Val
1               5                   10                  15

Ala Gly Pro Thr Gly Arg Asp Leu Phe Ala Glu Gly Leu Leu Glu Phe
            20                  25                  30

Leu Arg Pro Ala Val Gln Gln Leu Asp Ser His Val His Ala Val Arg
        35                  40                  45

Glu Xaa Gln Val Glu Leu Arg Glu Gln Ile Asp Asn Leu Ala Thr Glu
    50                  55                  60

Leu Cys Arg Ile Asn Glu Asp Gln Lys Val Ala Leu Asp Leu Asp Pro
65                  70                  75                  80

Tyr Val Lys Lys Leu Leu Asn Ala Arg Arg Val Val Leu Val Asn
                85                  90                  95

Asn Ile Leu Gln Asn Ala Gln Glu Arg Leu Arg Arg Leu Asn His Xaa
            100                 105                 110

Val Ala Lys Glu Thr Ala Arg Arg Ala Met Leu Asp Xaa Gly Ile
        115                 120                 125

Tyr Pro Pro Gly Ser Pro Gly Lys
        130                 135
```

```
<210> SEQ ID NO 120
<211> LENGTH: 9
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 120

Arg Gly Val Arg Leu Xaa Leu Pro Arg
1               5

<210> SEQ ID NO 121
<211> LENGTH: 9
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 121

Arg Gln Glu Arg Ala Xaa Leu Gln Asp
1               5

<210> SEQ ID NO 122
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 122

Ser Arg Ser Arg Thr Pro Xaa Leu Pro Thr
1               5                   10

<210> SEQ ID NO 123
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 123

Val Lys Ser Lys Ile Gly Xaa Thr Glu Asn
1               5                   10

<210> SEQ ID NO 124
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
```

```
<223> OTHER INFORMATION: Xaa can be any naturally occurring amino acid

<400> SEQUENCE: 124

Val Gln Ser Lys Ile Gly Xaa Leu Asp Asn
1               5                  10

<210> SEQ ID NO 125
<211> LENGTH: 18
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 125

Arg Arg Leu Gln Pro Arg Leu Xaa Thr Arg Pro Xaa Gly Val Xaa Leu
1               5                  10                  15
Cys Gly

<210> SEQ ID NO 126
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 126

Phe Ile Gly Arg Arg Gln Xaa Leu Ile Glu
1               5                  10

<210> SEQ ID NO 127
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 127

His Ile Glu Arg Arg Val Xaa Asn Ala Gly
1               5                  10

<210> SEQ ID NO 128
<211> LENGTH: 11
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: Xaa can be any naturally occurring amino acid
```

```
<400> SEQUENCE: 128

Gly Ala Lys Leu Arg Lys Val Xaa Lys Gln Glu
1               5                   10

<210> SEQ ID NO 129
<211> LENGTH: 11
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: Xaa can be any naturally occurring amino acid

<400> SEQUENCE: 129

Leu Ala Arg Arg Arg Lys Ala Xaa Gln Val Gly
1               5                   10

<210> SEQ ID NO 130
<211> LENGTH: 12
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (9)..(9)
<223> OTHER INFORMATION: Xaa can be any naturally occurring amino acid

<400> SEQUENCE: 130

His Thr Pro Ser Phe Ser Gly Asp Xaa Ser Ser Ser
1               5                   10

<210> SEQ ID NO 131
<211> LENGTH: 9
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 131

Leu Tyr Asp Arg Arg Xaa Ile Phe Glu
1               5

<210> SEQ ID NO 132
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 132

Lys Lys Lys Arg Lys Thr Xaa Ser Ser Lys
1               5                   10

<210> SEQ ID NO 133
<211> LENGTH: 7
<212> TYPE: PRT
<213> ORGANISM: artificial sequence
```

```
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa can be any naturally occurring amino acid

<400> SEQUENCE: 133

Leu Arg Arg Ala Xaa Leu Gly
1               5

<210> SEQ ID NO 134
<211> LENGTH: 7
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa can be any naturally occurring amino acid

<400> SEQUENCE: 134

Leu Ala Lys Ala Xaa Leu Gly
1               5

<210> SEQ ID NO 135
<211> LENGTH: 7
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa can be any naturally occurring amino acid

<400> SEQUENCE: 135

Leu His Arg Ala Xaa Leu Gly
1               5

<210> SEQ ID NO 136
<211> LENGTH: 6
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa can be any naturally occurring amino acid

<400> SEQUENCE: 136

Arg Arg Ala Xaa Leu Gly
1               5

<210> SEQ ID NO 137
<211> LENGTH: 6
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa can be any naturally occurring amino acid

<400> SEQUENCE: 137

Leu Arg Arg Ala Xaa Leu
1               5
```

<210> SEQ ID NO 138
<211> LENGTH: 10
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 138

Lys Arg Lys Gln Ile Xaa Val Ala Gly Leu
1               5                   10

<210> SEQ ID NO 139
<211> LENGTH: 13
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (11)..(11)
<223> OTHER INFORMATION: Xaa can be any naturally occurring amino acid

<400> SEQUENCE: 139

Gly Gly Gly Gly Gly Gly Gly Arg Arg Gly Xaa Gly Gly
1               5                   10

<210> SEQ ID NO 140
<211> LENGTH: 7
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa can be any naturally occurring amino acid

<400> SEQUENCE: 140

Leu Arg Arg Trp Xaa Leu Gly
1               5

<210> SEQ ID NO 141
<211> LENGTH: 7
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa can be any naturally occurring amino acid

<400> SEQUENCE: 141

Leu Arg Arg Ala Xaa Val Ala
1               5

<210> SEQ ID NO 142
<211> LENGTH: 25
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (14)..(14)

```
<223> OTHER INFORMATION: Xaa can be any naturally occurring amino acid

<400> SEQUENCE: 142

Leu Asp Ile Val Pro Arg Leu Leu Leu Met Lys Arg Pro Xaa Val Val
1               5                   10                  15

Lys Asp Asn Cys Arg Arg Leu Ile Glu
            20                  25

<210> SEQ ID NO 143
<211> LENGTH: 31
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid

<400> SEQUENCE: 143

Pro Val Ser Trp Thr Glu Thr Lys Lys Gln Xaa Phe Lys Gln Thr Gly
1               5                   10                  15

Glu Phe Gly Glu Lys Arg Lys Asn Xaa Ile Leu Asn Pro Ile Asn
            20                  25                  30

<210> SEQ ID NO 144
<211> LENGTH: 20
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (11)..(11)
<223> OTHER INFORMATION: Xaa can be any naturally occurring amino acid

<400> SEQUENCE: 144

Pro Thr Trp Leu Lys Leu Asp Lys Lys Val Xaa Ala Gln Glu Val Arg
1               5                   10                  15

Lys Glu Asn Pro
            20

<210> SEQ ID NO 145
<211> LENGTH: 22
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (8)..(8)
<223> OTHER INFORMATION: Xaa can be any naturally occurring amino acid

<400> SEQUENCE: 145

Arg Gln Arg Ala Arg Leu Val Xaa Lys Glu Gly Arg Cys Asn Ile Glu
1               5                   10                  15

Phe Gly Asn Val Asp Ala
            20

<210> SEQ ID NO 146
<211> LENGTH: 24
<212> TYPE: PRT
<213> ORGANISM: artificial sequence
```

```
<220> FEATURE:
<223> OTHER INFORMATION: Synthetic
<220> FEATURE:
<221> NAME/KEY: misc_feature
<222> LOCATION: (14)..(14)
<223> OTHER INFORMATION: Xaa can be any naturally occurring amino acid

<400> SEQUENCE: 146

Trp Ala Ala Gln Arg Tyr Gly Arg Glu Leu Arg Arg Met Xaa Asp Glu
1               5                   10                  15

Phe Val Asp Ser Phe Lys Lys Gly
            20

<210> SEQ ID NO 147
<211> LENGTH: 13
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 147

Pro Arg Glu Lys Lys Tyr Xaa Ala Thr Lys Val Val Tyr
1               5                   10

<210> SEQ ID NO 148
<211> LENGTH: 20
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (10)..(10)
<223> OTHER INFORMATION: Xaa can be any naturally occurring amino acid

<400> SEQUENCE: 148

Trp Gly Pro Thr Asp Pro Arg Arg Arg Xaa Arg Asn Leu Gly Lys Val
1               5                   10                  15

Ile Asp Thr Leu
            20

<210> SEQ ID NO 149
<211> LENGTH: 7
<212> TYPE: PRT
<213> ORGANISM: artificial sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa can be any naturally occurring amino acid

<400> SEQUENCE: 149

Leu Arg Arg Trp Xaa Leu Gly
1               5

<210> SEQ ID NO 150
<211> LENGTH: 26
<212> TYPE: PRT
<213> ORGANISM: artificial sequence
<220> FEATURE:
<223> OTHER INFORMATION: Synthetic

<400> SEQUENCE: 150
```

```
Thr Thr Tyr Ala Asp Phe Ile Ala Ser Gly Arg Thr Gly Arg Arg Asn
1               5                   10                  15

Ala Ile His Asp Met Leu Phe Pro Cys Arg
            20              25
```

<210> SEQ ID NO 151
<211> LENGTH: 76
<212> TYPE: PRT
<213> ORGANISM: human

<400> SEQUENCE: 151

```
Met Thr Asp Val Glu Thr Thr Tyr Ala Asp Phe Ile Ala Ser Gly Arg
1               5                   10                  15

Thr Gly Arg Arg Asn Ala Ile His Asp Ile Leu Val Ser Ser Ala Ser
                20                  25                  30

Gly Asn Ser Asn Glu Leu Ala Leu Lys Leu Ala Gly Leu Asp Ile Asn
            35                  40                  45

Lys Thr Glu Gly Glu Glu Asp Ala Gln Arg Ser Ser Thr Glu Gln Ser
    50                  55                  60

Gly Glu Ala Gln Gly Glu Ala Ala Lys Ser Glu Ser
65                  70                  75
```

<210> SEQ ID NO 152
<211> LENGTH: 76
<212> TYPE: PRT
<213> ORGANISM: mouse

<400> SEQUENCE: 152

```
Met Thr Asp Val Glu Thr Thr Tyr Ala Asp Phe Ile Ala Ser Gly Arg
1               5                   10                  15

Thr Gly Arg Arg Asn Ala Ile His Asp Ile Leu Val Ser Ser Ala Ser
                20                  25                  30

Gly Asn Ser Asn Glu Leu Ala Leu Lys Leu Ala Gly Leu Asp Ile Asn
            35                  40                  45

Lys Thr Glu Gly Glu Asp Asp Gly Gln Arg Ser Ser Thr Glu Gln Ser
    50                  55                  60

Gly Glu Ala Gln Gly Glu Ala Ala Lys Ser Glu Ser
65                  70                  75
```

<210> SEQ ID NO 153
<211> LENGTH: 7
<212> TYPE: PRT
<213> ORGANISM: artificial sequence
<220> FEATURE:
<223> OTHER INFORMATION: Synthetic

<400> SEQUENCE: 153

```
Leu Arg Arg Ala Ala Val Ala
1               5
```

<210> SEQ ID NO 154
<211> LENGTH: 9
<212> TYPE: PRT
<213> ORGANISM: artificial sequence
<220> FEATURE:
<223> OTHER INFORMATION: Synthetic

<400> SEQUENCE: 154

```
Gly Arg Thr Gly Arg Arg Asn Ala Ile
1               5
```

```
<210> SEQ ID NO 155
<211> LENGTH: 20
<212> TYPE: PRT
<213> ORGANISM: artificial sequence
<220> FEATURE:
<223> OTHER INFORMATION: Synthetic

<400> SEQUENCE: 155

Thr Thr Tyr Ala Asp Phe Ile Ala Ser Gly Arg Thr Gly Arg Arg Asn
1               5                   10                  15

Ala Ile His Asp
            20

<210> SEQ ID NO 156
<211> LENGTH: 15
<212> TYPE: PRT
<213> ORGANISM: artificial sequence
<220> FEATURE:
<223> OTHER INFORMATION: Synthetic

<400> SEQUENCE: 156

Ala Asp Phe Ile Ala Ser Gly Arg Thr Gly Arg Arg Asn Ala Ile
1               5                   10                  15

<210> SEQ ID NO 157
<211> LENGTH: 14
<212> TYPE: PRT
<213> ORGANISM: artificial sequence
<220> FEATURE:
<223> OTHER INFORMATION: Synthetic

<400> SEQUENCE: 157

Asp Phe Ile Ala Ser Gly Arg Thr Gly Arg Arg Asn Ala Ile
1               5                   10

<210> SEQ ID NO 158
<211> LENGTH: 17
<212> TYPE: PRT
<213> ORGANISM: artificial sequence
<220> FEATURE:
<223> OTHER INFORMATION: Synthetic

<400> SEQUENCE: 158

Thr Tyr Ala Asp Phe Ile Ala Ser Gly Arg Thr Gly Arg Arg Asn Ala
1               5                   10                  15

Ile

<210> SEQ ID NO 159
<211> LENGTH: 16
<212> TYPE: PRT
<213> ORGANISM: artificial sequence
<220> FEATURE:
<223> OTHER INFORMATION: Synthetic

<400> SEQUENCE: 159

Tyr Ala Asp Phe Ile Ala Ser Gly Arg Thr Gly Arg Arg Asn Ala Ile
1               5                   10                  15

<210> SEQ ID NO 160
<211> LENGTH: 18
<212> TYPE: PRT
<213> ORGANISM: artificial sequence
<220> FEATURE:
<223> OTHER INFORMATION: Synthetic

<400> SEQUENCE: 160
```

Thr Thr Tyr Ala Asp Phe Ile Ala Ser Gly Arg Thr Gly Arg Arg Asn
1               5                   10                  15

Ala Ile

<210> SEQ ID NO 161
<211> LENGTH: 15
<212> TYPE: PRT
<213> ORGANISM: artificial sequence
<220> FEATURE:
<223> OTHER INFORMATION: Synthetic

<400> SEQUENCE: 161

Phe Ile Ala Ser Gly Arg Thr Gly Arg Arg Asn Ala Ile His Asp
1               5                   10                  15

<210> SEQ ID NO 162
<211> LENGTH: 10
<212> TYPE: PRT
<213> ORGANISM: artificial sequence
<220> FEATURE:
<223> OTHER INFORMATION: Synthetic

<400> SEQUENCE: 162

Arg Thr Gly Arg Arg Asn Ala Ile His Asp
1               5                   10

<210> SEQ ID NO 163
<211> LENGTH: 13
<212> TYPE: PRT
<213> ORGANISM: artificial sequence
<220> FEATURE:
<223> OTHER INFORMATION: Synthetic

<400> SEQUENCE: 163

Ala Ser Gly Arg Thr Gly Arg Arg Asn Ala Ile His Asp
1               5                   10

<210> SEQ ID NO 164
<211> LENGTH: 14
<212> TYPE: PRT
<213> ORGANISM: artificial sequence
<220> FEATURE:
<223> OTHER INFORMATION: Synthetic

<400> SEQUENCE: 164

Ile Ala Ser Gly Arg Thr Gly Arg Arg Asn Ala Ile His Asp
1               5                   10

<210> SEQ ID NO 165
<211> LENGTH: 11
<212> TYPE: PRT
<213> ORGANISM: artificial sequence
<220> FEATURE:
<223> OTHER INFORMATION: Synthetic

<400> SEQUENCE: 165

Gly Arg Thr Gly Arg Arg Asn Ala Ile His Asp
1               5                   10

<210> SEQ ID NO 166
<211> LENGTH: 11
<212> TYPE: PRT
<213> ORGANISM: artificial sequence
<220> FEATURE:
<223> OTHER INFORMATION: Synthetic

<400> SEQUENCE: 166

Gly Lys Thr Gly Arg Arg Asn Ala Ile His Asp
1               5                   10

<210> SEQ ID NO 167
<211> LENGTH: 11
<212> TYPE: PRT
<213> ORGANISM: artificial sequence
<220> FEATURE:
<223> OTHER INFORMATION: Synthetic

<400> SEQUENCE: 167

Gly Arg Thr Gly Lys Arg Asn Ala Ile His Asp
1               5                   10

<210> SEQ ID NO 168
<211> LENGTH: 11
<212> TYPE: PRT
<213> ORGANISM: artificial sequence
<220> FEATURE:
<223> OTHER INFORMATION: Synthetic

<400> SEQUENCE: 168

Gly Arg Thr Gly Arg Lys Asn Ala Ile His Asp
1               5                   10

<210> SEQ ID NO 169
<211> LENGTH: 20
<212> TYPE: PRT
<213> ORGANISM: artificial sequence
<220> FEATURE:
<223> OTHER INFORMATION: Synthetic

<400> SEQUENCE: 169

Ile Ala Ser Gly Arg Thr Gly Arg Arg Asn Ala Ile His Asp Ile Leu
1               5                   10                  15

Val Ser Ser Ala
            20

<210> SEQ ID NO 170
<211> LENGTH: 17
<212> TYPE: PRT
<213> ORGANISM: artificial sequence
<220> FEATURE:
<223> OTHER INFORMATION: Synthetic

<400> SEQUENCE: 170

Gly Arg Thr Gly Arg Arg Asn Ala Ile His Asp Ile Leu Val Ser Ser
1               5                   10                  15

Ala

<210> SEQ ID NO 171
<211> LENGTH: 16
<212> TYPE: PRT
<213> ORGANISM: artificial sequence
<220> FEATURE:
<223> OTHER INFORMATION: Synthetic

<400> SEQUENCE: 171

Arg Thr Gly Arg Arg Asn Ala Ile His Asp Ile Leu Val Ser Ser Ala
1               5                   10                  15

<210> SEQ ID NO 172
<211> LENGTH: 18
<212> TYPE: PRT
<213> ORGANISM: artificial sequence

```
<220> FEATURE:
<223> OTHER INFORMATION: Synthetic

<400> SEQUENCE: 172

Ser Thr Tyr Ala Asp Phe Ile Ala Ser Gly Arg Thr Gly Arg Arg Asn
1               5                   10                  15

Ala Ile

<210> SEQ ID NO 173
<211> LENGTH: 18
<212> TYPE: PRT
<213> ORGANISM: artificial sequence
<220> FEATURE:
<223> OTHER INFORMATION: Synthetic

<400> SEQUENCE: 173

Thr Ala Tyr Ala Asp Phe Ile Ala Ser Gly Arg Thr Gly Arg Arg Asn
1               5                   10                  15

Ala Ile

<210> SEQ ID NO 174
<211> LENGTH: 18
<212> TYPE: PRT
<213> ORGANISM: artificial sequence
<220> FEATURE:
<223> OTHER INFORMATION: Synthetic

<400> SEQUENCE: 174

Thr Thr Ala Ala Asp Phe Ile Ala Ser Gly Arg Thr Gly Arg Arg Asn
1               5                   10                  15

Ala Ile

<210> SEQ ID NO 175
<211> LENGTH: 18
<212> TYPE: PRT
<213> ORGANISM: artificial sequence
<220> FEATURE:
<223> OTHER INFORMATION: Synthetic

<400> SEQUENCE: 175

Thr Thr Tyr Leu Asp Phe Ile Ala Ser Gly Arg Thr Gly Arg Arg Asn
1               5                   10                  15

Ala Ile

<210> SEQ ID NO 176
<211> LENGTH: 18
<212> TYPE: PRT
<213> ORGANISM: artificial sequence
<220> FEATURE:
<223> OTHER INFORMATION: Synthetic

<400> SEQUENCE: 176

Thr Thr Tyr Ala Ala Phe Ile Ala Ser Gly Arg Thr Gly Arg Arg Asn
1               5                   10                  15

Ala Ile

<210> SEQ ID NO 177
<211> LENGTH: 18
<212> TYPE: PRT
<213> ORGANISM: artificial sequence
<220> FEATURE:
<223> OTHER INFORMATION: Synthetic

<400> SEQUENCE: 177
```

```
Thr Thr Tyr Ala Asp Ala Ile Ala Ser Gly Arg Thr Gly Arg Arg Asn
1               5                   10                  15

Ala Ile

<210> SEQ ID NO 178
<211> LENGTH: 18
<212> TYPE: PRT
<213> ORGANISM: artificial sequence
<220> FEATURE:
<223> OTHER INFORMATION: Synthetic

<400> SEQUENCE: 178

Thr Thr Tyr Ala Asp Phe Ala Ala Ser Gly Arg Thr Gly Arg Arg Asn
1               5                   10                  15

Ala Ile

<210> SEQ ID NO 179
<211> LENGTH: 19
<212> TYPE: PRT
<213> ORGANISM: artificial sequence
<220> FEATURE:
<223> OTHER INFORMATION: Synthetic

<400> SEQUENCE: 179

Thr Thr Tyr Ala Asp Phe Ile Ala Ser Gly Arg Thr Gly Arg Arg Ala
1               5                   10                  15

Ser Ala Ile

<210> SEQ ID NO 180
<211> LENGTH: 18
<212> TYPE: PRT
<213> ORGANISM: artificial sequence
<220> FEATURE:
<223> OTHER INFORMATION: Synthetic

<400> SEQUENCE: 180

Thr Thr Tyr Ala Asp Phe Ile Ala Ser Gly Arg Thr Leu Arg Arg Asn
1               5                   10                  15

Ala Ile

<210> SEQ ID NO 181
<211> LENGTH: 18
<212> TYPE: PRT
<213> ORGANISM: artificial sequence
<220> FEATURE:
<223> OTHER INFORMATION: Synthetic

<400> SEQUENCE: 181

Thr Thr Tyr Ala Asp Phe Ile Ala Leu Ile Arg Thr Gly Arg Arg Asn
1               5                   10                  15

Ala Ile

<210> SEQ ID NO 182
<211> LENGTH: 9
<212> TYPE: PRT
<213> ORGANISM: artificial sequence
<220> FEATURE:
<223> OTHER INFORMATION: Synthetic

<400> SEQUENCE: 182

Gly Arg Thr Gly Arg Arg Asn Ala Ile
1               5
```

```
<210> SEQ ID NO 183
<211> LENGTH: 9
<212> TYPE: PRT
<213> ORGANISM: artificial sequence
<220> FEATURE:
<223> OTHER INFORMATION: Synthetic

<400> SEQUENCE: 183

Gly Arg Thr Gly Arg Arg Ala Ala Ile
1               5

<210> SEQ ID NO 184
<211> LENGTH: 9
<212> TYPE: PRT
<213> ORGANISM: artificial sequence
<220> FEATURE:
<223> OTHER INFORMATION: Synthetic

<400> SEQUENCE: 184

Gly Arg Thr Gly Arg Arg Gly Ala Ile
1               5

<210> SEQ ID NO 185
<211> LENGTH: 9
<212> TYPE: PRT
<213> ORGANISM: artificial sequence
<220> FEATURE:
<223> OTHER INFORMATION: Synthetic

<400> SEQUENCE: 185

Gly Arg Thr Leu Arg Arg Asn Ala Ile
1               5

<210> SEQ ID NO 186
<211> LENGTH: 9
<212> TYPE: PRT
<213> ORGANISM: artificial sequence
<220> FEATURE:
<223> OTHER INFORMATION: Synthetic

<400> SEQUENCE: 186

Gly Arg Ala Gly Arg Arg Asn Ala Ile
1               5

<210> SEQ ID NO 187
<211> LENGTH: 18
<212> TYPE: PRT
<213> ORGANISM: artificial sequence
<220> FEATURE:
<223> OTHER INFORMATION: Synthetic

<400> SEQUENCE: 187

Thr Thr Tyr Ala Asp Phe Ile Ala Ser Gly Arg Thr Gly Arg Arg Asn
1               5                   10                  15

Ala Leu

<210> SEQ ID NO 188
<211> LENGTH: 18
<212> TYPE: PRT
<213> ORGANISM: artificial sequence
<220> FEATURE:
<223> OTHER INFORMATION: Synthetic

<400> SEQUENCE: 188

Thr Thr Tyr Ala Asp Phe Ile Ala Ser Gly Arg Thr Gly Arg Arg Asn
1               5                   10                  15
```

Ala Gly

<210> SEQ ID NO 189
<211> LENGTH: 9
<212> TYPE: PRT
<213> ORGANISM: artificial sequence
<220> FEATURE:
<223> OTHER INFORMATION: Synthetic

<400> SEQUENCE: 189

Gly Arg Thr Gly Arg Arg Asn Ala Leu
1               5

<210> SEQ ID NO 190
<211> LENGTH: 9
<212> TYPE: PRT
<213> ORGANISM: artificial sequence
<220> FEATURE:
<223> OTHER INFORMATION: Synthetic

<400> SEQUENCE: 190

Gly Arg Thr Gly Arg Arg Asn Ala Gly
1               5

<210> SEQ ID NO 191
<211> LENGTH: 9
<212> TYPE: PRT
<213> ORGANISM: artificial sequence
<220> FEATURE:
<223> OTHER INFORMATION: Synthetic

<400> SEQUENCE: 191

Gly Arg Thr Gly Arg Arg Asn Ala Ile
1               5

<210> SEQ ID NO 192
<211> LENGTH: 9
<212> TYPE: PRT
<213> ORGANISM: artificial sequence
<220> FEATURE:
<223> OTHER INFORMATION: Synthetic

<400> SEQUENCE: 192

Gly Lys Thr Gly Arg Arg Asn Ala Ile
1               5

<210> SEQ ID NO 193
<211> LENGTH: 17
<212> TYPE: PRT
<213> ORGANISM: artificial sequence
<220> FEATURE:
<223> OTHER INFORMATION: Synthetic

<400> SEQUENCE: 193

Thr Tyr Ala Asp Phe Ile Ala Ser Gly Arg Thr Gly Arg Arg Asn Ala
1               5                   10                  15

Ile

<210> SEQ ID NO 194
<211> LENGTH: 17
<212> TYPE: PRT
<213> ORGANISM: artificial sequence
<220> FEATURE:
<223> OTHER INFORMATION: Synthetic

<400> SEQUENCE: 194

Thr Tyr Ala Asp Ala Ile Ala Ser Gly Arg Thr Gly Arg Arg Asn Ala
1               5                   10                  15

Ile

<210> SEQ ID NO 195
<211> LENGTH: 17
<212> TYPE: PRT
<213> ORGANISM: artificial sequence
<220> FEATURE:
<223> OTHER INFORMATION: Synthetic

<400> SEQUENCE: 195

Thr Tyr Ala Asp Trp Ile Ala Ser Gly Arg Thr Gly Arg Arg Asn Ala
1               5                   10                  15

Ile

<210> SEQ ID NO 196
<211> LENGTH: 18
<212> TYPE: PRT
<213> ORGANISM: artificial sequence
<220> FEATURE:
<223> OTHER INFORMATION: Synthetic

<400> SEQUENCE: 196

Thr Thr Tyr Ala Asp Phe Ile Ala Ser Gly Arg Thr Gly Arg Arg Asn
1               5                   10                  15

Ala Ile

<210> SEQ ID NO 197
<211> LENGTH: 20
<212> TYPE: PRT
<213> ORGANISM: artificial sequence
<220> FEATURE:
<223> OTHER INFORMATION: Synthetic

<400> SEQUENCE: 197

Ile Ala Ala Gly Arg Thr Gly Arg Arg Asn Ala Ile His Glu Ile Leu
1               5                   10                  15

Val Ser Ser Ala
            20

<210> SEQ ID NO 198
<211> LENGTH: 14
<212> TYPE: PRT
<213> ORGANISM: artificial sequence
<220> FEATURE:
<223> OTHER INFORMATION: Synthetic

<400> SEQUENCE: 198

Ile Ala Ala Gly Arg Thr Gly Arg Arg Asn Ala Ile His Glu
1               5                   10

<210> SEQ ID NO 199
<211> LENGTH: 20
<212> TYPE: PRT
<213> ORGANISM: artificial sequence
<220> FEATURE:
<223> OTHER INFORMATION: Synthetic

<400> SEQUENCE: 199

Ile Ala Ser Gly Arg Thr Gly Arg Arg Asn Ser Ile His Asp Ile Leu
1               5                   10                  15

Val Ser Ser Ala

20

<210> SEQ ID NO 200
<211> LENGTH: 24
<212> TYPE: PRT
<213> ORGANISM: artificial sequence
<220> FEATURE:
<223> OTHER INFORMATION: Synthetic

<400> SEQUENCE: 200

Tyr Ala Asp Phe Ile Ala Ser Gly Arg Thr Gly Arg Arg Asn Ala Ile
1               5                   10                  15

His Asp Ile Leu Val Ser Ser Ala
            20

<210> SEQ ID NO 201
<211> LENGTH: 18
<212> TYPE: PRT
<213> ORGANISM: artificial sequence
<220> FEATURE:
<223> OTHER INFORMATION: Synthetic

<400> SEQUENCE: 201

Tyr Ala Asp Phe Ile Ala Ser Gly Arg Thr Gly Arg Arg Asn Ala Ile
1               5                   10                  15

His Glu

<210> SEQ ID NO 202
<211> LENGTH: 20
<212> TYPE: PRT
<213> ORGANISM: artificial sequence
<220> FEATURE:
<223> OTHER INFORMATION: Synthetic

<400> SEQUENCE: 202

Thr Thr Tyr Ala Asp Phe Ile Ala Ser Gly Arg Thr Gly Arg Arg Asn
1               5                   10                  15

Ala Ile His Asp
            20

<210> SEQ ID NO 203
<211> LENGTH: 24
<212> TYPE: PRT
<213> ORGANISM: artificial sequence
<220> FEATURE:
<223> OTHER INFORMATION: Synthetic

<400> SEQUENCE: 203

Thr Asp Val Glu Thr Thr Tyr Ala Asp Phe Ile Ala Ser Gly Arg Thr
1               5                   10                  15

Gly Arg Arg Asn Ala Ile His Asp
            20

<210> SEQ ID NO 204
<211> LENGTH: 23
<212> TYPE: PRT
<213> ORGANISM: artificial sequence
<220> FEATURE:
<223> OTHER INFORMATION: Synthetic

<400> SEQUENCE: 204

Tyr Ala Asp Phe Ile Ala Ala Gly Arg Gly Arg Arg Asn Ala Ile His
1               5                   10                  15

Asp Ile Leu Val Ala Ala Ala

```
20

<210> SEQ ID NO 205
<211> LENGTH: 24
<212> TYPE: PRT
<213> ORGANISM: artificial sequence
<220> FEATURE:
<223> OTHER INFORMATION: Synthetic

<400> SEQUENCE: 205

Tyr Ala Asp Phe Ile Ala Ser Gly Arg Thr Gly Arg Gly Asn Ala Ile
1               5                  10                  15

His Asp Ile Leu Val Ser Ser Ala
            20

<210> SEQ ID NO 206
<211> LENGTH: 24
<212> TYPE: PRT
<213> ORGANISM: artificial sequence
<220> FEATURE:
<223> OTHER INFORMATION: Synthetic

<400> SEQUENCE: 206

Tyr Ala Asp Phe Ile Ala Ser Gly Arg Thr Gly Gly Arg Asn Ala Ile
1               5                  10                  15

His Asp Ile Leu Val Ser Ser Ala
            20

<210> SEQ ID NO 207
<211> LENGTH: 24
<212> TYPE: PRT
<213> ORGANISM: artificial sequence
<220> FEATURE:
<223> OTHER INFORMATION: Synthetic

<400> SEQUENCE: 207

Tyr Ala Asp Phe Ile Ala Ser Gly Gly Thr Gly Arg Arg Asn Ala Ile
1               5                  10                  15

His Asp Ile Leu Val Ser Ser Ala
            20

<210> SEQ ID NO 208
<211> LENGTH: 24
<212> TYPE: PRT
<213> ORGANISM: artificial sequence
<220> FEATURE:
<223> OTHER INFORMATION: Synthetic

<400> SEQUENCE: 208

Tyr Ala Asp Phe Ile Ala Ser Gly Arg Thr Gly Arg Arg Asn Ala Ile
1               5                  10                  15

Gly Asp Ile Leu Val Ser Ser Ala
            20

<210> SEQ ID NO 209
<211> LENGTH: 7
<212> TYPE: PRT
<213> ORGANISM: artificial sequence
<220> FEATURE:
<223> OTHER INFORMATION: Synthetic

<400> SEQUENCE: 209

Leu Arg Arg Ala Ala Leu Gly
1               5
```

<210> SEQ ID NO 210
<211> LENGTH: 7
<212> TYPE: PRT
<213> ORGANISM: artificial sequence
<220> FEATURE:
<223> OTHER INFORMATION: Synthetic

<400> SEQUENCE: 210

Leu Arg Arg Ala Val Leu Gly
1               5

<210> SEQ ID NO 211
<211> LENGTH: 7
<212> TYPE: PRT
<213> ORGANISM: artificial sequence
<220> FEATURE:
<223> OTHER INFORMATION: Synthetic

<400> SEQUENCE: 211

Leu Arg Arg Ala His Leu Gly
1               5

<210> SEQ ID NO 212
<211> LENGTH: 7
<212> TYPE: PRT
<213> ORGANISM: artificial sequence
<220> FEATURE:
<223> OTHER INFORMATION: Synthetic

<400> SEQUENCE: 212

Leu Arg Arg Ala Asp Leu Gly
1               5

<210> SEQ ID NO 213
<211> LENGTH: 7
<212> TYPE: PRT
<213> ORGANISM: artificial sequence
<220> FEATURE:
<223> OTHER INFORMATION: Synthetic

<400> SEQUENCE: 213

Leu Arg Arg Ala Gly Leu Gly
1               5

<210> SEQ ID NO 214
<211> LENGTH: 7
<212> TYPE: PRT
<213> ORGANISM: artificial sequence
<220> FEATURE:
<223> OTHER INFORMATION: Synthetic

<400> SEQUENCE: 214

Leu Arg Arg Ala Asn Leu Gly
1               5

<210> SEQ ID NO 215
<211> LENGTH: 621
<212> TYPE: PRT
<213> ORGANISM: viral

<400> SEQUENCE: 215

Met Pro Gly Phe Tyr Glu Ile Val Lys Val Pro Ser Asp Leu Asp
1               5                   10                  15

Gly His Leu Pro Gly Ile Ser Asp Ser Phe Val Asn Trp Val Ala Glu
                20                  25                  30

-continued

```
Lys Glu Trp Glu Leu Pro Pro Asp Ser Asp Met Asp Leu Asn Leu Ile
            35                  40                  45

Glu Gln Ala Pro Leu Thr Val Ala Glu Lys Leu Gln Arg Asp Phe Leu
 50                  55                  60

Thr Glu Trp Arg Arg Val Ser Lys Ala Pro Glu Ala Leu Phe Phe Val
 65                  70                  75                  80

Gln Phe Glu Lys Gly Glu Ser Tyr Phe His Met His Val Leu Val Glu
                 85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
            115                 120                 125

Pro Asn Trp Phe Ala Val Thr Lys Thr Arg Asn Gly Ala Gly Gly Gly
130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
                165                 170                 175

Ser Ala Cys Leu Asn Leu Thr Glu Arg Lys Arg Leu Val Ala Gln His
            180                 185                 190

Leu Thr His Val Ser Gln Thr Gln Glu Gln Asn Lys Glu Asn Gln Asn
            195                 200                 205

Pro Asn Ser Asp Ala Pro Val Ile Arg Ser Lys Thr Ser Ala Arg Tyr
210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ser Leu Thr Lys Thr Ala Pro Asp Tyr Leu Val Gly Gln Gln
            275                 280                 285

Pro Val Glu Asp Ile Ser Ser Asn Arg Ile Tyr Lys Ile Leu Glu Leu
290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Thr Val Pro
            340                 345                 350

Phe Tyr Gly Cys Val Asn Trp Thr Asn Glu Asn Phe Pro Phe Asn Asp
            355                 360                 365

Cys Val Asp Lys Met Val Ile Trp Trp Glu Glu Gly Lys Met Thr Ala
370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
            435                 440                 445

Glu Leu Thr Arg Arg Leu Asp His Asp Phe Gly Lys Val Thr Lys Gln
```

```
                      450                 455                 460
Glu Val Lys Asp Phe Phe Arg Trp Ala Lys Asp His Val Val Glu Val
465                 470                 475                 480

Glu His Glu Phe Tyr Val Lys Lys Gly Gly Ala Lys Lys Arg Pro Ala
                    485                 490                 495

Pro Ser Asp Ala Asp Ile Ser Glu Pro Lys Arg Val Arg Glu Ser Val
                500                 505                 510

Ala Gln Pro Ser Thr Ser Asp Ala Glu Ala Ser Ile Asn Tyr Ala Asp
            515                 520                 525

Arg Tyr Gln Asn Lys Cys Ser Arg His Val Gly Met Asn Leu Met Leu
        530                 535                 540

Phe Pro Cys Arg Gln Cys Glu Arg Met Asn Gln Asn Ser Asn Ile Cys
545                 550                 555                 560

Phe Thr His Gly Gln Lys Asp Cys Leu Glu Cys Phe Pro Val Ser Glu
                565                 570                 575

Ser Gln Pro Val Ser Val Val Lys Lys Ala Tyr Gln Lys Leu Cys Tyr
                580                 585                 590

Ile His His Ile Met Gly Lys Val Pro Asp Ala Cys Thr Ala Cys Asp
            595                 600                 605

Leu Val Asn Val Asp Leu Asp Asp Cys Ile Phe Glu Gln
        610                 615                 620

<210> SEQ ID NO 216
<211> LENGTH: 27
<212> TYPE: PRT
<213> ORGANISM: artificial sequence
<220> FEATURE:
<223> OTHER INFORMATION: Synthetic

<400> SEQUENCE: 216

Asn Tyr Ala Asp Arg Tyr Gln Asn Lys Cys Ser Arg His Val Gly Met
1               5                   10                  15

Asn Leu Met Leu Phe Pro Cys Arg Gln Cys Glu
                20                  25
```